(12) United States Patent
Miyazaki

(10) Patent No.: US 8,017,656 B2
(45) Date of Patent: Sep. 13, 2011

(54) ORGANIC SULFUR COMPOUNDS AND USE THEREOF

(75) Inventor: Hiroyuki Miyazaki, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 378 days.

(21) Appl. No.: 12/094,255

(22) PCT Filed: Nov. 1, 2006

(86) PCT No.: PCT/JP2006/322322
§ 371 (c)(1),
(2), (4) Date: May 19, 2008

(87) PCT Pub. No.: WO2007/060839
PCT Pub. Date: May 31, 2007

(65) Prior Publication Data
US 2009/0186941 A1    Jul. 23, 2009

(30) Foreign Application Priority Data

Nov. 22, 2005 (JP) ................. 2005-336721
Jun. 6, 2006 (JP) ................. 2006-156916

(51) Int. Cl.
| | | |
|---|---|---|
| C07C 325/00 | (2006.01) | |
| C07C 315/00 | (2006.01) | |
| C07C 317/00 | (2006.01) | |
| C07C 331/00 | (2006.01) | |
| C07C 17/00 | (2006.01) | |
| C09B 49/00 | (2006.01) | |
| C09B 59/00 | (2006.01) | |
| A01N 33/08 | (2006.01) | |
| A01N 37/18 | (2006.01) | |
| A61K 31/13 | (2006.01) | |

(52) U.S. Cl. ............ 514/628; 514/665; 568/27; 568/20; 568/29; 568/30; 568/31; 568/32; 568/35; 568/36; 568/37; 568/74; 568/75; 570/123

(58) Field of Classification Search ............ 568/20, 568/27, 29, 30, 31, 32, 35, 36, 37, 74, 75; 570/123; 514/628, 665
See application file for complete search history.

(56) References Cited

U.S. PATENT DOCUMENTS

| | | |
|---|---|---|
| 3,513,172 A | 5/1970 | Brokke |
| 3,654,293 A | 4/1972 | Brokke |
| 3,666,818 A | 5/1972 | Brokke |
| 3,692,912 A | 9/1972 | Brokke |
| 3,697,536 A | 10/1972 | Brokke |
| 3,700,646 A | 10/1972 | Anello et al. |
| 3,780,050 A | 12/1973 | Brokke |
| 3,891,662 A | 6/1975 | Brokke |
| 5,807,899 A | 9/1998 | Bohlmann et al. |
| 6,288,051 B1 | 9/2001 | Bittler et al. |
| 2003/0229050 A1 | 12/2003 | Lahm et al. |
| 2010/0160434 A1 | 6/2010 | Miyazaki |

FOREIGN PATENT DOCUMENTS

| | | |
|---|---|---|
| EP | 0 134 200 A1 | 3/1985 |
| FR | 2 516 920 | 5/1983 |
| FR | 2 619 811 A1 | 3/1989 |
| JP | 2004-091785 A | 3/2004 |
| JP | 2004-130306 A | 4/2004 |
| JP | 2005-179321 A | 7/2005 |
| WO | WO-98/07740 A1 | 2/1998 |
| WO | WO-98/25916 A1 | 6/1998 |
| WO | WO-99/33855 A1 | 7/1999 |
| WO | WO-99/42109 A1 | 8/1999 |
| WO | WO-00/03979 A1 | 1/2000 |
| WO | WO-02/40431 A2 | 5/2002 |

OTHER PUBLICATIONS

U.S. Appl. No. 12/600,622, filed Nov. 2009, Miyazaki.*
Serratrice et al., "Etude RMN Du $^{13}$C De Composes Fluoroaliphatiques Et De Tensio-Actifs Non Ioniques Perfluoroalkyles," Journal of Fluorine Chemistry, vol. 25, 1984, pp. 275-288.
Rocaboy et al., "Syntheses, oxidations, and palladium complexes of fluorous dialkyl sulfides: new precursors to hightly active catalysts for the Suzuki coupling," Tetrahedron, vol. 58, 2002, pp. 4007-4014.
Brace, "Oxidation chemistry of perfluoroalkyl-segmented thiols, disulfides, thiosulfinates and thiosulfonates, The role of the perfluoroalkyl group in searching out new chemistry," Journal of Fluorine Chemistry, vol. 105, 2000, pp. 11-23.
Calas et al., "Synthesis of terminally perfluorinated long-chain alkanethiols, sulfides and disulfides from the corresponding halides," Journal of Fluorine Chemistry, vol. 104, 2000, pp. 173-183.
Szonyi et al., "Fonctionnalisation Des Iodures De F-Alkyl-2 Ethane Par Catalyse Par Transfert De Phase: Importance De Cette Technique En Serie F-Alkylee," Journal of Fluorine Chemistry, vol. 42, 1989, pp. 59-68.
Dieng et al., "Synthese Et Reactivite Des F-Alkyl Sulfures Et Sulfones Actives," Journal of Fluorine Chemistry, vol. 28, 1985, pp. 425-440.
Dieng et al., "Synthese Et Application De Nouveaux Sulfures A Chain Perfluoree," Journal of Fluorine Chemistry, vol. 28, 1985, pp. 341-355.
Fokin et al., English translation of "Some Properties of Fluorine-Containing α,β-Unsaturated Sulfones," Zhurnal Organicheskoi Khimii, vol. 22, No. 2, pp. 270-276, Feb. 1986.

(Continued)

Primary Examiner — Sreeni Padmanabhan
Assistant Examiner — Kara R McMillian
(74) Attorney, Agent, or Firm — Birch, Stewart, Kolasch & Birch, LLP

(57) ABSTRACT

A compound given by the formula (I):

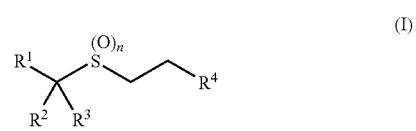

(I)

has an excellent controlling activity against noxious arthropods.

8 Claims, No Drawings

OTHER PUBLICATIONS

Benefice et al., "Reactivite Comparee Des Perfluoroiodoalcanes ($R_FI$) Et Des Perfluo-Roalcoyl-2 Iodo-1-Ethanes ($R_FCH_2CH_2I$) En Presence De Couple Metal-Lique Zinc-Cuivre Dans Un Solvant Dissociant Particulier: Le Sulfolane," Journal of Fluorine Chemistry, vol. 23, 1983, pp. 47-55.

Sodoyer et al., "Synthese De Nouvelles Sulfones F-Alkylees Saturees Et α,β-Insaturees," Journal of Fluorine Chemistry, vol. 22, 1983, pp. 401-419.

Serdyuk et al., "Polyfluoroalkylthiotrifluoroacetylketenes," Russian Chemical Bulletin, International Edition, vol. 52, No. 8, pp. 1854-1858, Aug. 2003.

Shkurak et al., English translation of "Activated Addition of Sulfur Chlorides and Sulfenyl Chlorides to Hexafluorodimethylketene," Izvestiya Akademii Nauk SSSR, Seriya Khimicheskaya, No. 6, pp. 1371-1378, Jun. 1984.

Il'In et al., English translation of "Comparison of $CF_3$-substituted Ethylenic Compounds in Reactions with Chlorines of Sulfur," Zhurnal Vses. Khim. Ob-va im. D. I. Mendeleeva, vol. 28, No. 2, pp. 115-116, 1983.

Mir et al., "Reactions of Hexafluoroacetone with Sulfur-Containing Compounds," Inorg. Chem., vol. 19, 1980, pp. 1510-1514.

Faurote et al., "Some New Polyfluoroalkyl Halides, $H(CF_2)_nCH_2X$, and the Reactions of $H(CF_2)_nCH_2I$ with Water, Sulfur and Selenium," Journal of Am. Chem. Soc., vol. 78, 1956, pp. 4999-5001.

Sakamoto et al., "Fluoro type surfactants", Chemical Abstracts, Database accession No. 2004:351462 (2004).

Beilstein Registry Nos. 6215504, 6236294, 4325236, 6203175, 6212969, 8220992.

European Patent Office Communication in Application No. 06 832 483.3 dated Apr. 16, 2009.

FR 2 516 920 (English translation, 16 pages), May 27, 1983.

Australian Office Action issued on Dec. 14, 2010 in corresponding Australian Patent Application No. 2006317486.

Database WPI Week 200560; Thomson Scientific; London, GB; AN; 2005-585455; XP002493506.

International Preliminary Report or Patentability and Written Opinion dated Nov. 24, 2009 for Application No. PCT/JP2008/059491.

International Preliminary Report on Patentability and Written Opinion dated Nov. 24, 2009 for Application No. PCT/JP2008/059492.

International Preliminary Report on Patentability and Written Opinion dated Nov. 24, 2009 for Application No. PCT/JP2008/059498.

International Search Report dated Sep. 4, 2008 for Application No. PCT/JP2008/059491.

International Search Report dated Sep. 4, 2008 for Application No. PCT/JP2008/059492.

International Search Report dated Sep. 4, 2008 for Application No. PCT/JP2008/059498.

Patani et al., "Bioisosterism: A Rational Approach in Drug Design," Chemical Reviews, 1996, vol. 96, No. 8, pp. 3147-3176.

English translation of Chinese Office Action issued on Jan. 28, 2011 in corresponding Chinese Patent Application No. 200680043328.5.

* cited by examiner

ORGANIC SULFUR COMPOUNDS AND USE THEREOF

TECHNICAL FIELD

The present invention relates to organic sulfur compounds and noxious arthropod controlling use thereof.

BACKGROUND ART

Many arthropods controlling agents have been developed and practically used.

DISCLOSURE OF INVENTION

The present invention provides novel compounds having an excellent activity against noxious arthropods.

Namely, the present invention provides an organic sulfur compound given by the following formula [I]:

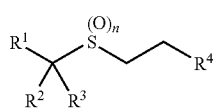

wherein
$R^1$ represents a C3-C6 fluoroalkyl group,
$R^2$ represents a cyano group, a group represented by C(=O)$R^5$ or a group represented by C(=S)$R^6$,
$R^3$ represents a hydrogen atom, a halogen atom or a C1-C4 alkyl group,
$R^4$ represents a C1-C5 fluoroalkyl group,
$R^5$ and $R^6$ independently represent a C1-C4 alkoxy group, an amino group optionally substituted by one or two C1-C4 alkyl group(s) or a C2-C5 cyclic amino group,
n represents 0, 1 or 2;
(may refer as the present compound, hereinafter), a noxious arthropod controlling agent comprising the present compound and an inert carrier and a method for controlling noxious arthropods applying an effective amount of the present compound to noxious arthropods or at a habitat of noxious arthropods.

MODE OF CARRYING OUT THE INVENTION

In the present invention, the mention of C1-C4 and the like means the total number of carbon atoms which comprises each substituents. And in the present invention, the mention of fluoroalkyl group means an alkyl group substituted one or more fluorine atom(s) are substituted at carbon atoms.

Examples of C3-C6 fluoroalkyl group represented by $R^1$ in the formula (I) includes
C3 fluoroalkyl group such as 2-fluoropropyl group, 2,2-difluoropropyl group, 3-fluoropropyl group, 3,3-difluoropropyl group, 3,3,3-trifluoropropyl group, 2,2,3,3,3-pentafluoropropyl group, 2,2,3,3-tetrafluoropropyl group and 2,2,2-trifluoro-(1-trifluoromethyl)ethyl group; C4 fluoroalkyl group such as 2-fluorobutyl group, 2,2-difluorobutyl group, 3-fluorobutyl group, 3,3-difluorobutyl group, 4-fluorobutyl group, 4,4-difluorobutyl group, 4,4,4-trifluorobutyl group, 3,3,4,4-pentafluorobutyl group, 2,2,3,4,4-pentafluorobutyl group and 2,2,3,3,4,4,4-heptafluorobutyl group;
C5 fluoroalkyl group such as 2-fluoropentyl group, 2,2-difluoropentyl group, 3-fluoropentyl group, 3,3-difluoropentyl group, 4-fluoropentyl group, 4,4-difluoropentyl group, 5-fluoropentyl group, 5,5-difluoropentyl group, 5,5,5-trifluoropentyl group, 4,4,5,5,5-pentafluoropentyl group, 3,3,4,4,5,5-heptafluoropentyl group, 2,2,3,3,4,4,5,5-octafluoropentyl group and 2,2,3,3,4,4,5,5,5-nonafluoropentyl group;
C6 fluoroalkyl group such as 2-fluorohexyl group, 2,2-difluorohexyl group, 3-fluorohexyl group, 3,3-difluorohexyl group, 4-fluorohexyl group, 4,4-difluorohexyl group, 5-fluorohexyl group, 5,5-difluorohexyl group, 6-fluorohexyl group, 6,6-difluorohexyl group, 6,6,6-trifluorohexyl group, 5,5,6,6,6-pentafluorohexyl group, 4,4,5,5,6,6,6-heptafluorohexyl group, 3,3,4,4,5,5,6,6,6-nonafluorohexyl group and 2,2,3,3,4,4,5,5,6,6,6-undecafluorohexyl group.

Examples of C1-C5 fluoroalkyl group represented by $R^4$ in the formula (I) includes C1-C2 fluoroalkyl group such as fluoromethyl group, difluoromethyl group, trifluoromethyl group, 1-fluoroethyl group, 2-fluoroethyl group, 1,1-difluoroethyl group, 2,2-difluoroethyl group, 2,2,2-trifluoroethyl group and 1,1,2,2,2-pentafluoroethyl group; C3 fluoroalkyl group such as 1-fluoropropyl group, 1,1-difluoropropyl group, 2-fluoropropyl group, 2,2-difluoropropyl group, 3-fluoropropyl group, 3,3-difluoropropyl group, 3,3,3-trifluoropropyl group, 1,1,2,2,3,3,3-heptafluoropropyl group, 2,2,3,3,3-pentafluoropropyl group, 2,2,2-trifluoro-(1-trifluoromethyl)ethyl group, 1,2,2,2-tetrafluoro-(1-trifluoromethyl)ethyl group and 2,2,3,3-tetrafluoropropyl group;
C4 fluoroalkyl group such as 1-fluorobutyl group, 1,1-difluorobutyl group, 2-fluorobutyl group, 2,2-difluorobutyl group, 3-fluorobutyl group, 3,3-difluorobutyl group, 4-fluorobutyl group, 4,4-difluorobutyl group, 4,4,4-trifluorobutyl group, 3,3,4,4,4-pentafluorobutyl group, 2,2,3,4,4-pentafluorobutyl group and 2,2,3,3,4,4,4-heptafluorobutyl group;
C5 fluoroalkyl group such as 1-fluoropentyl group, 1,1-difluoropentyl group, 2-fluoropentyl group, 2,2-difluoropentyl group, 3-fluoropentyl group, 3,3-difluoropentyl group, 4-fluoropentyl group, 4,4-difluoropentyl group, 5-fluoropentyl group, 5,5-difluoropentyl group, 5,5,5-trifluoropentyl group, 4,4,5,5,5-pentafluoropentyl group, 3,3,4,4,5,5,5-heptafluoropentyl group, 2,2,3,3,4,4,5,5-octafluoropentyl group and 2,2,3,3,4,4,5,5,5-nonafluoropentyl group.

Examples of C1-C4 alkyl group represented by $R^3$ in the formula (I) includes methyl group, ethyl group, propyl group, isopropyl group, butyl group, isobutyl group and tert-butyl group.

Examples of C1-C4 alkoxy group represented by $R^5$ and $R^6$ in the formula (I) includes methoxy group, ethoxy group, propoxy group, isopropoxy group, butoxy group, isobutoxy group and tert-butoxy group.

Examples of amino group optionally substituted by one or two C1-C4 alkyl group(s) represented by $R^5$ and $R^6$ in the formula (I) includes amino group, methylamino group, ethylamino group, propylamino group, 2-propylamino group, butylamino group, isobutylamino group, tert-butylamino group and dimethylamino group.

Examples of C2-C5 cyclic amino group represented by $R^5$ and $R^6$ in the formula (I) includes 1-aziridino group, 1-azetidinyl group, 1-pyrrolizinyl group and 1-piperidino group.

Examples of the embodiment of the present compounds include as following:
An organic sulfur compound wherein n is 2 in the formula (I);
An organic sulfur compound wherein $R^2$ is a cyano group or a group represented by C(=O)$R^5$ in the formula (I);
An organic sulfur compound wherein $R^2$ is a cyano group in the formula (I);
An organic sulfur compound wherein $R^2$ is a group represented by C(=O)$R^5$ and $R^5$ is an amino group optionally substituted by one or two C1-C4 alkyl group(s) in the formula (I);

An organic sulfur compound wherein $R^2$ is a group represented by $C(=O)R^5$ and $R^5$ is an amino group in the formula (I);

An organic sulfur compound wherein 3 is a halogen atom in the formula (I);

An organic sulfur compound wherein $R^3$ is a fluorine atom or a chlorine atom in the formula (I);

An organic sulfur compound wherein $R^4$ is a C1-C3 fluoroalkyl group in the formula (I);

An organic sulfur compound wherein $R^4$ is a trifluoromethyl group in the formula (I);

An organic sulfur compound wherein $R^4$ is a 1,1,2,2,2-pentafluoroethyl group in the formula (I);

An organic sulfur compound wherein $R^4$ is a 1,1,2,2,3,3,3-heptafluoropropyl group in the formula (I);

An organic sulfur compound wherein n is 2 and $R^4$ is a C1-C3 fluoroalkyl group in the formula (I);

An organic sulfur compound wherein n is 2 and $R^4$ is a trifluoromethyl group in the formula (I);

An organic sulfur compound wherein n is 2 and $R^4$ is a 1,1,2,2,2-pentafluoroethyl group in the formula (I);

An organic sulfur compound wherein n is 2 and $R^4$ is a 1,1,2,2,3,3,3-heptafluoropropyl group in the formula (I);

An organic sulfur compound wherein n is 2 and $R^2$ is a cyano group or a group represented by $C(=O)R^5$ in the formula (I);

An organic sulfur compound wherein n is 2 and $R^2$ is a cyano group in the formula (I);

An organic sulfur compound wherein n is 2, $R^2$ is a group represented by $C(=O)R^5$ and $R^5$ is an amino group optionally substituted by one or two C1-C4 alkyl group(s) in the formula (I);

An organic sulfur compound wherein n is 2, $R^2$ is a group represented by $C(=O)R^5$ and $R^5$ is an amino group in the formula (I);

An organic sulfur compound wherein n is 2 and $R^3$ is a halogen atom in the formula (I);

An organic sulfur compound wherein n is 2 and $R^3$ is a fluorine atom or a chlorine atom in the formula (I);

An organic sulfur compound wherein $R^2$ is a cyano group or a group represented by $C(=O)R^5$ and $R^3$ is a halogen atom in the formula (I);

An organic sulfur compound wherein $R^2$ is a cyano group and $R^3$ is a halogen atom in the formula (I);

An organic sulfur compound wherein $R^2$ is a group represented by $C(=O)R^5$, $R^5$ is an amino group optionally substituted by one or two C1-C4 alkyl group(s) and $R^3$ is a halogen atom in the formula (I);

An organic sulfur compound wherein $R^2$ is a group represented by $C(=O)R^5$, $R^5$ is an amino group and $R^3$ is a halogen atom in the formula (I);

An organic sulfur compound wherein $R^2$ is a cyano group or a group represented by $C(=O)R^5$ and $R^3$ is a fluorine atom or a chlorine atom in the formula (I);

An organic sulfur compound wherein $R^2$ is a cyano group and $R^3$ is a fluorine atom or a chlorine atom in the formula (I);

An organic sulfur compound wherein $R^2$ is a group represented by $C(=O)R^5$, $R^5$ is an amino group optionally substituted by one or two C1-C4 alkyl group(s) and $R^3$ is a fluorine atom or a chlorine atom in the formula (I);

An organic sulfur compound wherein $R^2$ is a group represented by $C(=O)R^5$, $R^5$ is an amino group and $R^3$ is a fluorine atom or a chlorine atom in the formula (I);

An organic sulfur compound wherein n is 2, $R^2$ is a cyano group or a group represented by $C(=O)R^5$ and $R^3$ is a halogen atom in the formula (I);

An organic sulfur compound wherein n is 2, $R^2$ is a cyano group and $R^3$ is a halogen atom in the formula (I);

An organic sulfur compound wherein n is 2, $R^2$ is a group represented by $C(=O)R^5$, $R^5$ is an amino group optionally substituted by one or two C1-C4 alkyl group(s) and $R^3$ is a halogen atom in the formula (I);

An organic sulfur compound wherein n is 2, $R^2$ is a group represented by $C(O)R^5$, $R^5$ is an amino group and $R^3$ is a halogen atom in the formula (I);

An organic sulfur compound wherein n is 2, $R^2$ is a cyano group or a group represented by $C(=O)R^5$ and $R^3$ is a fluorine atom or a chlorine atom in the formula (I);

An organic sulfur compound wherein n is 2, $R^2$ is a cyano group and $R^3$ is a fluorine atom or a chlorine atom in the formula (I);

An organic sulfur compound wherein n is 2, $R^2$ is a group represented by $C(=O)R^5$, $R^5$ is an amino group optionally substituted by one or two C1-C4 alkyl group(s) and $R^3$ is a fluorine atom or a chlorine atom in the formula (I);

An organic sulfur compound wherein n is 2, $R^2$ is a group represented by $C(=O)R^5$, $R^5$ is an amino group and $R^3$ is a fluorine atom or a chlorine atom in the formula (I);

An organic sulfur compound wherein $R^3$ is a hydrogen atom or a halogen atom in the formula (I);

An organic sulfur compound wherein $R^3$ is a hydrogen atom or a C1-C4 alkyl group in the formula (I);

An organic sulfur compound wherein $R^3$ is a halogen atom or a C1-C4 alkyl group in the formula (I);

An organic sulfur compound wherein $R^3$ is a hydrogen atom or a halogen atom and $R^4$ is a C1-C3 fluoroalkyl group in the formula (I);

An organic sulfur compound wherein $R^3$ is a hydrogen atom or a C1-C4 alkyl group and $R^4$ is a C1-C3 fluoroalkyl group in the formula (I);

An organic sulfur compound wherein $R^3$ is a halogen atom or a C1-C4 alkyl group and $R^4$ is a C1-C3 fluoroalkyl group in the formula (I).

Next, production method of the present compound is described.

For example, the present compound can be produced by following (Production Method 1) to (Production Method 12).

(Production Method 1)

The compound (I-2) which $R^3$ is C1-C4 alkyl group in the present compound can be produced, for example, by making react the following compound (a) and the compound (I-1).

$$R^{3-1}-X \ + \ \underset{(a)}{\overset{R^1}{\underset{R^2}{\big|}}}\!\!\!\overset{(O)_n}{\underset{H}{S}}\!\!\!-\!\!\!R^4 \longrightarrow$$

(I-1)

$$\underset{R^2}{\overset{R^1}{\big|}}\!\!\!\overset{(O)_n}{\underset{R^{3-1}}{S}}\!\!\!-\!\!\!R^4$$

(I-2)

wherein $R^1$, $R^2$, $R^4$ and n have the same meaning as described above, $R^{3-1}$ represents a C1-C4 alkyl group, X represents a leaving group such as a chlorine atom, a bromine atom, an iodine atom, a methanesulfonyloxy group, a p-toluenesulfonyloxy group and trifluoromethanesulfonyloxy group.

The reaction is usually carried out in a solvent and in the presence of a base.

The solvent used for the reaction includes, for example, acid amides such as N,N-dimethylformamide and the like, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like, aromatic hydrocarbons such as toluene, xylene and the like, water and the mixture thereof.

The base used for the reaction includes, for example, inorganic bases such as sodium hydride, sodium hydroxide, potassium hydroxide, potassium carbonate and the like, alkaline metal alkoxides such as sodium methoxide, potassium tert-butoxide and the like, alkaline metal amides such as lithium diisopropylamide and the like and organic bases such as triethylamine, 1,4-diazabicyclo[2.2.2]octane, 1,8-diazabicyclo[5.4.0]-7-undecene and the like. The amount of base used for the reaction is usually 1 to 10 moles based on 1 mole of the compound (I-1).

The amount of the compound (a) used for the reaction is usually 1 to 10 moles based on 1 mole of the compound (I-1).

The reaction temperature is usually in the range of −100 to 100° C. and the reaction period is usually 1 to 24 hours.

After the reaction has finished, the compound (I-2) can be isolated by subjecting post-treatment such as pouring the reaction mixture into water, extracting with an organic solvent, followed by concentrating the organic layer. The isolated compound (I-2) may be purified, if necessary, by chromatography, recrystallization and the like.

(Production Method 2)

The compound (I-3) which $R^3$ is a hydrogen atom or a C1-C4 alkyl group in the present compound can be produced, for example, by making react the following compound (c) and the compound (d).

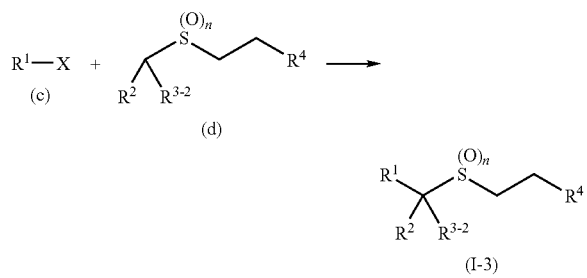

wherein $R^1$, $R^2$, $R^4$, n and X have the same meaning as described above, $R^{3-2}$ represents a hydrogen atom or a C1-C4 alkyl group.

The reaction is usually carried out in a solvent and in the presence of a base.

The solvent used for the reaction includes, for example, acid amides such as N,N-dimethylformamide and the like, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like, aromatic hydrocarbons such as toluene, xylene and the like, water and the mixture thereof.

The base used for the reaction includes, for example, inorganic bases such as sodium hydride, sodium hydroxide, potassium hydroxide, potassium carbonate and the like, alkaline metal alkoxides such as sodium methoxide, potassium tert-butoxide and the like, alkaline metal amides such as lithium diisopropylamide and the like and organic bases such as triethylamine, 1,4-diazabicyclo[2.2.2]octane, 1,8-diazabicyclo[5.4.0]-7-undecene and the like. The amount of base used for the reaction is usually 1 to 10 moles based on 1 mole of the compound (d).

The amount of the compound (c) used for the reaction is usually 1 to 10 moles based on 1 mole of the compound (d).

The reaction temperature is usually in the range of −100 to 100° C. and the reaction period is usually 1 to 24 hours.

After the reaction has finished, the compound (I-3) can be isolated by subjecting post-treatment such as pouring the reaction mixture into water, extracting with an organic solvent, followed by concentrating the organic layer. The isolated compound (I-3) may be purified, if necessary, by chromatography, recrystallization and the like.

The compound (I-4) which $R^3$ is a halogen atom in the present compound can be produced, for example, according to (Production Method 3) or (Production Method 4).

(Production Method 3)

The production method by making react the compound (I-1) and halogenating agent (e) in the presence of a base.

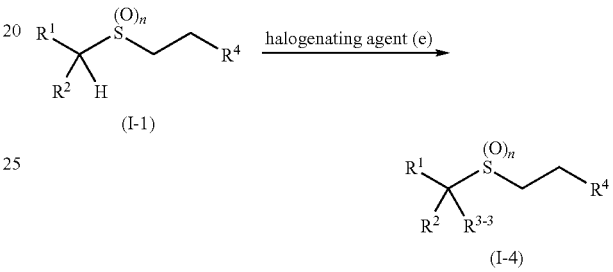

wherein $R^1$, $R^2$, $R^4$ and n have the same meaning as described above, $R^{3-3}$ represents a halogen atom.

The reaction is usually carried out in a solvent and in the presence of a base.

The solvent used for the reaction includes, for example, acid amides such as N,N-dimethylformamide and the like, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like, aromatic hydrocarbons such as toluene, xylene and the like, water and the mixture thereof.

The base used for the reaction includes, for example, inorganic bases such as sodium hydride, sodium hydroxide, potassium hydroxide, potassium carbonate and the like, alkaline metal alkoxides such as sodium methoxide, potassium tert-butoxide and the like, alkaline metal amides such as lithium diisopropylamide and the like and organic bases such as triethylamine, 1,4-diazabicyclo[2.2.2]octane, 1,8-diazabicyclo[5.4.0]-7-undecene and the like. The amount of base used for the reaction is usually 1 to 10 moles based on 1 mole of the compound (I-1).

The halogenating agent (e) used for the reaction includes, for example, halogenated hydrocarbons such as carbontetrachloride, hexachloroethane and the like, halogens such as fluorine, chlorine, bromine and iodine, halogenated succinimide such as N-chloro succinimide, N-bromo succinimide, N-iodo succinimide and the like, N-fluoropyridinium salt such as 1-fluoro-2,4,6-trimethylpyridinium trifluoromethanesulfonate, 1,1'-difluoro-2,2'-bipyridinium bistetrafluoroborate and the like, copper halide such as copper(II) chloride, copper(II) bromide and the like.

The amount of halogenating agent (e) used for the reaction is usually 1 to 10 moles based on 1 mole of the compound (I-1).

The reaction temperature is usually in the range of −100 to 100° C. and the reaction period is usually 1 to 24 hours.

After the reaction has finished, the compound (I-4) can be isolated by subjecting post-treatment such as pouring the reaction mixture into water, extracting with an organic solvent, followed by concentrating the organic layer. The isolated compound (I-4) may be purified, if necessary, by chromatography, recrystallization and the like.

(Production Method 4)

The production method by making react the compound (I-1) and halogenating agent (f).

$$R^1\underset{R^2\ H}{\overset{(O)_n}{\underset{|}{S}}}\diagup\diagdown R^4 \xrightarrow{\text{halogenating agent (f)}}$$

(I-1)

$$R^1\underset{R^2\ R^{3\text{-}3}}{\overset{(O)_n}{\underset{|}{S}}}\diagup\diagdown R^4$$

(I-4)

wherein $R^1$, $R^2$, $R^4$, $R^{3\text{-}3}$ and n have the same meaning as described above.

The reaction is carried out without a solvent or in a solvent.

The solvent used for the reaction includes, for example, halogenated hydrocarbons such as chloroform, carbontetrachloride, 1,2-dichloroethane, chlorobenzene and the like, aromatic hydrocarbons such as toluene, xylene and the like, aliphatic nitriles such as acetonitrile, propionitrile and the like, aliphatic carboxylic acids such as acetic acid, carbon disulfide, water and the mixture thereof.

The halogenating agent (f) used for the reaction includes, for example, halogens such as fluorine, chlorine, bromine and iodine, hydrogen halides such as hydrogen fluoride, hydrogen chloride, hydrogen bromide and hydrogen iodide, halogenated sulfur compound such as thionyl chloride, thionyl bromide, sulfuryl chloride and the like, halogenated phosphorus compound such as phosphorus trichloride, phosphorus tribromide, phosphorus pentachloride, phosphorus oxychloride and the like.

The amount of halogenating agent (f) used for the reaction is usually 1 to 10 moles based on 1 mole of the compound (I-1).

The reaction temperature is usually in the range of −100 to 200° C. and the reaction period is usually 1 to 24 hours.

After the reaction has finished, the compound (I-4) can be isolated by subjecting post-treatment such as pouring the reaction mixture into water, extracting with an organic solvent, followed by concentrating the organic layer. The isolated compound (I-4) may be purified, if necessary, by chromatography, recrystallization and the like.

The compound (I-5) which $R^2$ is a group represented by $C(=O)R^5$ and $R^5$ is a C1-C4 alkoxy group, an amino group optionally substituted by one or two C1-C4 alkyl group(s) or a C2-C5 cyclic amino group in the present compound can be produced, for example, according to (Production Method 5) or (Production Method 6).

(Production Method 5)

$$R^1\underset{HO_2C\ R^3}{\overset{(O)_n}{\underset{|}{S}}}\diagup\diagdown R^4 \xrightarrow[\text{Step 5-1}]{\text{halogenating agent (h)}}$$

(g)

-continued $$R^1\underset{ZOC\ R^3}{\overset{(O)_n}{\underset{|}{S}}}\diagup\diagdown R^4 \xrightarrow[\text{Step 5-2}]{R^5-H\ (j)} R^1\underset{R^5OC\ R^3}{\overset{(O)_n}{\underset{|}{S}}}\diagup\diagdown R^4$$

(i)                                                              (I-5)

wherein $R^1$, $R^3$, $R^4$, $R^5$ and n have the same meaning as described above, Z represents a halogen atom.

(Step 5-1)

The compound (i) can be produced by making react the compound (g) and halogenating agent (h).

The reaction is carried out without a solvent or in a solvent.

The solvent used for the reaction includes, for example, halogenated hydrocarbons such as chloroform, dichloromethane, 1,2-dichloroethane, chlorobenzene and the like, aromatic hydrocarbons such as toluene, xylene and the like.

The halogenating agent (h) used for the reaction includes, for example, oxalyl chloride, thionyl chloride, thionyl bromide, phosphorus trichloride, phosphorus tribromide and phosphorus pentachloride. The amount of halogenating agent (h) used for the reaction is usually 1 mole to excess based on 1 mole of the compound (g).

The reaction temperature is usually in the range of −20 to 100° C. and the reaction period is usually 1 to 24 hours.

After the reaction has finished, the compound (i) can be isolated by subjecting a treatment such as concentrating the reaction mixture. The isolated compound (i) may be purified by distillation and the like.

(Step 5-2)

The reaction is usually carried out in a solvent and in the presence of a base.

The solvent used for the reaction includes, for example, acid amides such as N,N-dimethylformamide and the like, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like, aromatic hydrocarbons such as toluene, xylene and the like, water and the mixture thereof.

The base used for the reaction includes, for example, inorganic bases such as sodium hydride, sodium hydroxide, potassium hydroxide, potassium carbonate and the like and organic bases such as triethylamine, 1,4-diazabicyclo[2.2.2]octane, 1,8-diazabicyclo[5.4.0]-7-undecene and the like. The amount of base used for the reaction is usually 1 to 10 moles based on 1 mole of the compound (i).

The amount of the compound (j) used for the reaction is usually 1 to 10 moles based on 1 mole of the compound (i).

The reaction temperature is usually in the range of −20 to 100° C. and the reaction period is usually 1 to 24 hours.

After the reaction has finished, the compound (I-5) can be isolated by subjecting post-treatment such as pouring the reaction mixture into water, extracting with an organic solvent, followed by concentrating the organic layer. The isolated compound (I-5) may be purified, if necessary, by chromatography, recrystallization and the like.

(Production Method 6)

The production method by making react the compound (g) and the compound (j).

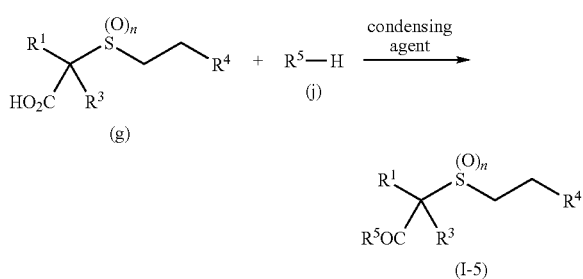

wherein $R^1$, $R^3$, $R^4$, $R^5$ and n have the same meaning as described above.

The reaction is usually carried out in a solvent and in the presence of a condensing agent.

The solvent used for the reaction includes, for example, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like and aromatic hydrocarbons such as toluene, xylene and the like.

The condensing agent used for the reaction includes, for example, dicyclohexylcarbodiimide, N-(3-dimethylaminopropyl)-N'-ethylcarbodiimide, carbonyldiimidazole and the like.

The amount of condensing agent used for the reaction is usually 1 to 10 moles based on 1 mole of the compound (g).

The amount of the compound (j) used for the reaction is usually 1 to 10 moles based on 1 mole of the compound (g).

The reaction temperature is usually in the range of –20 to 100° C. and the reaction period is usually 1 to 24 hours.

After the reaction has finished, the compound (I-5) can be isolated by subjecting a treatment such as pouring the reaction mixture into water, extracting with an organic solvent, followed by concentrating the organic layer. The isolated compound (I-5) may be purified, if necessary, by chromatography, recrystallization and the like.

(Production Method 7)

The compound (I-1) which $R^3$ is a hydrogen atom in the present compound can be produced, for example, by making react the compound (c) and the compound (k).

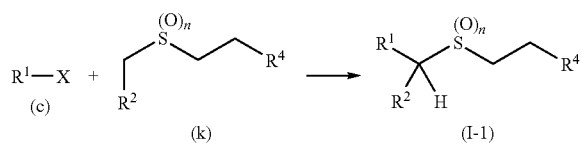

wherein $R^1$, $R^2$, $R^4$, X and n have the same meaning as described above.

The reaction is usually carried out in a solvent and in the presence of a base.

The solvent used for the reaction includes, for example, acid amides such as N,N-dimethylformamide and the like, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like, aromatic hydrocarbons such as toluene, xylene and the like, water and the mixture thereof.

The base used for the reaction includes, for example, inorganic bases such as sodium hydride, sodium hydroxide, potassium hydroxide, potassium carbonate and the like, alkali metal alkoxides such as sodium methoxide, potassium tert-butoxide and the like, alkali metal amides such as lithium diisopropyl amide and the like and organic bases such as triethylamine, 1,4-diazabicyclo[2.2.2]octane, 1,8-diazabicyclo[5.4.0]-7-undecene and the like. The amount of base used for the reaction is usually 1 to 10 moles based on 1 mole of the compound (k).

The amount of the compound (c) used for the reaction is usually 1 to 10 moles based on 1 mole of the compound (k).

The reaction temperature is usually in the range of –100 to 100° C. and the reaction period is usually 1 to 24 hours.

After the reaction has finished, the compound (I-1) can be isolated by subjecting post-treatment such as pouring the reaction mixture into water, extracting with an organic solvent, followed by concentrating the organic layer. The isolated compound (I-1) may be purified, if necessary, by chromatography, recrystallization and the like.

(Production Method 8)

The compound (I-8) which $R^2$ is a group represented by $C(=O)R^5$, $R^5$ is an amino group optionally substituted by one or two C1-C4 alkyl group(s) or a C2-C5 cyclic amino group and n is 2 in the present compound can also be produced by making the compound (I-7), which $R^2$ is a group represented by $C(=O)R^5$, $R^5$ is a C1-C4 alkoxy group and n is 2, react with the compound (p).

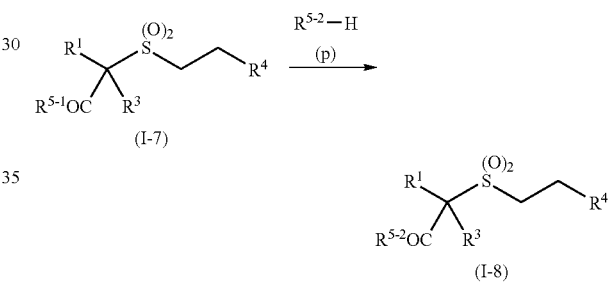

wherein $R^1$, $R^3$ and $R^4$ have the same meaning as described above, $R^{5-1}$ represents a C1-C4 alkoxy group, $R^{5-2}$ represents an amino group optionally substituted by one or two C1-C4 alkyl group(s) or a C2-C5 cyclic amino group.

The reaction is usually carried out in a solvent.

The solvent used for the reaction includes, for example, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like, aromatic hydrocarbons such as toluene, xylene and the like.

The amount of the compound (p) used for the reaction is usually 1 to 10 moles based on 1 mole of the compound (I-7).

The reaction temperature is usually in the range of –20 to 100° C. and the reaction period is usually 1 to 24 hours.

After the reaction has finished, the compound (I-8) can be isolated by subjecting a post-treatment such as of concentrating the reaction mixture. The isolated compound (I-8) may also be purified, if necessary, by chromatography, recrystallization and the like.

(Production Method 9)

The compound (I-9) which $R^2$ is a group represented by $C(=S)R^5$ in the present compound can also be produced by making the compound (I-5) which $R^2$ is a group represented by $C(=O)R^5$ react with the sulfurating agent (q).

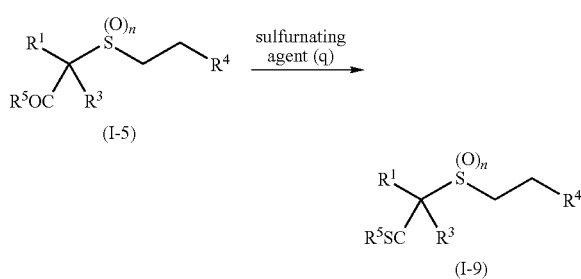

wherein $R^1$, $R^3$, $R^4$, $R^5$ and n have the same meaning as described above.

The reaction is usually carried out in a solvent.

The solvent used for the reaction includes, for example, halogenated hydrocarbons such as chloroform, 1,2-dichloroethane, chlorobenzene and the like, aromatic hydrocarbons such as toluene, xylene and the like.

The sulfurating agent (q) used for the reaction includes, for example, inorganic sulfur compounds such as hydrogen sulfide, organic sulfur compounds such as phosphorus pentasulfide and the like and 2,4-bis(4-methoxyphenyl)-1,3-dithia-2,4-diphosphetane 2,4-disulfide and the like.

The amount of the sulfurating agent (q) used for the reaction is usually 0.5 to 10 moles based on 1 mole of the compound (I-5).

The reaction temperature is usually in the range of 0 to 250° C. and the reaction period is usually 1 to 72 hours.

After the reaction has finished, the compound (I-9) can be isolated by subjecting a post-treatment such as of concentrating the reaction mixture. The isolated compound (I-9) may be purified, if necessary, by chromatography, recrystallization and the like.

The compound (I-10) which n is 0 in the present compound can be produced, for example, by according to (Production Method 10) or (Production Method 11).

(Production Method 10)

The production method by making react the compound (r) and the compound (m).

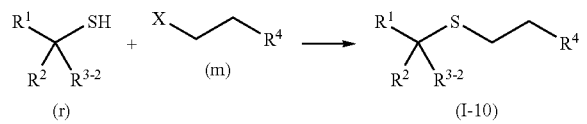

wherein $R^1$, $R^2$, $R^{3-2}$, $R^4$ and X have the same meaning as described above.

The reaction is usually carried out in a solvent and in the presence of a base.

The solvent used for the reaction includes, for example, acid amides such as N,N-dimethylformamide and the like, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like, aromatic hydrocarbons such as toluene, xylene and the like, water and the mixture thereof.

The base used for the reaction includes, for example, inorganic bases such as sodium hydride, sodium hydroxide, potassium hydroxide, potassium carbonate and the like, alkali metal alkoxides such as sodium methoxide, potassium tert-butoxide and the like, alkali metal amides such as lithium diisopropyl amide and the like and organic bases such as triethylamine, 1,4-diazabicyclo[2.2.2]octane, 1,8-diazabicyclo[5.4.0]-7-undecene and the like.

The amount of base used for the reaction is usually 1 to 10 moles based on 1 mole of the compound (r).

The amount of the compound (m) used for the reaction is usually 1 to 10 moles based on 1 mole of the compound (r).

The reaction temperature is usually in the range of −20 to 100° C. and the reaction period is usually 1 to 24 hours.

After the reaction has finished, the compound (I-10) can be isolated by subjecting post-treatment such as pouring the reaction mixture into water, extracting with an organic solvent, followed by concentrating the organic layer. The isolated compound (I-10) may be purified, if necessary, by chromatography, recrystallization and the like.

(Production Method 11)

The production method by making react the compound (s) and the compound (o).

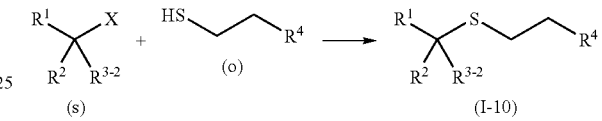

wherein $R^1$, $R^2$, $R^{3-2}$, $R^4$ and X have the same meaning as described above.

The reaction is usually carried out in a solvent and in the presence of a base.

The solvent used for the reaction includes, for example, acid amides such as N,N-dimethylformamide and the like, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like, aromatic hydrocarbons such as toluene, xylene and the like, water and the mixture thereof.

The base used for the reaction includes, for example, inorganic bases such as sodium hydride, sodium hydroxide, potassium hydroxide, potassium carbonate and the like, alkali metal alkoxides such as sodium methoxide, potassium tert-butoxide and the like, alkali metal amides such as lithium diisopropyl amide and the like and organic bases such as triethylamine, 1,4-diazabicyclo[2.2.2]octane, 1,8-diazabicyclo[5.4.0]-7-undecene and the like. The amount of base used for the reaction is usually 1 to 10 moles based on 1 mole of the compound (o).

The amount of the compound (s) used for the reaction is usually 1 to 10 moles based on 1 mole of the compound (o).

The reaction temperature is usually in the range of −20 to 100° C. and the reaction period is usually 1 to 24 hours.

After the reaction has finished, the compound (I-10) can be isolated by subjecting post-treatment such as pouring the reaction mixture into water, extracting with an organic solvent, followed by concentrating the organic layer. The isolated compound (I-10) may be purified, if necessary, by chromatography, recrystallization and the like.

(Production Method 12)

The compound (I-11) which n is 1 or 2 in the present compound can be produced by making the compound (I-10) oxidize.

$$\underset{(\text{I-10})}{\overset{R^1}{\underset{R^2}{\bigvee}}\underset{R^{3-2}}{\overset{S}{\bigvee}}R^4} \longrightarrow \underset{(\text{I-11})}{\overset{R^1}{\underset{R^2}{\bigvee}}\underset{R^{3-2}}{\overset{(O)_{n'}}{\underset{}{\bigvee}}}R^4}$$

wherein $R^1$, $R^2$, $R^{3-2}$ and $R^4$ have the same meaning as described above, n' represents 1 or 2.

The reaction is usually carried out in a solvent and in the presence of a oxidizing agent.

The solvent used for the reaction includes, for example, alcohols such as methanol, ethanol and the like, halogenated hydrocarbons such as dichloromethane, chloroform and the like, aromatic hydrocarbons such as toluene, xylene and the like, aliphatic carboxylic acids such as acetic acid, trifluoroacetic acid and the like, water and the mixture thereof.

The oxidizing agent used for the reaction includes, for example, peracids such as peracetic acid, trifluoroperacetic acid, m-chloroperbenzoic acid and the like, halogen molecules such as chlorine and bromine, halogenated succinimides such as N-chlorosuccinimide, perhalogenated compounds such as perchloric acid or its salts, periodic acid or its salts and the like, permanganates such as potassium permanganate and the like, chromic acid salts such as potassium chromate and the like and hydrogen peroxide. The amount of oxidizing agent used for the reaction is usually 1 to 10 moles based on 1 mole of the compound (I-10).

The reaction temperature is usually in the range of −50 to 200° C. and the reaction period is usually 1 to 72 hours.

After the reaction has finished, the compound (I-11) can be isolated by subjecting post-treatment such as pouring the reaction mixture into water, extracting with an organic solvent, followed by concentrating the organic layer. The isolated compound (I-11) may be purified, if necessary, by chromatography, recrystallization and the like.

Next, the production method of intermediate compounds for production of the present compounds is explained as Reference Production Method.

(Reference Production Method 1-1)

The compound (g) can be produced by making the compound (I-6) hydrolyze in the presence of an acid.

$$\underset{(\text{I-6})}{\overset{R^1}{\underset{R^{5-3}OC}{\bigvee}}\underset{R^3}{\overset{(O)_n}{\underset{}{\bigvee}}}R^4} \xrightarrow{\text{acid}} \underset{(g)}{\overset{R^1}{\underset{HO_2C}{\bigvee}}\underset{R^3}{\overset{(O)_n}{\underset{}{\bigvee}}}R^4}$$

wherein $R^1$, $R^3$, $R^4$ and n have the same meaning as described above, $R^{5-3}$ represents a methoxy group or an ethoxy group.

The reaction is usually carried out in the presence of water and usually in an organic solvent.

The organic solvent used for the reaction includes, for example, alcohols such as methanol, ethanol and the like, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like, aromatic hydrocarbons such as toluene, xylene and the like, aliphatic carboxylic acids such as formic acid, acetic acid and the like and the mixture thereof.

The acid used the reaction includes, for example, inorganic acids such as hydrochloric acid, sulfuric acid and the like.

The amount of an acid used for the reaction is usually 1 to 10 moles based on 1 mole of the compound (I-6).

The reaction temperature is usually in the range of −20 to 100° C. and the reaction period is usually 1 to 24 hours.

After the reaction has finished, the compound (g) can be isolated by subjecting post-treatment such as pouring water to the reaction mixture, extracting with an organic solvent, followed by concentrating the organic layer. The isolated compound (g) may be purified, if necessary, by chromatography, recrystallization and the like.

(Reference Production Method 1-2)

The compound (g) can be produced by making the compound (I-6) hydrolyze in the presence of a base.

The reaction is usually carried out in the presence of water and usually in an organic solvent.

The organic solvent used for the reaction includes, for example, alcohols such as methanol, ethanol and the like, ethers such as diethyl ether, tetrahydrofuran and the like, organic sulfurs such as dimethylsulfoxide, sulfolane and the like, aromatic hydrocarbons such as toluene, xylene and the like and the mixture thereof.

The base used for the reaction includes, for example, inorganic bases such as sodium hydroxide, potassium hydroxide and the like.

The amount of a base used for the reaction is usually 1 to 10 moles based on 1 mole of the compound (I-6).

The reaction temperature is usually in the range of −20 to 100° C. and the reaction period is usually 1 to 24 hours.

After the reaction has finished, the compound (g) can be isolated by subjecting post-treatment such as pouring water and an acid to the reaction mixture, extracting with an organic solvent, followed by concentrating the organic layer. The isolated compound (g) may be purified, if necessary, by chromatography, recrystallization and the like.

(Reference Production Method 2)

The compound (d-1) which $R^{3-2}$ is a C1-C4 alkyl group in the compound (d) can be produced by making react the below compound (a) and the compound (k).

$$R^{3-1}-X + \underset{(k)}{\overset{(O)_n}{\underset{R^2}{\bigvee}}\underset{}{\overset{S}{\underset{}{\bigvee}}}R^4} \longrightarrow \underset{(d-1)}{\overset{(O)_n}{\underset{R^2}{\bigvee}}\underset{R^{3-1}}{\overset{S}{\underset{}{\bigvee}}}R^4}$$
$$(a)$$

wherein $R^2$, $R^4$, $R^{3-1}$, n and X have the same meaning as described above.

The reaction is usually carried out in a solvent and in the presence of a base.

The solvent used for the reaction includes, for example, acid amides such as N,N-dimethylformamide and the like, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like, aromatic hydrocarbons such as toluene, xylene and the like, water and the mixture thereof.

The base used for the reaction includes, for example, inorganic bases such as sodium hydride, sodium hydroxide, potassium hydroxide, potassium carbonate and the like, alkaline metal alkoxides such as sodium methoxide, potassium tert-butoxide and the like, alkaline metal amides such as lithium diisopropylamide and the like and organic bases such as triethylamine, 1,4-diazabicyclo[2.2.2]octane, 1,8-diazabicyclo[5.4.0]-7-undecene and the like. The amount of base used for the reaction is usually 1 to 10 moles based on 1 mole of the compound (k).

The amount of the compound (a) used for the reaction is usually 1 to 10 moles based on 1 mole of the compound (k).

The reaction temperature is usually in the range of −20 to 100° C. and the reaction period is usually 1 to 24 hours.

After the reaction has finished, the compound (d-1) can be isolated by subjecting post-treatment such as pouring the reaction mixture into water, extracting with an organic solvent, followed by concentrating the organic layer. The isolated compound (d-1) may be purified, it necessary, by chromatography, recrystallization and the like.
(Reference Production Method 3)
The compound (k-1) which n is 0 and the compound (k-2) which n is 1 or 2 can be produced, for example, according to following scheme.

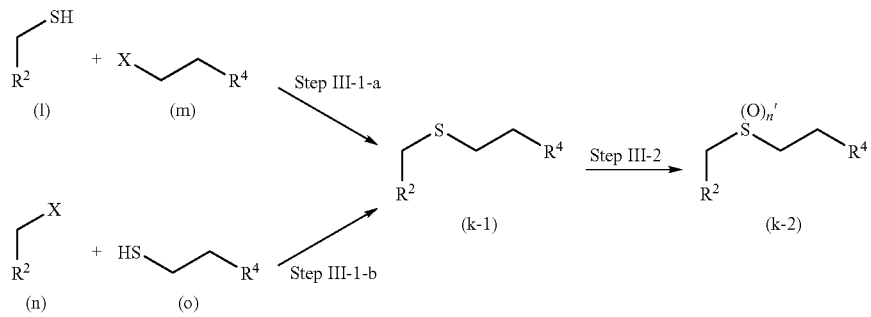

wherein $R^2$, $R^4$, X and n' have the same meaning as described above.
(Step III-1-a)
The compound (k-1) can be produced by making react the compound (l) and the compound (m).

The reaction is usually carried out in a solvent and in the presence of a base.

The solvent used for the reaction includes, for example, acid amides such as N,N-dimethylformamide and the like, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like, aromatic hydrocarbons such as toluene, xylene and the like, water and the mixture thereof.

The base used for the reaction includes, for example, inorganic bases such as sodium hydride, sodium hydroxide, potassium hydroxide, potassium carbonate and the like, alkaline metal alkoxides such as sodium methoxide, potassium tert-butoxide and the like, alkaline metal amides such as lithium diisopropylamide and the like and organic bases such as triethylamine, 1,4-diazabicyclo[2.2.2]octane, 1,8-diazabicyclo[5.4.0]-7-undecene and the like.

The amount of base used for the reaction is usually 1 to 10 moles based on 1 mole of the compound (l).

The amount of the compound (m) used for the reaction is usually 1 to 10 moles based on 1 mole of the compound (l).

The reaction temperature is usually in the range of −20 to 100° C. and the reaction period is usually 1 to 24 hours.

After the reaction has finished, the compound (k-1) can be isolated by subjecting post-treatment such as pouring the reaction mixture into water, extracting with an organic solvent, followed by concentrating the organic layer. The isolated compound (k-1) may be purified, if necessary, by chromatography, recrystallization and the like.
(Step III-1-b)
The compound (k-1) can also be produced by making react the compound (n) and the compound (o).

The reaction is usually carried out in a solvent and in the presence of a base. The solvent used for the reaction includes, for example, acid amides such as N,N-dimethylformamide and the like, ethers such as diethyl ether, tetrahydrofuran and the like, organic sulfurs such as dimethylsulfoxide, sulfolane and the like, halogenated hydrocarbons such as chloroform, 1,2-dichloroethane, chlorobenzene and the like, aromatic hydrocarbons such as toluene, xylene and the like, water and the mixture thereof.

The base used for the reaction includes, for example, inorganic bases such as sodium hydride, sodium hydroxide, potassium hydroxide, potassium carbonate and the like, alkaline metal alkoxides such as sodium methoxide, potassium tert-butoxide and the like, alkaline metal amides such as lithium diisopropylamide and the like and organic bases such as triethylamine, 1,4-diazabicyclo[2.2.2]octane, 1,8-diazabicyclo[5.4.0]-7-undecene and the like. The amount of base used for the reaction is usually 1 to 10 moles based on 1 mole of the compound (o).

The amount of the compound (n) used for the reaction is usually 1 to 10 moles based on 1 mole of the compound (o).

The reaction temperature is usually in the range of 20 to 100° C. and the reaction period is usually 1 to 24 hours.

After the reaction has finished, the compound (k-1) can be isolated by subjecting post-treatment such as pouring the reaction mixture into water, extracting with an organic solvent, followed by concentrating the organic layer. The isolated compound (k-1) may be purified, if necessary, by chromatography, recrystallization and the like.
(Step III-2)
The compound (k-2) can be produced, for examples by making the compound (k-1) oxidize.

The reaction is usually carried out in the presence of a solvent and in the presence of a oxidizing agent.

The solvent used for the reaction includes, for example, alcohols such as methanol, ethanol and the like, halogenated hydrocarbons such as dichloromethane, chloroform and the like, aromatic hydrocarbons such as toluene, xylene and the like, aliphatic carboxylic acids such as acetic acid, trifluoroacetic acid and the like, water and the mixture thereof.

The oxidizing agent used for the reaction includes, for example, peracids such as peracetic acid, trifluoroperacetic acid, m-chloroperbenzoic acid and the like, halogen molecules such as chlorine and bromine, halogenated succinimides such as N-chlorosuccinimide, perhalogenated compounds such as perchloric acid or its salts, periodic acid or its salts and the like, permanganates such as potassium permanganate and the like, chromic acid salts such as potassium chromate and the like and hydrogen peroxide. The amount of oxidizing agent used for the reaction is usually 1 to 10 moles based on 1 mole of the compound (k-1).

The reaction temperature is usually in the range of −50 to 200° C. and the reaction period is usually 1 to 72 hours.

After the reaction has finished, the compound (k-2) can be isolated by subjecting a treatment such as pouring the reaction mixture into water, extracting with an organic solvent, followed by concentrating the organic layer. The isolated compound (k-2) may be purified, if necessary, by chromatography, recrystallization and the like.

The above mentioned compound (o) and (s) each can be produced, for example, by the same method described in The Journal of Organic Chemistry, 27(1), p. 93-95 (1962) and HETEROCYCLES, 24(5), p. 1331-1346 (1986).

The above mentioned compound (t) can be produced, for example, by the same method described in The Journal of Organic Chemistry, 18, p. 1112-1116 (1953).

The noxious arthropods against which the present compound has control activity may include insect pests, acarine pests and the like. Specific examples are listed below:

Hemiptera:

Delphacidae such as *Laodelphax striatellus, Nilaparvata lugens, Sogatella furcifera* and the like, Deltocephalinae such as *Nephotettix cincticeps, Nephotettix virescens* and the like, Aphididae such as *Aphis gossypii, Myzus persicae, Brevicoryne brassicae, Macrosiphum euphorbiae, Aulacorthum solani, Rhopalosiphum padi, Toxoptera citricidus* and the like, Pentatomidae such as *Nezara antennata, Riptortus clavatus, Eysarcoris lewisi, Eysarcoris parvus, Plautia stali, Halyomorpha mista, Stenotus rubrovittatus, Trigonotylus ruficornis* and the like, Aleyrodidae such as *Trialeurodes vaporariorum, Bemisia argentifolii* and the like, Coccidae such as *Aonidiella aurantii, Comstockaspis perniciosa, Unaspis citri, Ceroplastes rubens, Icerya purchasi* and the like, Tingidae, Cimicidae such as *Cimex lectularius,*

Psyllidae, and the like;

Lepidoptera:

Pyralidae such as *Chilo suppressalis, Cnaphalocrocis medinalis, Notarcha derogata, Rocha interpunctella, Maruca testulalis, Hellula undalis, Parapediasia tetewella* and the like, Noctuidae such as *Spodoptera litura, Pseudaletia separata, Thoricoplusia* spp., *Heliothis* spp., *Helicoverpa* spp. and the like, Pieridae such as *Pieris rapae* and the like, Tortricidae such as *Adoxophyes* spp., *Grapholita molesta, Cydia pomonella* and the like, Carposinidae such as *Carposina niponensis* and the like, Lyonetiidae such as *Lyonetia* spp. and the like, Lymantriidae such as *tymantria* spp., *Euproctis* spp., and the like, Yponomeutidae such as *Plutella xvlostella* and the like, Gracillariidae such as *Caloptilia theivora, Phyllonorycter ringoneella*, and the like, Gelechiidae such as *Pectinophora gossypiella* and the like, Arctiidae such as *Hyphantria cunea* and the like, Tineidae such as *Tinea translucens, Tineola bisselliella* and the like;

Diptera:

Culicidae such as *Culex pipiens pallens, Culex tritaeniorhynchus, Culex quinquefasciatus* and the like,

*Aedes* spp. such as *Aedes aegypti, Aedes albopictus* and the like,

*Anopheles* spp. such as *Anopheles sinensis* and the like,

Chironomidae,

Muscidae such as *Musca domestica, Muscina stabulans* and the like,

Calliphoridae,

Sarcophagidae,

Fanniidae,

Anthomyiidae such as *Delia platura, Delia antiqua* and the like,

Agromyzidae such as *Liriomyza trifolii,*

Tephritidae,

Drosophilidae,

Phoridae such as *Megaselia spiracularis,*

Psychodidae such as *Clogmia albipunctata,*

Tabanidae,

Simuliidae,

Stomoxyidae, and the like;

Coleoptera:

*Diabrotica* spp. such as *Diabrotica virgifera, Diabrotica undecimpunctata howardi* and the like, Scarabaeidae such as *Anomala cuprea, Anomala rufocuprea* and the like, Curculionidae such as *Sitophilus zeamais, Lissorhoptrus oryzophilus, Callosobruchuys chienensis* and the like, Tenebrionidae such as *Tenebrio molitor, Tribolium castaneum* and the like, Chrysomelidae such as *Oulema oryzae, Aulacophora femoralis, Phyllotreta striolata, Leptinotarsa decemlineata* and the like, Dermestidae such as *Dermestes maculates,*

Anobiidae,

*Epilachna* spp. such as *Epilachna vigintioctopunctata* and the like,

Lyctidae,

Bostrychidae,

Cerambycidae,

Paederus fuscipes and the like;

Blattodea: *Blattella germanica, Periplaneta fuliginosa, Periplaneta americana, Periplaneta brunnea, Blatta orientalis* and the like;

Thysanoptera: *Thrips palmi, Thrips tabaci, Frankliniella occidentalis, Frankliniella intonsa, Scirtothrips dorsalis* and the like;

Hymenoptera:

Formicidae such as *Monomorium pharaosis, Formica fusca japonica, Ochetellus glaber, Pristomyrmex pungens, Pheidole noda, Linepithema humile* and the like, Vespidae, bethylid wasp, Tenthredinidae such as *Athalia japonica*, and the like;

Orthoptera: Gryllotalpidae, Acrididae, Gryllidae and the like;

Aphaniptera: *Ctenocephalides felis, Ctenocephalides canis, Pulex irritans, Xenopsylla cheopis*, and the like;

Anoplura: *Pediculus humanus corporis, Phthirus pubis, Haematopinus eurysternus, Damalinia ovis, Haemaopinus suis* and the like;

Isoptera: *Reticulitermes speratus, Coptotermes formosanus,* Rhinotermitidae such as *Reticulitermes flavipes, Reticulitermes hesperus, Reticulitermes virginicus, Reticulitermes tibialis, Heterotermes aureus* and the like, Kalotermitidae such as *Incisitermes minor* and the like; dampwood termites such as *Zootermopsis nevadensis* and the like;

Acarina:

Tetranychidae such as *Tetranychus urticae*, *Tetranychus kanzawai*, *Panonychus citri*, *Panonychus ulmi*, *Oligonychus* spp., and the like, Eriophyidae such as *Aculops lycopers*, *Aculops pelekassi*, *Aculus schlechtendali*, and the like, Tarsonemidae such as *Polyphagotarsonemus latus*, and the like, Tenuipalpidae, Tuckerellidae, Ixodidae such as *Haemaphysalis longicornis*, *Haemaphysalis flava*, *Dermacentor variabilis*, *Haemaphysalis flava*, *Dermacentor taiwanicus*, *Ixodes ovatus*, *Ixodes persulcatus*, *Ixodes scapularis*, *Boophilus microplus*, *Amblyomma americanum*, *Rhipicephalus sanguineus* and the like, Acaridae such as *Tyrophagus putrescentiae*, and the like, Epidermoptidae such as *Dermatophagoides farinae*, *Dermatophagoides ptrenyssnus*, and the like, Cheyletidae such as *Cheyletus eruditus*, *Cheyletus malaccensis*, *Cheyletus moorei*, and the like,

*Ornithonyssus bacoti*, *Ornithonyssus sylvairum*,

Dermanyssidae such as *Dermanyssus gallinae*;

chiggers such as *Leptotrombidium akamushi*,

Araneae: *Chiracanthium japonicum*, *Latrodectus hasseltii*, and the like;

Chilopoda: *Thereuonema hilgendorfi*, *Scolopendra subspinipes*, and the like;

Diplopoda: *Oxidus gracilis*, *Nedyopus tambanus*, and the like;

Isopoda: *Armadillidium vulgare*, and the like;

Gastropoda: *Limax marginatus*, *Limax flavus*, and the like.

The noxious arthropod controlling agent of the present invention comprises the present compound and a inert carrier. Usually the present compound is mixed with a solid carrier, a liquid carrier and/or a gaseous carrier, and if necessary, added a surfactant and other adjuvant for formulation to formulate to an emulsifiable concentrate, an oil solution, a shampoo formulation, a flowable, a dust, a wettable powder, a granule, a paste formulation, a microcapsule, a foam, an aerosol, a carbon dioxide gas formulation, a tablet and a resin formulation. These formulations may be converted to use into a poison bait, a mosquito coil, an electric mosquito mat, a smoking agent, a fumigant or sheet.

In the noxious arthropod controlling agent of the present invention, the present compound is usually contained in an amount of 0.1% to 95% by weight.

The solid carrier for formulation includes, for example, a fine power and a granule of clays (e.g., kaolin clay, diatomite, bentonite, Fubasami clay, acid clay, etc.), synthetic hydrated silicon oxide, talc, ceramic, other inorganic minerals (e.g., sericite, quartz, sulfur, activated carbon, calcium carbonate, hydrated silica) or chemical fertilizers (e.g., ammonium sulfate, ammonium phosphate, ammonium nitrate, ammonium chloride, urea).

The liquid carrier for formulation includes, for example, aromatic or aliphatic hydrocarbons (e.g., xylene, toluene, alkylnaphthalene, phenylxylylethane, kerosine, light oil, hexane, cyclohexane), halogenated hydrocarbons (e.g., chlorobenzene, dichloromethane, dichloroethane, trichloroethane), alcohols (e.g., methanol, ethanol, isopropyl alcohol, butanol, hexanol, ethylene glycol), ethers (e.g., diethyl ether, ethylene glycol dimethyl ether, diethylene glycol monomethyl ether, diethylene glycol monoethyl ether, propylene glycol monomethyl ether, tetrahydrofuran, dioxane), esters (e.g., ethyl acetate, butyl acetate), ketones (e.g., acetone, methyl ethyl ketone, methyl isobutyl ketone, cyclohexanone), nitrites (e.g., acetonitrile, isobutyronitrile), sulfoxides (e.g., dimethylsulfoxide), acid amides (e.g., N,N-dimethylformamide, N,N-dimethylacetamide), vegetable oils (e.g., soy bean oil, cotton seed oil), vegetable essential oils (e.g., orange oil, hyssop oil, lemon oil) and water.

The gaseous carrier for formulation includes, for example, butane gas, flon gas, liquefied petroleum gas (LPG), dimethyl ether, carbon dioxide and the like.

The surfactant includes, for example, alkyl sulfate salts, alkylsulfonic acid salts, alkylarylsulfonic acid salts, alkyl aryl ethers and their polyoxyethylene derivatives, polyethylene glycol ethers, polyhydric alcohol esters, and sugar alcohol derivatives.

The other adjuvant for formulation includes, binders, dispersants, stabilizers and the like, and specifically for example, casein, gelatin, polysaccharides (e.g., starch, gum arabic, cellulose derivatives, alginic acid), lignin derivatives, bentonite, sugars, synthetic water-soluble polymers (e.g., polyvinyl alcohol, polyvinylpyrrolidone, polyacrylic acid), PAP (isopropyl acid phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids, and fatty acid esters.

The base for resin formulation includes, for example, polyvinyl chloride based copolymer, polyurethane and the like. To these bases, if necessary, a plasticizer such as phthalates (e.g., dimethyl phthalate, dioctyl phthalate), adipates and stearic acid may be added. The resin formulation can be obtained by kneading the compound into the base using a known kneader and then formulating by injection molding, extrusion molding, press molding and the like, and further, if necessary, via a process for molding, cutting and the like, the resin formulation having a specific form can be converted into a resin formulation such as board, film, tape, net, string and the like. These resin formulations can be converted into, for example, an animal collar, an animal ear tag, a sheet formulation, an attraction string, a gardening stick.

A base for the poison bait includes for example, grain powders, vegetable oils, sugars, and crystalline cellulose, and further, if necessary, antioxidants such as dibutylhydroxytoluene and nordihydroguaiaretic acid, preservatives such as dehydroacetic acid, agents for preventing children and pets from erroneously eating such as hot pepper powder, and pest-attractive flavors such as cheese flavor, onion flavor and peanut oil may be added to the base.

The noxious arthropod controlling agent of the present invention is used, for example, by applying to noxious arthropods directly and/or at a habitat of noxious arthropods such as plant, animal soil and the like.

When the noxious arthropod controlling agent of the present invention is used for a control of pests in agriculture and forestry, the application amount is usually 1 to 10,000 g/ha, preferably 10 to 500 g/ha, as an active ingredient. The emulsifiable concentrates, wettable powders, flowables, and microcapsule formulations are usually applied after dilution with water to have an active ingredient concentration of 1 to 1,000 ppm, while dusts and granules are usually applied as such. These formulations may be sprayed directly to the plant to be protected from noxious arthropods. The noxious arthropods living in the soil can be controlled by treating the soil with these formulations, and the formulations can also be applied to treat seedbeds prior to the planting plants or to treat planting holes or plant bottoms in the planting. Furthermore, the sheet formulation of the noxious arthropod controlling agent of the present invention can be applied by a method such as winding around plants, stretching in the vicinity of plants and laying on the soil surface at the plant bottom.

When the noxious arthropod controlling agent of the present invention is used for a control of epidemic, the application amount is usually 0.001 to 10 mg/m$^3$ as an active ingredient in case of application for open space, and 0.001 to 100 mg/m$^2$ as an active ingredient in case of application for plane surface. The emulsifiable concentrates, wettable powders and flowables are usually applied after dilution with water to have an active ingredient concentration of 0.01 to 10,000 ppm, while oil solutions, aerosols, smoking agents and poison baits are usually applied as such.

When the noxious arthropod controlling agent of the present invention is used for a control of parasite living outside of a livestock such as cow, horse, pig, sheep, goat and chicken, and a small animal such as dog, cat, rat and mouse, the noxious arthropod controlling agent of the present invention can be applied to said animal by a veterinarily known method. Specifically, for systemic control, the noxious arthropod controlling agent of the present invention is administered by means of, for example, a tablet, a mixture with feed, a suppository or an injection (e.g., intramuscular, subcutaneous, intravenous, intraperitoneal), and for non-systemic control, it is applied by a method such as spraying an oil solution or an aqueous liquid formulation, carrying out pour-on treatment or spot-on treatment, washing said animal with a shampoo formulation, attaching the resin formulation on said animal as a collar or an ear-tag, and the like. When it is administered to an animal, the amount of the present compound is usually in the range of 0.1 to 1,000 mg/kg body weight of the animal.

The noxious arthropod controlling agent of the present invention can also be used in admixture or combination with other insecticides, nematocides, acaricides, fungicides, herbicides, plant growth regulators, synergists, fertilizers, soil conditioners, animal feeds, and the like.

The active ingredients of such other insecticide and acaricide include, for example, pyrethroid compounds such as allethrin, tetramethrin, prallethrin, phenothrin, resmethrin, cyphenothrin, permethrin, cypermethrin, alpha-cypermethrin, zeta-cypermethrin, deltamethrin, tralomethrin, cyfluthrin, beta-cyfluthrin, cyhalothrin, lambda-cyhalothrin, flumethrin, imiprothrin, etofenprox, fenvalerate, esfenvalerate, fenpropathrin, silafluofen, bifenthrin, transfluthrin, flucythrinate, tau-fluvalinate, acrinathrin, tefluthrin, cycloprothrin, empenthrin, 2,3,5,6-tetrafluoro-4-methoxymethylbenzyl 3-(2-methyl-1-propenyl)-2,2-dimethylcyclopropancarboxylate, 2,3,5,6-tetrafluoro-4-methoxymethylbenzyl 3-(1-propenyl)-2,2-dimethylcyclopropancarboxylate and 2,3,5,6-tetrafluoro-4-methylbenzyl 3-(1-propenyl)-2,2-dimethylcyclopropancarboxylate; organophosphorus compounds such as dichlorvos, fenitrothion, cyanophos, profenofos, sulprofos, phenthoate, isoxathion, tetrachlorvinphos, fenthion, chlorpyriphos, diazinon, acephate, terbufos, phorate, chlorethoxyfos, fosthiazate, ethoprophos, cadusafos and methidathion; carbamate compounds such as propoxur, carbaryl, metoxadiazone, fenobucarb, methomyl, thiodicarb, alanycarb, benfuracarb, oxamyl, aldicarb and methiocarb; benzoylphenylurea compounds such as lufenuron, chlorfluazuron, hexaflumuron, diflubenzuron, triflumuron, teflubenzuron, flufenoxuron, fluazuron, novaluron and triazuron; juvenile hormone-like substances such as pyriproxyfen, methoprene, hydroprene and fenoxycarb; neonicotinoid compounds such as acetamiprid, nitenpyram, thiacloprid, thiamethoxam, dinotefuran and clothianidin; N-phenylpyrazole compounds such as acetoprole and ethiprole; benzoylhydrazine compounds such as tebufenozide, chromafenozide, methoxyfenozide and halofenozide; diafenthiuron; pymetrozine; flonicamid; triazamate; buprofezin; spinosad; emamectin benzoate; chlorfenapyr; indoxacarb; pyridalyl; cyromazine; fenpyroximate; tebufenpyrad; tolfenpyrad; pyridaben; pyrimidifen; fluacrypyrim; etoxazole; fenazaquin; acequinocyl; hexythiazox; clofentezine; fenbutatin oxide; dicofol, propargite; abamectin; milbemectin; amitraz; cartap; bensultap; thiocyclam; endosulfan; spirodiclofen; spiromesifen; Flubendiamide; and azadirachtin.

The other fungicide include, for example, strobilurin compounds such as azoxystrobin; organophosphorus compounds such as tolclofos-methyl; azole compounds such as triflumizole, pefurazoate and difenoconazole; phthalide; flutolanil; validamycin; probenazole; diclomezine; pencycuron; dazomet; kasugamycin; IBP; pyroquilon; oxolinic acid; tricyclazole; ferimzone; mepronil; EDDP; isoprothiolane; carpropamid; diclocymet; furametpyr; fludioxonil; procymidone; and diethofencarb.

The present invention is constructed in more detail by production examples, formulation examples, test examples and the like.

Firstly, production examples of the present compound are illustrated.

Production Example 1

0.6 g of 1-iodo-3,3,3-trifluoropropane and 0.5 g of (3,3,3-trifluoropropylsulfonyl)acetonitrile were dissolved to 20 ml of N,N-dimethylformamide. 0.1 g of sodium hydride (60% in oil) was added thereto at room temperature, and the mixture the mixture was stirred for 24 hours at the same temperature. Then 10% hydrochloric acid was added to the reaction mixture and the mixture the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 1.44 g of 5,5,5-trifluoro-2-(3,3,3-trifluoropropylsulfonyl)pentanenitrile (referred as the present compound (1), hereinafter).

The Present Compound (1)

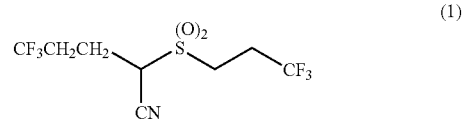

(1)

$^1$H-NMR (CDCl$_3$, TMS): δ (ppm) 4.00-4.07 (m, 1H), 3.44-3.62 (m, 2H), 2.72-2.87 (m, 2H), 2.36-2.64 (m, 4H)

Production Example 2

0.7 g of 2,2,3,3,3-pentafluoropropyl trifluoromethansulfonate and 0.5 g of (3,3,3-trifluoropropylsulfonyl)acetonitrile were dissolved to 20 ml of N,N-dimethylformamide. 0.3 g of potassium carbonate was added thereto at room temperature, and the mixture the mixture was stirred for 40 hours at the same temperature. Then 10% hydrochloric acid was added to the reaction mixture and the mixture the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.40 g of 4,4,5,5,5-pentafluoro-2-(3,3,3-trifluoropropylsulfonyl)pentanenitrile (referred as the present compound (2), hereinafter).

The Present Compound (2)

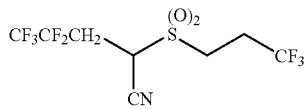

$^1$H-NMR (CDCl$_3$, TMS): δ (ppm) 4.22 (dd, 1H), 3.54-3.72 (m, 2H), 2.76-3.06 (m, 4H)

Production Example 3

0.6 g of 1-iodo-3,3,4,4,4-pentafluorobutane and 0.4 g of (3,3,3-trifluoropropylsulfonyl)acetonitrile were dissolved to 20 ml of N,N-dimethylformamide. 0.09 g of sodium hydride (60% in oil) was added thereto at room temperature, and the mixture the mixture was stirred for 20 hours at the same temperature. Then 10% hydrochloric acid was added to the reaction mixture and the mixture the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 1.44 g of 5,5,6,6,6-pentafluoro-2-(3,3,3-trifluoropropylsulfonyl)hexanenitrile (referred as the present compound (3), hereinafter).

The Present Compound (3)

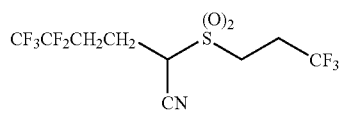

$^1$H-NMR (CDCl$_3$, TMS): δ (ppm) 4.01-4.08 (m, 1H), 3.44-3.62 (m, 2H), 2.73-2.88 (m, 2H), 2.28-2.62 (m, 4H)

Production Example 4

0.9 g of 2,2,3,3,4,4,4-heptafluorobutyl trifluoromethansulfonate and 0.5 g of (3,3,3-trifluoropropylsulfonyl)acetonitrile were dissolved to 20 ml of N,N-dimethylformamide. 0.3 g of potassium carbonate was added thereto at room temperature, and the mixture the mixture was stirred for 28 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.40 g of 4,4,5,5,6,6,6-heptafluoro-2-(3,3,3-trifluoropropylsulfonyl)hexanenitrile (referred as the present compound (4), hereinafter).

The Present Compound (4)

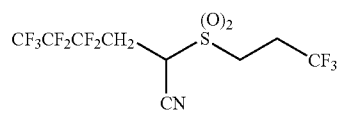

$^1$H-NMR (CDCl$_3$, TMS): δ (ppm) 4.22 (dd, 1H), 3.55-3.72 (m, 2H), 2.78-3.10 (m, 4H)

Production Example 5

0.8 g of 1-iodo-3,3,4,4,5,5,5-heptafluoropentane and 0.5 g of (3,3,3-trifluoropropylsulfonyl)acetonitrile were dissolved to 20 ml of N,N-dimethylformamide. 0.1 g of sodium hydride (60% in oil) was added thereto at room temperature, and the mixture was stirred for 24 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.45 g of 5,5,6,6,7,7,7-heptafluoro-2-(3,3,3-trifluoropropylsulfonyl)heptanenitrile (referred as the present compound (5), hereinafter).

The Present Compound (5)

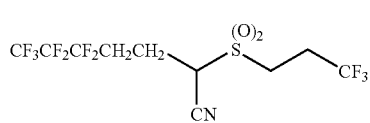

$^1$H-NMR (CDCl$_3$, TMS): δ (ppm) 4.04-4.08 (m, 1H), 3.46-3.63 (m, 2H), 2.73-2.88 (m, 2H), 2.34-2.64 (m, 4H)

Production Example 6

1.3 g of 2,2,3,3,4,4,5,5-octafluoropentyl trifluoromethansulfonate and 0.7 g of (3,3,3-trifluoropropylsulfonyl)acetonitrile were dissolved to 30 ml of N,N-dimethylformamide. 0.5 g of potassium carbonate was added thereto at room temperature, and the mixture was stirred for 20 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.32 g of 4,4,5,5,6,6,7,7-octafluoro-2-(3,3,3-trifluoropropylsulfonyl)heptanenitrile (referred as the present compound (6), hereinafter).

The Present Compound (6)

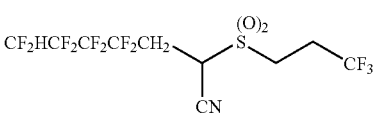

$^1$H-NMR (CDCl$_3$, TMS): δ (ppm) 6.05 (tt, 1H), 4.21 (dd, 1H), 3.50-3.71 (m, 2H), 2.70-3.09 (m, 4H)

Production Example 7

1.3 g of 1-iodo-3,3,4,4,5,5,6,6,6-nonafluorohexane and 0.7 g of (3,3,3-trifluoropropylsulfonyl)acetonitrile were dissolved to 30 ml of N,N-dimethylformamide. 0.1 g of potassium carbonate was added thereto at room temperature, and the mixture was stirred for 6 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.59 g of 5,5,6,6,7,7,8,8,8-nonafluoro-2-(3,3,3-trifluoropropylsulfonyl)octanenitrile (referred as the present compound (7), hereinafter).

The Present Compound (7)

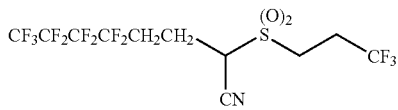

(7)

$^1$H-NMR (CDCl$_3$, TMS): δ (ppm) 4.02-4.08 (m, 1H), 3.45-3.63 (m, 2H), 2.73-2.86 (m, 2H), 2.34-2.63 (m, 4H)

Production Example 8

0.6 g of 1-iodo-3,3,4,4,4-pentafluorobutane and 0.4 g of (3,3,4,4,4-pentafluorobutylsulfonyl)acetonitrile were dissolved to 50 ml of N,N-dimethylformamide. 0.5 g of sodium hydride (60% in oil) was added thereto at room temperature, and the mixture was stirred for 4 days at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 2.66 g of 5,5,6,6,6-pentafluoro-2-(3,3,4,4,4-pentafluorobutylsulfonyl)hexanenitrile (referred as the present compound (8), hereinafter).

The Present Compound (8)

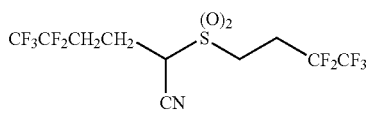

(8)

$^1$H-NMR (CDCl$_3$, TMS): δ (ppm) 4.04-4.09 (m, 1H), 3.48-3.68 (m, 2H), 2.67-2.82 (m, 2H), 2.31-2.61 (m, 4H)

Production Example 9

0.7 g of 2,2,3,3,4,4,4-heptafluorobutyl trifluoromethansulfonate and 0.5 g of (3,3,4,4,4-pentafluorobutylsulfonyl)acetonitrile were dissolved to 20 ml of N,N-dimethylformamide. 0.3 g of potassium carbonate was added thereto at room temperature, and the mixture was stirred for 40 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.38 g of 4,4,5,5,6,6,6-heptafluoro-2-(3,3,4,4,4-pentafluorobutylsulfonyl)hexanenitrile (referred as the present compound (9), hereinafter).

The Present Compound (9)

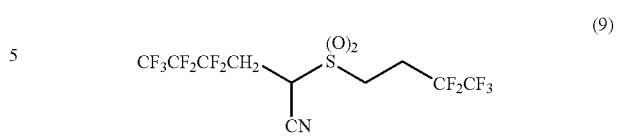

(9)

$^1$H-NMR (CDCl$_3$, TMS): δ (ppm) 4.22 (dd, 1H), 3.56-3.76 (m, 2H), 2.68-3.10 (m, 4H)

Production Example 10

1.8 g of 1-iodo-3,3,4,4,4-pentafluorobutane and 2.0 g of (3,3,4,4,5,5,5-heptafluoropentylsulfonyl)acetonitrile were dissolved to 50 ml of N,N-dimethylformamide. 0.3 g of sodium hydride (60% in oil) was added thereto at room temperature, and the mixture was stirred for 20 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 1.43 g of 2-(3,3,4,4,5,5,5-heptafluoropentylsulfonyl)-5,5,6,6,6-pentafluorohexanenitrile (referred as the present compound (10), hereinafter).

The Present Compound (10)

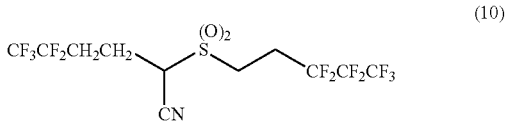

(10)

$^1$H-NMR (CDCl$_3$, TMS): δ (ppm) 4.07 (dd, 1H), 3.48-3.67 (m, 2H), 2.32-2.85 (m, 6H)

Production Example 11

0.2 g of iodomethane and 0.5 g of 5,5,6,6,6-pentafluoro-2-(3,3,3-trifluoropropylsulfonyl)hexanenitrile were dissolved to 20 ml of N,N-dimethylformamide. 0.06 g of sodium hydride (60% in oil) was added thereto at room temperature, and the mixture was stirred for 20 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.35 g of 2-methyl-5,5,6,6,6-pentafluoro-2-(3,3,3-trifluoropropylsulfonyl)hexanenitrile (referred as the present compound (11), hereinafter).

The Present Compound (11)

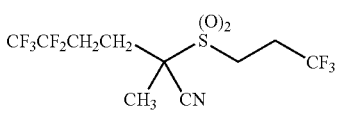

(11)

$^1$H-NMR (CDCl$_3$, TMS): δ (ppm) 3.40-3.58 (m, 2H), 2.73-2.88 (m, 2H), 2.16-2.58 (m, 4H), 1.83 (s, 3H)

Production Example 12

0.3 g of iodomethane and 0.7 g of 4,4,5,5,6,6,6-heptafluoro-2-(3,3,3-trifluoropropylsulfonyl)hexanenitrile were dissolved to 30 ml of N,N-dimethylformamide. 0.07 g of sodium hydride (60% in oil) was added thereto at room temperature, and the mixture was stirred for 24 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.32 g of 4,4,5,5,6,6,6-heptafluoro-2-methyl-2-(3,3,3-trifluoropropylsulfonyl)hexanenitrile (referred as the present compound (12), hereinafter).
The Present Compound (12)

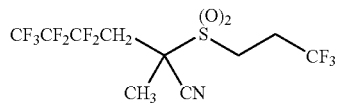

(12)

$^1$H-NMR (CDCl$_3$, TMS): δ (ppm) 3.48-3.65 (m, 2H), 2.61-3.13 (m, 4H), 2.00 (d, 3H)

Production Example 13

0.2 g of iodomethane and 0.5 g of 5,5,6,6,6-pentafluoro-2-(3,3,4,4,4-pentafluorobutylsulfonyl)hexanenitrile were dissolved to 20 ml of N,N-dimethylformamide. 0.05 g of sodium hydride (60% in oil) was added thereto at room temperature, and the mixture was stirred for 20 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.49 g of 2-methyl-5,5,6,6,6-pentafluoro-2-(3,3,4,4,4-pentafluorobutylsulfonyl)hexanenitrile (referred as the present compound (13), hereinafter).
The Present Compound (13)

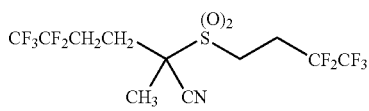

(13)

$^1$H-NMR (CDCl$_3$, TMS): δ (ppm) 3.42-3.61 (m, 2H), 2.68-2.82 (m, 2H), 2.18-2.58 (m, 4H), 1.84 (s, 3H)

Production Example 14

0.2 g of iodomethane and 0.5 g of 5,5,6,6,6-pentafluoro-2-(3,3,4,4,5,5,5-heptafluoropentylsulfonyl)hexanenitrile were dissolved to 20 ml of N,N-dimethylformamide. 0.05 g of sodium hydride (60% in oil) was added thereto at room temperature, and the mixture was stirred for 2 days at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.49 g of 2-(3,3,4,4,5,5,5-heptafluoropentylsulfonyl)-2-methyl-5,5,6,6,6-pentafluorohexanenitrile (referred as the present compound (14), hereinafter).
The Present Compound (14)

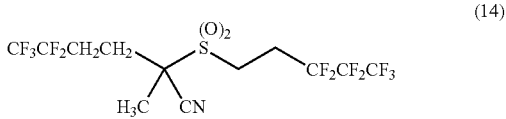

(14)

$^1$H-NMR (CDCl$_3$, TMS): δ (ppm) 3.42-3.61 (m, 2H), 2.68-2.82 (m, 2H), 2.18-2.58 (m, 4H), 1.84 (s, 3H)

Production Example 15

0.2 g of iodoethane and 0.5 g of 5,5,6,6,6-pentafluoro-2-(3,3,3-trifluoropropylsulfonyl)hexanenitrile were dissolved to 20 ml of N,N-dimethylformamide. 0.06 g of sodium hydride (60% in oil) was added thereto at room temperature, and the mixture was stirred for 10 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.37 g of 2-ethyl-5,5,6,6,6-pentafluoro-2-(3,3,3-trifluoropropylsulfonyl)hexanenitrile (referred as the present compound (15), hereinafter).
The Present Compound (15)

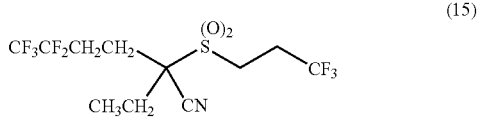

(15)

$^1$H-NMR (CDCl$_3$, TMS): δ (ppm) 3.39-3.58 (m, 2H), 2.72-2.84 (m, 2H), 2.32-2.56 (m, 4H), 2.06-2.26 (m, 2H), 1.28 (t, 3H)

Production Example 16

0.2 g of 1-iodopropane and 0.5 g of 5,5,6,6,6-pentafluoro-2-(3,3,3-trifluoropropylsulfonyl)hexanenitrile were dissolved to 20 ml of N,N-dimethylformamide. 0.06 g of sodium hydride (60% in oil) was added thereto at room temperature, and the mixture was stirred for 24 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.38 g of 5,5,6,6,6-pentafluoro-2-propyl-2-(3,3,3-trifluoropropylsulfonyl)hexanenitrile (referred as the present compound (16), hereinafter).

The Present Compound (16)

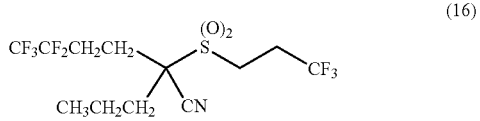

¹H-NMR (CDCl₃, TMS): δ (ppm) 3.38-3.58 (m, 2H), 2.72-2.86 (m, 2H), 2.32-2.58 (m, 4H), 1.95-2.11 (m, 2H), 1.58-1.72 (m, 2H), 1.10 (t, 3H)

Production Example 17

0.2 g of 2-iodopropane and 0.5 g of 5,5,6,6,6-pentafluoro-2-(3,3,3-trifluoropropylsulfonyl)hexanenitrile were dissolved to 20 ml of N,N-dimethylformamide. 0.06 g of sodium hydride (60% in oil) was added thereto at room temperature, and the mixture was stirred for 6 hours at the same temperature, for 2 hours at 60° C. and for 6 hours at 90° C. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.13 g of 5,5,6,6,6-pentafluoro-2-(2-propyl)-2-(3,3,3-trifluoropropylsulfonyl)hexanenitrile (referred as the present compound (17), hereinafter).
The Present Compound (17)

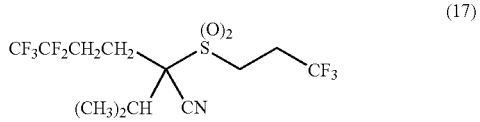

¹H-NMR (CDCl₃, TMS): δ (ppm) 3.39-3.60 (m, 2H), 2.70-2.87 (m, 2H), 2.26-2.62 (m, 5H), 1.35 (d, 3H), 1.27 (d, 3H)

Production Example 18

0.3 g of 1-iodobutane and 0.5 g of 5,5,6,6,6-pentafluoro-2-(3,3,3-trifluoropropylsulfonyl)hexanenitrile were dissolved to 20 ml of N,N-dimethylformamide. 0.06 g of sodium hydride (60% in oil) was added thereto at room temperature, and the mixture was stirred for 8 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.28 g of 2-butyl-5,5,6,6,6-pentafluoro-2-(3,3,3-trifluoropropylsulfonyl)hexanenitrile (referred as the present compound (18), hereinafter).
The Present Compound (18)

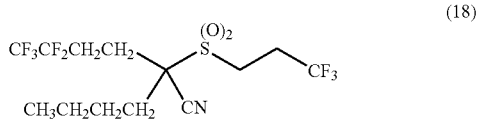

¹H-NMR (CDCl₃, TMS): δ (ppm) 3.38-3.58 (m, 2H), 2.72-2.86 (m, 2H), 2.32-2.58 (m, 4H), 1.94-2.11 (m, 2H), 1.38-1.65 (m, 4H), 1.00 (t, 3H)

Production Example 19

0.3 g of 1-iodopentane and 0.5 g of 5,5,6,6,6-pentafluoro-2-(3,3,3-trifluoropropylsulfonyl)hexanenitrile were dissolved to 20 ml of N,N-dimethylformamide. 0.06 g of sodium hydride (60% in oil) was added thereto at room temperature, and the mixture was stirred for 20 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.28 g of 2-(3,3,4,4,4-pentafluorobutyl)-2-(3,3,3-trifluoropropylsulfonyl)heptanenitrile (referred as the present compound (19), hereinafter).
The Present Compound (19)

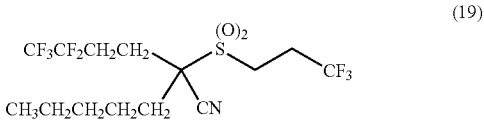

¹H-NMR (CDCl₃, TMS): δ (ppm) 3.38-3.58 (m, 2H), 2.72-2.86 (m, 2H), 2.32-2.58 (m, 4H), 1.94-2.11 (m, 2H), 1.38-1.65 (m, 6H), 1.00 (t, 3H)

Production Example 20

0.5 g of 5,5,6,6,6-pentafluoro-2-(3,3,3-trifluoropropylsulfonyl)hexanenitrile was dissolved to 20 ml of tetrahydrofuran. 0.06 g of sodium hydride (60% in oil) was added thereto at 0° C., and the mixture was stirred for 0.5 hours at the same temperature. Then 0.4 g of 1-fluoro-2,4,6-trimethylpyridinium trifluoromethanesulfonate was added to the mixture at the same temperature and the mixture was stirred for 0.5 hours. Furthermore, the mixture was stirred at room temperature for 10 hours. After that, 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.37 g of 2,5,5,6,6,6-hexafluoro-2-(3,3,3-trifluoropropylsulfonyl)hexanenitrile (referred as the present compound (20), hereinafter).
The Present Compound (20)

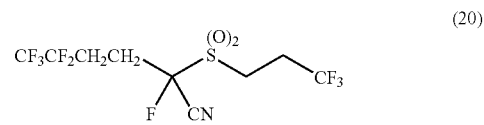

¹H-NMR (CDCl₃, TMS): δ (ppm) 3.54-3.67 (m, 2H), 2.39-2.88 (m, 6H)

Production Example 21

0.5 g of 5,5,6,6,6-pentafluoro-2-(3,3,3-trifluoropropylsulfonyl)hexanenitrile was dissolved to 20 ml of tetrahydrofuran. 0.06 g of sodium hydride (60% in oil) was added thereto at 0° C., and the mixture was stirred for 0.5 hours at the same temperature. Then 0.2 g of N-chloro succinimide was added to the mixture at the same temperature and the mixture was stirred for 0.5 hours. Furthermore, the mixture was stirred at room temperature for 3 days. After that, 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.15 g of 2-chloro-5,5,6,6,6-pentafluoro-2-(3,33-trifluoropropylsulfonyl)hexanenitrile (referred as the present compound (21), hereinafter).

The Present Compound (21)

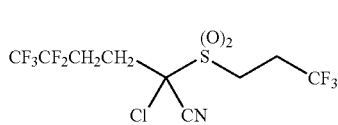

(21)

$^1$H-NMR (CDCl$_3$, TMS): δ (ppm) 3.66-3.84 (m, 2H), 2.42-2.92 (m, 6H)

Production Example 22

2.0 g of 1-iodo-4,4,4-trifluorobutane and 2.0 g of methyl (3,3,3-trifluoropropylsulfonyl)acetate were dissolved to 20 ml of N,N-dimethylformamide. 1.2 g of potassium carbonate was added thereto at room temperature, and the mixture was stirred for 20 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.80 g of methyl 6,6,6-trifluoro-2-(3,3,3-trifluoropropylsulfonyl) hexanoate (referred as the present compound (22), hereinafter).

The Present Compound (22)

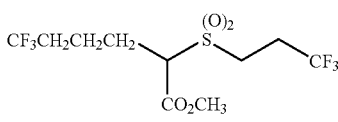

(22)

$^1$H-NMR (CDCl$_3$, TMS): δ (ppm) 3.89 (s, 3H), 3.82-3.88 (m, 1H), 3.30-3.50 (m, 2H), 2.62-2.77 (m, 2H), 2.10-2.24 (m, 4H), 1.64-1.75 (m, 2H)

Production Example 23

1.2 g of 1-iodo-3,3,4,4,4-pentafluorobutane and 1.0 g of methyl (3,3,3-trifluoropropylsulfonyl)acetate were dissolved to 20 ml of N,N-dimethylformamide. 0.6 g of potassium carbonate was added thereto at room temperature, and it was stirred for 30 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 1.20 g of methyl 5,5,6,6,6-pentafluoro-2-(3,3,3-trifluoropropylsulfonyl)hexanoate (referred as the present compound (23), hereinafter).

The Present Compound (23)

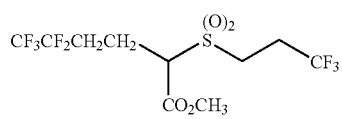

(23)

$^1$H-NMR (CDCl$_3$, TMS): δ (ppm) 3.90 (s, 3H), 3.86-3.94 (m, 1H), 3.38-3.51 (m, 2H), 2.63-2.78 (m, 2H), 2.38-2.53 (m, 2H), 2.18-2.34 (m, 2H)

Production Example 24

4.8 g of 1-iodo-3,3,4,4,4-pentafluorobutane and 5.0 g of methyl (3,3,4,4,4-pentafluorobutylsulfonyl)acetate were dissolved to 50 ml of N,N-dimethylformamide. 0.7 g of sodium hydride (60% in oil) was added thereto at room temperature, and the mixture was stirred for 2 days at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 4.69 g of methyl 5,5,6,6,6-pentafluoro-2-(3,3,4,4,4-pentafluorobutylsulfonyl)hexanoate (referred as the present compound (24), hereinafter).

The Present Compound (24)

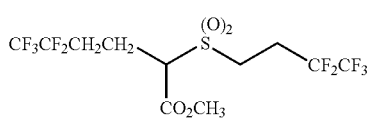

(24)

$^1$H-NMR (CDCl$_3$, TMS): δ (ppm) 3.91 (s, 3H), 3.89-3.97 (m, 1H), 3.44-3.51 (m, 2H), 2.58-2.73 (m, 2H), 2.39-2.53 (m, 2H), 2.20-2.34 (m, 2H)

Production Example 25

0.5 g of 5,5,6,6,6-pentafluoro-2-(3,3,3-trifluoropropylsulfonyl)hexanoic acid was dissolved to 10 ml of dichloromethane. 2 drops of N,N-dimethylformamide and 0.2 ml of oxalyl chloride were subsequently added dropwise thereto at room temperature, then the mixture was stirred for 2 hours at the same temperature. Then the reaction mixture was concentrated under reduced pressure. The obtained residue was dissolved to 20 ml of tetrahydrofuran and 0.1 g of tert-butyl alcohol and 0.2 ml of triethylamine were added dropwise at room temperature. The mixture was stirred at the same temperature for 1 hour. Saturated aqueous solution of ammonium chloride was added to the reaction mixture and the mixture was extracted by ethyl acetate. The organic layer was washed with saturated aqueous solution of sodium chloride, dried over anhydrous magnesium sulfate and concentrated under reduced pressure. The obtained residue was subjected to silica gel chromatography to obtain 0.42 g of tert-butyl 5,5,6,6,6-pentafluoro-2-(3,3,3-trifluoropropylsulfonyl)hexanoate (referred as the present compound (25), hereinafter).

The Present Compound (25)

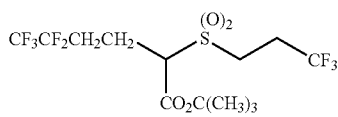

(25)

¹H-NMR (CDCl₃, TMS): δ (ppm) 3.75-3.82 (m, 1H), 3.38-3.52 (m, 2H), 2.63-2.78 (m, 2H), 2.18-2.46 (m, 4H), 1.53 (s, 9H)

Production Example 26

0.4 g of iodomethane and 1.0 g of methyl 5,5,6,6,6-pentafluoro-2-(3,3,3-trifluoropropylsulfonyl)hexanoate were dissolved to 20 ml of N,N-dimethylformamide. 0.1 g of sodium hydride (60% in oil) was added thereto at room temperature, and the mixture was stirred for 3 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.73 g of methyl 2-methyl-5,5,6,6,6-pentafluoro-2-(3,3,3-trifluoropropylsulfonyl)hexanoate (referred as the present compound (26), hereinafter).
The Present Compound (26)

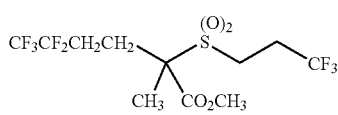

(26)

¹H-NMR (CDCl₃, TMS): δ (ppm) 3.88 (s, 3H), 3.43-3.52 (m, 2H), 2.63-2.78 (m, 2H), 2.08-2.54 (m, 4H), 1.70 (s, 3H)

Production Example 27

0.4 g of iodoethane and 1.0 g of methyl 5,5,6,6,6-pentafluoro-2-(3,3,3-trifluoropropylsulfonyl)hexanoate were dissolved to 20 ml of N,N-dimethylformamide. 0.1 g of sodium hydride (60% in oil) was added thereto at room temperature, and the mixture was stirred for 20 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.45 g of methyl 2-ethyl-5,5,6,6,6-pentafluoro-2-(3,3,3-trifluoropropylsulfonyl)hexanoate (referred as the present compound (27), hereinafter).
The Present Compound (27)

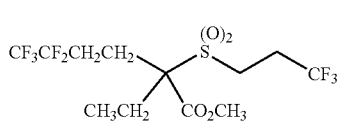

(27)

¹H-NMR (CDCl₃, TMS): δ (ppm) 3.88 (s, 3H), 3.33-3.65 (m, 2H), 2.06-2.77 (m, 8H), 1.04 (t, 3H)

Production Example 28

0.4 g of 1-iodopropane and 1.0 g of methyl 5,5,6,6,6-pentafluoro-2-(3,3,3-trifluoropropylsulfonyl)hexanoate were dissolved to 20 ml of N,N-dimethylformamide. 0.1 g of sodium hydride (60% in oil) was added thereto at room temperature, and the mixture was stirred for 20 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.89 g of methyl 5,5,6,6,6-pentafluoro-2-propyl-2-(3,3,3-trifluoropropylsulfonyl)hexanoate (referred as the present compound (28), hereinafter).
The Present Compound (28)

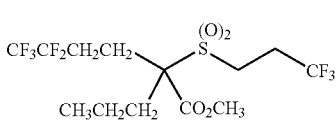

(28)

¹H-NMR (CDCl₃, TMS): δ (ppm) 3.87 (s, 3H), 3.32-3.66 (m, 2H), 1.96-2.76 (m, 8H) 1.16-1.58 (m, 2H), 1.01 (t, 3H)

Production Example 29

0.05 g of sodium hydride (60% in oil) was added to a solution of 0.5 g of methyl 5,5,6,6,6-pentafluoro-2-(3,3,3-trifluoropropylsulfonyl)hexanoate in 20 ml of tetrahydrofuran at 0° C. and the mixture was stirred for 0.5 hours at the same temperature. Then 0.4 g of 1-fluoro-2,4,6-trimethylpyridinium trifluoromethanesulfonate was added thereto and the mixture was stirred for 0.5 hour. Furthermore, the mixture was stirred at room temperature for 10 hours. 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.39 g of methyl 2,5,5,6,6,6-hexafluoro-2-(3,3,3-trifluoropropylsulfonyl)hexanoate (referred as the present compound (29), hereinafter).
The Present Compound (29)

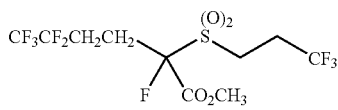

(29)

¹H-NMR (CDCl₃, TMS): δ (ppm) 4.00 (s, 3H), 3.26-3.56 (m, 2H), 2.09-2.80 (m, 6H)

Production Example 30

0.7 g of iodomethane and 2.0 g of methyl 5,5,6,6,6-pentafluoro-2-(3,3,4,4,4-pentafluorobutylsulfonyl)hexanenoate were dissolved to 50 ml of N,N-dimethylformamide. 0.2 g of sodium hydride (60% in oil) was added thereto at room temperature, and the mixture was stirred for 4 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 1.20 g of methyl 2-methyl-5,5,6,6,6-pentafluoro-2-(3,3,4,4,4-pentafluorobutylsulfonyl)hexanoate (referred as the present compound (30), hereinafter).
The Present Compound (30)

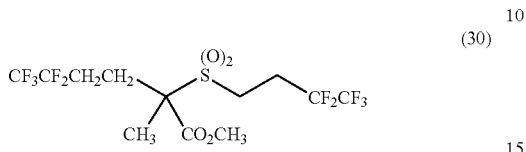

(30)

¹H-NMR (CDCl₃, TMS): δ (ppm) 3.90 (s, 3H), 3.46-3.53 (m, 2H), 2.45-2.72 (m, 3H), 2.09-2.34 (m, 3H), 1.71 (s, 3H)

Production Example 31

0.5 g of 5,5,6,6,6-pentafluoro-2-(3,3,3-trifluoropropylsulfonyl)hexanoic acid was dissolved to 10 ml of dichloromethane. 2 drops of N,N-dimethylformamide and 0.2 ml of oxalyl chloride were subsequently added dropwise thereto at room temperature, then the mixture was stirred for 2 hours at the same temperature. Then the reaction mixture was concentrated under reduced pressure. The obtained residue was dissolved to 20 ml of tetrahydrofuran and 0.2 g of ammonia (30% (w/w) aqueous solution) was added dropwise thereto at room temperature. The mixture was stirred at the same temperature for 2 hours. Saturated aqueous solution of ammonium chloride was added to the reaction mixture and the mixture was extracted by ethyl acetate. The organic layer was washed with saturated aqueous solution of sodium chloride, dried over anhydrous magnesium sulfate and concentrated under reduced pressure. The obtained residue was subjected to silica gel chromatography to obtain 0.24 g of 5,5,6,6,6-pentafluoro-2-(3,3,3-trifluoropropylsulfonyl)hexanamide (referred as the present compound (31), hereinafter).
The Present Compound (31)

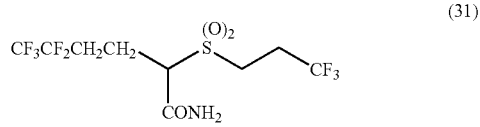

(31)

¹H-NMR (CDCl₃, TMS): δ (ppm) 6.34 (bs, 1H), 5.73 (bs, 1H), 3.73 (dd, 1H), 3.21-3.42 (m, 2H), 2.64-2.73 (m, 2H), 2.12-2.48 (m, 4H)

Production Example 32

0.5 g of 5,5,6,6,6-pentafluoro-2-(3,3,3-trifluoropropylsulfonyl)hexanoic acid was dissolved to 10 ml of dichloromethane. 2 drops of N,N-dimethylformamide and 0.2 ml of oxalyl chloride were subsequently added dropwise thereto at room temperature, then the mixture was stirred for 1 hour at the same temperature. Then the reaction mixture was concentrated under reduced pressure. The obtained residue was dissolved to 20 ml of tetrahydrofuran and 0.3 g of methylamine (40% (w/w) aqueous solution) was added dropwise thereto at room temperature. The mixture was stirred at the same temperature for 2 hours. Saturated aqueous solution of ammonium chloride was added to the reaction mixture and the mixture was extracted by ethyl acetate. The organic layer was washed with saturated aqueous solution of sodium chloride, dried over anhydrous magnesium sulfate and concentrated under reduced pressure. The obtained residue was subjected to silica gel chromatography to obtain 0.26 g of N-methyl-5,5,6,6,6-pentafluoro-2-(3,3,3-trifluoropropylsulfonyl)hexanamide (referred as the present compound (32), hereinafter).
The Present Compound (32)

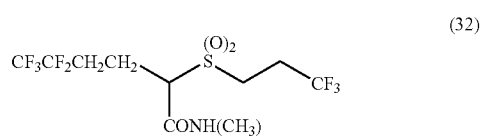

(32)

¹H-NMR (CDCl₃, TMS): δ (ppm) 6.22 (bs, 1H), 3.63 (dd, 1H), 3.18-3.39 (m, 2H), 2.94 (d, 3H), 2.60-2.73 (m, 2H), 2.08-2.50 (m, 4H)

Production Example 33

0.5 g of 5,5,6,6,6-pentafluoro-2-(3,3,3-trifluoropropylsulfonyl)hexanoic acid was dissolved to 10 ml of dichloromethane. 2 drops of N,N-dimethylformamide and 0.2 ml of oxalyl chloride were subsequently added dropwise thereto at room temperature, then the mixture was stirred for 1 hour at the same temperature. Then the reaction mixture was concentrated under reduced pressure. The obtained residue was dissolved to 20 ml of tetrahydrofuran and 0.5 g of dimethylamine (40% (w/w) aqueous solution) was added dropwise thereto at room temperature. The mixture was stirred at the same temperature for 2 hours. Saturated aqueous solution of ammonium chloride was added to the reaction mixture and the mixture was extracted by ethyl acetate. The organic layer was washed with saturated aqueous solution of sodium chloride, dried over anhydrous magnesium sulfate and concentrated under reduced pressure. The obtained residue was subjected to silica gel chromatography to obtain 0.30 g of N,N-dimethyl-5,5,6,6,6-pentafluoro-2-(3,3,3-trifluoropropylsulfonyl)hexanamide (referred as the present compound (33), hereinafter).
The Present Compound (33)

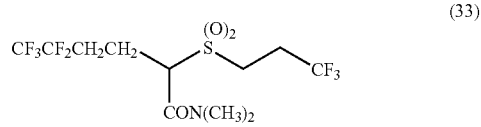

(33)

¹H-NMR (CDCl₃, TMS): δ (ppm) 4.31 (dd, 1H), 3.19-3.53 (m, 2H), 3.21 (s, 3H), 3.09 (s, 3H), 2.57-2.70 (m, 2H), 1.98-2.54 (m, 4H)

Production Example 34

1.1 g of 2-methyl-5,5,6,6,6-pentafluoro-2-(3,3,3-trifluoropropylsulfonyl)hexanoic acid was dissolved to 20 ml of dichloromethane. 2 drops of N,N-dimethylformamide and 0.5 ml of oxalyl chloride was subsequently added dropwise thereto at room temperature, then the mixture was stirred for 2 hours at the same temperature. Then the reaction mixture was concentrated under reduced pressure. The obtained residue was dissolved to 20 ml of tetrahydrofuran and 0.5 g of ammonia (30% (w/w) aqueous solution) was added dropwise thereto at room temperature. The mixture was stirred at the same temperature for 2 hours. Saturated aqueous solution of ammonium chloride was added to the reaction mixture and the mixture was extracted by ethyl acetate. The organic layer was washed with saturated aqueous solution of sodium chloride, dried over anhydrous magnesium sulfate and concentrated under reduced pressure. The obtained residue was subjected to silica gel chromatography to obtain 0.76 g of 2-methyl-5,5,6,6,6-pentafluoro-2-(3,3,3-trifluoropropylsulfonyl)hexanamide (referred as the present compound (34), hereinafter).
The Present Compound (34)

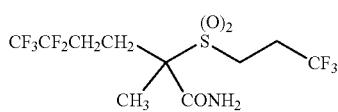

(34)

$^1$H-NMR (CDCl$_3$, TMS): δ (ppm) 6.62 (bs, 1H), 5.74 (bs, 1H), 3.20-3.41 (m, 2H), 2.64-2.78 (m, 2H), 2.08-2.54 (m, 4H), 1.68 (s, 3H)

Production Example 35

1.1 g of 2-methyl-5,5,6,6,6-pentafluoro-2-(3,3,3-trifluoropropylsulfonyl)hexanoic acid was dissolved to 20 ml of dichloromethane. 2 drops of N,N-dimethylformamide and 0.5 ml of oxalyl chloride was subsequently added dropwise thereto at room temperature, then the mixture was stirred for 2 hours at the same temperature. Then the reaction mixture was concentrated under reduced pressure. The obtained residue was dissolved to 20 ml of tetrahydrofuran and 0.7 g of methylamine (30% (w/w) aqueous solution) was added dropwise thereto at room temperature. The mixture was stirred at the same temperature for 2 hours. Saturated aqueous solution of ammonium chloride was added to the reaction mixture and the mixture was extracted by ethyl acetate. The organic layer was washed with saturated aqueous solution of sodium chloride, dried over anhydrous magnesium sulfate and concentrated under reduced pressure. The obtained residue was subjected to silica gel chromatography to obtain 0.70 g of N-methyl-2-methyl-5,5,6,6,6-pentafluoro-2-(3,3,3-trifluoropropylsulfonyl)hexanamide (referred as the present compound (35), hereinafter).
The Present Compound (35)

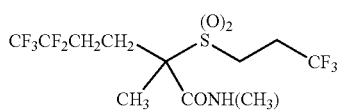

(35)

$^1$H-NMR (CDCl$_3$, TMS): δ (ppm) 6.56 (bs, 1H), 3.14-3.39 (m, 2H), 2.91 (d, 3H), 2.60-2.74 (m, 2H), 2.03-2.53 (m, 4H), 1.67 (s, 3H)

Production Example 36

0.5 g of 5,5,6,6,6-pentafluoro-2-(3,3,3-trifluoropropylsulfonyl)hexanoic acid was dissolved to 10 ml of dichloromethane. 2 drops of N,N-dimethylformamide and 0.2 ml of oxalyl chloride was subsequently added dropwise thereto at room temperature, then the mixture was stirred for 1 hour at the same temperature. Then the reaction mixture was concentrated under reduced pressure. The obtained residue was dissolved to 20 ml of tetrahydrofuran and 1.0 g of dimethylamine (40% (w/w) aqueous solution) was added dropwise thereto at room temperature. The mixture was stirred at the same temperature for 4 hours. Saturated aqueous solution of ammonium chloride was added to the reaction mixture and the mixture was extracted by ethyl acetate. The organic layer was washed with saturated aqueous solution of sodium chloride, dried over anhydrous magnesium sulfate and concentrated under reduced pressure. The obtained residue was subjected to silica gel chromatography to obtain 0.97 g of 5,5,6,6,6-pentafluoro-2-(3,3,3-trifluoropropylsulfonyl)-N,N-2-dimethyl-2-methylhexanamide (referred as the present compound (36), hereinafter).
The Present Compound (36)

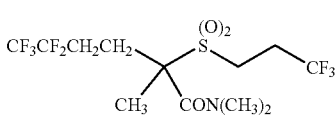

(36)

$^1$H-NMR (CDCl$_3$, TMS): δ (ppm) 3.37 (dd, 2H), 3.16 (bs, 6H), 1.98-2.88 (m, 6H), 1.82 (s, 3H)

Production Example 37

0.5 g of 2-methyl-5,5,6,6,6-pentafluoro-2-(3,3,3-trifluoropropylsulfonyl)hexanoic acid was dissolved to 20 ml of dichloromethane. 1 drop of N,N-dimethylformamide and 0.2 ml of oxalyl chloride were subsequently added dropwise thereto at room temperature, then the mixture was stirred for 2 hours at the same temperature. Then the reaction mixture was concentrated under reduced pressure. The obtained residue was dissolved to 20 ml of tetrahydrofuran and 0.2 g of ethylamine (70% (w/w) aqueous solution) was added dropwise thereto at room temperature. The mixture was stirred at the same temperature for 8 hours. Saturated aqueous solution of ammonium chloride was added to the reaction mixture and the mixture was extracted by ethyl acetate. The organic layer was washed with saturated aqueous solution of sodium chloride, dried over anhydrous magnesium sulfate and concentrated under reduced pressure. The obtained residue was subjected to silica gel chromatography to obtain 0.41 g of N-ethyl-2-methyl-5,5,6,6,6-pentafluoro-2-(3,3,3-trifluoropropylsulfonyl)hexanamide (referred as the present compound (37), hereinafter).
The Present Compound (37)

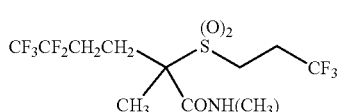

(37)

$^1$H-NMR (CDCl$_3$, TMS): δ (ppm) 6.57 (bs, 1H), 3.13-3.44 (m, 4H), 2.61-2.74 (m, 2H), 2.01-2.52 (m, 4H), 1.66 (s, 3H), 1.18 (t, 3H)

Production Example 38

0.5 g of 2-ethyl-5,5,6,6,6-pentafluoro-2-(3,3,3-trifluoropropylsulfonyl)hexanoic acid was dissolved to 20 ml of dichloromethane. 1 drop of N,N-dimethylformamide and 0.2 ml of oxalyl chloride was subsequently added dropwise thereto at room temperature, then the mixture was stirred for 2 hours at the same temperature. Then the reaction mixture was concentrated under reduced pressure. The obtained residue was dissolved to 20 ml of tetrahydrofuran and 0.2 g of ammonia (30% (w/w) aqueous solution) was added dropwise thereto at room temperature. The mixture was stirred at the same temperature for 1 hour. Saturated aqueous solution of ammonium chloride was added to the reaction mixture and the mixture was extracted by ethyl acetate. The organic layer was washed with saturated aqueous solution of sodium chloride, dried over anhydrous magnesium sulfate and concentrated under reduced pressure. The obtained residue was subjected to silica gel chromatography to obtain 0.37 g of 2-ethyl-5,5,6,6,6-pentafluoro-2-(3,3,3-trifluoropropylsulfonyl)hexanamide (referred as the present compound (38), hereinafter).

The Present Compound (38)

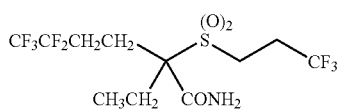

(38)

$^1$H-NMR (CDCl$_3$, TMS): δ (ppm) 6.59 (bs, 1H), 5.82 (bs, 1H), 3.19-3.48 (m, 2H), 2.62-2.76 (m, 2H), 2.11-2.52 (m, 6H), 1.10 (t, 3H)

Production Example 39

0.6 g of 1-iodo-4,4,4-trifluorobutane and 0.5 g of (3,3,3-trifluoropropylsulfonyl)acetonitrile were dissolved to 20 ml of N,N-dimethylformamide. 0.1 g of sodium hydride (60% in oil) was added thereto at room temperature, and the mixture was stirred for 10 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.57 g of 6,6,6-trifluoro-2-(3,3,3-trifluoropropylsulfonyl)hexanenitrile (referred as the present compound (39), hereinafter).

The Present Compound (39)

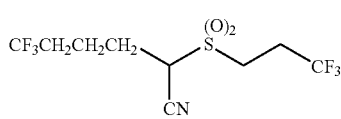

(39)

$^1$H-NMR (CDCl$_3$, TMS): δ (ppm) 3.90-3.97 (m, 1H), 3.41-3.59 (m, 2H), 2.68-2.88 (m, 2H), 1.78-2.36 (m, 6H)

Production Example 40

0.5 g of 2-methyl-5,5,6,6,6-pentafluoro-2-(3,3,3-trifluoropropylsulfonyl)hexanoic acid was dissolved to 20 ml of dichloromethane. 2 drops of N,N-dimethylformamide and 0.2 ml of oxalyl chloride were subsequently added dropwise thereto at room temperature, then the mixture was stirred for 2 hours at the same temperature. Then the reaction mixture was concentrated under reduced pressure. The obtained residue was dissolved to 20 ml of tetrahydrofuran and 0.2 g of propylamine was added dropwise to it. The mixture was stirred at the same temperature for 14 hours. Saturated aqueous solution of ammonium chloride was added to the reaction mixture and the mixture was extracted by ethyl acetate. The organic layer was washed with saturated aqueous solution of sodium chloride, dried over anhydrous magnesium sulfate and concentrated under reduced pressure. The obtained residue was subjected to silica gel chromatography to obtain 0.26 g of 2-methyl-N-propyl-5,5,6,6,6-pentafluoro-2-(3,3,3-trifluoropropylsulfonyl)hexanamide (referred as the present compound (40), hereinafter).

The Present Compound (40)

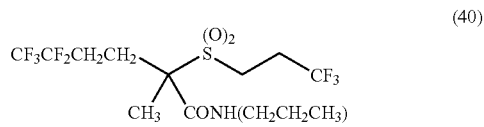

(40)

$^1$H-NMR (CDCl$_3$, TMS): δ (ppm) 6.62 (bs, 1H), 3.11-3.38 (m, 4H), 2.00-2.74 (m, 6H), 1.66 (s, 3H), 1.45-1.70 (m, 2H), 0.94 (t, 3H)

Production Example 41

0.5 g of 2-methyl-5,5,6,6,6-pentafluoro-2-(3,3,3-trifluoropropylsulfonyl)hexanoic acid was dissolved to 20 ml of dichloromethane. 2 drops of N,N-dimethylformamide and 0.2 ml of oxalyl chloride were subsequently added dropwise thereto at room temperature, then the mixture was stirred for 2 hours at the same temperature. Then the reaction mixture was concentrated under reduced pressure. The obtained residue was dissolved to 20 ml of tetrahydrofuran and 0.2 g of isopropylamine was added dropwise thereto at room temperature. The mixture was stirred at the same temperature for 14 hours. Saturated aqueous solution of ammonium chloride was added to the reaction mixture and the mixture was extracted by ethyl acetate. The organic layer was washed with saturated aqueous solution of sodium chloride, dried over anhydrous magnesium sulfate and concentrated under reduced pressure. The obtained residue was subjected to silica gel chromatography to obtain 0.25 g of N-isopropyl-2-methyl-5,5,6,6,6-pentafluoro-2-(3,3,3-trifluoropropylsulfonyl)hexanamide (referred as the present compound (41), hereinafter).

The Present Compound (41)

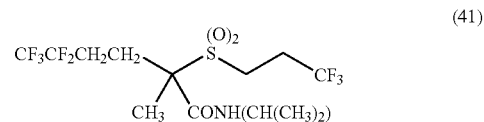

(41)

$^1$H-NMR (CDCl$_3$, TMS): δ (ppm) 6.40 (bs, 1H), 4.05-4.18 (m, 1H), 3.10-3.39 (m, 2H), 2.60-2.78 (m, 2H), 1.98-2.52 (m, 4H), 1.65 (s, 3H), 1.19 (dd, 6H)

Production Example 42

0.9 g of 1-iodo-3,3,4,4,4-pentafluorobutane and 1.1 g of methyl (3,3,4,4,5,5,5-heptafluoropentylsulfonyl)acetate were dissolved to 20 ml of N,N-dimethylformamide. 0.1 g of sodium hydride (60% in oil) was added thereto at room temperature, and the mixture was stirred for 3 days at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 1.12 g of methyl 2-(3,3,4,4,5,5,5-heptafluoropentylsulfonyl)-5,5,6,6,6-pentafluorohexanoate (referred as the present compound (42), hereinafter).

The Present Compound (42)

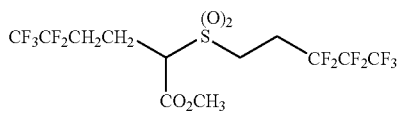

$^1$H-NMR (CDCl$_3$, TMS): δ (ppm) 3.91-3.95 (m, 1H), 3.91 (s, 3H), 3.41-3.53 (m, 2H), 2.62-2.77 (m, 2H), 2.38-2.54 (m, 2H), 2.19-2.34 (m, 2H)

Production Example 43

0.2 g of iodomethane and 0.6 g of methyl 2-(3,3,4,4,5,5,5-heptafluoropentylsulfonyl)-5,5,6,6,6-pentafluorohexanoate were dissolved to 20 ml of N,N-dimethylformamide. 0.1 g of sodium hydride (60% in oil) was added thereto at room temperature, and the mixture was stirred for 10 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.41 g of methyl 2-(3,3,4,4,5,5,5-heptafluoropentylsulfonyl)-2-methyl-5,5,6,6,6-pentafluorohexanoate (referred as the present compound (43), hereinafter).

The Present Compound (43)

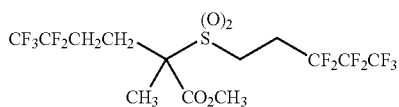

$^1$H-NMR (CDCl$_3$, TMS): δ (ppm) 3.89 (s, 3H), 3.47-3.56 (m, 2H), 2.61-2.78 (m, 2H), 1.95-2.56 (m, 4H), 1.71 (s, 3H)

Production Example 44

0.4 g of iodomethane and 1.0 g of methyl 6,6,6-trifluoro-2-(3,3,3-trifluoropropylsulfonyl)hexanoate were dissolved to 20 ml of N,N-dimethylformamide. 0.1 g of sodium hydride (60% in oil) was added thereto at room temperature, and the mixture was stirred for 10 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.85 g of methyl 2-methyl-6,6,6-trifluoro-2-(3,3,3-trifluoropropylsulfonyl)hexanoate (referred as the present compound (44), hereinafter).

The Present Compound (44)

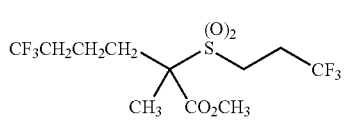

$^1$H-NMR (CDCl$_3$, TMS): δ (ppm) 3.86 (s, 3H), 3.31-3.55 (m, 2H), 2.62-2.75 (m, 2H), 1.95-2.33 (m, 4H), 1.67 (s, 3H), 1.43-1.80 (m, 2H)

Production Example 45

0.2 g of iodomethane and 0.5 g of 6,6,6-trifluoro-2-(3,3,3-trifluoropropylsulfonyl)hexanenitrile were dissolved to 20 ml of N,N-dimethylformamide. 0.06 g of sodium hydride (60% in oil) was added thereto at room temperature, and the mixture was stirred for 10 hours at the same temperature. Then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.37 g of 2-methyl-6,6,6-trifluoro-2-(3,3,3-trifluoropropylsulfonyl)hexanenitrile (referred as the present compound (45), hereinafter).

The Present Compound (45)

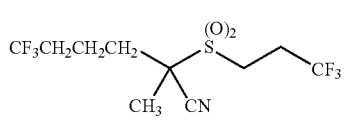

$^1$H-NMR (CDCl$_3$, TMS): δ (ppm) 3.40-3.55 (m, 2H), 2.73-2.88 (m, 2H), 1.85-2.34 (m, 6H), 1.80 (s, 3H)

Production Example 46

1.0 g of 1-iodo-3,3,4,4,4-pentafluorobutane and 1.0 g of ethyl 2-(3,3,3-trifluoropropylsulfonyl)propionate were dissolved to 20 ml of dimethylsulfoxide. 0.2 g of sodium hydride (60% in oil) was added thereto at room temperature, and the mixture was stirred for 10 hours at the same temperature, for 4 hours at 60° C. then for 4 hours at 90° C. After that, the reaction mixture was cooled to room temperature, then 10% hydrochloric acid was added to the reaction mixture and the mixture was extracted by ethyl acetate. The organic layer was washed with saturated aqueous solution of sodium chloride, dried over anhydrous magnesium sulfate, then concentrated under reduced pressure. The obtained residue was subjected to silica gel chromatography to obtain 0.47 g of ethyl 2-methyl-5,5,6,6,6-pentafluoro-2-(3,3,3-trifluoropropylsulfonyl)hexanoate (referred as the present compound (46), hereinafter).

The Present Compound (46)

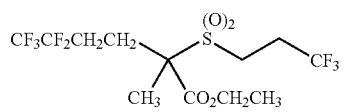

$^1$H-NMR (CDCl$_3$, TMS): δ (ppm) 4.33 (q, 2H), 3.46-3.53 (m, 2H), 2.63-2.78 (m, 2H), 2.08-2.54 (m, 4H), 1.69 (s, 3H), 1.34 (t, 3H)

Production Example 47

After dissolving 1.8 g of S-(3,3,3-trifluoropropyl)benzenethioate to 100 ml of tetrahydrofuran, this solution was added with 1.5 ml of sodium methoxide (28% (w/w) methanol solution) under ice cooling; and then being added dropwise with 2.0 g of 2-bromo-5,5,6,6,6-pentafluorohexanenitrile at the same temperature, followed by stirring at room temperature for 0.5 hours. The reaction mixture was added with 10% hydrochloric acid, followed by extraction with ethyl acetate. The organic layer was subsequently washed with 10% hydrochloric acid and saturated aqueous solution of sodium chloride, dried over anhydrous magnesium sulfate, and then concentrated under reduced pressure. The obtained residue was subjected to a silica gel chromatography to obtain 1.6 g of 5,5,6,6,6-pentafluoro-2-(3,3,3-trifluoropropylthio)hexanenitrile (referred as the present compound (47), hereinafter).

The Present Compound (47)

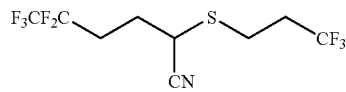

$^1$H-NMR (CDCl$_3$, TMS): δ (ppm) 3.67 (t, 1H), 2.89-3.04 (m, 2H), 2.10-2.58 (m, 6H)

Production Example 48

After dissolving 0.5 g of S-(3,3,3-trifluoropropyl)benzenethioate to 20 ml of tetrahydrofuran, this solution was added with 0.4 ml of sodium methoxide (28% (w/w) methanol solution) under ice cooling; and then being added dropwise with 0.6 g of 2-bromo-5,5,6,6,6-pentafluorohexanenitrile at the same temperature, followed by stirring at room temperature for 1 hour. The reaction mixture was added with 10% hydrochloric acid, followed by extraction with ethyl acetate. The organic layer was subsequently washed with 10% hydrochloric acid and saturated aqueous solution of sodium chloride, dried over anhydrous magnesium sulfate, and then concentrated under reduced pressure. The obtained residue was dissolved to 20 ml of chloroform, added with 0.5 g of peracetic acid (32% (w/w) acetic acid solution) under ice cooling, and then stirred at the same temperature for 4 hours. The reaction mixture was raised to room temperature, and poured into water, then the mixture was extracted by ethyl acetate. The organic layer was subsequently washed with saturated aqueous solution of sodium hydrogencarbonate and saturated aqueous solution of sodium chloride, dried over anhydrous magnesium sulfate, and then concentrated under reduced pressure. The obtained residue was subjected to silica gel chromatography to obtain 0.4 g of 5,5,6,6,6-pentafluoro-2-(3,3,3-trifluoropropylsulfinyl)hexanenitrile (referred as the present compound (48), hereinafter).

The Present Compound (48)

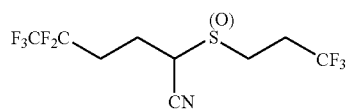

$^1$H-NMR (CDCl$_3$, TMS): δ (ppm) 3.62-3.69 (m, 1H), 2.98-3.38 (m, 2H), 2.25-2.82 (m, 6H)

Production Example 49

1.1 g of 2-methyl-5,5,6,6,6-pentafluoro-2-(3,3,3-trifluoropropylsulfonyl)hexanoic acid was dissolved to 20 ml of dichloromethane. This solution was subsequently added dropwise with 2 drops of N,N-dimethylformamide and 0.5 ml of oxalyl chloride at room temperature, and then stirred at the same temperature for 2 hours. The reaction mixture was concentrated under reduced pressure. The obtained residue was dissolved to 20 ml of tetrahydrofuran, followed by dropwise addition of 0.5 g of ammonia (30% (w/w) aqueous solution) at room temperature; and then being stirred at the same temperature for 10 hours. The reaction mixture was added with saturated aqueous solution of ammonium chloride, followed by extraction with ethyl acetate. The organic layer was concentrated under reduced pressure. The obtained residue was added with the mixture of 1.2 g of 2,4-bis(4-methoxyphenyl)-1,3-dithia-2,4-diphosphetane 2,4-disulfide and 20 ml of toluene, followed by heating under refluxing for 10 hours. The reaction mixture was dropped to a room temperature, followed by concentration under reduced pressure. The obtained residue was subjected to a silica gel chromatography to obtain 0.47 g of 2-methyl-5,5,6,6,6-pentafluoro-2-(3,3,3-trifluoropropylsulfonyl)hexanthioamide (referred as the present compound (49), hereinafter).

The Present Compound (49)

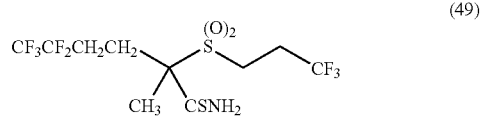

(49)

$^1$H-NMR (CDCl$_3$, TMS): δ (ppm) 8.03 (bs, 1H), 7.80 (bs, 1H), 3.19-3.44 (m, 2H), 2.08-2.78 (m, 6H), 1.85 (s, 3H)

Production Example 50

After dissolving 0.5 g of 5,5,6,6,6-pentafluoro-2-(3,3,3-trifluoropropylthio)hexanenitrile and 0.2 g of iodomethane with 20 ml of tetrahydrofuran, this solution was added with 1.6 ml of sodium bis(trimethylsilyl)amide (1 M tetrahydrofuran solution) at −78° C. This mixture was stirred at the same temperature for 0.5 hours. The reaction mixture was added with 10% hydrochloric acid, followed by extraction with ethyl acetate. The organic layer was subsequently washed with 10% hydrochloric acid and saturated aqueous solution of sodium chloride, dried over anhydrous magnesium sulfate, and then concentrated under reduced pressure. The obtained residue was subjected to a silica gel chromatography to obtain 0.4 g of 2-methyl-5,5,6,6,6-pentafluoro-2-(3,3,3-trifluoropropylthio)hexanenitrile (referred as the present compound (50), hereinafter).

The Present Compound (50)

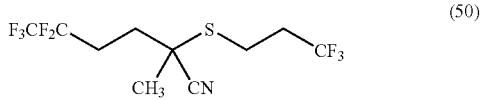

(50)

$^1$H-NMR (CDCl$_3$, TMS): δ (ppm) 2.98 (t, 2H), 2.08-2.58 (m, 6H), 1.71 (s, 3H)

Production Example 51

5.7 g of 1-iodo-3,3,4,4,5,5,5-heptafluoropentane and 5.0 g of methyl (3,3,4,4,4-pentafluorobutylsulfonyl)acetate were dissolved to 50 ml of N,N-dimethylformamide. This solution was added with 0.7 g of sodium hydride (60% in oil) at room temperature, followed by stirring at the same temperature for 3 days. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 1.80 g of methyl 5,5,6,6,7,7,7-heptafluoro-2-(3,3,4,4,4-pentafluorobutylsulfonyl)heptanoate (referred as the present compound (51), hereinafter).
The Present Compound (51)

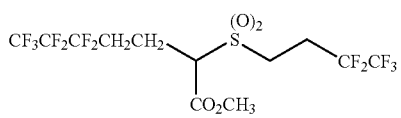

(51)

$^1$H-NMR (CDCl$_3$, TMS): δ (ppm) 3.91 (s, 3H), 3.90-3.97 (m, 1H), 3.41-3.54 (m, 2H), 2.20-2.73 (m, 6H)

Production Example 52

0.4 g of iodomethane and 1.3 g of methyl 5,5,6,6,7,7,7-heptafluoro-2-(3,3,4,4,4-pentafluorobutylsulfonyl)heptanoate were dissolved to 50 ml of N,N-dimethylformamide. This solution was added with 0.1 g of sodium hydride (60% in oil) at room temperature, followed by stirring at the same temperature for 3 hours. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 1.30 g of methyl 5,5,6,6,7,7,7-heptafluoro-2-methyl-2-(3,3,4,4,4-pentafluorobutylsulfonyl)heptanoate (referred as the present compound (52), hereinafter).
The Present Compound (52)

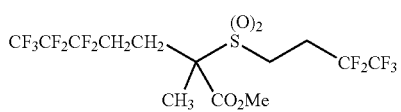

(52)

$^1$H-NMR (CDCl$_3$, TMS): δ (ppm) 3.88 (s, 3H), 3.47-3.54 (m, 2H), 2.08-2.73 (m, 6H), 1.71 (s, 3H)

Production Example 53

0.4 g of 1-iodo-3,3,3-trifluoropropane and 0.5 g of (3,3,4,4,4-pentafluorobutylsulfonyl)acetonitrile were dissolved to 20 ml of N,N-dimethylformamide. This solution was added with 0.08 g of sodium hydride (60% in oil) at room temperature, followed by stirring at the same temperature for 20 hours. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 0.26 g of 2-(3,3,4,4,4-pentafluorobutylsulfonyl)-5,5,5-trifluoropentanenitrile (referred as the present compound (53), hereinafter).
The Present Compound (53)

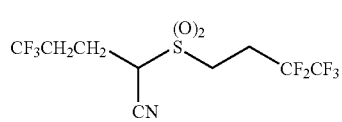

(53)

$^1$H-NMR (CDCl$_3$, TMS): δ (ppm) 4.04-4.08 (m, 1H), 3.47-3.66 (m, 2H), 2.35-2.81 (m, 6H)

Production Example 54

0.6 g of 1-iodo-3,3,4,4,5,5,5-heptafluoropentane and 0.5 g of (3,3,4,4,4-pentafluorobutylsulfonyl)acetonitrile were dissolved to 20 ml of N,N-dimethylformamide. This solution was added with 0.08 g of sodium hydride (60% in oil) at room temperature, followed by stirring at the same temperature for 24 hours. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 0.30 g of 5,5,6,6,7,7,7-heptafluoro-2-(3,3,4,4,4-pentafluorobutylsulfonyl)heptanenitrile (referred as the present compound (54), hereinafter).
The Present Compound (54)

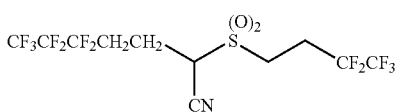

(54)

$^1$H-NMR (CDCl$_3$, TMS): δ (ppm) 4.16-4.22 (m, 1H), 3.50-3.68 (m, 2H), 2.33-2.88 (m, 6H)

Production Example 55

0.5 g of 5,5,6,6,7,7,7-heptafluoro-2-(3,3,4,4,4-pentafluorobutylsulfonyl)heptanoic acid was dissolved to 20 ml of dichloromethane. This solution was subsequently added dropwise with 2 drops of N,N-dimethylformamide and 0.1 ml of oxalyl chloride at room temperature, and then stirred at the same temperature for 2 hours. The reaction mixture was concentrated under reduced pressure. The obtained residue was dissolved to 20 ml of tetrahydrofuran, followed by dropwise addition of 0.2 g of ammonia (30% (w/w) aqueous solution) at room temperature; and then being stirred at the same temperature for 2 hours. The reaction mixture was added with saturated aqueous solution of ammonium chloride, followed by extraction with ethyl acetate. The organic layer was concentrated under reduced pressure. The obtained residue was subjected to a silica gel chromatography to obtain 0.31 g of 5,5,6,6,7,7,7-heptafluoro-2-(3,3,4,4,4-pentafluorobutylsulfonyl)heptaneamide (referred as the present compound (55), hereinafter).

The Present Compound (55)

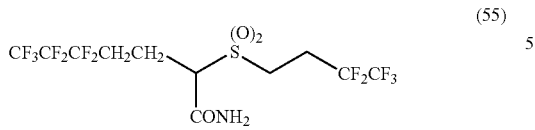

$^1$H-NMR (CDCl$_3$, TMS): δ (ppm) 6.31 (bs, 1H), 5.73 (bs, 1H), 3.72-3.78 (m, 1H), 3.24-3.45 (m, 2H), 2.12-2.74 (m, 6H Production Example 56

1.1 g of 5,5,6,6,7,7,7-heptafluoro-2-methyl-2-(3,3,4,4,4-pentafluorobutylsulfonyl)heptanoic acid was dissolved to 20 ml of dichloromethane. This solution was subsequently added dropwise with 2 drops of N,N-dimethylformamide and 0.4 ml of oxalyl chloride at room temperature, and then stirred at the same temperature for 2 hours. The reaction mixture was concentrated under reduced pressure. The obtained residue was dissolved to 50 ml of tetrahydrofuran, followed by dropwise addition of 0.4 g of ammonia (30% (w/w) aqueous solution) at room temperature; and then being stirred at the same temperature for 2 hours. The reaction mixture was added with saturated aqueous solution of ammonium chloride, followed by extraction with ethyl acetate. The organic layer was concentrated under reduced pressure. The obtained residue was subjected to a silica gel chromatography to obtain 0.60 g of 5,5,6,6,7,7,7-heptafluoro-2-methyl-2-(3,3,4,4,4-pentafluorobutylsulfonyl)heptaneamide (referred as the present compound (56), hereinafter).

The Present Compound (56)

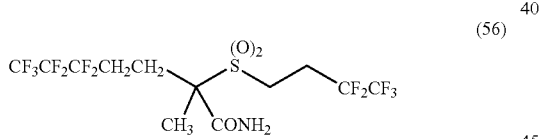

$^1$H-NMR (CDCl$_3$, TMS): δ (ppm) 6.63 (bs, 1H), 5.76 (bs, 1H), 3.20-3.45 (m, 2H), 2.08-2.73 (m, 6H), 1.70 (s, 3H)

Production Example 57

After dissolving 0.6 g of 2-methyl-5,5,6,6,6-pentafluoro-2-(3,3,3-trifluoropropylthio)hexanenitrile with 30 ml of chloroform, this solution was added with 0.4 g of peracetic acid (32% (w/w) acetic acid solution) under ice cooling, stirred at the same temperature for 2 hours, and then further stirred at room temperature for 10 hours. The reaction mixture was poured into water, followed by extraction with ethyl acetate. The organic layer was subsequently washed with saturated aqueous solution of sodium hydrogencarbonate and saturated aqueous solution of sodium chloride, dried over anhydrous magnesium sulfate, and then concentrated under reduced pressure. The obtained residue was subjected to a silica gel chromatography to obtain 0.25 g of 2-methyl-5,5,6,6,6-pentafluoro-2-(3,3,3-trifluoropropylsulfinyl)hexanenitrile (referred as the present compound (57), hereinafter).

The Present Compound (57)

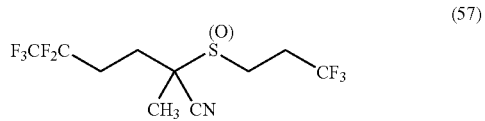

$^1$H-NMR (CDCl$_3$, TMS): δ (ppm) 2.98-3.21 (m, 2H), 2.60-2.82 (m, 2H), 2.04-2.54 (m, 4H), 1.68 (s, 2H), 1.59 (s, 1H)

Production Example 58

0.8 g of methyl 5,5,6,6,6-pentafluoro-2-(3,3,3-trifluoropropylsulfonyl)hexanoate was dissolved to 50 ml of tetrahydrofuran. This solution was added with 0.08 g of sodium hydride (60% in oil) at room temperature, followed by stirring at the same temperature for 0.5 hours; and then being added with 0.3 g of N-chlorosuccinimide at the same temperature, followed by stirring for 4 hours. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 0.60 g of methyl 2-chloro-5,5,6,6,6-pentafluoro-2-(3,3,3-trifluoropropylsulfonyl)hexanoate (referred as the present compound (58), hereinafter).

The Present Compound (58)

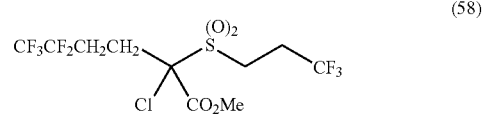

$^1$H-NMR (CDCl$_3$, TMS): δ (ppm) 3.97 (s, 3H), 3.52-3.92 (m, 2H), 2.18-2.91 (m, 6H)

Production Example 59

0.5 g of methyl 2-chloro-5,5,6,6,6-pentafluoro-2-(3,3,3-trifluoropropylsulfonyl)hexanoate was dissolved to 50 ml of methanol. This solution was added with 0.5 ml of ammonia (7 M methanol solution) at room temperature, followed by stirring at the same temperature for 2 hours. The reaction mixture was concentrated under reduced pressure. The obtained residue was subjected to a silica gel chromatography to obtain 0.15 g of 2-chloro-5,5,6,6,6-pentafluoro-2-(3,3,3-trifluoropropylsulfonyl)hexanamide (referred as the present compound (59), hereinafter).

The Present Compound (59)

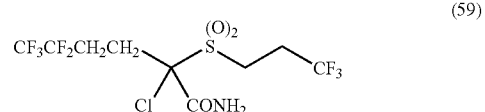

$^1$H-NMR (CDCl$_3$, TMS): δ (ppm) 6.88 (bs, 1H), 6.02 (bs, 1H), 3.38-3.74 (m, 2H), 2.13-2.95 (m, 6H)

Production Example 60

0.5 g of 5,5,6,6,6-pentafluoro-2-(3,3,4,4,4-pentafluorobutylsulfonyl)hexanoic acid was dissolved to 20 ml of dichloromethane. This solution was subsequently added dropwise with 2 drops of N,N-dimethylformamide and 0.2 ml of oxalyl chloride at room temperature, followed by stirring at the same temperature for 4 hours. The reaction mixture was concentrated under reduced pressure. The obtained residue was dissolved to 20 ml of tetrahydrofuran, followed by dropwise addition of 0.2 g of ammonia (30% (w/w) aqueous solution) at room temperature; and then being stirred at the same temperature for 2 days. The reaction mixture was added with saturated aqueous solution of ammonium chloride, followed by extraction with ethyl acetate. The organic layer was concentrated under reduced pressure. The obtained residue was subjected to a silica gel chromatography to obtain 0.20 g of 5,5,6,6,6-pentafluoro-2-(3,3,4,4,4-pentafluorobutylsulfonyl)hexanamide (referred as the present compound (60), hereinafter).
The Present Compound (60)

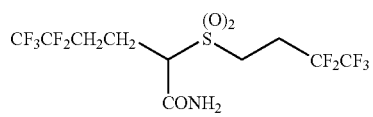

(60)

$^1$H-NMR (CDCl$_3$, TMS): δ (ppm) 6.41 (bs, 1H), 5.73 (bs, 1H), 3.74-3.79 (m, 1H), 3.20-3.45 (m, 2H), 2.08-2.74 (m, 6H)

Production Example 61

0.8 g of 2-methyl-5,5,6,6,6-pentafluoro-2-(3,3,4,4,4-pentafluorobutylsulfonyl)hexanoic acid was dissolved to 20 ml of dichloromethane. This solution was subsequently added dropwise with 2 drops of N,N-dimethylformamide and 0.3 ml of oxalyl chloride at room temperature, followed by stirring at the same temperature for 4 hours. The reaction mixture was concentrated under reduced pressure. The obtained residue was dissolved to 20 ml of tetrahydrofuran, followed by dropwise addition of 0.3 g of ammonia (30% (w/w) aqueous solution) at room temperature; and then being stirred at the same temperature for 2 days. The reaction mixture was added with saturated aqueous solution of ammonium chloride, followed by extraction with ethyl acetate. The organic layer was concentrated under reduced pressure. The obtained residue was subjected to a silica gel chromatography to obtain 0.60 g of 2-methyl-5,5,6,6,6-pentafluoro-2-(3,3,4,4,4-pentafluorobutylsulfonyl)hexanamide (referred as the present compound (61), hereinafter).
The Present Compound (61)

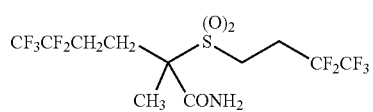

(61)

$^1$H-NMR (CDCl$_3$, TMS): δ (ppm) 6.69 (bs, 1H), 6.01 (bs, 1H), 3.22-3.46 (m, 2H), 2.08-2.73 (m, 6H), 1.69 (s, 3H)

Production Example 62

After dissolving 2.0 g of 5,5,6,6,6-pentafluoro-2-(3,3,3-trifluoropropylthio)hexanenitrile with 50 ml of methanol, this solution was added with 12.5 ml of sodium methoxide (28% (w/w) methanol solution) at room temperature, followed by stirring at the same temperature for 15 hours. This reaction mixture was added with 10% hydrochloric acid, followed by extraction with ethyl acetate. The organic layer was subsequently washed with 10% hydrochloric acid and saturated aqueous solution of sodium chloride, dried over anhydrous magnesium sulfate, and then concentrated under reduced pressure. The obtained residue was subjected to a silica gel chromatography to obtain 0.8 g of methyl 5,5,6,6,6-pentafluoro-2-(3,3,3-trifluoropropylthio)hexanoate (referred as the present compound (62), hereinafter).
The Present Compound (62)

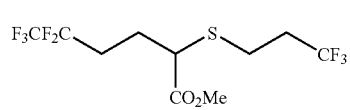

(62)

$^1$H-NMR (CDCl$_3$, TMS): δ (ppm) 3.79 (s, 3H), 3.31 (t, 1H), 2.72-2.90 (m, 2H), 1.93-2.48 (m, 6H)

Production Example 63

After dissolving 0.3 g of methyl 5,5,6,6,6-pentafluoro-2-(3,3,3-trifluoropropylthio)hexanoate with 20 ml of chloroform, this solution was added with 0.2 g of peracetic acid (32% (w/w) acetic acid solution) under ice cooling, followed by stirring at room temperature for 6 hours. The reaction mixture was poured into water, followed by extraction with ethyl acetate. The organic layer was subsequently washed with saturated aqueous solution of sodium hydrogencarbonate and saturated aqueous solution of sodium chloride, dried over anhydrous magnesium sulfate, and then concentrated under reduced pressure. The obtained residue was subjected to a silica gel chromatography to obtain 0.18 g of methyl 5,5,6,6,6-pentafluoro-2-(3,3,3-trifluoropropylsulfinyl)hexanoate (referred as the present compound (63), hereinafter).
The Present Compound (63)

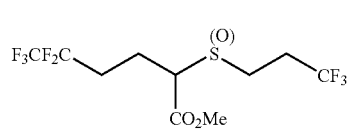

(63)

$^1$H-NMR (CDCl$_3$, TMS): δ (ppm) 3.86 (s, 1.2H), 3.84 (s, 1.8H), 3.57-3.69 (m, 1H), 2.13-3.14 (m, 8H)

Production Example 64

0.5 g of methyl 2,5,5,6,6,6-hexafluoro-2-(3,3,3-trifluoropropylsulfonyl)hexanoate was dissolved to 20 ml of methanol. This solution was added with 0.5 ml of ammonia (7 M methanol solution) at room temperature, followed by stirring at the same temperature for 0.5 hours; and then being further added with 5 ml of ammonia (7 M methanol solution), followed by stirring at the same temperature for 2 hours. The reaction mixture was concentrated under reduced pressure. The obtained residue was subjected to a silica gel chromatography to obtain 0.37 g of 2,5,5,6,6,6-hexafluoro-2-(3,3,3-trifluoropropylsulfonyl)hexanamide (referred as the present compound (64), hereinafter).

The Present Compound (64)

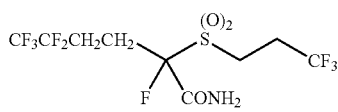
(64)

¹H-NMR (CDCl₃, TMS): δ (ppm) 6.54 (bs, 1H), 5.88 (bs, 1H), 3.30-3.58 (m, 2H), 2.14-2.83 (m, 6H)

Production Example 65

2.0 g of methyl 5,5,6,6,6-pentafluoro-2-(3,3,3-trifluoropropylsulfonyl)hexanoate was dissolved to 50 ml of tetrahydrofuran. This solution was added with 0.21 g of sodium hydride (60% in oil) under ice cooling, followed by stirring at the same temperature for 0.5 hours; and then being added with 0.9 g of N-bromosuccinimide, followed by stirring at room temperature for 12 hours. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 0.30 g of methyl 2-bromo-5,5,6,6,6-pentafluoro-2-(3,3,3-trifluoropropylsulfonyl)hexanoate (referred as the present compound (65), hereinafter).

The Present Compound (65)

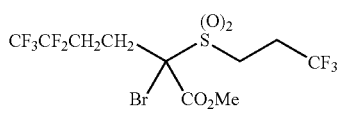
(65)

¹H-NMR (CDCl₃, TMS): δ (ppm) 3.96 (s, 3H), 3.75-4.01 (m, 2H), 2.35-2.92 (m, 6H)

Production Example 66

1.0 g of methyl 2-(3,3,4,4,5,5,5-heptafluoropentylsulfonyl)-5,5,6,6,6-pentafluorohexanoate was dissolved to 50 ml of tetrahydrofuran. This solution was added with 0.08 g of sodium hydride (60% in oil) at 0° C., followed by stirring at the same temperature for 0.5 hours; and subsequently being added with 0.6 g of 1-fluoro-2,4,6-trimethylpyridinium trifluoromethanesulfonate at the same temperature, followed by stirring for 1 hour. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 0.75 g of methyl 2-(3,3,4,4,5,5,5-heptafluoropentylsulfonyl)-2,5,5,6,6,6-hexafluorohexanoate (referred as the present compound (66), hereinafter).

The Present Compound (66)

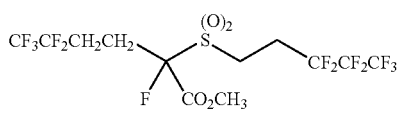
(66)

¹H-NMR (CDCl₃, TMS): δ (ppm) 4.00 (s, 3H), 3.34-3.61 (m, 2H), 2.09-2.81 (m, 6H)

Production Example 67

1.5 g of methyl 2-(3,3,4,4,5,5,5-heptafluoropentylsulfonyl)-2,5,5,6,6,6-hexafluorohexanoate was dissolved to 30 ml of methanol. This solution was added with 1.3 ml of ammonia (7 M methanol solution) at room temperature, followed by stirring at the same temperature for 24 hours. The reaction mixture was concentrated under reduced pressure. The obtained residue was subjected to a silica gel chromatography to obtain 1.10 g of 2-(3,3,4,4,5,5,5-heptafluoropentylsulfonyl)-2,5,5,6,6,6-hexafluorohexanamide (referred as the present compound (67), hereinafter).

The Present Compound (67)

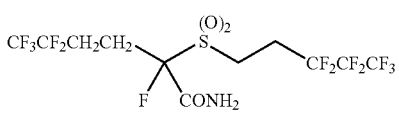
(67)

¹H-NMR (CDCl₃, TMS): δ (ppm) 6.54 (bs, 1H), 5.89 (bs, 1H), 3.34-3.62 (m, 2H), 2.10-2.82 (m, 6H)

Production Example 68

After dissolving 0.3 g of methyl 5,5,6,6,6-pentafluoro-2-(3,3,3-trifluoropropylthio)hexanoate and 0.12 g of iodomethane with 20 ml of tetrahydrofuran, this mixture was added with 0.9 ml of sodium bis(trimethylsilyl)amide (1 M tetrahydrofuran solution) at 0° C. The mixture was stirred at the same temperature for 1 hour. The reaction mixture was added with 10% hydrochloric acid, followed by extraction with ethyl acetate. The organic layer was subsequently washed with 10% hydrochloric acid and saturated aqueous solution of sodium chloride, dried over anhydrous magnesium sulfate, and then concentrated under reduced pressure. The obtained residue was subjected to a silica gel chromatography to obtain 0.3 g of methyl 2-methyl-5,5,6,6,6-pentafluoro-2-(3,3,3-trifluoropropylthio)hexanoate (referred as the present compound (68), hereinafter).

The Present Compound (68)

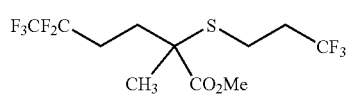
(68)

¹H-NMR (CDCl₃, TMS): δ (ppm) 3.78 (s, 3H), 2.73-2.79 (m, 2H), 1.96-2.41 (m, 6H), 1.50 (s, 3H)

Production Example 69

1.0 g of methyl 2,5,5,6,6,6-hexafluoro-2-(3,3,3-trifluoropropylsulfonyl)hexanoate was dissolved to 30 ml of methanol. This solution was added with 3.8 ml of methylamine (2 M methanol solution) at room temperature, followed by stirring at the same temperature for 2 hours. The reaction mixture was concentrated under reduced pressure. The obtained residue was subjected to a silica gel chromatography to obtain 0.92 g of 2,5,5,6,6,6-hexafluoro-N-methyl-2-(3,3,3-trifluoropropylsulfonyl)hexanamide (referred as the present compound (69), hereinafter).

The Present Compound (69)

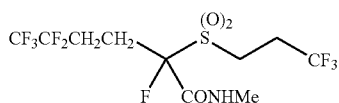

$^1$H-NMR (CDCl$_3$, TMS): δ (ppm) 6.58 (bs, 1H), 3.26-3.58 (m, 2H), 2.99 (d, 3H), 2.04-2.82 (m, 6H)

Production Example 70

After dissolving 1.0 g of methyl 2-methyl-5,5,6,6,6-pentafluoro-2-(3,3,3-trifluoropropylthio)hexanoate with 50 ml of methanol, this solution was added with an aqueous solution of potassium hydroxide (a mixed solution of 0.9 g of potassium hydroxide and 5 ml of water) at room temperature, and then stirred at the same temperature for 1 day. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was dissolved to 20 ml of dichloromethane; and then being subsequently added dropwise with 2 drops of N,N-dimethylformamide and 0.4 ml of oxalyl chloride at room temperature, and then stirred at the same temperature for 1 hour. The reaction mixture was concentrated under reduced pressure. The obtained residue was dissolved to 20 ml of tetrahydrofuran, and then added dropwise with 0.4 g of ammonia (30% (w/w) aqueous solution) at room temperature; and then being stirred at the same temperature for 1 hour. The reaction mixture was added with saturated aqueous solution of ammonium chloride, followed by extraction with ethyl acetate. The organic layer was concentrated under reduced pressure. The obtained residue was subjected to a silica gel chromatography to obtain 0.25 g of 2-methyl-5,5,6,6,6-pentafluoro-2-(3,3,3-trifluoropropylthio)hexanamide (referred as the present compound (70), hereinafter).
The Present Compound (70)

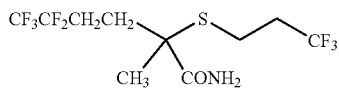

$^1$H-NMR (CDCl$_3$, TMS): δ (ppm) 6.60 (bs, 1H), 5.49 (bs, 1H), 2.73 (t, 2H), 1.96-2.44 (m, 6H), 1.51 (s, 3H)

Production Example 71

After dissolving 4.4 g of methyl 2-methyl-5,5,6,6,6-pentafluoro-2-(3,3,3-trifluoropropylthio)hexanoate with 30 ml of chloroform, this solution was added with 2.9 g of peracetic acid (32% (w/w) acetic acid solution) under ice cooling, and then being stirred at the same temperature for 4 hours. The reaction mixture was poured into water, followed by extraction with ethyl acetate. The organic layer was subsequently washed with saturated aqueous solution of sodium hydrogencarbonate and saturated aqueous solution of sodium chloride, dried over anhydrous magnesium sulfate, and then concentrated under reduced pressure. The obtained residue was subjected to a silica gel chromatography to obtain 1.10 g of methyl 2-methyl-5,5,6,6,6-pentafluoro-2-(3,3,3-trifluoropropylsulfinyl)hexanoate (referred as the present compound (71), hereinafter).
The Present Compound (71)

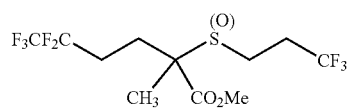

$^1$H-NMR (CDCl$_3$, TMS): δ (ppm) 3.84 (s, 1.2H), 3.82 (s, 1.8H), 2.06-2.84 (m, 8H), 1.53 (s, 1.2H), 1.52 (s, 1.8H)

Production Example 72

1.0 g of methyl 2-(3,3,4,4,4-pentafluorobutylsulfonyl)-5,5,6,6,6-pentafluorohexanoate was dissolved to 50 ml of tetrahydrofuran. This solution was added with 0.09 g of sodium hydride (60% in oil) at room temperature, and then stirred at the same temperature for 0.5 hours; and subsequently being added with 0.7 g of 1-fluoro-2,4,6-trimethylpyridinium trifluoromethanesulfonate at the same temperature, followed by stirring for 3 hours. The reaction mixture was added with 10% hydrochloric acid, followed by extraction with ethyl acetate.
The organic layer was washed with saturated aqueous solution of sodium chloride, dried over anhydrous magnesium sulfate, and then concentrated under reduced pressure. The obtained residue was subjected to a silica gel chromatography to obtain 0.78 g of methyl 2,5,5,6,6,6-hexafluoro-2-(3,3,4,4,4-pentafluorobutylsulfonyl)hexanoate (referred as the present compound (72), hereinafter).
The Present Compound (72)

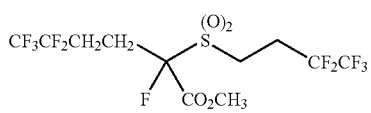

$^1$H-NMR (CDCl$_3$, TMS): δ (ppm) 4.00 (s, 3H), 3.33-3.60 (m, 2H), 2.08-2.81 (m, 6H)

Production Example 73

0.6 g of methyl 2,5,5,6,6,6-hexafluoro-2-(3,3,4,4,4-pentafluorobutylsulfonyl)hexanoate was dissolved to 20 ml of methanol. This solution was added with 0.6 ml of ammonia (7 M methanol solution) at room temperature, and then stirred at the same temperature for 12 hours. The reaction mixture was concentrated under reduced pressure. The obtained residue was subjected to a silica gel chromatography to obtain 0.45 g of 2,5,5,6,66-hexafluoro-2-(3,3,4,4,4-pentafluorobutylsulfonyl)hexanamide (referred as the present compound (73), hereinafter).
The Present Compound (73)

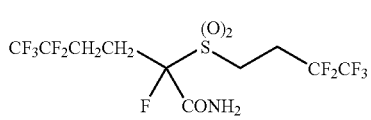

$^1$H-NMR (CDCl$_3$, TMS): δ (ppm) 6.55 (bs, 1H), 5.91 (bs, 1H), 3.33-3.61 (m, 2H), 2.04-2.83 (m, 6H)

Production Example 74

After dissolving 0.5 g of methyl 2,5,5,6,6,6-hexafluoro-2-(3,3,3-trifluoropropylsulfonyl)hexanoate with 30 ml of methanol, this solution was added with an aqueous solution of potassium hydroxide (a mixed solution of 0.4 g of potassium hydroxide and 5 ml of water) at room temperature, followed by stirring at the same temperature for 12 hours. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The residue was dissolved to 20 ml of dichloromethane; and then being subsequently added dropwise with 2 drops of N,N-dimethylformamide and 0.2 ml of oxalyl chloride at room temperature, followed by stirring at the same temperature for 2 hours. The reaction mixture was concentrated under reduced pressure. The obtained residue was dissolved to 30 ml of tetrahydrofuran, and then added dropwise with 0.4 g of dimethylamine (40% (w/w) aqueous solution) at room temperature; and then being stirred at the same temperature for 2 hours. The reaction mixture was added with saturated aqueous solution of ammonium chloride, followed by extraction with ethyl acetate. The organic layer was concentrated under reduced pressure. The obtained residue was subjected to a silica gel chromatography to obtain 0.26 g of N,N-dimethyl-2,5,5,6,6,6-hexafluoro-2-(3,3,3-trifluoropropylsulfonyl)hexanamide (referred as the present compound (74), hereinafter).

The Present Compound (74)

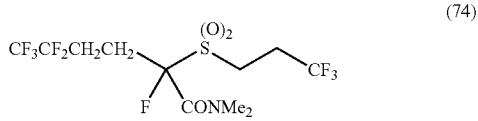

$^1$H-NMR (CDCl$_3$, TMS): δ (ppm) 3.32-3.55 (m, 2H), 3.29 (d, 3H), 3.10 (s, 3H), 2.14-2.97 (m, 6H)

Production Example 75

1.0 g of methyl 2-chloro-5,5,6,6,6-pentafluoro-2-(3,3,3-trifluoropropylsulfonyl)hexanoate was dissolved to 30 ml of methanol. This solution was added with 3.6 ml of methylamine (2 M methanol solution) at room temperature, and then stirred at the same temperature for 16 hours. The reaction mixture was concentrated under reduced pressure. The obtained residue was subjected to a silica gel chromatography to obtain 0.15 g of 2-chloro-N-methyl-5,5,6,6,6-pentafluoro-2-(3,3,3-trifluoropropylsulfonyl)hexanamide (referred as the present compound (75), hereinafter).

The Present Compound (75)

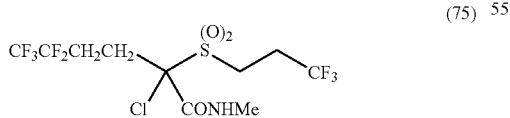

$^1$H-NMR (CDCl$_3$, TMS): δ (ppm) 6.95 (bs, 1H), 3.35-3.75 (m, 2H), 2.96 (d, 3H), 2.05-2.98 (m, 6H)

Production Example 76

1.0 g of 1-iodo-3,3,3-trifluoropropane and 1.0 g of methyl (3,3,3-trifluoropropylsulfonyl)acetate were dissolved to 20 ml of dimethylsulfoxide. This solution was added with 0.6 g of potassium carbonate at room temperature, and then stirred at the same temperature for 16 hours. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 0.42 g of methyl 5,5,5-trifluoro-2-(3,3,3-trifluoropropylsulfonyl)pentanoate (referred as the present compound (76), hereinafter).

The Present Compound (76)

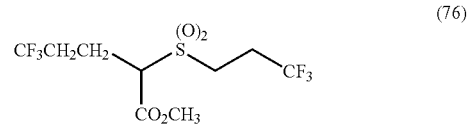

$^1$H-NMR (CDCl$_3$, TMS): δ (ppm) 3.90 (s, 3H), 3.88-3.94 (m, 1H), 3.36-3.52 (m, 2H), 2.62-2.78 (m, 2H), 2.38-2.53 (m, 2H), 2.24-2.48 (m, 2H)

Production Example 77

1.0 g of methyl 5,5,5-trifluoro-2-(3,3,3-trifluoropropylsulfonyl)pentanoate was dissolved to 30 ml of tetrahydrofuran. This solution was added with 0.12 g of sodium hydride (60% in oil) at room temperature, followed by stirring at the same temperature for 0.5 hours; and then being added with 0.4 g of N-chlorosuccinimide at the same temperature, followed by stirring for 2 hours. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 0.65 g of methyl 2-chloro-5,5,5-trifluoro-2-(3,3,3-trifluoropropylsulfonyl)pentanate (referred as the present compound (77), hereinafter).

The Present Compound (77)

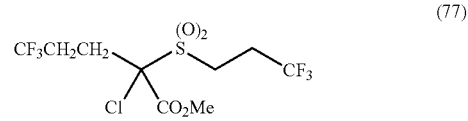

$^1$H-NMR (CDCl$_3$, TMS): δ (ppm) 3.97 (s, 3H), 3.58-3.88 (m, 2H), 2.35-2.88 (m, 6H)

Production Example 78

2.0 g of 1-iodo-4,4,4-trifluorobutane and 2.0 g of methyl (3,3,3-trifluoropropylsulfonyl)acetate were dissolved to 30 ml of dimethylsulfoxide. This solution was added with 1.2 g of potassium carbonate at room temperature, followed by stirring at the same temperature for 3 days. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 1.50 g of methyl 6,6,6-trifluoro-2-(3,3,3-trifluoropropylsulfonyl)hexanate (referred as the present compound (78), hereinafter).
The Present Compound (78)

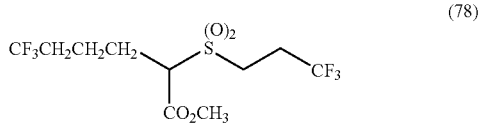

(78)

¹H-NMR (CDCl₃, TMS): δ (ppm) 3.89 (s, 3H), 3.80-3.90 (m, 1H), 3.28-3.50 (m, 2H), 2.60-2.78 (m, 2H), 2.09-2.27 (m, 4H), 1.62-1.75 (m, 2H)

Production Example 79

1.0 g of methyl 6,6,6-trifluoro-2-(3,3,3-trifluoropropylsulfonyl)hexanoate was dissolved to 30 ml of tetrahydrofuran. This solution was added with 0.12 g of sodium hydride (60% in oil) at room temperature, followed by stirring at the same temperature for 0.5 hours; and then being added with 0.4 g of N-chlorosuccinimide at the same temperature, followed by stirring for 4 hours. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 0.96 g of methyl 2-chloro-6,6,6-trifluoro-2-(3,3,3-trifluoropropylsulfonyl)hexanoate (referred as the present compound (79), hereinafter).
The Present Compound (79)

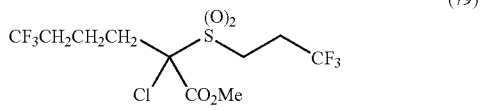

(79)

¹H-NMR (CDCl₃, TMS): δ (ppm) 3.96 (s, 3H), 3.53-3.84 (m, 2H), 2.12-2.79 (m, 6H), 1.72-2.02 (m, 2H)

Production Example 80

0.8 g of methyl 2-chloro-6,6,6-trifluoro-2-(3,3,3-trifluoropropylsulfonyl)hexanoate was dissolved to 20 ml of methanol. This solution was added with 0.9 ml of ammonia (7 M methanol solution) at room temperature, followed by stirring at the same temperature for 10 hours. The reaction mixture was concentrated under reduced pressure. The obtained residue was subjected to a silica gel chromatography to obtain 0.51 g of 2-chloro-6,6,6-trifluoro-2-(3,3,3-trifluoropropylsulfonyl)hexanamide (referred as the present compound (80), hereinafter).
The Present Compound (80)

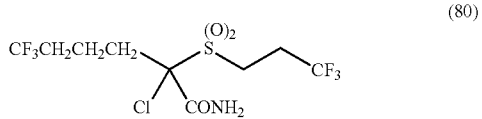

(80)

¹H-NMR (CDCl₃, TMS): δ (ppm) 6.93 (bs, 1H), 6.20 (bs, 1H), 3.36-3.74 (m, 2H), 2.13-2.81 (m, 6H), 1.61-2.01 (m, 2H)

Production Example 81

1.0 g of methyl 2-chloro-5,5,5-trifluoro-2-(3,3,3-trifluoropropylsulfonyl)pentanoate was dissolved to 30 ml of methanol. This solution was added with 1.2 ml of ammonia (7 M methanol solution) at room temperature, followed by stirring at the same temperature for 14 hours. The reaction mixture was concentrated under reduced pressure. The obtained residue was subjected to a silica gel chromatography to obtain 0.62 g of 2-chloro-5,5,5-trifluoro-2-(3,3,3-trifluoropropylsulfonyl)pentanamide (referred as the present compound (81), hereinafter).
The Present Compound (81)

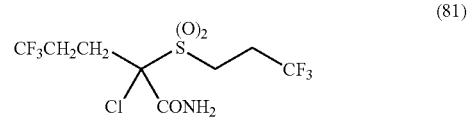

(81)

¹H-NMR (CDCl₃, TMS): δ (ppm) 6.93 (bs, 1H), 6.36 (bs, 1H), 3.38-3.73 (m, 2H), 2.21-2.92 (m, 6H)

Production Example 32

2.8 g of 1-iodo-3,3,4,4,5,5,5-heptafluoropentane and 2.0 g of methyl (3,3,3-trifluoropropylsulfonyl)acetate were dissolved to 30 ml of dimethylsulfoxide. This solution was added with 0.34 g of sodium hydride (60% in oil) at room temperature, and then stirred at the same temperature for 14 hours. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 2.30 g of methyl 5,5,6,6,7,7,7-heptafluoro-2-(3,3,3-trifluoropropylsulfonyl)heptanoate (referred as the present compound (82), hereinafter).
The Present Compound (82)

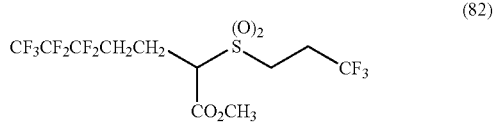

(82)

¹H-NMR (CDCl₃, TMS): δ (ppm) 3.91 (s, 3H), 3.87-3.95 (m, 1H), 3.36-3.52 (m, 2H), 2.21-2.78 (m, 6H)

Production Example 83

1.0 g of methyl 5,5,6,6,7,7,7-heptafluoro-2-(3,3,3-trifluoropropylsulfonyl)heptanoate was dissolved to 30 ml of tetrahydrofuran. This solution was added with 0.09 g of sodium hydride (60% in oil) at room temperature, and then stirred at the same temperature for 0.5 hours; and then being added with 0.3 g of N-chlorosuccinimide at the same temperature, followed by stirring for 1 hour, and then the reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 0.93 g of methyl 2-chloro-5,5,6,6,7,7,7-heptafluoro-2-(3,3,3-trifluoropropyl-sulfonyl)heptanoate (referred as the present compound (83), hereinafter).
The Present Compound (83)

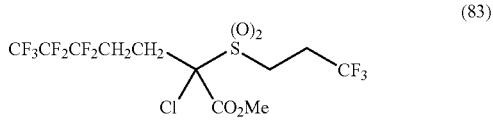

$^1$H-NMR (CDCl$_3$, TMS): δ (ppm) 3.97 (s, 3H), 3.53-3.90 (m, 2H), 2.30-2.91 (m, 6H)

Production Example 84

0.7 g of methyl 2-chloro-5,5,6,6,7,7,7-heptafluoro-2-(3,3,3-trifluoropropylsulfonyl)heptanoate was dissolved to 30 ml of methanol. This solution was added with 0.6 ml of ammonia (7 M methanol solution) at room temperature, and then stirred at the same temperature for 10 hours. The reaction mixture was concentrated under reduced pressure. The obtained residue was subjected to a silica gel chromatography to obtain 0.50 g of 2-chloro-5,5,6,6,7,7,7-heptafluoro-2-(3,3,3-trifluoropropylsulfonyl)heptanamide (referred as the present compound (84), hereinafter).
The Present Compound (84)

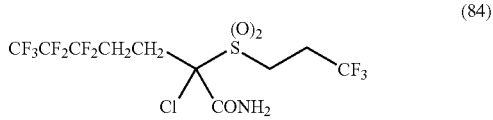

$^1$H-NMR (CDCl$_3$, TMS): δ (ppm) 6.88 (bs, 1H), 5.94 (bs, 1H), 3.37-3.73 (m, 2H), 2.14-2.96 (m, 6H)

Production Example 85

7.0 g of 1-iodo-3,3,4,4,5,5,6,6-nonafluorohexane and 4.4 g of methyl (3,3,3-trifluoropropylsulfonyl)acetate were dissolved to 50 ml of dimethylsulfoxide. This solution was added with 2.59 g of potassium carbonate at room temperature. This mixture was stirred at 60° C. for 2 days. The reaction mixture was dropped to about a room temperature. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 1.50 g of methyl 5,5,6,6,7,7,8,8,8-nonafluoro-2-(3,3,3-trifluoropropylsulfonyl)octanoate (referred as the present compound (85), hereinafter).
The Present Compound (85)

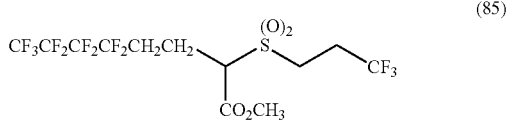

$^1$H-NMR (CDCl$_3$, TMS): δ (ppm) 3.92 (s, 3H), 3.87-3.95 (m, 1H), 3.38-3.52 (m, 2H), 2.20-2.78 (m, 6H)

Production Example 86

1.0 g of methyl 5,5,6,6,7,7,8,8,8-nonafluoro-2-(3,3,3-trifluoropropylsulfonyl)octanoate was dissolved to 30 ml of tetrahydrofuran. This solution was added with 0.08 g of sodium hydride (60% in oil) at room temperature, followed by stirring at the same temperature for 0.5 hours; and then being added with 0.3 g of N-chlorosuccinimide at the same temperature, followed by stirring for 16 hours. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 0.89 g of methyl 2-chloro-5,5,6,6,7,7,8,8,8-nonafluoro-2-(3,3,3-trifluoropropylsulfonyl)octanoate (referred as the present compound (86), hereinafter).
The Present Compound (86)

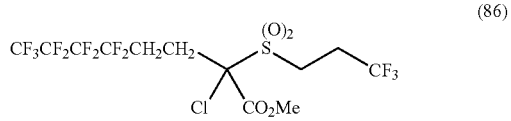

$^1$H-NMR (CDCl$_3$, TMS): δ (ppm) 3.97 (s, 3H), 3.58-3.92 (m, 2H), 2.33-2.94 (m, 6H)

Production Example 87

0.8 g of methyl 2-chloro-5,5,6,6,7,7,8,8,8-nonafluoro-2-(3,3,3-trifluoropropylsulfonyl)octanoate was dissolved to 20 ml of methanol. This solution was added with 1.1 ml of ammonia (7 M methanol solution) at room temperature, followed by stirring at the same temperature for 12 hours. The reaction mixture was concentrated under reduced pressure. The obtained residue was subjected to a silica gel chromatography to obtain 0.45 g of 2-chloro-5,5,6,6,7,7,8,8,8-nonafluoro-2-(3,3,3-trifluoropropylsulfonyl)octanamide (referred as the present compound (87), hereinafter).
The Present Compound (87)

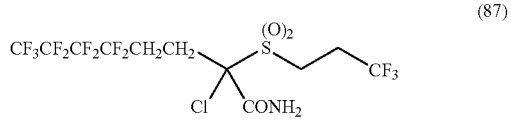

$^1$H-NMR (CDCl$_3$, TMS): δ (ppm) 6.88 (bs, 1H), 5.93 (bs, 1H), 3.38-3.77 (m, 2H), 2.15-2.98 (m, 6H)

Production Example 88

2.0 g of methyl 5,5,6,6,6-pentafluoro-2-(3,3,4,4,4-pentafluorobutylsulfonyl)hexanoate was dissolved to 30 ml of dimethylsulfoxide. This solution was added with 0.19 g of sodium hydride (60% in oil) at room temperature, followed by stirring at the same temperature for 0.5 hours; and then being added with 1.9 g of copper(II) chloride at the same temperature, followed by stirring for 12 hours. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure. The obtained residue was subjected to a silica gel chromatography to obtain 1.70 g of methyl 2-chloro-5,5,6,6,6-pentafluoro-2-(3,3,4,4,4-pentafluorobutylsulfonyl)hexanate (referred as the present compound (88), hereinafter).

The Present Compound (88)

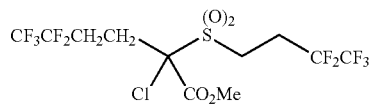
(88)

$^1$H-NMR (CDCl$_3$, TMS): δ (ppm) 3.98 (s, 3H), 3.63-3.93 (m, 2H), 2.29-2.92 (m, 6H)

Production Example 89

1.5 g of methyl 2-chloro-5,5,6,6,6-pentafluoro-2-(3,3,4,4,4-pentafluorobutylsulfonyl)hexanoate was dissolved to 30 ml of methanol. This solution was added with 1.4 ml of ammonia (7 M methanol solution) at room temperature, followed by stirring at the same temperature for 16 hours. The reaction mixture was concentrated under reduced pressure. The obtained residue was subjected to a silica gel chromatography to obtain 1.10 g of 2-chloro-5,5,6,6,6-pentafluoro-2-(3,3,4,4,4-pentafluorobutylsulfonyl)hexanamide (referred as the present compound (89), hereinafter).

The Present Compound (89)

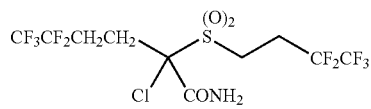
(89)

$^1$H-NMR (CDCl$_3$, TMS): δ (ppm) 6.86 (bs, 1H), 5.93 (bs, 1H), 3.40-3.78 (m, 2H), 2.13-2.95 (m, 6H)

The present compounds (90) to (103) shown below were produced by the similar method described above.

The Present Compound (90)

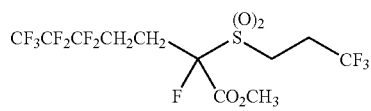
(90)

$^1$H-NMR (CDCl$_3$, TMS): δ (ppm) 4.00 (s, 3H), 3.26-3.58 (m, 2H), 2.12-2.80 (m, 6H)

The Present Compound (91)

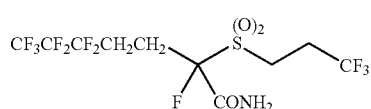
(91)

$^1$H-NMR (CDCl$_3$, TMS): δ (ppm) 6.58 (bs, 1H), 5.92 (bs, 1H), 3.26-3.58 (m, 2H), 2.19-2.83 (m, 6H)

The Present Compound (92)

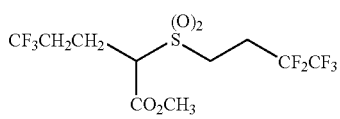
(92)

$^1$H-NMR (CDCl$_3$, TMS): δ (ppm) 3.90 (s, 3H), 3.88-3.96 (m, 1H), 3.38-3.55 (m, 2H), 2.54-2.73 (m, 2H), 2.23-2.50 (m, 4H)

The Present Compound (93)

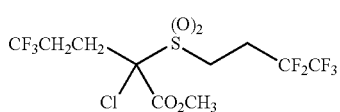
(93)

$^1$H-NMR (CDCl$_3$, TMS): δ (ppm) 3.97 (s, 3H), 3.62-3.91 (m, 2H), 2.37-2.88 (m, 6H)

The Present Compound (94)

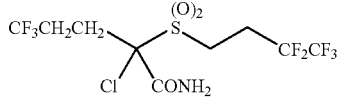
(94)

$^1$H-NMR (CDCl$_3$, TMS): δ (ppm) 6.87 (bs, 1H), 6.01 (bs, 1H), 3.35-3.80 (m, 2H), 2.19-2.92 (m, 6H)

The Present Compound (95)

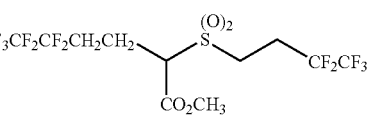
(95)

$^1$H-NMR (CDCl$_3$, TMS): δ (ppm) 3.93-3.97 (m, 1H), 3.91 (s, 3H), 3.41-3.55 (m, 2H), 2.21-2.73 (m, 6H)

The Present Compound (96)

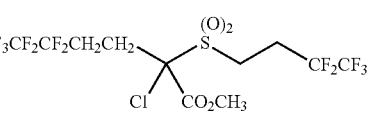
(96)

$^1$H-NMR (CDCl$_3$, TMS): δ (ppm) 3.98 (s, 3H), 3.62-3.92 (m, 2H), 2.19-2.94 (m, 6H)

The Present Compound (97)

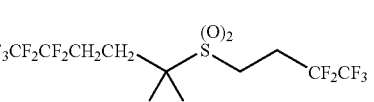
(97)

$^1$H-NMR (CDCl$_3$, TMS): δ (ppm) 6.88 (bs, 1H), 5.95 (bs, 1H), 3.39-3.78 (m, 2H), 2.14-2.96 (m, 6H)

The Present Compound (98)

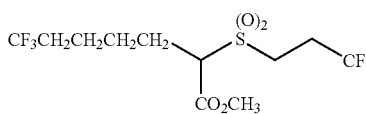

$^1$H-NMR (CDCl$_3$, TMS): δ (ppm) 3.87 (s, 3H), 3.80-3.88 (m, 1H), 3.26-3.50 (m, 2H), 2.59-2.78 (m, 2H), 2.03-2.18 (m, 4H), 1.44-1.72 (m, 4H)

The Present Compound (99)

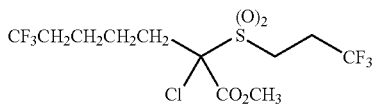

$^1$H-NMR (CDCl$_3$, TMS): δ (ppm) 3.94 (s, 3H), 3.50-3.81 (m, 2H), 2.55-2.80 (m, 3H), 2.05-2.32 (m, 3H), 1.50-1.80 (m, 4H)

The Present Compound (100)

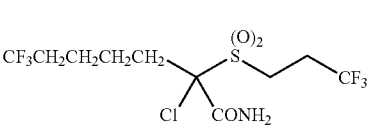

$^1$H-NMR (CDCl$_3$, TMS): δ (ppm) 6.88 (bs, 1H), 5.98 (bs, 1H), 3.34-3.78 (m, 2H), 2.58-2.81 (m, 3H), 2.01-2.28 (m, 3H), 1.40-1.82 (m, 4H)

The Present Compound (101)

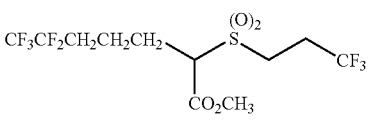

$^1$H-NMR (CDCl$_3$, TMS): δ (ppm) 3.89 (s, 3H), 3.80-3.88 (m, 1H), 3.26-3.54 (m, 2H), 2.59-2.80 (m, 3H), 2.00-2.26 (m, 3H), 1.65-1.78 (m, 2H)

The Present Compound (102)

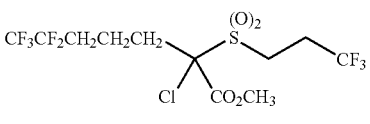

$^1$H-NMR (CDCl$_3$, TMS): δ (ppm) 3.96 (s, 3H), 3.50-3.85 (m, 2H), 2.61-2.78 (m, 3H), 1.75-2.40 (m, 5H)

The Present Compound (103)

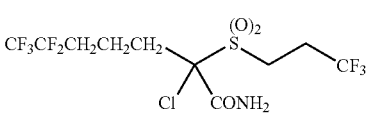

$^1$H-NMR (CDCl$_3$, TMS): δ (ppm) 6.95 (bs, 1H), 6.30 (bs, 1H), 3.35-3.78 (m, 2H), 2.61-2.80 (m, 3H), 1.62-2.32 (m, 5H)

Next, examples of the present compound are described.

The compound given by the formula (I-A);

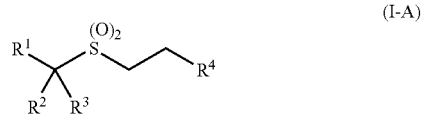

wherein R$^1$, R$^2$, R$^3$ and R$^4$ are the combination described in Table 1 to Table 83.

TABLE 1

| R$^1$ | R$^2$ | R$^3$ | R$^4$ |
|---|---|---|---|
| CH$_2$CH$_2$CF$_2$CF$_3$ | CN | H | CF$_3$ |
| CH$_2$CH$_2$CF$_2$CF$_3$ | CN | H | CF$_2$CF$_3$ |
| CH$_2$CH$_2$CF$_2$CF$_3$ | CN | H | CF$_2$CF$_2$CF$_3$ |
| CH$_2$CH$_2$CF$_2$CF$_3$ | CN | CH$_3$ | CF$_3$ |
| CH$_2$CH$_2$CF$_2$CF$_3$ | CN | CH$_3$ | CF$_2$CF$_3$ |
| CH$_2$CH$_2$CF$_2$CF$_3$ | CN | CH$_3$ | CF$_2$CF$_2$CF$_3$ |
| CH$_2$CH$_2$CF$_2$CF$_3$ | CN | CH$_2$CH$_3$ | CF$_3$ |
| CH$_2$CH$_2$CF$_2$CF$_3$ | CN | CH$_2$CH$_3$ | CF$_2$CF$_3$ |
| CH$_2$CH$_2$CF$_2$CF$_3$ | CN | CH$_2$CH$_3$ | CF$_2$CF$_2$CF$_3$ |
| CH$_2$CH$_2$CF$_2$CF$_3$ | CN | CH$_2$CH$_2$CH$_3$ | CF$_3$ |
| CH$_2$CH$_2$CF$_2$CF$_3$ | CN | CH$_2$CH$_2$CH$_3$ | CF$_2$CF$_3$ |
| CH$_2$CH$_2$CF$_2$CF$_3$ | CN | CH$_2$CH$_2$CH$_3$ | CF$_2$CF$_2$CF$_3$ |
| CH$_2$CH$_2$CF$_2$CF$_3$ | CN | CH(CH$_3$)$_2$ | CF$_3$ |
| CH$_2$CH$_2$CF$_2$CF$_3$ | CN | CH(CH$_3$)$_2$ | CF$_2$CF$_3$ |
| CH$_2$CH$_2$CF$_2$CF$_3$ | CN | CH(CH$_3$)$_2$ | CF$_2$CF$_2$CF$_3$ |
| CH$_2$CH$_2$CF$_2$CF$_3$ | CN | CH$_2$CH$_2$CH$_2$CH$_3$ | CF$_3$ |
| CH$_2$CH$_2$CF$_2$CF$_3$ | CN | CH$_2$CH$_2$CH$_2$CH$_3$ | CF$_2$CF$_3$ |
| CH$_2$CH$_2$CF$_2$CF$_3$ | CN | CH$_2$CH$_2$CH$_2$CH$_3$ | CF$_2$CF$_2$CF$_3$ |
| CH$_2$CH$_2$CF$_2$CF$_3$ | CN | CH$_2$CH$_2$CH$_2$CH$_2$CH$_3$ | CF$_3$ |
| CH$_2$CH$_2$CF$_2$CF$_3$ | CN | CH$_2$CH$_2$CH$_2$CH$_2$CH$_3$ | CF$_2$CF$_3$ |
| CH$_2$CH$_2$CF$_2$CF$_3$ | CN | CH$_2$CH$_2$CH$_2$CH$_2$CH$_3$ | CF$_2$CF$_2$CF$_3$ |
| CH$_2$CH$_2$CF$_2$CF$_3$ | CN | F | CF$_3$ |
| CH$_2$CH$_2$CF$_2$CF$_3$ | CN | F | CF$_2$CF$_3$ |
| CH$_2$CH$_2$CF$_2$CF$_3$ | CN | F | CF$_2$CF$_2$CF$_3$ |
| CH$_2$CH$_2$CF$_2$CF$_3$ | CN | Cl | CF$_3$ |
| CH$_2$CH$_2$CF$_2$CF$_3$ | CN | Cl | CF$_2$CF$_3$ |
| CH$_2$CH$_2$CF$_2$CF$_3$ | CN | Cl | CF$_2$CF$_2$CF$_3$ |

TABLE 2

| R$^1$ | R$^2$ | R$^3$ | R$^4$ |
|---|---|---|---|
| CH$_2$CH$_2$CF$_2$CF$_3$ | CO$_2$CH$_3$ | H | CF$_3$ |
| CH$_2$CH$_2$CF$_2$CF$_3$ | CO$_2$CH$_3$ | H | CF$_2$CF$_3$ |
| CH$_2$CH$_2$CF$_2$CF$_3$ | CO$_2$CH$_3$ | H | CF$_2$CF$_2$CF$_3$ |
| CH$_2$CH$_2$CF$_2$CF$_3$ | CO$_2$CH$_3$ | CH$_3$ | CF$_3$ |
| CH$_2$CH$_2$CF$_2$CF$_3$ | CO$_2$CH$_3$ | CH$_3$ | CF$_2$CF$_3$ |
| CH$_2$CH$_2$CF$_2$CF$_3$ | CO$_2$CH$_3$ | CH$_3$ | CF$_2$CF$_2$CF$_3$ |
| CH$_2$CH$_2$CF$_2$CF$_3$ | CO$_2$CH$_3$ | CH$_2$CH$_3$ | CF$_3$ |
| CH$_2$CH$_2$CF$_2$CF$_3$ | CO$_2$CH$_3$ | CH$_2$CH$_3$ | CF$_2$CF$_3$ |
| CH$_2$CH$_2$CF$_2$CF$_3$ | CO$_2$CH$_3$ | CH$_2$CH$_3$ | CF$_2$CF$_2$CF$_3$ |
| CH$_2$CH$_2$CF$_2$CF$_3$ | CO$_2$CH$_3$ | CH$_2$CH$_2$CH$_3$ | CF$_3$ |
| CH$_2$CH$_2$CF$_2$CF$_3$ | CO$_2$CH$_3$ | CH$_2$CH$_2$CH$_3$ | CF$_2$CF$_3$ |
| CH$_2$CH$_2$CF$_2$CF$_3$ | CO$_2$CH$_3$ | CH$_2$CH$_2$CH$_3$ | CF$_2$CF$_2$CF$_3$ |
| CH$_2$CH$_2$CF$_2$CF$_3$ | CO$_2$CH$_3$ | F | CF$_3$ |
| CH$_2$CH$_2$CF$_2$CF$_3$ | CO$_2$CH$_3$ | F | CF$_2$CF$_3$ |
| CH$_2$CH$_2$CF$_2$CF$_3$ | CO$_2$CH$_3$ | F | CF$_2$CF$_2$CF$_3$ |
| CH$_2$CH$_2$CF$_2$CF$_3$ | CO$_2$CH$_3$ | Cl | CF$_3$ |
| CH$_2$CH$_2$CF$_2$CF$_3$ | CO$_2$CH$_3$ | Cl | CF$_2$CF$_3$ |
| CH$_2$CH$_2$CF$_2$CF$_3$ | CO$_2$CH$_3$ | Cl | CF$_2$CF$_2$CF$_3$ |
| CH$_2$CH$_2$CF$_2$CF$_3$ | CO$_2$C(CH$_3$)$_3$ | H | CF$_3$ |
| CH$_2$CH$_2$CF$_2$CF$_3$ | CO$_2$C(CH$_3$)$_3$ | H | CF$_2$CF$_3$ |
| CH$_2$CH$_2$CF$_2$CF$_3$ | CO$_2$C(CH$_3$)$_3$ | H | CF$_2$CF$_2$CF$_3$ |
| CH$_2$CH$_2$CF$_2$CF$_3$ | CO$_2$C(CH$_3$)$_3$ | CH$_3$ | CF$_3$ |
| CH$_2$CH$_2$CF$_2$CF$_3$ | CO$_2$C(CH$_3$)$_3$ | CH$_3$ | CF$_2$CF$_3$ |
| CH$_2$CH$_2$CF$_2$CF$_3$ | CO$_2$C(CH$_3$)$_3$ | CH$_3$ | CF$_2$CF$_2$CF$_3$ |
| CH$_2$CH$_2$CF$_2$CF$_3$ | CO$_2$C(CH$_3$)$_3$ | F | CF$_3$ |
| CH$_2$CH$_2$CF$_2$CF$_3$ | CO$_2$C(CH$_3$)$_3$ | F | CF$_2$CF$_3$ |
| CH$_2$CH$_2$CF$_2$CF$_3$ | CO$_2$C(CH$_3$)$_3$ | F | CF$_2$CF$_2$CF$_3$ |

TABLE 3

| R¹ | R² | R³ | R⁴ |
|---|---|---|---|
| $CH_2CH_2CF_2CF_3$ | $CO_2C(CH_3)_3$ | Cl | $CF_3$ |
| $CH_2CH_2CF_2CF_3$ | $CO_2C(CH_3)_3$ | Cl | $CF_2CF_3$ |
| $CH_2CH_2CF_2CF_3$ | $CO_2C(CH_3)_3$ | Cl | $CF_2CF_2CF_3$ |
| $CH_2CH_2CF_2CF_3$ | $CONH_2$ | H | $CF_3$ |
| $CH_2CH_2CF_2CF_3$ | $CONH_2$ | H | $CF_2CF_3$ |
| $CH_2CH_2CF_2CF_3$ | $CONH_2$ | H | $CF_2CF_2CF_3$ |
| $CH_2CH_2CF_2CF_3$ | $CONH_2$ | $CH_3$ | $CF_3$ |
| $CH_2CH_2CF_2CF_3$ | $CONH_2$ | $CH_3$ | $CF_2CF_3$ |
| $CH_2CH_2CF_2CF_3$ | $CONH_2$ | $CH_3$ | $CF_2CF_2CF_3$ |
| $CH_2CH_2CF_2CF_3$ | $CONH_2$ | $CH_2CH_3$ | $CF_3$ |
| $CH_2CH_2CF_2CF_3$ | $CONH_2$ | $CH_2CH_3$ | $CF_2CF_3$ |
| $CH_2CH_2CF_2CF_3$ | $CONH_2$ | $CH_2CH_3$ | $CF_2CF_2CF_3$ |
| $CH_2CH_2CF_2CF_3$ | $CONH_2$ | F | $CF_3$ |
| $CH_2CH_2CF_2CF_3$ | $CONH_2$ | F | $CF_2CF_3$ |
| $CH_2CH_2CF_2CF_3$ | $CONH_2$ | F | $CF_2CF_2CF_3$ |
| $CH_2CH_2CF_2CF_3$ | $CONH_2$ | Cl | $CF_3$ |
| $CH_2CH_2CF_2CF_3$ | $CONH_2$ | Cl | $CF_2CF_3$ |
| $CH_2CH_2CF_2CF_3$ | $CONH_2$ | Cl | $CF_2CF_2CF_3$ |
| $CH_2CH_2CF_2CF_3$ | $CONH(CH_3)$ | H | $CF_3$ |
| $CH_2CH_2CF_2CF_3$ | $CONH(CH_3)$ | H | $CF_2CF_3$ |
| $CH_2CH_2CF_2CF_3$ | $CONH(CH_3)$ | H | $CF_2CF_2CF_3$ |
| $CH_2CH_2CF_2CF_3$ | $CONH(CH_3)$ | $CH_3$ | $CF_3$ |
| $CH_2CH_2CF_2CF_3$ | $CONH(CH_3)$ | $CH_3$ | $CF_2CF_3$ |
| $CH_2CH_2CF_2CF_3$ | $CONH(CH_3)$ | $CH_3$ | $CF_2CF_2CF_3$ |
| $CH_2CH_2CF_2CF_3$ | $CONH(CH_3)$ | $CH_2CH_3$ | $CF_3$ |
| $CH_2CH_2CF_2CF_3$ | $CONH(CH_3)$ | $CH_2CH_3$ | $CF_2CF_3$ |
| $CH_2CH_2CF_2CF_3$ | $CONH(CH_3)$ | $CH_2CH_3$ | $CF_2CF_2CF_3$ |

TABLE 4

| R¹ | R² | R³ | R⁴ |
|---|---|---|---|
| $CH_2CH_2CF_2CF_3$ | $CONH(CH_3)$ | F | $CF_3$ |
| $CH_2CH_2CF_2CF_3$ | $CONH(CH_3)$ | F | $CF_2CF_3$ |
| $CH_2CH_2CF_2CF_3$ | $CONH(CH_3)$ | F | $CF_2CF_2CF_3$ |
| $CH_2CH_2CF_2CF_3$ | $CONH(CH_3)$ | Cl | $CF_3$ |
| $CH_2CH_2CF_2CF_3$ | $CONH(CH_3)$ | Cl | $CF_2CF_3$ |
| $CH_2CH_2CF_2CF_3$ | $CONH(CH_3)$ | Cl | $CF_2CF_2CF_3$ |
| $CH_2CH_2CF_2CF_3$ | $CONH(CH_2CH_3)$ | H | $CF_3$ |
| $CH_2CH_2CF_2CF_3$ | $CONH(CH_2CH_3)$ | H | $CF_2CF_3$ |
| $CH_2CH_2CF_2CF_3$ | $CONH(CH_2CH_3)$ | H | $CF_2CF_2CF_3$ |
| $CH_2CH_2CF_2CF_3$ | $CONH(CH_2CH_3)$ | $CH_3$ | $CF_3$ |
| $CH_2CH_2CF_2CF_3$ | $CONH(CH_2CH_3)$ | $CH_3$ | $CF_2CF_3$ |
| $CH_2CH_2CF_2CF_3$ | $CONH(CH_2CH_3)$ | $CH_3$ | $CF_2CF_2CF_3$ |
| $CH_2CH_2CF_2CF_3$ | $CONH(CH_2CH_3)$ | $CH_2CH_3$ | $CF_3$ |
| $CH_2CH_2CF_2CF_3$ | $CONH(CH_2CH_3)$ | $CH_2CH_3$ | $CF_2CF_3$ |
| $CH_2CH_2CF_2CF_3$ | $CONH(CH_2CH_3)$ | $CH_2CH_3$ | $CF_2CF_2CF_3$ |
| $CH_2CH_2CF_2CF_3$ | $CONH(CH_2CH_3)$ | F | $CF_3$ |
| $CH_2CH_2CF_2CF_3$ | $CONH(CH_2CH_3)$ | F | $CF_2CF_3$ |
| $CH_2CH_2CF_2CF_3$ | $CONH(CH_2CH_3)$ | F | $CF_2CF_2CF_3$ |
| $CH_2CH_2CF_2CF_3$ | $CONH(CH_2CH_3)$ | Cl | $CF_3$ |
| $CH_2CH_2CF_2CF_3$ | $CONH(CH_2CH_3)$ | Cl | $CF_2CF_3$ |
| $CH_2CH_2CF_2CF_3$ | $CONH(CH_2CH_3)$ | Cl | $CF_2CF_2CF_3$ |
| $CH_2CH_2CF_2CF_3$ | $CON(CH_3)_2$ | H | $CF_3$ |
| $CH_2CH_2CF_2CF_3$ | $CON(CH_3)_2$ | H | $CF_2CF_3$ |
| $CH_2CH_2CF_2CF_3$ | $CON(CH_3)_2$ | H | $CF_2CF_2CF_3$ |
| $CH_2CH_2CF_2CF_3$ | $CON(CH_3)_2$ | $CH_3$ | $CF_3$ |
| $CH_2CH_2CF_2CF_3$ | $CON(CH_3)_2$ | $CH_3$ | $CF_2CF_3$ |
| $CH_2CH_2CF_2CF_3$ | $CON(CH_3)_2$ | $CH_3$ | $CF_2CF_2CF_3$ |

TABLE 5

| R¹ | R² | R³ | R⁴ |
|---|---|---|---|
| $CH_2CH_2CF_2CF_3$ | $CON(CH_3)_2$ | $CH_2CH_3$ | $CF_3$ |
| $CH_2CH_2CF_2CF_3$ | $CON(CH_3)_2$ | $CH_2CH_3$ | $CF_2CF_3$ |
| $CH_2CH_2CF_2CF_3$ | $CON(CH_3)_2$ | $CH_2CH_3$ | $CF_2CF_2CF_3$ |
| $CH_2CH_2CF_2CF_3$ | $CON(CH_3)_2$ | F | $CF_3$ |
| $CH_2CH_2CF_2CF_3$ | $CON(CH_3)_2$ | F | $CF_2CF_3$ |
| $CH_2CH_2CF_2CF_3$ | $CON(CH_3)_2$ | F | $CF_2CF_2CF_3$ |
| $CH_2CH_2CF_2CF_3$ | $CON(CH_3)_2$ | Cl | $CF_3$ |
| $CH_2CH_2CF_2CF_3$ | $CON(CH_3)_2$ | Cl | $CF_2CF_3$ |
| $CH_2CH_2CF_2CF_3$ | $CON(CH_3)_2$ | Cl | $CF_2CF_2CF_3$ |

TABLE 5-continued

| R¹ | R² | R³ | R⁴ |
|---|---|---|---|
| $CH_2CH_2CF_3$ | CN | H | $CF_3$ |
| $CH_2CH_2CF_3$ | CN | H | $CF_2CF_3$ |
| $CH_2CH_2CF_3$ | CN | H | $CF_2CF_2CF_3$ |
| $CH_2CH_2CF_3$ | CN | $CH_3$ | $CF_3$ |
| $CH_2CH_2CF_3$ | CN | $CH_3$ | $CF_2CF_3$ |
| $CH_2CH_2CF_3$ | CN | $CH_3$ | $CF_2CF_2CF_3$ |
| $CH_2CH_2CF_3$ | CN | $CH_2CH_3$ | $CF_3$ |
| $CH_2CH_2CF_3$ | CN | $CH_2CH_3$ | $CF_2CF_3$ |
| $CH_2CH_2CF_3$ | CN | $CH_2CH_3$ | $CF_2CF_2CF_3$ |
| $CH_2CH_2CF_3$ | CN | F | $CF_3$ |
| $CH_2CH_2CF_3$ | CN | F | $CF_2CF_3$ |
| $CH_2CH_2CF_3$ | CN | F | $CF_2CF_2CF_3$ |
| $CH_2CH_2CF_3$ | CN | Cl | $CF_3$ |
| $CH_2CH_2CF_3$ | CN | Cl | $CF_2CF_3$ |
| $CH_2CH_2CF_3$ | CN | Cl | $CF_2CF_2CF_3$ |
| $CH_2CH_2CF_3$ | $CO_2CH_3$ | H | $CF_3$ |
| $CH_2CH_2CF_3$ | $CO_2CH_3$ | H | $CF_2CF_3$ |
| $CH_2CH_2CF_3$ | $CO_2CH_3$ | H | $CF_2CF_2CF_3$ |

TABLE 6

| R¹ | R² | R³ | R⁴ |
|---|---|---|---|
| $CH_2CH_2CF_3$ | $CO_2CH_3$ | $CH_3$ | $CF_3$ |
| $CH_2CH_2CF_3$ | $CO_2CH_3$ | $CH_3$ | $CF_2CF_3$ |
| $CH_2CH_2CF_3$ | $CO_2CH_3$ | $CH_3$ | $CF_2CF_2CF_3$ |
| $CH_2CH_2CF_3$ | $CO_2CH_3$ | F | $CF_3$ |
| $CH_2CH_2CF_3$ | $CO_2CH_3$ | F | $CF_2CF_3$ |
| $CH_2CH_2CF_3$ | $CO_2CH_3$ | F | $CF_2CF_2CF_3$ |
| $CH_2CH_2CF_3$ | $CO_2CH_3$ | Cl | $CF_3$ |
| $CH_2CH_2CF_3$ | $CO_2CH_3$ | Cl | $CF_2CF_3$ |
| $CH_2CH_2CF_3$ | $CO_2CH_3$ | Cl | $CF_2CF_2CF_3$ |
| $CH_2CH_2CF_3$ | $CONH_2$ | H | $CF_3$ |
| $CH_2CH_2CF_3$ | $CONH_2$ | H | $CF_2CF_3$ |
| $CH_2CH_2CF_3$ | $CONH_2$ | H | $CF_2CF_2CF_3$ |
| $CH_2CH_2CF_3$ | $CONH_2$ | $CH_3$ | $CF_3$ |
| $CH_2CH_2CF_3$ | $CONH_2$ | $CH_3$ | $CF_2CF_3$ |
| $CH_2CH_2CF_3$ | $CONH_2$ | $CH_3$ | $CF_2CF_2CF_3$ |
| $CH_2CH_2CF_3$ | $CONH_2$ | $CH_2CH_3$ | $CF_3$ |
| $CH_2CH_2CF_3$ | $CONH_2$ | $CH_2CH_3$ | $CF_2CF_3$ |
| $CH_2CH_2CF_3$ | $CONH_2$ | $CH_2CH_3$ | $CF_2CF_2CF_3$ |
| $CH_2CH_2CF_3$ | $CONH_2$ | F | $CF_3$ |
| $CH_2CH_2CF_3$ | $CONH_2$ | F | $CF_2CF_3$ |
| $CH_2CH_2CF_3$ | $CONH_2$ | F | $CF_2CF_2CF_3$ |
| $CH_2CH_2CF_3$ | $CONH_2$ | Cl | $CF_3$ |
| $CH_2CH_2CF_3$ | $CONH_2$ | Cl | $CF_2CF_3$ |
| $CH_2CH_2CF_3$ | $CONH_2$ | Cl | $CF_2CF_2CF_3$ |
| $CH_2CH_2CF_3$ | $CONH(CH_3)$ | H | $CF_3$ |
| $CH_2CH_2CF_3$ | $CONH(CH_3)$ | H | $CF_2CF_3$ |
| $CH_2CH_2CF_3$ | $CONH(CH_3)$ | H | $CF_2CF_2CF_3$ |

TABLE 7

| R¹ | R² | R³ | R⁴ |
|---|---|---|---|
| $CH_2CH_2CF_3$ | $CONH(CH_3)$ | $CH_3$ | $CF_3$ |
| $CH_2CH_2CF_3$ | $CONH(CH_3)$ | $CH_3$ | $CF_2CF_3$ |
| $CH_2CH_2CF_3$ | $CONH(CH_3)$ | $CH_3$ | $CF_2CF_2CF_3$ |
| $CH_2CH_2CF_3$ | $CONH(CH_3)$ | $CH_2CH_3$ | $CF_3$ |
| $CH_2CH_2CF_3$ | $CONH(CH_3)$ | $CH_2CH_3$ | $CF_2CF_3$ |
| $CH_2CH_2CF_3$ | $CONH(CH_3)$ | $CH_2CH_3$ | $CF_2CF_2CF_3$ |
| $CH_2CH_2CF_3$ | $CONH(CH_3)$ | F | $CF_3$ |
| $CH_2CH_2CF_3$ | $CONH(CH_3)$ | F | $CF_2CF_3$ |
| $CH_2CH_2CF_3$ | $CONH(CH_3)$ | F | $CF_2CF_2CF_3$ |
| $CH_2CH_2CF_3$ | $CONH(CH_3)$ | Cl | $CF_3$ |
| $CH_2CH_2CF_3$ | $CONH(CH_3)$ | Cl | $CF_2CF_3$ |
| $CH_2CH_2CF_3$ | $CONH(CH_3)$ | Cl | $CF_2CF_2CF_3$ |
| $CH_2CH_2CF_3$ | $CON(CH_3)_2$ | H | $CF_3$ |
| $CH_2CH_2CF_3$ | $CON(CH_3)_2$ | H | $CF_2CF_3$ |
| $CH_2CH_2CF_3$ | $CON(CH_3)_2$ | H | $CF_2CF_2CF_3$ |
| $CH_2CH_2CF_3$ | $CON(CH_3)_2$ | $CH_3$ | $CF_3$ |
| $CH_2CH_2CF_3$ | $CON(CH_3)_2$ | $CH_3$ | $CF_2CF_3$ |
| $CH_2CH_2CF_3$ | $CON(CH_3)_2$ | $CH_3$ | $CF_2CF_2CF_3$ |

TABLE 7-continued

| $R^1$ | $R^2$ | $R^3$ | $R^4$ |
|---|---|---|---|
| $CH_2CH_2CF_3$ | $CON(CH_3)_2$ | $CH_2CH_3$ | $CF_3$ |
| $CH_2CH_2CF_3$ | $CON(CH_3)_2$ | $CH_2CH_3$ | $CF_2CF_3$ |
| $CH_2CH_2CF_3$ | $CON(CH_3)_2$ | $CH_2CH_3$ | $CF_2CF_2CF_3$ |
| $CH_2CH_2CF_3$ | $CON(CH_3)_2$ | F | $CF_3$ |
| $CH_2CH_2CF_3$ | $CON(CH_3)_2$ | F | $CF_2CF_3$ |
| $CH_2CH_2CF_3$ | $CON(CH_3)_2$ | F | $CF_2CF_2CF_3$ |
| $CH_2CH_2CF_3$ | $CON(CH_3)_2$ | Cl | $CF_3$ |
| $CH_2CH_2CF_3$ | $CON(CH_3)_2$ | Cl | $CF_2CF_3$ |
| $CH_2CH_2CF_3$ | $CON(CH_3)_2$ | Cl | $CF_2CF_2CF_3$ |

TABLE 8

| $R^1$ | $R^2$ | $R^3$ | $R^4$ |
|---|---|---|---|
| $CH_2CF_2CF_3$ | CN | H | $CF_3$ |
| $CH_2CF_2CF_3$ | CN | H | $CF_2CF_3$ |
| $CH_2CF_2CF_3$ | CN | H | $CF_2CF_2CF_3$ |
| $CH_2CF_2CF_3$ | CN | $CH_3$ | $CF_3$ |
| $CH_2CF_2CF_3$ | CN | $CH_3$ | $CF_2CF_3$ |
| $CH_2CF_2CF_3$ | CN | $CH_3$ | $CF_2CF_2CF_3$ |
| $CH_2CF_2CF_3$ | CN | $CH_2CH_3$ | $CF_3$ |
| $CH_2CF_2CF_3$ | CN | $CH_2CH_3$ | $CF_2CF_3$ |
| $CH_2CF_2CF_3$ | CN | $CH_2CH_3$ | $CF_2CF_2CF_3$ |
| $CH_2CF_2CF_3$ | CN | F | $CF_3$ |
| $CH_2CF_2CF_3$ | CN | F | $CF_2CF_3$ |
| $CH_2CF_2CF_3$ | CN | F | $CF_2CF_2CF_3$ |
| $CH_2CF_2CF_3$ | CN | Cl | $CF_3$ |
| $CH_2CF_2CF_3$ | CN | Cl | $CF_2CF_3$ |
| $CH_2CF_2CF_3$ | CN | Cl | $CF_2CF_2CF_3$ |
| $CH_2CF_2CF_3$ | $CO_2CH_3$ | H | $CF_3$ |
| $CH_2CF_2CF_3$ | $CO_2CH_3$ | H | $CF_2CF_3$ |
| $CH_2CF_2CF_3$ | $CO_2CH_3$ | H | $CF_2CF_2CF_3$ |
| $CH_2CF_2CF_3$ | $CO_2CH_3$ | $CH_3$ | $CF_3$ |
| $CH_2CF_2CF_3$ | $CO_2CH_3$ | $CH_3$ | $CF_2CF_3$ |
| $CH_2CF_2CF_3$ | $CO_2CH_3$ | $CH_3$ | $CF_2CF_2CF_3$ |
| $CH_2CF_2CF_3$ | $CO_2CH_3$ | F | $CF_3$ |
| $CH_2CF_2CF_3$ | $CO_2CH_3$ | F | $CF_2CF_3$ |
| $CH_2CF_2CF_3$ | $CO_2CH_3$ | F | $CF_2CF_2CF_3$ |
| $CH_2CF_2CF_3$ | $CO_2CH_3$ | Cl | $CF_3$ |
| $CH_2CF_2CF_3$ | $CO_2CH_3$ | Cl | $CF_2CF_3$ |
| $CH_2CF_2CF_3$ | $CO_2CH_3$ | Cl | $CF_2CF_2CF_3$ |

TABLE 9

| $R^1$ | $R^2$ | $R^3$ | $R^4$ |
|---|---|---|---|
| $CH_2CF_2CF_3$ | CN | H | $CF_3$ |
| $CH_2CF_2CF_3$ | CN | H | $CF_2CF_3$ |
| $CH_2CF_2CF_3$ | CN | H | $CF_2CF_2CF_3$ |
| $CH_2CF_2CF_3$ | CN | $CH_3$ | $CF_3$ |
| $CH_2CF_2CF_3$ | CN | $CH_3$ | $CF_2CF_3$ |
| $CH_2CF_2CF_3$ | CN | $CH_3$ | $CF_2CF_2CF_3$ |
| $CH_2CF_2CF_3$ | CN | $CH_2CH_3$ | $CF_3$ |
| $CH_2CF_2CF_3$ | CN | $CH_2CH_3$ | $CF_2CF_3$ |
| $CH_2CF_2CF_3$ | CN | $CH_2CH_3$ | $CF_2CF_2CF_3$ |
| $CH_2CF_2CF_3$ | CN | F | $CF_3$ |
| $CH_2CF_2CF_3$ | CN | F | $CF_2CF_3$ |
| $CH_2CF_2CF_3$ | CN | F | $CF_2CF_2CF_3$ |
| $CH_2CF_2CF_3$ | CN | Cl | $CF_3$ |
| $CH_2CF_2CF_3$ | CN | Cl | $CF_2CF_3$ |
| $CH_2CF_2CF_3$ | CN | Cl | $CF_2CF_2CF_3$ |
| $CH_2CF_2CF_3$ | $CO_2CH_3$ | H | $CF_3$ |
| $CH_2CF_2CF_3$ | $CO_2CH_3$ | H | $CF_2CF_3$ |
| $CH_2CF_2CF_3$ | $CO_2CH_3$ | H | $CF_2CF_2CF_3$ |
| $CH_2CF_2CF_3$ | $CO_2CH_3$ | $CH_3$ | $CF_3$ |
| $CH_2CF_2CF_3$ | $CO_2CH_3$ | $CH_3$ | $CF_2CF_3$ |
| $CH_2CF_2CF_3$ | $CO_2CH_3$ | $CH_3$ | $CF_2CF_2CF_3$ |
| $CH_2CF_2CF_3$ | $CO_2CH_3$ | F | $CF_3$ |
| $CH_2CF_2CF_3$ | $CO_2CH_3$ | F | $CF_2CF_3$ |
| $CH_2CF_2CF_3$ | $CO_2CH_3$ | F | $CF_2CF_2CF_3$ |
| $CH_2CF_2CF_3$ | $CO_2CH_3$ | Cl | $CF_3$ |

TABLE 9-continued

| $R^1$ | $R^2$ | $R^3$ | $R^4$ |
|---|---|---|---|
| $CH_2CF_2CF_3$ | $CO_2CH_3$ | Cl | $CF_2CF_3$ |
| $CH_2CF_2CF_3$ | $CO_2CH_3$ | Cl | $CF_2CF_2CF_3$ |

TABLE 10

| $R^1$ | $R^2$ | $R^3$ | $R^4$ |
|---|---|---|---|
| $CH_2CF_2CF_3$ | $CONH_2$ | H | $CF_3$ |
| $CH_2CF_2CF_3$ | $CONH_2$ | H | $CF_2CF_3$ |
| $CH_2CF_2CF_3$ | $CONH_2$ | H | $CF_2CF_2CF_3$ |
| $CH_2CF_2CF_3$ | $CONH_2$ | $CH_3$ | $CF_3$ |
| $CH_2CF_2CF_3$ | $CONH_2$ | $CH_3$ | $CF_2CF_3$ |
| $CH_2CF_2CF_3$ | $CONH_2$ | $CH_3$ | $CF_2CF_2CF_3$ |
| $CH_2CF_2CF_3$ | $CONH_2$ | $CH_2CH_3$ | $CF_3$ |
| $CH_2CF_2CF_3$ | $CONH_2$ | $CH_2CH_3$ | $CF_2CF_3$ |
| $CH_2CF_2CF_3$ | $CONH_2$ | $CH_2CH_3$ | $CF_2CF_2CF_3$ |
| $CH_2CF_2CF_3$ | $CONH_2$ | F | $CF_3$ |
| $CH_2CF_2CF_3$ | $CONH_2$ | F | $CF_2CF_3$ |
| $CH_2CF_2CF_3$ | $CONH_2$ | F | $CF_2CF_2CF_3$ |
| $CH_2CF_2CF_3$ | $CONH_2$ | Cl | $CF_3$ |
| $CH_2CF_2CF_3$ | $CONH_2$ | Cl | $CF_2CF_3$ |
| $CH_2CF_2CF_3$ | $CONH_2$ | Cl | $CF_2CF_2CF_3$ |
| $CH_2CF_2CF_3$ | $CONH(CH_3)$ | H | $CF_3$ |
| $CH_2CF_2CF_3$ | $CONH(CH_3)$ | H | $CF_2CF_3$ |
| $CH_2CF_2CF_3$ | $CONH(CH_3)$ | H | $CF_2CF_2CF_3$ |
| $CH_2CF_2CF_3$ | $CONH(CH_3)$ | $CH_3$ | $CF_3$ |
| $CH_2CF_2CF_3$ | $CONH(CH_3)$ | $CH_3$ | $CF_2CF_3$ |
| $CH_2CF_2CF_3$ | $CONH(CH_3)$ | $CH_3$ | $CF_2CF_2CF_3$ |
| $CH_2CF_2CF_3$ | $CONH(CH_3)$ | $CH_2CH_3$ | $CF_3$ |
| $CH_2CF_2CF_3$ | $CONH(CH_3)$ | $CH_2CH_3$ | $CF_2CF_3$ |
| $CH_2CF_2CF_3$ | $CONH(CH_3)$ | $CH_2CH_3$ | $CF_2CF_2CF_3$ |
| $CH_2CF_2CF_3$ | $CONH(CH_3)$ | F | $CF_3$ |
| $CH_2CF_2CF_3$ | $CONH(CH_3)$ | F | $CF_2CF_3$ |
| $CH_2CF_2CF_3$ | $CONH(CH_3)$ | F | $CF_2CF_2CF_3$ |

TABLE 11

| $R^1$ | $R^2$ | $R^3$ | $R^4$ |
|---|---|---|---|
| $CH_2CF_2CF_3$ | $CONH(CH_3)$ | Cl | $CF_3$ |
| $CH_2CF_2CF_3$ | $CONH(CH_3)$ | Cl | $CF_2CF_3$ |
| $CH_2CF_2CF_3$ | $CONH(CH_3)$ | Cl | $CF_2CF_2CF_3$ |
| $CH_2CF_2CF_3$ | $CON(CH_3)_2$ | H | $CF_3$ |
| $CH_2CF_2CF_3$ | $CON(CH_3)_2$ | H | $CF_2CF_3$ |
| $CH_2CF_2CF_3$ | $CON(CH_3)_2$ | H | $CF_2CF_2CF_3$ |
| $CH_2CF_2CF_3$ | $CON(CH_3)_2$ | $CH_3$ | $CF_3$ |
| $CH_2CF_2CF_3$ | $CON(CH_3)_2$ | $CH_3$ | $CF_2CF_3$ |
| $CH_2CF_2CF_3$ | $CON(CH_3)_2$ | $CH_3$ | $CF_2CF_2CF_3$ |
| $CH_2CF_2CF_3$ | $CON(CH_3)_2$ | $CH_2CH_3$ | $CF_3$ |
| $CH_2CF_2CF_3$ | $CON(CH_3)_2$ | $CH_2CH_3$ | $CF_2CF_3$ |
| $CH_2CF_2CF_3$ | $CON(CH_3)_2$ | $CH_2CH_3$ | $CF_2CF_2CF_3$ |
| $CH_2CF_2CF_3$ | $CON(CH_3)_2$ | F | $CF_3$ |
| $CH_2CF_2CF_3$ | $CON(CH_3)_2$ | F | $CF_2CF_3$ |
| $CH_2CF_2CF_3$ | $CON(CH_3)_2$ | F | $CF_2CF_2CF_3$ |
| $CH_2CF_2CF_3$ | $CON(CH_3)_2$ | Cl | $CF_3$ |
| $CH_2CF_2CF_3$ | $CON(CH_3)_2$ | Cl | $CF_2CF_3$ |
| $CH_2CF_2CF_3$ | $CON(CH_3)_2$ | Cl | $CF_2CF_2CF_3$ |
| $CH_2CF_2CF_2CF_3$ | CN | H | $CF_3$ |
| $CH_2CF_2CF_2CF_3$ | CN | H | $CF_2CF_3$ |
| $CH_2CF_2CF_2CF_3$ | CN | H | $CF_2CF_2CF_3$ |
| $CH_2CF_2CF_2CF_3$ | CN | $CH_3$ | $CF_3$ |
| $CH_2CF_2CF_2CF_3$ | CN | $CH_3$ | $CF_2CF_3$ |
| $CH_2CF_2CF_2CF_3$ | CN | $CH_3$ | $CF_2CF_2CF_3$ |
| $CH_2CF_2CF_2CF_3$ | CN | $CH_2CH_3$ | $CF_3$ |
| $CH_2CF_2CF_2CF_3$ | CN | $CH_2CH_3$ | $CF_2CF_3$ |
| $CH_2CF_2CF_2CF_3$ | CN | $CH_2CH_3$ | $CF_2CF_2CF_3$ |

TABLE 12

| R¹ | R² | R³ | R⁴ |
|---|---|---|---|
| CH₂CF₂CF₂CF₃ | CN | F | CF₃ |
| CH₂CF₂CF₂CF₃ | CN | F | CF₂CF₃ |
| CH₂CF₂CF₂CF₃ | CN | F | CF₂CF₂CF₃ |
| CH₂CF₂CF₂CF₃ | CN | Cl | CF₃ |
| CH₂CF₂CF₂CF₃ | CN | Cl | CF₂CF₃ |
| CH₂CF₂CF₂CF₃ | CN | Cl | CF₂CF₂CF₃ |
| CH₂CF₂CF₂CF₃ | CO₂CH₃ | H | CF₃ |
| CH₂CF₂CF₂CF₃ | CO₂CH₃ | H | CF₂CF₃ |
| CH₂CF₂CF₂CF₃ | CO₂CH₃ | H | CF₂CF₂CF₃ |
| CH₂CF₂CF₂CF₃ | CO₂CH₃ | CH₃ | CF₃ |
| CH₂CF₂CF₂CF₃ | CO₂CH₃ | CH₃ | CF₂CF₃ |
| CH₂CF₂CF₂CF₃ | CO₂CH₃ | CH₃ | CF₂CF₂CF₃ |
| CH₂CF₂CF₂CF₃ | CO₂CH₃ | F | CF₃ |
| CH₂CF₂CF₂CF₃ | CO₂CH₃ | F | CF₂CF₃ |
| CH₂CF₂CF₂CF₃ | CO₂CH₃ | F | CF₂CF₂CF₃ |
| CH₂CF₂CF₂CF₃ | CO₂CH₃ | Cl | CF₃ |
| CH₂CF₂CF₂CF₃ | CO₂CH₃ | Cl | CF₂CF₃ |
| CH₂CF₂CF₂CF₃ | CO₂CH₃ | Cl | CF₂CF₂CF₃ |
| CH₂CF₂CF₂CF₃ | CN | H | CF₃ |
| CH₂CF₂CF₂CF₃ | CN | H | CF₂CF₃ |
| CH₂CF₂CF₂CF₃ | CN | H | CF₂CF₂CF₃ |
| CH₂CF₂CF₂CF₃ | CN | CH₃ | CF₃ |
| CH₂CF₂CF₂CF₃ | CN | CH₃ | CF₂CF₃ |
| CH₂CF₂CF₂CF₃ | CN | CH₃ | CF₂CF₂CF₃ |
| CH₂CF₂CF₂CF₃ | CN | CH₂CH₃ | CF₃ |
| CH₂CF₂CF₂CF₃ | CN | CH₂CH₃ | CF₂CF₃ |
| CH₂CF₂CF₂CF₃ | CN | CH₂CH₃ | CF₂CF₂CF₃ |

TABLE 13

| R¹ | R² | R³ | R⁴ |
|---|---|---|---|
| CH₂CF₂CF₂CF₃ | CN | F | CF₃ |
| CH₂CF₂CF₂CF₃ | CN | F | CF₂CF₃ |
| CH₂CF₂CF₂CF₃ | CN | F | CF₂CF₂CF₃ |
| CH₂CF₂CF₂CF₃ | CN | Cl | CF₃ |
| CH₂CF₂CF₂CF₃ | CN | Cl | CF₂CF₃ |
| CH₂CF₂CF₂CF₃ | CN | Cl | CF₂CF₂CF₃ |
| CH₂CF₂CF₂CF₃ | CO₂CH₃ | H | CF₃ |
| CH₂CF₂CF₂CF₃ | CO₂CH₃ | H | CF₂CF₃ |
| CH₂CF₂CF₂CF₃ | CO₂CH₃ | H | CF₂CF₂CF₃ |
| CH₂CF₂CF₂CF₃ | CO₂CH₃ | CH₃ | CF₃ |
| CH₂CF₂CF₂CF₃ | CO₂CH₃ | CH₃ | CF₂CF₃ |
| CH₂CF₂CF₂CF₃ | CO₂CH₃ | CH₃ | CF₂CF₂CF₃ |
| CH₂CF₂CF₂CF₃ | CO₂CH₃ | F | CF₃ |
| CH₂CF₂CF₂CF₃ | CO₂CH₃ | F | CF₂CF₃ |
| CH₂CF₂CF₂CF₃ | CO₂CH₃ | F | CF₂CF₂CF₃ |
| CH₂CF₂CF₂CF₃ | CO₂CH₃ | Cl | CF₃ |
| CH₂CF₂CF₂CF₃ | CO₂CH₃ | Cl | CF₂CF₃ |
| CH₂CF₂CF₂CF₃ | CO₂CH₃ | Cl | CF₂CF₂CF₃ |
| CH₂CF₂CF₂CF₃ | CONH₂ | H | CF₃ |
| CH₂CF₂CF₂CF₃ | CONH₂ | H | CF₂CF₃ |
| CH₂CF₂CF₂CF₃ | CONH₂ | H | CF₂CF₂CF₃ |
| CH₂CF₂CF₂CF₃ | CONH₂ | CH₃ | CF₃ |
| CH₂CF₂CF₂CF₃ | CONH₂ | CH₃ | CF₂CF₃ |
| CH₂CF₂CF₂CF₃ | CONH₂ | CH₃ | CF₂CF₂CF₃ |
| CH₂CF₂CF₂CF₃ | CONH₂ | CH₂CH₃ | CF₃ |
| CH₂CF₂CF₂CF₃ | CONH₂ | CH₂CH₃ | CF₂CF₃ |
| CH₂CF₂CF₂CF₃ | CONH₂ | CH₂CH₃ | CF₂CF₂CF₃ |

TABLE 14

| R¹ | R² | R³ | R⁴ |
|---|---|---|---|
| CH₂CF₂CF₂CF₃ | CONH₂ | F | CF₃ |
| CH₂CF₂CF₂CF₃ | CONH₂ | F | CF₂CF₃ |
| CH₂CF₂CF₂CF₃ | CONH₂ | F | CF₂CF₂CF₃ |
| CH₂CF₂CF₂CF₃ | CONH₂ | Cl | CF₃ |
| CH₂CF₂CF₂CF₃ | CONH₂ | Cl | CF₂CF₃ |
| CH₂CF₂CF₂CF₃ | CONH₂ | Cl | CF₂CF₂CF₃ |
| CH₂CF₂CF₂CF₃ | CONH(CH₃) | H | CF₃ |
| CH₂CF₂CF₂CF₃ | CONH(CH₃) | H | CF₂CF₃ |
| CH₂CF₂CF₂CF₃ | CONH(CH₃) | H | CF₂CF₂CF₃ |

TABLE 14-continued

| R¹ | R² | R³ | R⁴ |
|---|---|---|---|
| CH₂CF₂CF₂CF₃ | CONH(CH₃) | CH₃ | CF₃ |
| CH₂CF₂CF₂CF₃ | CONH(CH₃) | CH₃ | CF₂CF₃ |
| CH₂CF₂CF₂CF₃ | CONH(CH₃) | CH₃ | CF₂CF₂CF₃ |
| CH₂CF₂CF₂CF₃ | CONH(CH₃) | CH₂CH₃ | CF₃ |
| CH₂CF₂CF₂CF₃ | CONH(CH₃) | CH₂CH₃ | CF₂CF₃ |
| CH₂CF₂CF₂CF₃ | CONH(CH₃) | CH₂CH₃ | CF₂CF₂CF₃ |
| CH₂CF₂CF₂CF₃ | CONH(CH₃) | F | CF₃ |
| CH₂CF₂CF₂CF₃ | CONH(CH₃) | F | CF₂CF₃ |
| CH₂CF₂CF₂CF₃ | CONH(CH₃) | F | CF₂CF₂CF₃ |
| CH₂CF₂CF₂CF₃ | CONH(CH₃) | Cl | CF₃ |
| CH₂CF₂CF₂CF₃ | CONH(CH₃) | Cl | CF₂CF₃ |
| CH₂CF₂CF₂CF₃ | CONH(CH₃) | Cl | CF₂CF₂CF₃ |
| CH₂CF₂CF₂CF₃ | CON(CH₃)₂ | H | CF₃ |
| CH₂CF₂CF₂CF₃ | CON(CH₃)₂ | H | CF₂CF₃ |
| CH₂CF₂CF₂CF₃ | CON(CH₃)₂ | H | CF₂CF₂CF₃ |
| CH₂CF₂CF₂CF₃ | CON(CH₃)₂ | CH₃ | CF₃ |
| CH₂CF₂CF₂CF₃ | CON(CH₃)₂ | CH₃ | CF₂CF₃ |
| CH₂CF₂CF₂CF₃ | CON(CH₃)₂ | CH₃ | CF₂CF₂CF₃ |

TABLE 15

| R¹ | R² | R³ | R⁴ |
|---|---|---|---|
| CH₂CF₂CF₂CF₃ | CON(CH₃)₂ | CH₂CH₃ | CF₃ |
| CH₂CF₂CF₂CF₃ | CON(CH₃)₂ | CH₂CH₃ | CF₂CF₃ |
| CH₂CF₂CF₂CF₃ | CON(CH₃)₂ | CH₂CH₃ | CF₂CF₂CF₃ |
| CH₂CF₂CF₂CF₃ | CON(CH₃)₂ | F | CF₃ |
| CH₂CF₂CF₂CF₃ | CON(CH₃)₂ | F | CF₂CF₃ |
| CH₂CF₂CF₂CF₃ | CON(CH₃)₂ | F | CF₂CF₂CF₃ |
| CH₂CF₂CF₂CF₃ | CON(CH₃)₂ | Cl | CF₃ |
| CH₂CF₂CF₂CF₃ | CON(CH₃)₂ | Cl | CF₂CF₃ |
| CH₂CF₂CF₂CF₃ | CON(CH₃)₂ | Cl | CF₂CF₂CF₃ |
| CH₂CH₂CF₂CF₂CF₃ | CN | H | CF₃ |
| CH₂CH₂CF₂CF₂CF₃ | CN | H | CF₂CF₃ |
| CH₂CH₂CF₂CF₂CF₃ | CN | H | CF₂CF₂CF₃ |
| CH₂CH₂CF₂CF₂CF₃ | CN | CH₃ | CF₃ |
| CH₂CH₂CF₂CF₂CF₃ | CN | CH₃ | CF₂CF₃ |
| CH₂CH₂CF₂CF₂CF₃ | CN | CH₃ | CF₂CF₂CF₃ |
| CH₂CH₂CF₂CF₂CF₃ | CN | CH₂CH₃ | CF₃ |
| CH₂CH₂CF₂CF₂CF₃ | CN | CH₂CH₃ | CF₂CF₃ |
| CH₂CH₂CF₂CF₂CF₃ | CN | CH₂CH₃ | CF₂CF₂CF₃ |
| CH₂CH₂CF₂CF₂CF₃ | CN | F | CF₃ |
| CH₂CH₂CF₂CF₂CF₃ | CN | F | CF₂CF₃ |
| CH₂CH₂CF₂CF₂CF₃ | CN | F | CF₂CF₂CF₃ |
| CH₂CH₂CF₂CF₂CF₃ | CN | Cl | CF₃ |
| CH₂CH₂CF₂CF₂CF₃ | CN | Cl | CF₂CF₃ |
| CH₂CH₂CF₂CF₂CF₃ | CN | Cl | CF₂CF₂CF₃ |
| CH₂CH₂CF₂CF₂CF₃ | CO₂CH₃ | H | CF₃ |
| CH₂CH₂CF₂CF₂CF₃ | CO₂CH₃ | H | CF₂CF₃ |
| CH₂CH₂CF₂CF₂CF₃ | CO₂CH₃ | H | CF₂CF₂CF₃ |

TABLE 16

| R¹ | R² | R³ | R⁴ |
|---|---|---|---|
| CH₂CH₂CF₂CF₂CF₃ | CO₂CH₃ | CH₃ | CF₃ |
| CH₂CH₂CF₂CF₂CF₃ | CO₂CH₃ | CH₃ | CF₂CF₃ |
| CH₂CH₂CF₂CF₂CF₃ | CO₂CH₃ | CH₃ | CF₂CF₂CF₃ |
| CH₂CH₂CF₂CF₂CF₃ | CO₂CH₃ | F | CF₃ |
| CH₂CH₂CF₂CF₂CF₃ | CO₂CH₃ | F | CF₂CF₃ |
| CH₂CH₂CF₂CF₂CF₃ | CO₂CH₃ | F | CF₂CF₂CF₃ |
| CH₂CH₂CF₂CF₂CF₃ | CO₂CH₃ | Cl | CF₃ |
| CH₂CH₂CF₂CF₂CF₃ | CO₂CH₃ | Cl | CF₂CF₃ |
| CH₂CH₂CF₂CF₂CF₃ | CO₂CH₃ | Cl | CF₂CF₂CF₃ |
| CH₂CH₂CF₂CF₂CF₃ | CN | H | CF₃ |
| CH₂CH₂CF₂CF₂CF₃ | CN | H | CF₂CF₃ |
| CH₂CH₂CF₂CF₂CF₃ | CN | H | CF₂CF₂CF₃ |
| CH₂CH₂CF₂CF₂CF₃ | CN | CH₃ | CF₃ |
| CH₂CH₂CF₂CF₂CF₃ | CN | CH₃ | CF₂CF₃ |
| CH₂CH₂CF₂CF₂CF₃ | CN | CH₃ | CF₂CF₂CF₃ |
| CH₂CH₂CF₂CF₂CF₃ | CN | CH₂CH₃ | CF₃ |
| CH₂CH₂CF₂CF₂CF₃ | CN | CH₂CH₃ | CF₂CF₃ |
| CH₂CH₂CF₂CF₂CF₃ | CN | CH₂CH₃ | CF₂CF₂CF₃ |

TABLE 16-continued

| R¹ | R² | R³ | R⁴ |
|---|---|---|---|
| $CH_2CH_2CF_2CF_2CF_3$ | CN | F | $CF_3$ |
| $CH_2CH_2CF_2CF_2CF_3$ | CN | F | $CF_2CF_3$ |
| $CH_2CH_2CF_2CF_2CF_3$ | CN | F | $CF_2CF_2CF_3$ |
| $CH_2CH_2CF_2CF_2CF_3$ | CN | Cl | $CF_3$ |
| $CH_2CH_2CF_2CF_2CF_3$ | CN | Cl | $CF_2CF_3$ |
| $CH_2CH_2CF_2CF_2CF_3$ | CN | Cl | $CF_2CF_2CF_3$ |
| $CH_2CH_2CF_2CF_2CF_3$ | $CO_2CH_3$ | H | $CF_3$ |
| $CH_2CH_2CF_2CF_2CF_3$ | $CO_2CH_3$ | H | $CF_2CF_3$ |
| $CH_2CH_2CF_2CF_2CF_3$ | $CO_2CH_3$ | H | $CF_2CF_2CF_3$ |

TABLE 17

| R¹ | R² | R³ | R⁴ |
|---|---|---|---|
| $CH_2CH_2CF_2CF_2CF_3$ | $CO_2CH_3$ | $CH_3$ | $CF_3$ |
| $CH_2CH_2CF_2CF_2CF_3$ | $CO_2CH_3$ | $CH_3$ | $CF_2CF_3$ |
| $CH_2CH_2CF_2CF_2CF_3$ | $CO_2CH_3$ | $CH_3$ | $CF_2CF_2CF_3$ |
| $CH_2CH_2CF_2CF_2CF_3$ | $CO_2CH_3$ | F | $CF_3$ |
| $CH_2CH_2CF_2CF_2CF_3$ | $CO_2CH_3$ | F | $CF_2CF_3$ |
| $CH_2CH_2CF_2CF_2CF_3$ | $CO_2CH_3$ | F | $CF_2CF_2CF_3$ |
| $CH_2CH_2CF_2CF_2CF_3$ | $CO_2CH_3$ | Cl | $CF_3$ |
| $CH_2CH_2CF_2CF_2CF_3$ | $CO_2CH_3$ | Cl | $CF_2CF_3$ |
| $CH_2CH_2CF_2CF_2CF_3$ | $CO_2CH_3$ | Cl | $CF_2CF_2CF_3$ |
| $CH_2CH_2CF_2CF_2CF_3$ | $CONH_2$ | H | $CF_3$ |
| $CH_2CH_2CF_2CF_2CF_3$ | $CONH_2$ | H | $CF_2CF_3$ |
| $CH_2CH_2CF_2CF_2CF_3$ | $CONH_2$ | H | $CF_2CF_2CF_3$ |
| $CH_2CH_2CF_2CF_2CF_3$ | $CONH_2$ | $CH_3$ | $CF_3$ |
| $CH_2CH_2CF_2CF_2CF_3$ | $CONH_2$ | $CH_3$ | $CF_2CF_3$ |
| $CH_2CH_2CF_2CF_2CF_3$ | $CONH_2$ | $CH_3$ | $CF_2CF_2CF_3$ |
| $CH_2CH_2CF_2CF_2CF_3$ | $CONH_2$ | $CH_2CH_3$ | $CF_3$ |
| $CH_2CH_2CF_2CF_2CF_3$ | $CONH_2$ | $CH_2CH_3$ | $CF_2CF_3$ |
| $CH_2CH_2CF_2CF_2CF_3$ | $CONH_2$ | $CH_2CH_3$ | $CF_2CF_2CF_3$ |
| $CH_2CH_2CF_2CF_2CF_3$ | $CONH_2$ | F | $CF_3$ |
| $CH_2CH_2CF_2CF_2CF_3$ | $CONH_2$ | F | $CF_2CF_3$ |
| $CH_2CH_2CF_2CF_2CF_3$ | $CONH_2$ | F | $CF_2CF_2CF_3$ |
| $CH_2CH_2CF_2CF_2CF_3$ | $CONH_2$ | Cl | $CF_3$ |
| $CH_2CH_2CF_2CF_2CF_3$ | $CONH_2$ | Cl | $CF_2CF_3$ |
| $CH_2CH_2CF_2CF_2CF_3$ | $CONH_2$ | Cl | $CF_2CF_2CF_3$ |
| $CH_2CH_2CF_2CF_2CF_3$ | $CONH(CH_3)$ | H | $CF_3$ |
| $CH_2CH_2CF_2CF_2CF_3$ | $CONH(CH_3)$ | H | $CF_2CF_3$ |
| $CH_2CH_2CF_2CF_2CF_3$ | $CONH(CH_3)$ | H | $CF_2CF_2CF_3$ |

TABLE 18

| R¹ | R² | R³ | R⁴ |
|---|---|---|---|
| $CH_2CH_2CF_2CF_2CF_3$ | $CONH(CH_3)$ | $CH_3$ | $CF_3$ |
| $CH_2CH_2CF_2CF_2CF_3$ | $CONH(CH_3)$ | $CH_3$ | $CF_2CF_3$ |
| $CH_2CH_2CF_2CF_2CF_3$ | $CONH(CH_3)$ | $CH_3$ | $CF_2CF_2CF_3$ |
| $CH_2CH_2CF_2CF_2CF_3$ | $CONH(CH_3)$ | $CH_2CH_3$ | $CF_3$ |
| $CH_2CH_2CF_2CF_2CF_3$ | $CONH(CH_3)$ | $CH_2CH_3$ | $CF_2CF_3$ |
| $CH_2CH_2CF_2CF_2CF_3$ | $CONH(CH_3)$ | $CH_2CH_3$ | $CF_2CF_2CF_3$ |
| $CH_2CH_2CF_2CF_2CF_3$ | $CONH(CH_3)$ | F | $CF_3$ |
| $CH_2CH_2CF_2CF_2CF_3$ | $CONH(CH_3)$ | F | $CF_2CF_3$ |
| $CH_2CH_2CF_2CF_2CF_3$ | $CONH(CH_3)$ | F | $CF_2CF_2CF_3$ |
| $CH_2CH_2CF_2CF_2CF_3$ | $CONH(CH_3)$ | F | $CF_3$ |
| $CH_2CH_2CF_2CF_2CF_3$ | $CONH(CH_3)$ | F | $CF_2CF_3$ |
| $CH_2CH_2CF_2CF_2CF_3$ | $CONH(CH_3)$ | F | $CF_2CF_2CF_3$ |
| $CH_2CH_2CF_2CF_2CF_3$ | $CONH(CH_3)$ | Cl | $CF_3$ |
| $CH_2CH_2CF_2CF_2CF_3$ | $CONH(CH_3)$ | Cl | $CF_2CF_3$ |
| $CH_2CH_2CF_2CF_2CF_3$ | $CONH(CH_3)$ | Cl | $CF_2CF_2CF_3$ |
| $CH_2CH_2CF_2CF_2CF_3$ | $CON(CH_3)_2$ | H | $CF_3$ |
| $CH_2CH_2CF_2CF_2CF_3$ | $CON(CH_3)_2$ | H | $CF_2CF_3$ |
| $CH_2CH_2CF_2CF_2CF_3$ | $CON(CH_3)_2$ | H | $CF_2CF_2CF_3$ |
| $CH_2CH_2CF_2CF_2CF_3$ | $CON(CH_3)_2$ | $CH_3$ | $CF_3$ |
| $CH_2CH_2CF_2CF_2CF_3$ | $CON(CH_3)_2$ | $CH_3$ | $CF_2CF_3$ |
| $CH_2CH_2CF_2CF_2CF_3$ | $CON(CH_3)_2$ | $CH_3$ | $CF_2CF_2CF_3$ |
| $CH_2CH_2CF_2CF_2CF_3$ | $CON(CH_3)_2$ | $CH_2CH_3$ | $CF_3$ |
| $CH_2CH_2CF_2CF_2CF_3$ | $CON(CH_3)_2$ | $CH_2CH_3$ | $CF_2CF_3$ |
| $CH_2CH_2CF_2CF_2CF_3$ | $CON(CH_3)_2$ | $CH_2CH_3$ | $CF_2CF_2CF_3$ |
| $CH_2CH_2CF_2CF_2CF_3$ | $CON(CH_3)_2$ | F | $CF_3$ |

TABLE 18-continued

| R¹ | R² | R³ | R⁴ |
|---|---|---|---|
| $CH_2CH_2CF_2CF_2CF_3$ | $CON(CH_3)_2$ | F | $CF_2CF_3$ |
| $CH_2CH_2CF_2CF_2CF_3$ | $CON(CH_3)_2$ | F | $CF_2CF_2CF_3$ |

TABLE 19

| R¹ | R² | R³ | R⁴ |
|---|---|---|---|
| $CH_2CH_2CF_2CF_2CF_3$ | $CON(CH_3)_2$ | Cl | $CF_3$ |
| $CH_2CH_2CF_2CF_2CF_3$ | $CON(CH_3)_2$ | Cl | $CF_2CF_3$ |
| $CH_2CH_2CF_2CF_2CF_3$ | $CON(CH_3)_2$ | Cl | $CF_2CF_2CF_3$ |
| $CH_2CF_2CF_2CF_2CF_2H$ | CN | H | $CF_3$ |
| $CH_2CF_2CF_2CF_2CF_2H$ | CN | H | $CF_2CF_3$ |
| $CH_2CF_2CF_2CF_2CF_2H$ | CN | H | $CF_2CF_2CF_3$ |
| $CH_2CF_2CF_2CF_2CF_2H$ | CN | $CH_3$ | $CF_3$ |
| $CH_2CF_2CF_2CF_2CF_2H$ | CN | $CH_3$ | $CF_2CF_3$ |
| $CH_2CF_2CF_2CF_2CF_2H$ | CN | $CH_3$ | $CF_2CF_2CF_3$ |
| $CH_2CF_2CF_2CF_2CF_2H$ | CN | $CH_2CH_3$ | $CF_3$ |
| $CH_2CF_2CF_2CF_2CF_2H$ | CN | $CH_2CH_3$ | $CF_2CF_3$ |
| $CH_2CF_2CF_2CF_2CF_2H$ | CN | $CH_2CH_3$ | $CF_2CF_2CF_3$ |
| $CH_2CF_2CF_2CF_2CF_2H$ | CN | F | $CF_3$ |
| $CH_2CF_2CF_2CF_2CF_2H$ | CN | F | $CF_2CF_3$ |
| $CH_2CF_2CF_2CF_2CF_2H$ | CN | F | $CF_2CF_2CF_3$ |
| $CH_2CF_2CF_2CF_2CF_2H$ | CN | Cl | $CF_3$ |
| $CH_2CF_2CF_2CF_2CF_2H$ | CN | Cl | $CF_2CF_3$ |
| $CH_2CF_2CF_2CF_2CF_2H$ | CN | Cl | $CF_2CF_2CF_3$ |
| $CH_2CF_2CF_2CF_2CF_2H$ | $CO_2CH_3$ | H | $CF_3$ |
| $CH_2CF_2CF_2CF_2CF_2H$ | $CO_2CH_3$ | H | $CF_2CF_3$ |
| $CH_2CF_2CF_2CF_2CF_2H$ | $CO_2CH_3$ | H | $CF_2CF_2CF_3$ |
| $CH_2CF_2CF_2CF_2CF_2H$ | $CO_2CH_3$ | $CH_3$ | $CF_3$ |
| $CH_2CF_2CF_2CF_2CF_2H$ | $CO_2CH_3$ | $CH_3$ | $CF_2CF_3$ |
| $CH_2CF_2CF_2CF_2CF_2H$ | $CO_2CH_3$ | $CH_3$ | $CF_2CF_2CF_3$ |
| $CH_2CF_2CF_2CF_2CF_2H$ | $CO_2CH_3$ | F | $CF_3$ |
| $CH_2CF_2CF_2CF_2CF_2H$ | $CO_2CH_3$ | F | $CF_2CF_3$ |
| $CH_2CF_2CF_2CF_2CF_2H$ | $CO_2CH_3$ | F | $CF_2CF_2CF_3$ |

TABLE 20

| R¹ | R² | R³ | R⁴ |
|---|---|---|---|
| $CH_2CF_2CF_2CF_2CF_2H$ | $CO_2CH_3$ | Cl | $CF_3$ |
| $CH_2CF_2CF_2CF_2CF_2H$ | $CO_2CH_3$ | Cl | $CF_2CF_3$ |
| $CH_2CF_2CF_2CF_2CF_2H$ | $CO_2CH_3$ | Cl | $CF_2CF_2CF_3$ |
| $CH_2CF_2CF_2CF_2CF_2H$ | CN | H | $CF_3$ |
| $CH_2CF_2CF_2CF_2CF_2H$ | CN | H | $CF_2CF_3$ |
| $CH_2CF_2CF_2CF_2CF_2H$ | CN | H | $CF_2CF_2CF_3$ |
| $CH_2CF_2CF_2CF_2CF_2H$ | CN | $CH_3$ | $CF_3$ |
| $CH_2CF_2CF_2CF_2CF_2H$ | CN | $CH_3$ | $CF_2CF_3$ |
| $CH_2CF_2CF_2CF_2CF_2H$ | CN | $CH_3$ | $CF_2CF_2CF_3$ |
| $CH_2CF_2CF_2CF_2CF_2H$ | CN | $CH_2CH_3$ | $CF_3$ |
| $CH_2CF_2CF_2CF_2CF_2H$ | CN | $CH_2CH_3$ | $CF_2CF_3$ |
| $CH_2CF_2CF_2CF_2CF_2H$ | CN | $CH_2CH_3$ | $CF_2CF_2CF_3$ |
| $CH_2CF_2CF_2CF_2CF_2H$ | CN | F | $CF_3$ |
| $CH_2CF_2CF_2CF_2CF_2H$ | CN | F | $CF_2CF_3$ |
| $CH_2CF_2CF_2CF_2CF_2H$ | CN | F | $CF_2CF_2CF_3$ |
| $CH_2CF_2CF_2CF_2CF_2H$ | CN | Cl | $CF_3$ |
| $CH_2CF_2CF_2CF_2CF_2H$ | CN | Cl | $CF_2CF_3$ |
| $CH_2CF_2CF_2CF_2CF_2H$ | CN | Cl | $CF_2CF_2CF_3$ |
| $CH_2CF_2CF_2CF_2CF_2H$ | $CO_2CH_3$ | H | $CF_3$ |
| $CH_2CF_2CF_2CF_2CF_2H$ | $CO_2CH_3$ | H | $CF_2CF_3$ |
| $CH_2CF_2CF_2CF_2CF_2H$ | $CO_2CH_3$ | H | $CF_2CF_2CF_3$ |
| $CH_2CF_2CF_2CF_2CF_2H$ | $CO_2CH_3$ | $CH_3$ | $CF_3$ |
| $CH_2CF_2CF_2CF_2CF_2H$ | $CO_2CH_3$ | $CH_3$ | $CF_2CF_3$ |
| $CH_2CF_2CF_2CF_2CF_2H$ | $CO_2CH_3$ | $CH_3$ | $CF_2CF_2CF_3$ |
| $CH_2CF_2CF_2CF_2CF_2H$ | $CO_2CH_3$ | F | $CF_3$ |
| $CH_2CF_2CF_2CF_2CF_2H$ | $CO_2CH_3$ | F | $CF_2CF_3$ |
| $CH_2CF_2CF_2CF_2CF_2H$ | $CO_2CH_3$ | F | $CF_2CF_2CF_3$ |

TABLE 21

| R¹ | R² | R³ | R⁴ |
|---|---|---|---|
| CH₂CF₂CF₂CF₂CF₂H | CO₂CH₃ | Cl | CF₃ |
| CH₂CF₂CF₂CF₂CF₂H | CO₂CH₃ | Cl | CF₂CF₃ |
| CH₂CF₂CF₂CF₂CF₂H | CO₂CH₃ | Cl | CF₂CF₂CF₃ |
| CH₂CF₂CF₂CF₂CF₂H | CONH₂ | H | CF₃ |
| CH₂CF₂CF₂CF₂CF₂H | CONH₂ | H | CF₂CF₃ |
| CH₂CF₂CF₂CF₂CF₂H | CONH₂ | H | CF₂CF₂CF₃ |
| CH₂CF₂CF₂CF₂CF₂H | CONH₂ | CH₃ | CF₃ |
| CH₂CF₂CF₂CF₂CF₂H | CONH₂ | CH₃ | CF₂CF₃ |
| CH₂CF₂CF₂CF₂CF₂H | CONH₂ | CH₃ | CF₂CF₂CF₃ |
| CH₂CF₂CF₂CF₂CF₂H | CONH₂ | CH₂CH₃ | CF₃ |
| CH₂CF₂CF₂CF₂CF₂H | CONH₂ | CH₂CH₃ | CF₂CF₃ |
| CH₂CF₂CF₂CF₂CF₂H | CONH₂ | CH₂CH₃ | CF₂CF₂CF₃ |
| CH₂CF₂CF₂CF₂CF₂H | CONH₂ | F | CF₃ |
| CH₂CF₂CF₂CF₂CF₂H | CONH₂ | F | CF₂CF₃ |
| CH₂CF₂CF₂CF₂CF₂H | CONH₂ | F | CF₂CF₂CF₃ |
| CH₂CF₂CF₂CF₂CF₂H | CONH₂ | Cl | CF₃ |
| CH₂CF₂CF₂CF₂CF₂H | CONH₂ | Cl | CF₂CF₃ |
| CH₂CF₂CF₂CF₂CF₂H | CONH₂ | Cl | CF₂CF₂CF₃ |
| CH₂CF₂CF₂CF₂CF₂H | CONH(CH₃) | H | CF₃ |
| CH₂CF₂CF₂CF₂CF₂H | CONH(CH₃) | H | CF₂CF₃ |
| CH₂CF₂CF₂CF₂CF₂H | CONH(CH₃) | H | CF₂CF₂CF₃ |
| CH₂CF₂CF₂CF₂CF₂H | CONH(CH₃) | CH₃ | CF₃ |
| CH₂CF₂CF₂CF₂CF₂H | CONH(CH₃) | CH₃ | CF₂CF₃ |
| CH₂CF₂CF₂CF₂CF₂H | CONH(CH₃) | CH₃ | CF₂CF₂CF₃ |
| CH₂CF₂CF₂CF₂CF₂H | CONH(CH₃) | CH₂CH₃ | CF₃ |
| CH₂CF₂CF₂CF₂CF₂H | CONH(CH₃) | CH₂CH₃ | CF₂CF₃ |
| CH₂CF₂CF₂CF₂CF₂H | CONH(CH₃) | CH₂CH₃ | CF₂CF₂CF₃ |

TABLE 22

| R¹ | R² | R³ | R⁴ |
|---|---|---|---|
| CH₂CF₂CF₂CF₂CF₂H | CONH(CH₃) | F | CF₃ |
| CH₂CF₂CF₂CF₂CF₂H | CONH(CH₃) | F | CF₂CF₃ |
| CH₂CF₂CF₂CF₂CF₂H | CONH(CH₃) | F | CF₂CF₂CF₃ |
| CH₂CF₂CF₂CF₂CF₂H | CONH(CH₃) | Cl | CF₃ |
| CH₂CF₂CF₂CF₂CF₂H | CONH(CH₃) | Cl | CF₂CF₃ |
| CH₂CF₂CF₂CF₂CF₂H | CONH(CH₃) | Cl | CF₂CF₂CF₃ |
| CH₂CF₂CF₂CF₂CF₂H | CON(CH₃)₂ | H | CF₃ |
| CH₂CF₂CF₂CF₂CF₂H | CON(CH₃)₂ | H | CF₂CF₃ |
| CH₂CF₂CF₂CF₂CF₂H | CON(CH₃)₂ | H | CF₂CF₂CF₃ |
| CH₂CF₂CF₂CF₂CF₂H | CON(CH₃)₂ | CH₃ | CF₃ |
| CH₂CF₂CF₂CF₂CF₂H | CON(CH₃)₂ | CH₃ | CF₂CF₃ |
| CH₂CF₂CF₂CF₂CF₂H | CON(CH₃)₂ | CH₃ | CF₂CF₂CF₃ |
| CH₂CF₂CF₂CF₂CF₂H | CON(CH₃)₂ | CH₂CH₃ | CF₃ |
| CH₂CF₂CF₂CF₂CF₂H | CON(CH₃)₂ | CH₂CH₃ | CF₂CF₃ |
| CH₂CF₂CF₂CF₂CF₂H | CON(CH₃)₂ | CH₂CH₃ | CF₂CF₂CF₃ |
| CH₂CF₂CF₂CF₂CF₂H | CON(CH₃)₂ | F | CF₃ |
| CH₂CF₂CF₂CF₂CF₂H | CON(CH₃)₂ | F | CF₂CF₃ |
| CH₂CF₂CF₂CF₂CF₂H | CON(CH₃)₂ | F | CF₂CF₂CF₃ |
| CH₂CF₂CF₂CF₂CF₂H | CON(CH₃)₂ | Cl | CF₃ |
| CH₂CF₂CF₂CF₂CF₂H | CON(CH₃)₂ | Cl | CF₂CF₃ |
| CH₂CF₂CF₂CF₂CF₂H | CON(CH₃)₂ | Cl | CF₂CF₂CF₃ |
| CH₂CH₂CF₂CF₂CF₂CF₃ | CN | H | CF₃ |
| CH₂CH₂CF₂CF₂CF₂CF₃ | CN | H | CF₂CF₃ |
| CH₂CH₂CF₂CF₂CF₂CF₃ | CN | H | CF₂CF₂CF₃ |
| CH₂CH₂CF₂CF₂CF₂CF₃ | CN | CH₃ | CF₃ |
| CH₂CH₂CF₂CF₂CF₂CF₃ | CN | CH₃ | CF₂CF₃ |
| CH₂CH₂CF₂CF₂CF₂CF₃ | CN | CH₃ | CF₂CF₂CF₃ |

TABLE 23

| R¹ | R² | R³ | R⁴ |
|---|---|---|---|
| CH₂CH₂CF₂CF₂CF₂CF₃ | CN | CH₂CH₃ | CF₃ |
| CH₂CH₂CF₂CF₂CF₂CF₃ | CN | CH₂CH₃ | CF₂CF₃ |
| CH₂CH₂CF₂CF₂CF₂CF₃ | CN | CH₂CH₃ | CF₂CF₂CF₃ |
| CH₂CH₂CF₂CF₂CF₂CF₃ | CN | F | CF₃ |
| CH₂CH₂CF₂CF₂CF₂CF₃ | CN | F | CF₂CF₃ |
| CH₂CH₂CF₂CF₂CF₂CF₃ | CN | F | CF₂CF₂CF₃ |
| CH₂CH₂CF₂CF₂CF₂CF₃ | CN | Cl | CF₃ |
| CH₂CH₂CF₂CF₂CF₂CF₃ | CN | Cl | CF₂CF₃ |
| CH₂CH₂CF₂CF₂CF₂CF₃ | CN | Cl | CF₂CF₂CF₃ |

TABLE 23-continued

| R¹ | R² | R³ | R⁴ |
|---|---|---|---|
| CH₂CH₂CF₂CF₂CF₂CF₃ | CO₂CH₃ | H | CF₃ |
| CH₂CH₂CF₂CF₂CF₂CF₃ | CO₂CH₃ | H | CF₂CF₃ |
| CH₂CH₂CF₂CF₂CF₂CF₃ | CO₂CH₃ | H | CF₂CF₂CF₃ |
| CH₂CH₂CF₂CF₂CF₂CF₃ | CO₂CH₃ | CH₃ | CF₃ |
| CH₂CH₂CF₂CF₂CF₂CF₃ | CO₂CH₃ | CH₃ | CF₂CF₃ |
| CH₂CH₂CF₂CF₂CF₂CF₃ | CO₂CH₃ | CH₃ | CF₂CF₂CF₃ |
| CH₂CH₂CF₂CF₂CF₂CF₃ | CO₂CH₃ | F | CF₃ |
| CH₂CH₂CF₂CF₂CF₂CF₃ | CO₂CH₃ | F | CF₂CF₃ |
| CH₂CH₂CF₂CF₂CF₂CF₃ | CO₂CH₃ | F | CF₂CF₂CF₃ |
| CH₂CH₂CF₂CF₂CF₂CF₃ | CO₂CH₃ | Cl | CF₃ |
| CH₂CH₂CF₂CF₂CF₂CF₃ | CO₂CH₃ | Cl | CF₂CF₃ |
| CH₂CH₂CF₂CF₂CF₂CF₃ | CO₂CH₃ | Cl | CF₂CF₂CF₃ |
| CH₂CH₂CF₂CF₂CF₂CF₃ | CN | H | CF₃ |
| CH₂CH₂CF₂CF₂CF₂CF₃ | CN | H | CF₂CF₃ |
| CH₂CH₂CF₂CF₂CF₂CF₃ | CN | H | CF₂CF₂CF₃ |
| CH₂CH₂CF₂CF₂CF₂CF₃ | CN | CH₃ | CF₃ |
| CH₂CH₂CF₂CF₂CF₂CF₃ | CN | CH₃ | CF₂CF₃ |
| CH₂CH₂CF₂CF₂CF₂CF₃ | CN | CH₃ | CF₂CF₂CF₃ |

TABLE 24

| R¹ | R² | R³ | R⁴ |
|---|---|---|---|
| CH₂CH₂CF₂CF₂CF₂CF₃ | CN | CH₂CH₃ | CF₃ |
| CH₂CH₂CF₂CF₂CF₂CF₃ | CN | CH₂CH₃ | CF₂CF₃ |
| CH₂CH₂CF₂CF₂CF₂CF₃ | CN | CH₂CH₃ | CF₂CF₂CF₃ |
| CH₂CH₂CF₂CF₂CF₂CF₃ | CN | F | CF₃ |
| CH₂CH₂CF₂CF₂CF₂CF₃ | CN | F | CF₂CF₃ |
| CH₂CH₂CF₂CF₂CF₂CF₃ | CN | F | CF₂CF₂CF₃ |
| CH₂CH₂CF₂CF₂CF₂CF₃ | CN | Cl | CF₃ |
| CH₂CH₂CF₂CF₂CF₂CF₃ | CN | Cl | CF₂CF₃ |
| CH₂CH₂CF₂CF₂CF₂CF₃ | CN | Cl | CF₂CF₂CF₃ |
| CH₂CH₂CF₂CF₂CF₂CF₃ | CO₂CH₃ | H | CF₃ |
| CH₂CH₂CF₂CF₂CF₂CF₃ | CO₂CH₃ | H | CF₂CF₃ |
| CH₂CH₂CF₂CF₂CF₂CF₃ | CO₂CH₃ | H | CF₂CF₂CF₃ |
| CH₂CH₂CF₂CF₂CF₂CF₃ | CO₂CH₃ | CH₃ | CF₃ |
| CH₂CH₂CF₂CF₂CF₂CF₃ | CO₂CH₃ | CH₃ | CF₂CF₃ |
| CH₂CH₂CF₂CF₂CF₂CF₃ | CO₂CH₃ | CH₃ | CF₂CF₂CF₃ |
| CH₂CH₂CF₂CF₂CF₂CF₃ | CO₂CH₃ | F | CF₃ |
| CH₂CH₂CF₂CF₂CF₂CF₃ | CO₂CH₃ | F | CF₂CF₃ |
| CH₂CH₂CF₂CF₂CF₂CF₃ | CO₂CH₃ | F | CF₂CF₂CF₃ |
| CH₂CH₂CF₂CF₂CF₂CF₃ | CO₂CH₃ | Cl | CF₃ |
| CH₂CH₂CF₂CF₂CF₂CF₃ | CO₂CH₃ | Cl | CF₂CF₃ |
| CH₂CH₂CF₂CF₂CF₂CF₃ | CO₂CH₃ | Cl | CF₂CF₂CF₃ |
| CH₂CH₂CF₂CF₂CF₂CF₃ | CONH₂ | H | CF₃ |
| CH₂CH₂CF₂CF₂CF₂CF₃ | CONH₂ | H | CF₂CF₃ |
| CH₂CH₂CF₂CF₂CF₂CF₃ | CONH₂ | H | CF₂CF₂CF₃ |
| CH₂CH₂CF₂CF₂CF₂CF₃ | CONH₂ | CH₃ | CF₃ |
| CH₂CH₂CF₂CF₂CF₂CF₃ | CONH₂ | CH₃ | CF₂CF₃ |
| CH₂CH₂CF₂CF₂CF₂CF₃ | CONH₂ | CH₃ | CF₂CF₂CF₃ |

TABLE 25

| R¹ | R² | R³ | R⁴ |
|---|---|---|---|
| CH₂CH₂CF₂CF₂CF₂CF₃ | CONH₂ | CH₂CH₃ | CF₃ |
| CH₂CH₂CF₂CF₂CF₂CF₃ | CONH₂ | CH₂CH₃ | CF₂CF₃ |
| CH₂CH₂CF₂CF₂CF₂CF₃ | CONH₂ | CH₂CH₃ | CF₂CF₂CF₃ |
| CH₂CH₂CF₂CF₂CF₂CF₃ | CONH₂ | F | CF₃ |
| CH₂CH₂CF₂CF₂CF₂CF₃ | CONH₂ | F | CF₂CF₃ |
| CH₂CH₂CF₂CF₂CF₂CF₃ | CONH₂ | F | CF₂CF₂CF₃ |
| CH₂CH₂CF₂CF₂CF₂CF₃ | CONH₂ | Cl | CF₃ |
| CH₂CH₂CF₂CF₂CF₂CF₃ | CONH₂ | Cl | CF₂CF₃ |
| CH₂CH₂CF₂CF₂CF₂CF₃ | CONH₂ | Cl | CF₂CF₂CF₃ |
| CH₂CH₂CF₂CF₂CF₂CF₃ | CONH(CH₃) | H | CF₃ |
| CH₂CH₂CF₂CF₂CF₂CF₃ | CONH(CH₃) | H | CF₂CF₃ |
| CH₂CH₂CF₂CF₂CF₂CF₃ | CONH(CH₃) | H | CF₂CF₂CF₃ |
| CH₂CH₂CF₂CF₂CF₂CF₃ | CONH(CH₃) | CH₃ | CF₃ |
| CH₂CH₂CF₂CF₂CF₂CF₃ | CONH(CH₃) | CH₃ | CF₂CF₃ |
| CH₂CH₂CF₂CF₂CF₂CF₃ | CONH(CH₃) | CH₃ | CF₂CF₂CF₃ |
| CH₂CH₂CF₂CF₂CF₂CF₃ | CONH(CH₃) | CH₂CH₃ | CF₃ |
| CH₂CH₂CF₂CF₂CF₂CF₃ | CONH(CH₃) | CH₂CH₃ | CF₂CF₃ |
| CH₂CH₂CF₂CF₂CF₂CF₃ | CONH(CH₃) | CH₂CH₃ | CF₂CF₂CF₃ |

TABLE 25-continued

| R¹ | R² | R³ | R⁴ |
| --- | --- | --- | --- |
| $CH_2CH_2CF_2CF_2CF_2CF_3$ | $CONH(CH_3)$ | F | $CF_3$ |
| $CH_2CH_2CF_2CF_2CF_2CF_3$ | $CONH(CH_3)$ | F | $CF_2CF_3$ |
| $CH_2CH_2CF_2CF_2CF_2CF_3$ | $CONH(CH_3)$ | F | $CF_2CF_2CF_3$ |
| $CH_2CH_2CF_2CF_2CF_2CF_3$ | $CONH(CH_3)$ | Cl | $CF_3$ |
| $CH_2CH_2CF_2CF_2CF_2CF_3$ | $CONH(CH_3)$ | Cl | $CF_2CF_3$ |
| $CH_2CH_2CF_2CF_2CF_2CF_3$ | $CONH(CH_3)$ | Cl | $CF_2CF_2CF_3$ |
| $CH_2CH_2CF_2CF_2CF_2CF_3$ | $CON(CH_3)_2$ | H | $CF_3$ |
| $CH_2CH_2CF_2CF_2CF_2CF_3$ | $CON(CH_3)_2$ | H | $CF_2CF_3$ |
| $CH_2CH_2CF_2CF_2CF_2CF_3$ | $CON(CH_3)_2$ | H | $CF_2CF_2CF_3$ |

TABLE 26

| R¹ | R² | R³ | R⁴ |
| --- | --- | --- | --- |
| $CH_2CH_2CF_2CF_2CF_2CF_3$ | $CON(CH_3)_2$ | $CH_3$ | $CF_3$ |
| $CH_2CH_2CF_2CF_2CF_2CF_3$ | $CON(CH_3)_2$ | $CH_3$ | $CF_2CF_3$ |
| $CH_2CH_2CF_2CF_2CF_2CF_3$ | $CON(CH_3)_2$ | $CH_3$ | $CF_2CF_2CF_3$ |
| $CH_2CH_2CF_2CF_2CF_2CF_3$ | $CON(CH_3)_2$ | $CH_2CH_3$ | $CF_3$ |
| $CH_2CH_2CF_2CF_2CF_2CF_3$ | $CON(CH_3)_2$ | $CH_2CH_3$ | $CF_2CF_3$ |
| $CH_2CH_2CF_2CF_2CF_2CF_3$ | $CON(CH_3)_2$ | $CH_2CH_3$ | $CF_2CF_2CF_3$ |
| $CH_2CH_2CF_2CF_2CF_2CF_3$ | $CON(CH_3)_2$ | F | $CF_3$ |
| $CH_2CH_2CF_2CF_2CF_2CF_3$ | $CON(CH_3)_2$ | F | $CF_2CF_3$ |
| $CH_2CH_2CF_2CF_2CF_2CF_3$ | $CON(CH_3)_2$ | F | $CF_2CF_2CF_3$ |
| $CH_2CH_2CF_2CF_2CF_2CF_3$ | $CON(CH_3)_2$ | Cl | $CF_3$ |
| $CH_2CH_2CF_2CF_2CF_2CF_3$ | $CON(CH_3)_2$ | Cl | $CF_2CF_3$ |
| $CH_2CH_2CF_2CF_2CF_2CF_3$ | $CON(CH_3)_2$ | Cl | $CF_2CF_2CF_3$ |
| $CH_2CH_2CF_2CF_3$ | $C(S)OCH_3$ | H | $CF_3$ |
| $CH_2CH_2CF_2CF_3$ | $C(S)OCH_3$ | H | $CF_2CF_3$ |
| $CH_2CH_2CF_2CF_3$ | $C(S)OCH_3$ | H | $CF_2CF_2CF_3$ |
| $CH_2CH_2CF_2CF_3$ | $C(S)OCH_3$ | $CH_3$ | $CF_3$ |
| $CH_2CH_2CF_2CF_3$ | $C(S)OCH_3$ | $CH_3$ | $CF_2CF_3$ |
| $CH_2CH_2CF_2CF_3$ | $C(S)OCH_3$ | $CH_3$ | $CF_2CF_2CF_3$ |
| $CH_2CH_2CF_2CF_3$ | $C(S)OCH_3$ | F | $CF_3$ |
| $CH_2CH_2CF_2CF_3$ | $C(S)OCH_3$ | F | $CF_2CF_3$ |
| $CH_2CH_2CF_2CF_3$ | $C(S)OCH_3$ | F | $CF_2CF_2CF_3$ |
| $CH_2CH_2CF_2CF_3$ | $C(S)OCH_3$ | Cl | $CF_3$ |
| $CH_2CH_2CF_2CF_3$ | $C(S)OCH_3$ | Cl | $CF_2CF_3$ |
| $CH_2CH_2CF_2CF_3$ | $C(S)OCH_3$ | Cl | $CF_2CF_2CF_3$ |
| $CH_2CH_2CF_2CF_3$ | $C(S)NH_2$ | H | $CF_3$ |
| $CH_2CH_2CF_2CF_3$ | $C(S)NH_2$ | H | $CF_2CF_3$ |
| $CH_2CH_2CF_2CF_3$ | $C(S)NH_2$ | H | $CF_2CF_2CF_3$ |

TABLE 27

| R¹ | R² | R³ | R⁴ |
| --- | --- | --- | --- |
| $CH_2CH_2CF_2CF_3$ | $C(S)NH_2$ | $CH_3$ | $CF_3$ |
| $CH_2CH_2CF_2CF_3$ | $C(S)NH_2$ | $CH_3$ | $CF_2CF_3$ |
| $CH_2CH_2CF_2CF_3$ | $C(S)NH_2$ | $CH_3$ | $CF_2CF_2CF_3$ |
| $CH_2CH_2CF_2CF_3$ | $C(S)NH_2$ | $CH_2CH_3$ | $CF_3$ |
| $CH_2CH_2CF_2CF_3$ | $C(S)NH_2$ | $CH_2CH_3$ | $CF_2CF_3$ |
| $CH_2CH_2CF_2CF_3$ | $C(S)NH_2$ | $CH_2CH_3$ | $CF_2CF_2CF_3$ |
| $CH_2CH_2CF_2CF_3$ | $C(S)NH_2$ | F | $CF_3$ |
| $CH_2CH_2CF_2CF_3$ | $C(S)NH_2$ | F | $CF_2CF_3$ |
| $CH_2CH_2CF_2CF_3$ | $C(S)NH_2$ | F | $CF_2CF_2CF_3$ |
| $CH_2CH_2CF_2CF_3$ | $C(S)NH_2$ | Cl | $CF_3$ |
| $CH_2CH_2CF_2CF_3$ | $C(S)NH_2$ | Cl | $CF_2CF_3$ |
| $CH_2CH_2CF_2CF_3$ | $C(S)NH_2$ | Cl | $CF_2CF_2CF_3$ |
| $CH_2CH_2CF_2CF_3$ | $C(S)NH(CH_3)$ | H | $CF_3$ |
| $CH_2CH_2CF_2CF_3$ | $C(S)NH(CH_3)$ | H | $CF_2CF_3$ |
| $CH_2CH_2CF_2CF_3$ | $C(S)NH(CH_3)$ | H | $CF_2CF_2CF_3$ |
| $CH_2CH_2CF_2CF_3$ | $C(S)NH(CH_3)$ | $CH_3$ | $CF_3$ |
| $CH_2CH_2CF_2CF_3$ | $C(S)NH(CH_3)$ | $CH_3$ | $CF_2CF_3$ |
| $CH_2CH_2CF_2CF_3$ | $C(S)NH(CH_3)$ | $CH_3$ | $CF_2CF_2CF_3$ |
| $CH_2CH_2CF_2CF_3$ | $C(S)NH(CH_3)$ | $CH_2CH_3$ | $CF_3$ |
| $CH_2CH_2CF_2CF_3$ | $C(S)NH(CH_3)$ | $CH_2CH_3$ | $CF_2CF_3$ |
| $CH_2CH_2CF_2CF_3$ | $C(S)NH(CH_3)$ | $CH_2CH_3$ | $CF_2CF_2CF_3$ |
| $CH_2CH_2CF_2CF_3$ | $C(S)NH(CH_3)$ | F | $CF_3$ |
| $CH_2CH_2CF_2CF_3$ | $C(S)NH(CH_3)$ | F | $CF_2CF_3$ |
| $CH_2CH_2CF_2CF_3$ | $C(S)NH(CH_3)$ | F | $CF_2CF_2CF_3$ |
| $CH_2CH_2CF_2CF_3$ | $C(S)NH(CH_3)$ | Cl | $CF_3$ |

TABLE 27-continued

| R¹ | R² | R³ | R⁴ |
| --- | --- | --- | --- |
| $CH_2CH_2CF_2CF_3$ | $C(S)NH(CH_3)$ | Cl | $CF_2CF_3$ |
| $CH_2CH_2CF_2CF_3$ | $C(S)NH(CH_3)$ | Cl | $CF_2CF_2CF_3$ |

TABLE 28

| R¹ | R² | R³ | R⁴ |
| --- | --- | --- | --- |
| $CH_2CH_2CF_2CF_3$ | $C(S)N(CH_3)_2$ | H | $CF_3$ |
| $CH_2CH_2CF_2CF_3$ | $C(S)N(CH_3)_2$ | H | $CF_2CF_3$ |
| $CH_2CH_2CF_2CF_3$ | $C(S)N(CH_3)_2$ | H | $CF_2CF_2CF_3$ |
| $CH_2CH_2CF_2CF_3$ | $C(S)N(CH_3)_2$ | $CH_3$ | $CF_3$ |
| $CH_2CH_2CF_2CF_3$ | $C(S)N(CH_3)_2$ | $CH_3$ | $CF_2CF_3$ |
| $CH_2CH_2CF_2CF_3$ | $C(S)N(CH_3)_2$ | $CH_3$ | $CF_2CF_2CF_3$ |
| $CH_2CH_2CF_2CF_3$ | $C(S)N(CH_3)_2$ | $CH_2CH_3$ | $CF_3$ |
| $CH_2CH_2CF_2CF_3$ | $C(S)N(CH_3)_2$ | $CH_2CH_3$ | $CF_2CF_3$ |
| $CH_2CH_2CF_2CF_3$ | $C(S)N(CH_3)_2$ | $CH_2CH_3$ | $CF_2CF_2CF_3$ |
| $CH_2CH_2CF_2CF_3$ | $C(S)N(CH_3)_2$ | F | $CF_3$ |
| $CH_2CH_2CF_2CF_3$ | $C(S)N(CH_3)_2$ | F | $CF_2CF_3$ |
| $CH_2CH_2CF_2CF_3$ | $C(S)N(CH_3)_2$ | F | $CF_2CF_2CF_3$ |
| $CH_2CH_2CF_2CF_3$ | $C(S)N(CH_3)_2$ | Cl | $CF_3$ |
| $CH_2CH_2CF_2CF_3$ | $C(S)N(CH_3)_2$ | Cl | $CF_2CF_3$ |
| $CH_2CH_2CF_2CF_3$ | $C(S)N(CH_3)_2$ | Cl | $CF_2CF_2CF_3$ |
| $CH_2CH_2CF_3$ | $C(S)OCH_3$ | H | $CF_3$ |
| $CH_2CH_2CF_3$ | $C(S)OCH_3$ | H | $CF_2CF_3$ |
| $CH_2CH_2CF_3$ | $C(S)OCH_3$ | H | $CF_2CF_2CF_3$ |
| $CH_2CH_2CF_3$ | $C(S)OCH_3$ | $CH_3$ | $CF_3$ |
| $CH_2CH_2CF_3$ | $C(S)OCH_3$ | $CH_3$ | $CF_2CF_3$ |
| $CH_2CH_2CF_3$ | $C(S)OCH_3$ | $CH_3$ | $CF_2CF_2CF_3$ |
| $CH_2CH_2CF_3$ | $C(S)OCH_3$ | F | $CF_3$ |
| $CH_2CH_2CF_3$ | $C(S)OCH_3$ | F | $CF_2CF_3$ |
| $CH_2CH_2CF_3$ | $C(S)OCH_3$ | F | $CF_2CF_2CF_3$ |
| $CH_2CH_2CF_3$ | $C(S)OCH_3$ | Cl | $CF_3$ |
| $CH_2CH_2CF_3$ | $C(S)OCH_3$ | Cl | $CF_2CF_3$ |
| $CH_2CH_2CF_3$ | $C(S)OCH_3$ | Cl | $CF_2CF_2CF_3$ |

TABLE 29

| R¹ | R² | R³ | R⁴ |
| --- | --- | --- | --- |
| $CH_2CH_2CF_3$ | $C(S)NH_2$ | H | $CF_3$ |
| $CH_2CH_2CF_3$ | $C(S)NH_2$ | H | $CF_2CF_3$ |
| $CH_2CH_2CF_3$ | $C(S)NH_2$ | H | $CF_2CF_2CF_3$ |
| $CH_2CH_2CF_3$ | $C(S)NH_2$ | $CH_3$ | $CF_3$ |
| $CH_2CH_2CF_3$ | $C(S)NH_2$ | $CH_3$ | $CF_2CF_3$ |
| $CH_2CH_2CF_3$ | $C(S)NH_2$ | $CH_3$ | $CF_2CF_2CF_3$ |
| $CH_2CH_2CF_3$ | $C(S)NH_2$ | $CH_2CH_3$ | $CF_3$ |
| $CH_2CH_2CF_3$ | $C(S)NH_2$ | $CH_2CH_3$ | $CF_2CF_3$ |
| $CH_2CH_2CF_3$ | $C(S)NH_2$ | $CH_2CH_3$ | $CF_2CF_2CF_3$ |
| $CH_2CH_2CF_3$ | $C(S)NH_2$ | F | $CF_3$ |
| $CH_2CH_2CF_3$ | $C(S)NH_2$ | F | $CF_2CF_3$ |
| $CH_2CH_2CF_3$ | $C(S)NH_2$ | F | $CF_2CF_2CF_3$ |
| $CH_2CH_2CF_3$ | $C(S)NH_2$ | Cl | $CF_3$ |
| $CH_2CH_2CF_3$ | $C(S)NH_2$ | Cl | $CF_2CF_3$ |
| $CH_2CH_2CF_3$ | $C(S)NH_2$ | Cl | $CF_2CF_2CF_3$ |
| $CH_2CH_2CF_3$ | $C(S)NH(CH_3)$ | H | $CF_3$ |
| $CH_2CH_2CF_3$ | $C(S)NH(CH_3)$ | H | $CF_2CF_3$ |
| $CH_2CH_2CF_3$ | $C(S)NH(CH_3)$ | H | $CF_2CF_2CF_3$ |
| $CH_2CH_2CF_3$ | $C(S)NH(CH_3)$ | $CH_3$ | $CF_3$ |
| $CH_2CH_2CF_3$ | $C(S)NH(CH_3)$ | $CH_3$ | $CF_2CF_3$ |
| $CH_2CH_2CF_3$ | $C(S)NH(CH_3)$ | $CH_3$ | $CF_2CF_2CF_3$ |
| $CH_2CH_2CF_3$ | $C(S)NH(CH_3)$ | $CH_2CH_3$ | $CF_3$ |
| $CH_2CH_2CF_3$ | $C(S)NH(CH_3)$ | $CH_2CH_3$ | $CF_2CF_3$ |
| $CH_2CH_2CF_3$ | $C(S)NH(CH_3)$ | $CH_2CH_3$ | $CF_2CF_2CF_3$ |
| $CH_2CH_2CF_3$ | $C(S)NH(CH_3)$ | F | $CF_3$ |
| $CH_2CH_2CF_3$ | $C(S)NH(CH_3)$ | F | $CF_2CF_3$ |
| $CH_2CH_2CF_3$ | $C(S)NH(CH_3)$ | F | $CF_2CF_2CF_3$ |

TABLE 30

| R¹ | R² | R³ | R⁴ |
|---|---|---|---|
| CH₂CH₂CF₃ | C(S)NH(CH₃) | Cl | CF₃ |
| CH₂CH₂CF₃ | C(S)NH(CH₃) | Cl | CF₂CF₃ |
| CH₂CH₂CF₃ | C(S)NH(CH₃) | Cl | CF₂CF₂CF₃ |
| CH₂CH₂CF₃ | C(S)N(CH₃)₂ | H | CF₃ |
| CH₂CH₂CF₃ | C(S)N(CH₃)₂ | H | CF₂CF₃ |
| CH₂CH₂CF₃ | C(S)N(CH₃)₂ | H | CF₂CF₂CF₃ |
| CH₂CH₂CF₃ | C(S)N(CH₃)₂ | CH₃ | CF₃ |
| CH₂CH₂CF₃ | C(S)N(CH₃)₂ | CH₃ | CF₂CF₃ |
| CH₂CH₂CF₃ | C(S)N(CH₃)₂ | CH₃ | CF₂CF₂CF₃ |
| CH₂CH₂CF₃ | C(S)N(CH₃)₂ | CH₂CH₃ | CF₃ |
| CH₂CH₂CF₃ | C(S)N(CH₃)₂ | CH₂CH₃ | CF₂CF₃ |
| CH₂CH₂CF₃ | C(S)N(CH₃)₂ | CH₂CH₃ | CF₂CF₂CF₃ |
| CH₂CH₂CF₃ | C(S)N(CH₃)₂ | F | CF₃ |
| CH₂CH₂CF₃ | C(S)N(CH₃)₂ | F | CF₂CF₃ |
| CH₂CH₂CF₃ | C(S)N(CH₃)₂ | F | CF₂CF₂CF₃ |
| CH₂CH₂CF₃ | C(S)N(CH₃)₂ | Cl | CF₃ |
| CH₂CH₂CF₃ | C(S)N(CH₃)₂ | Cl | CF₂CF₃ |
| CH₂CH₂CF₃ | C(S)N(CH₃)₂ | Cl | CF₂CF₂CF₃ |
| CH₂CF₂CF₃ | C(S)OCH₃ | H | CF₃ |
| CH₂CF₂CF₃ | C(S)OCH₃ | H | CF₂CF₃ |
| CH₂CF₂CF₃ | C(S)OCH₃ | H | CF₂CF₂CF₃ |
| CH₂CF₂CF₃ | C(S)OCH₃ | CH₃ | CF₃ |
| CH₂CF₂CF₃ | C(S)OCH₃ | CH₃ | CF₂CF₃ |
| CH₂CF₂CF₃ | C(S)OCH₃ | CH₃ | CF₂CF₂CF₃ |
| CH₂CF₂CF₃ | C(S)OCH₃ | F | CF₃ |
| CH₂CF₂CF₃ | C(S)OCH₃ | F | CF₂CF₃ |
| CH₂CF₂CF₃ | C(S)OCH₃ | F | CF₂CF₂CF₃ |

TABLE 31

| R¹ | R² | R³ | R⁴ |
|---|---|---|---|
| CH₂CF₂CF₃ | C(S)OCH₃ | Cl | CF₃ |
| CH₂CF₂CF₃ | C(S)OCH₃ | Cl | CF₂CF₃ |
| CH₂CF₂CF₃ | C(S)OCH₃ | Cl | CF₂CF₂CF₃ |
| CH₂CF₂CF₃ | C(S)NH₂ | H | CF₃ |
| CH₂CF₂CF₃ | C(S)NH₂ | H | CF₂CF₃ |
| CH₂CF₂CF₃ | C(S)NH₂ | H | CF₂CF₂CF₃ |
| CH₂CF₂CF₃ | C(S)NH₂ | CH₃ | CF₃ |
| CH₂CF₂CF₃ | C(S)NH₂ | CH₃ | CF₂CF₃ |
| CH₂CF₂CF₃ | C(S)NH₂ | CH₃ | CF₂CF₂CF₃ |
| CH₂CF₂CF₃ | C(S)NH₂ | CH₂CH₃ | CF₃ |
| CH₂CF₂CF₃ | C(S)NH₂ | CH₂CH₃ | CF₂CF₃ |
| CH₂CF₂CF₃ | C(S)NH₂ | CH₂CH₃ | CF₂CF₂CF₃ |
| CH₂CF₂CF₃ | C(S)NH₂ | F | CF₃ |
| CH₂CF₂CF₃ | C(S)NH₂ | F | CF₂CF₃ |
| CH₂CF₂CF₃ | C(S)NH₂ | F | CF₂CF₂CF₃ |
| CH₂CF₂CF₃ | C(S)NH₂ | Cl | CF₃ |
| CH₂CF₂CF₃ | C(S)NH₂ | Cl | CF₂CF₃ |
| CH₂CF₂CF₃ | C(S)NH₂ | Cl | CF₂CF₂CF₃ |
| CH₂CF₂CF₃ | C(S)NH(CH₃) | H | CF₃ |
| CH₂CF₂CF₃ | C(S)NH(CH₃) | H | CF₂CF₃ |
| CH₂CF₂CF₃ | C(S)NH(CH₃) | H | CF₂CF₂CF₃ |
| CH₂CF₂CF₃ | C(S)NH(CH₃) | CH₃ | CF₃ |
| CH₂CF₂CF₃ | C(S)NH(CH₃) | CH₃ | CF₂CF₃ |
| CH₂CF₂CF₃ | C(S)NH(CH₃) | CH₃ | CF₂CF₂CF₃ |
| CH₂CF₂CF₃ | C(S)NH(CH₃) | CH₂CH₃ | CF₃ |
| CH₂CF₂CF₃ | C(S)NH(CH₃) | CH₂CH₃ | CF₂CF₃ |
| CH₂CF₂CF₃ | C(S)NH(CH₃) | CH₂CH₃ | CF₂CF₂CF₃ |

TABLE 32

| R¹ | R² | R³ | R⁴ |
|---|---|---|---|
| CH₂CF₂CF₃ | C(S)NH(CH₃) | F | CF₃ |
| CH₂CF₂CF₃ | C(S)NH(CH₃) | F | CF₂CF₃ |
| CH₂CF₂CF₃ | C(S)NH(CH₃) | F | CF₂CF₂CF₃ |
| CH₂CF₂CF₃ | C(S)NH(CH₃) | Cl | CF₃ |
| CH₂CF₂CF₃ | C(S)NH(CH₃) | Cl | CF₂CF₃ |
| CH₂CF₂CF₃ | C(S)NH(CH₃) | Cl | CF₂CF₂CF₃ |
| CH₂CF₂CF₃ | C(S)N(CH₃)₂ | H | CF₃ |
| CH₂CF₂CF₃ | C(S)N(CH₃)₂ | H | CF₂CF₃ |
| CH₂CF₂CF₃ | C(S)N(CH₃)₂ | H | CF₂CF₂CF₃ |

TABLE 32-continued

| R¹ | R² | R³ | R⁴ |
|---|---|---|---|
| CH₂CF₂CF₃ | C(S)N(CH₃)₂ | CH₃ | CF₃ |
| CH₂CF₂CF₃ | C(S)N(CH₃)₂ | CH₃ | CF₂CF₃ |
| CH₂CF₂CF₃ | C(S)N(CH₃)₂ | CH₃ | CF₂CF₂CF₃ |
| CH₂CF₂CF₃ | C(S)N(CH₃)₂ | CH₂CH₃ | CF₃ |
| CH₂CF₂CF₃ | C(S)N(CH₃)₂ | CH₂CH₃ | CF₂CF₃ |
| CH₂CF₂CF₃ | C(S)N(CH₃)₂ | CH₂CH₃ | CF₂CF₂CF₃ |
| CH₂CF₂CF₃ | C(S)N(CH₃)₂ | F | CF₃ |
| CH₂CF₂CF₃ | C(S)N(CH₃)₂ | F | CF₂CF₃ |
| CH₂CF₂CF₃ | C(S)N(CH₃)₂ | F | CF₂CF₂CF₃ |
| CH₂CF₂CF₃ | C(S)N(CH₃)₂ | Cl | CF₃ |
| CH₂CF₂CF₃ | C(S)N(CH₃)₂ | Cl | CF₂CF₃ |
| CH₂CF₂CF₃ | C(S)N(CH₃)₂ | Cl | CF₂CF₂CF₃ |
| CH₂CF₂CF₂CF₃ | C(S)OCH₃ | H | CF₃ |
| CH₂CF₂CF₂CF₃ | C(S)OCH₃ | H | CF₂CF₃ |
| CH₂CF₂CF₂CF₃ | C(S)OCH₃ | H | CF₂CF₂CF₃ |
| CH₂CF₂CF₂CF₃ | C(S)OCH₃ | CH₃ | CF₃ |
| CH₂CF₂CF₂CF₃ | C(S)OCH₃ | CH₃ | CF₂CF₃ |
| CH₂CF₂CF₂CF₃ | C(S)OCH₃ | CH₃ | CF₂CF₂CF₃ |

TABLE 33

| R¹ | R² | R³ | R⁴ |
|---|---|---|---|
| CH₂CF₂CF₂CF₃ | C(S)OCH₃ | F | CF₃ |
| CH₂CF₂CF₂CF₃ | C(S)OCH₃ | F | CF₂CF₃ |
| CH₂CF₂CF₂CF₃ | C(S)OCH₃ | F | CF₂CF₂CF₃ |
| CH₂CF₂CF₂CF₃ | C(S)OCH₃ | Cl | CF₃ |
| CH₂CF₂CF₂CF₃ | C(S)OCH₃ | Cl | CF₂CF₃ |
| CH₂CF₂CF₂CF₃ | C(S)OCH₃ | Cl | CF₂CF₂CF₃ |
| CH₂CF₂CF₂CF₃ | C(S)NH₂ | H | CF₃ |
| CH₂CF₂CF₂CF₃ | C(S)NH₂ | H | CF₂CF₃ |
| CH₂CF₂CF₂CF₃ | C(S)NH₂ | H | CF₂CF₂CF₃ |
| CH₂CF₂CF₂CF₃ | C(S)NH₂ | CH₃ | CF₃ |
| CH₂CF₂CF₂CF₃ | C(S)NH₂ | CH₃ | CF₂CF₃ |
| CH₂CF₂CF₂CF₃ | C(S)NH₂ | CH₃ | CF₂CF₂CF₃ |
| CH₂CF₂CF₂CF₃ | C(S)NH₂ | CH₂CH₃ | CF₃ |
| CH₂CF₂CF₂CF₃ | C(S)NH₂ | CH₂CH₃ | CF₂CF₂CF₃ |
| CH₂CF₂CF₂CF₃ | C(S)NH₂ | F | CF₃ |
| CH₂CF₂CF₂CF₃ | C(S)NH₂ | F | CF₂CF₃ |
| CH₂CF₂CF₂CF₃ | C(S)NH₂ | F | CF₂CF₂CF₃ |
| CH₂CF₂CF₂CF₃ | C(S)NH₂ | Cl | CF₃ |
| CH₂CF₂CF₂CF₃ | C(S)NH₂ | Cl | CF₂CF₃ |
| CH₂CF₂CF₂CF₃ | C(S)NH₂ | Cl | CF₂CF₂CF₃ |
| CH₂CF₂CF₂CF₃ | C(S)NH(CH₃) | H | CF₃ |
| CH₂CF₂CF₂CF₃ | C(S)NH(CH₃) | H | CF₂CF₃ |
| CH₂CF₂CF₂CF₃ | C(S)NH(CH₃) | H | CF₂CF₂CF₃ |
| CH₂CF₂CF₂CF₃ | C(S)NH(CH₃) | CH₃ | CF₃ |
| CH₂CF₂CF₂CF₃ | C(S)NH(CH₃) | CH₃ | CF₂CF₃ |
| CH₂CF₂CF₂CF₃ | C(S)NH(CH₃) | CH₃ | CF₂CF₂CF₃ |

TABLE 34

| R¹ | R² | R³ | R⁴ |
|---|---|---|---|
| CH₂CF₂CF₂CF₃ | C(S)NH(CH₃) | CH₂CH₃ | CF₃ |
| CH₂CF₂CF₂CF₃ | C(S)NH(CH₃) | CH₂CH₃ | CF₂CF₃ |
| CH₂CF₂CF₂CF₃ | C(S)NH(CH₃) | CH₂CH₃ | CF₂CF₂CF₃ |
| CH₂CF₂CF₂CF₃ | C(S)NH(CH₃) | F | CF₃ |
| CH₂CF₂CF₂CF₃ | C(S)NH(CH₃) | F | CF₂CF₃ |
| CH₂CF₂CF₂CF₃ | C(S)NH(CH₃) | F | CF₂CF₂CF₃ |
| CH₂CF₂CF₂CF₃ | C(S)NH(CH₃) | Cl | CF₃ |
| CH₂CF₂CF₂CF₃ | C(S)NH(CH₃) | Cl | CF₂CF₃ |
| CH₂CF₂CF₂CF₃ | C(S)NH(CH₃) | Cl | CF₂CF₂CF₃ |
| CH₂CF₂CF₂CF₃ | C(S)N(CH₃)₂ | H | CF₃ |
| CH₂CF₂CF₂CF₃ | C(S)N(CH₃)₂ | H | CF₂CF₃ |
| CH₂CF₂CF₂CF₃ | C(S)N(CH₃)₂ | H | CF₂CF₂CF₃ |
| CH₂CF₂CF₂CF₃ | C(S)N(CH₃)₂ | CH₃ | CF₃ |
| CH₂CF₂CF₂CF₃ | C(S)N(CH₃)₂ | CH₃ | CF₂CF₃ |
| CH₂CF₂CF₂CF₃ | C(S)N(CH₃)₂ | CH₃ | CF₂CF₂CF₃ |
| CH₂CF₂CF₂CF₃ | C(S)N(CH₃)₂ | CH₂CH₃ | CF₃ |
| CH₂CF₂CF₂CF₃ | C(S)N(CH₃)₂ | CH₂CH₃ | CF₂CF₃ |
| CH₂CF₂CF₂CF₃ | C(S)N(CH₃)₂ | CH₂CH₃ | CF₂CF₂CF₃ |

TABLE 34-continued

| R¹ | R² | R³ | R⁴ |
|---|---|---|---|
| CH₂CF₂CF₂CF₃ | C(S)N(CH₃)₂ | F | CF₃ |
| CH₂CF₂CF₂CF₃ | C(S)N(CH₃)₂ | F | CF₂CF₃ |
| CH₂CF₂CF₂CF₃ | C(S)N(CH₃)₂ | F | CF₂CF₂CF₃ |
| CH₂CF₂CF₂CF₃ | C(S)N(CH₃)₂ | Cl | CF₃ |
| CH₂CF₂CF₂CF₃ | C(S)N(CH₃)₂ | Cl | CF₂CF₃ |
| CH₂CF₂CF₂CF₃ | C(S)N(CH₃)₂ | Cl | CF₂CF₂CF₃ |
| CH₂CH₂CF₂CF₂CF₃ | C(S)OCH₃ | H | CF₃ |
| CH₂CH₂CF₂CF₂CF₃ | C(S)OCH₃ | H | CF₂CF₃ |
| CH₂CH₂CF₂CF₂CF₃ | C(S)OCH₃ | H | CF₂CF₂CF₃ |

TABLE 35

| R¹ | R² | R³ | R⁴ |
|---|---|---|---|
| CH₂CH₂CF₂CF₂CF₃ | C(S)OCH₃ | CH₃ | CF₃ |
| CH₂CH₂CF₂CF₂CF₃ | C(S)OCH₃ | CH₃ | CF₂CF₃ |
| CH₂CH₂CF₂CF₂CF₃ | C(S)OCH₃ | CH₃ | CF₂CF₂CF₃ |
| CH₂CH₂CF₂CF₂CF₃ | C(S)OCH₃ | F | CF₃ |
| CH₂CH₂CF₂CF₂CF₃ | C(S)OCH₃ | F | CF₂CF₃ |
| CH₂CH₂CF₂CF₂CF₃ | C(S)OCH₃ | F | CF₂CF₂CF₃ |
| CH₂CH₂CF₂CF₂CF₃ | C(S)OCH₃ | Cl | CF₃ |
| CH₂CH₂CF₂CF₂CF₃ | C(S)OCH₃ | Cl | CF₂CF₃ |
| CH₂CH₂CF₂CF₂CF₃ | C(S)OCH₃ | Cl | CF₂CF₂CF₃ |
| CH₂CH₂CF₂CF₂CF₃ | C(S)NH₂ | H | CF₃ |
| CH₂CH₂CF₂CF₂CF₃ | C(S)NH₂ | H | CF₂CF₃ |
| CH₂CH₂CF₂CF₂CF₃ | C(S)NH₂ | H | CF₂CF₂CF₃ |
| CH₂CH₂CF₂CF₂CF₃ | C(S)NH₂ | CH₃ | CF₃ |
| CH₂CH₂CF₂CF₂CF₃ | C(S)NH₂ | CH₃ | CF₂CF₃ |
| CH₂CH₂CF₂CF₂CF₃ | C(S)NH₂ | CH₃ | CF₂CF₂CF₃ |
| CH₂CH₂CF₂CF₂CF₃ | C(S)NH₂ | CH₂CH₃ | CF₃ |
| CH₂CH₂CF₂CF₂CF₃ | C(S)NH₂ | CH₂CH₃ | CF₂CF₃ |
| CH₂CH₂CF₂CF₂CF₃ | C(S)NH₂ | CH₂CH₃ | CF₂CF₂CF₃ |
| CH₂CH₂CF₂CF₂CF₃ | C(S)NH₂ | F | CF₃ |
| CH₂CH₂CF₂CF₂CF₃ | C(S)NH₂ | F | CF₂CF₃ |
| CH₂CH₂CF₂CF₂CF₃ | C(S)NH₂ | F | CF₂CF₂CF₃ |
| CH₂CH₂CF₂CF₂CF₃ | C(S)NH₂ | Cl | CF₃ |
| CH₂CH₂CF₂CF₂CF₃ | C(S)NH₂ | Cl | CF₂CF₃ |
| CH₂CH₂CF₂CF₂CF₃ | C(S)NH₂ | Cl | CF₂CF₂CF₃ |
| CH₂CH₂CF₂CF₂CF₃ | C(S)NH(CH₃) | H | CF₃ |
| CH₂CH₂CF₂CF₂CF₃ | C(S)NH(CH₃) | H | CF₂CF₃ |
| CH₂CH₂CF₂CF₂CF₃ | C(S)NH(CH₃) | H | CF₂CF₂CF₃ |

TABLE 36

| R¹ | R² | R³ | R⁴ |
|---|---|---|---|
| CH₂CH₂CF₂CF₂CF₃ | C(S)NH(CH₃) | CH₃ | CF₃ |
| CH₂CH₂CF₂CF₂CF₃ | C(S)NH(CH₃) | CH₃ | CF₂CF₃ |
| CH₂CH₂CF₂CF₂CF₃ | C(S)NH(CH₃) | CH₃ | CF₂CF₂CF₃ |
| CH₂CH₂CF₂CF₂CF₃ | C(S)NH(CH₃) | CH₂CH₃ | CF₃ |
| CH₂CH₂CF₂CF₂CF₃ | C(S)NH(CH₃) | CH₂CH₃ | CF₂CF₃ |
| CH₂CH₂CF₂CF₂CF₃ | C(S)NH(CH₃) | CH₂CH₃ | CF₂CF₂CF₃ |
| CH₂CH₂CF₂CF₂CF₃ | C(S)NH(CH₃) | F | CF₃ |
| CH₂CH₂CF₂CF₂CF₃ | C(S)NH(CH₃) | F | CF₂CF₃ |
| CH₂CH₂CF₂CF₂CF₃ | C(S)NH(CH₃) | F | CF₂CF₂CF₃ |
| CH₂CH₂CF₂CF₂CF₃ | C(S)NH(CH₃) | F | CF₃ |
| CH₂CH₂CF₂CF₂CF₃ | C(S)NH(CH₃) | F | CF₂CF₃ |
| CH₂CH₂CF₂CF₂CF₃ | C(S)NH(CH₃) | F | CF₂CF₂CF₃ |
| CH₂CH₂CF₂CF₂CF₃ | C(S)NH(CH₃) | Cl | CF₃ |
| CH₂CH₂CF₂CF₂CF₃ | C(S)NH(CH₃) | Cl | CF₂CF₃ |
| CH₂CH₂CF₂CF₂CF₃ | C(S)NH(CH₃) | Cl | CF₂CF₂CF₃ |
| CH₂CH₂CF₂CF₂CF₃ | C(S)N(CH₃)₂ | H | CF₃ |
| CH₂CH₂CF₂CF₂CF₃ | C(S)N(CH₃)₂ | H | CF₂CF₃ |
| CH₂CH₂CF₂CF₂CF₃ | C(S)N(CH₃)₂ | H | CF₂CF₂CF₃ |
| CH₂CH₂CF₂CF₂CF₃ | C(S)N(CH₃)₂ | CH₃ | CF₃ |
| CH₂CH₂CF₂CF₂CF₃ | C(S)N(CH₃)₂ | CH₃ | CF₂CF₃ |
| CH₂CH₂CF₂CF₂CF₃ | C(S)N(CH₃)₂ | CH₃ | CF₂CF₂CF₃ |
| CH₂CH₂CF₂CF₂CF₃ | C(S)N(CH₃)₂ | CH₂CH₃ | CF₃ |
| CH₂CH₂CF₂CF₂CF₃ | C(S)N(CH₃)₂ | CH₂CH₃ | CF₂CF₃ |
| CH₂CH₂CF₂CF₂CF₃ | C(S)N(CH₃)₂ | CH₂CH₃ | CF₂CF₂CF₃ |
| CH₂CH₂CF₂CF₂CF₃ | C(S)N(CH₃)₂ | F | CF₃ |

TABLE 36-continued

| R¹ | R² | R³ | R⁴ |
|---|---|---|---|
| CH₂CH₂CF₂CF₂CF₃ | C(S)N(CH₃)₂ | F | CF₂CF₃ |
| CH₂CH₂CF₂CF₂CF₃ | C(S)N(CH₃)₂ | F | CF₂CF₂CF₃ |

TABLE 37

| R¹ | R² | R³ | R⁴ |
|---|---|---|---|
| CH₂CH₂CF₂CF₂CF₃ | C(S)N(CH₃)₂ | Cl | CF₃ |
| CH₂CH₂CF₂CF₂CF₃ | C(S)N(CH₃)₂ | Cl | CF₂CF₃ |
| CH₂CH₂CF₂CF₂CF₃ | C(S)N(CH₃)₂ | Cl | CF₂CF₂CF₃ |
| CH₂CF₂CF₂CF₂CF₂H | C(S)OCH₃ | H | CF₃ |
| CH₂CF₂CF₂CF₂CF₂H | C(S)OCH₃ | H | CF₂CF₃ |
| CH₂CF₂CF₂CF₂CF₂H | C(S)OCH₃ | H | CF₂CF₂CF₃ |
| CH₂CF₂CF₂CF₂CF₂H | C(S)OCH₃ | CH₃ | CF₃ |
| CH₂CF₂CF₂CF₂CF₂H | C(S)OCH₃ | CH₃ | CF₂CF₃ |
| CH₂CF₂CF₂CF₂CF₂H | C(S)OCH₃ | CH₃ | CF₂CF₂CF₃ |
| CH₂CF₂CF₂CF₂CF₂H | C(S)OCH₃ | F | CF₃ |
| CH₂CF₂CF₂CF₂CF₂H | C(S)OCH₃ | F | CF₂CF₃ |
| CH₂CF₂CF₂CF₂CF₂H | C(S)OCH₃ | F | CF₂CF₂CF₃ |
| CH₂CF₂CF₂CF₂CF₂H | C(S)OCH₃ | Cl | CF₃ |
| CH₂CF₂CF₂CF₂CF₂H | C(S)OCH₃ | Cl | CF₂CF₃ |
| CH₂CF₂CF₂CF₂CF₂H | C(S)OCH₃ | Cl | CF₂CF₂CF₃ |
| CH₂CF₂CF₂CF₂CF₂H | C(S)NH₂ | H | CF₃ |
| CH₂CF₂CF₂CF₂CF₂H | C(S)NH₂ | H | CF₂CF₃ |
| CH₂CF₂CF₂CF₂CF₂H | C(S)NH₂ | H | CF₂CF₂CF₃ |
| CH₂CF₂CF₂CF₂CF₂H | C(S)NH₂ | CH₃ | CF₃ |
| CH₂CF₂CF₂CF₂CF₂H | C(S)NH₂ | CH₃ | CF₂CF₃ |
| CH₂CF₂CF₂CF₂CF₂H | C(S)NH₂ | CH₃ | CF₂CF₂CF₃ |
| CH₂CF₂CF₂CF₂CF₂H | C(S)NH₂ | CH₂CH₃ | CF₃ |
| CH₂CF₂CF₂CF₂CF₂H | C(S)NH₂ | CH₂CH₃ | CF₂CF₃ |
| CH₂CF₂CF₂CF₂CF₂H | C(S)NH₂ | CH₂CH₃ | CF₂CF₂CF₃ |
| CH₂CF₂CF₂CF₂CF₂H | C(S)NH₂ | F | CF₃ |
| CH₂CF₂CF₂CF₂CF₂H | C(S)NH₂ | F | CF₂CF₃ |
| CH₂CF₂CF₂CF₂CF₂H | C(S)NH₂ | F | CF₂CF₂CF₃ |

TABLE 38

| R¹ | R² | R³ | R⁴ |
|---|---|---|---|
| CH₂CF₂CF₂CF₂CF₂H | C(S)NH₂ | Cl | CF₃ |
| CH₂CF₂CF₂CF₂CF₂H | C(S)NH₂ | Cl | CF₂CF₃ |
| CH₂CF₂CF₂CF₂CF₂H | C(S)NH₂ | Cl | CF₂CF₂CF₃ |
| CH₂CF₂CF₂CF₂CF₂H | C(S)NH(CH₃) | H | CF₃ |
| CH₂CF₂CF₂CF₂CF₂H | C(S)NH(CH₃) | H | CF₂CF₃ |
| CH₂CF₂CF₂CF₂CF₂H | C(S)NH(CH₃) | H | CF₂CF₂CF₃ |
| CH₂CF₂CF₂CF₂CF₂H | C(S)NH(CH₃) | CH₃ | CF₃ |
| CH₂CF₂CF₂CF₂CF₂H | C(S)NH(CH₃) | CH₃ | CF₂CF₃ |
| CH₂CF₂CF₂CF₂CF₂H | C(S)NH(CH₃) | CH₃ | CF₂CF₂CF₃ |
| CH₂CF₂CF₂CF₂CF₂H | C(S)NH(CH₃) | CH₂CH₃ | CF₃ |
| CH₂CF₂CF₂CF₂CF₂H | C(S)NH(CH₃) | CH₂CH₃ | CF₂CF₃ |
| CH₂CF₂CF₂CF₂CF₂H | C(S)NH(CH₃) | CH₂CH₃ | CF₂CF₂CF₃ |
| CH₂CF₂CF₂CF₂CF₂H | C(S)NH(CH₃) | F | CF₃ |
| CH₂CF₂CF₂CF₂CF₂H | C(S)NH(CH₃) | F | CF₂CF₃ |
| CH₂CF₂CF₂CF₂CF₂H | C(S)NH(CH₃) | F | CF₂CF₂CF₃ |
| CH₂CF₂CF₂CF₂CF₂H | C(S)NH(CH₃) | Cl | CF₃ |
| CH₂CF₂CF₂CF₂CF₂H | C(S)NH(CH₃) | Cl | CF₂CF₃ |
| CH₂CF₂CF₂CF₂CF₂H | C(S)NH(CH₃) | Cl | CF₂CF₂CF₃ |
| CH₂CF₂CF₂CF₂CF₂H | C(S)N(CH₃)₂ | H | CF₃ |
| CH₂CF₂CF₂CF₂CF₂H | C(S)N(CH₃)₂ | H | CF₂CF₃ |
| CH₂CF₂CF₂CF₂CF₂H | C(S)N(CH₃)₂ | H | CF₂CF₂CF₃ |
| CH₂CF₂CF₂CF₂CF₂H | C(S)N(CH₃)₂ | CH₃ | CF₃ |
| CH₂CF₂CF₂CF₂CF₂H | C(S)N(CH₃)₂ | CH₃ | CF₂CF₃ |
| CH₂CF₂CF₂CF₂CF₂H | C(S)N(CH₃)₂ | CH₃ | CF₂CF₂CF₃ |
| CH₂CF₂CF₂CF₂CF₂H | C(S)N(CH₃)₂ | CH₂CH₃ | CF₃ |
| CH₂CF₂CF₂CF₂CF₂H | C(S)N(CH₃)₂ | CH₂CH₃ | CF₂CF₃ |
| CH₂CF₂CF₂CF₂CF₂H | C(S)N(CH₃)₂ | CH₂CH₃ | CF₂CF₂CF₃ |

TABLE 39

| R¹ | R² | R³ | R⁴ |
|---|---|---|---|
| $CH_2CF_2CF_2CF_2CF_2H$ | $C(S)N(CH_3)_2$ | F | $CF_3$ |
| $CH_2CF_2CF_2CF_2CF_2H$ | $C(S)N(CH_3)_2$ | F | $CF_2CF_3$ |
| $CH_2CF_2CF_2CF_2CF_2H$ | $C(S)N(CH_3)_2$ | F | $CF_2CF_2CF_3$ |
| $CH_2CF_2CF_2CF_2CF_2H$ | $C(S)N(CH_3)_2$ | Cl | $CF_3$ |
| $CH_2CF_2CF_2CF_2CF_2H$ | $C(S)N(CH_3)_2$ | Cl | $CF_2CF_3$ |
| $CH_2CF_2CF_2CF_2CF_2H$ | $C(S)N(CH_3)_2$ | Cl | $CF_2CF_2CF_3$ |
| $CH_2CH_2CF_2CF_2CF_2CF_3$ | $C(S)OCH_3$ | H | $CF_3$ |
| $CH_2CH_2CF_2CF_2CF_2CF_3$ | $C(S)OCH_3$ | H | $CF_2CF_3$ |
| $CH_2CH_2CF_2CF_2CF_2CF_3$ | $C(S)OCH_3$ | H | $CF_2CF_2CF_3$ |
| $CH_2CH_2CF_2CF_2CF_2CF_3$ | $C(S)OCH_3$ | $CH_3$ | $CF_3$ |
| $CH_2CH_2CF_2CF_2CF_2CF_3$ | $C(S)OCH_3$ | $CH_3$ | $CF_2CF_3$ |
| $CH_2CH_2CF_2CF_2CF_2CF_3$ | $C(S)OCH_3$ | $CH_3$ | $CF_2CF_2CF_3$ |
| $CH_2CH_2CF_2CF_2CF_2CF_3$ | $C(S)OCH_3$ | F | $CF_3$ |
| $CH_2CH_2CF_2CF_2CF_2CF_3$ | $C(S)OCH_3$ | F | $CF_2CF_3$ |
| $CH_2CH_2CF_2CF_2CF_2CF_3$ | $C(S)OCH_3$ | F | $CF_2CF_2CF_3$ |
| $CH_2CH_2CF_2CF_2CF_2CF_3$ | $C(S)OCH_3$ | Cl | $CF_3$ |
| $CH_2CH_2CF_2CF_2CF_2CF_3$ | $C(S)OCH_3$ | Cl | $CF_2CF_3$ |
| $CH_2CH_2CF_2CF_2CF_2CF_3$ | $C(S)OCH_3$ | Cl | $CF_2CF_2CF_3$ |
| $CH_2CH_2CF_2CF_2CF_2CF_3$ | $C(S)NH_2$ | H | $CF_3$ |
| $CH_2CH_2CF_2CF_2CF_2CF_3$ | $C(S)NH_2$ | H | $CF_2CF_3$ |
| $CH_2CH_2CF_2CF_2CF_2CF_3$ | $C(S)NH_2$ | H | $CF_2CF_2CF_3$ |
| $CH_2CH_2CF_2CF_2CF_2CF_3$ | $C(S)NH_2$ | $CH_3$ | $CF_3$ |
| $CH_2CH_2CF_2CF_2CF_2CF_3$ | $C(S)NH_2$ | $CH_3$ | $CF_2CF_3$ |
| $CH_2CH_2CF_2CF_2CF_2CF_3$ | $C(S)NH_2$ | $CH_3$ | $CF_2CF_2CF_3$ |
| $CH_2CH_2CF_2CF_2CF_2CF_3$ | $C(S)NH_2$ | $CH_2CH_3$ | $CF_3$ |
| $CH_2CH_2CF_2CF_2CF_2CF_3$ | $C(S)NH_2$ | $CH_2CH_3$ | $CF_2CF_3$ |
| $CH_2CH_2CF_2CF_2CF_2CF_3$ | $C(S)NH_2$ | $CH_2CH_3$ | $CF_2CF_2CF_3$ |

TABLE 40

| R¹ | R² | R³ | R⁴ |
|---|---|---|---|
| $CH_2CH_2CF_2CF_2CF_2CF_3$ | $C(S)NH_2$ | F | $CF_3$ |
| $CH_2CH_2CF_2CF_2CF_2CF_3$ | $C(S)NH_2$ | F | $CF_2CF_3$ |
| $CH_2CH_2CF_2CF_2CF_2CF_3$ | $C(S)NH_2$ | F | $CF_2CF_2CF_3$ |
| $CH_2CH_2CF_2CF_2CF_2CF_3$ | $C(S)NH_2$ | Cl | $CF_3$ |
| $CH_2CH_2CF_2CF_2CF_2CF_3$ | $C(S)NH_2$ | Cl | $CF_2CF_3$ |
| $CH_2CH_2CF_2CF_2CF_2CF_3$ | $C(S)NH_2$ | Cl | $CF_2CF_2CF_3$ |
| $CH_2CH_2CF_2CF_2CF_2CF_3$ | $C(S)NH(CH_3)$ | H | $CF_3$ |
| $CH_2CH_2CF_2CF_2CF_2CF_3$ | $C(S)NH(CH_3)$ | H | $CF_2CF_3$ |
| $CH_2CH_2CF_2CF_2CF_2CF_3$ | $C(S)NH(CH_3)$ | H | $CF_2CF_2CF_3$ |
| $CH_2CH_2CF_2CF_2CF_2CF_3$ | $C(S)NH(CH_3)$ | $CH_3$ | $CF_3$ |
| $CH_2CH_2CF_2CF_2CF_2CF_3$ | $C(S)NH(CH_3)$ | $CH_3$ | $CF_2CF_3$ |
| $CH_2CH_2CF_2CF_2CF_2CF_3$ | $C(S)NH(CH_3)$ | $CH_3$ | $CF_2CF_2CF_3$ |
| $CH_2CH_2CF_2CF_2CF_2CF_3$ | $C(S)NH(CH_3)$ | $CH_2CH_3$ | $CF_3$ |
| $CH_2CH_2CF_2CF_2CF_2CF_3$ | $C(S)NH(CH_3)$ | $CH_2CH_3$ | $CF_2CF_3$ |
| $CH_2CH_2CF_2CF_2CF_2CF_3$ | $C(S)NH(CH_3)$ | $CH_2CH_3$ | $CF_2CF_2CF_3$ |
| $CH_2CH_2CF_2CF_2CF_2CF_3$ | $C(S)NH(CH_3)$ | F | $CF_3$ |
| $CH_2CH_2CF_2CF_2CF_2CF_3$ | $C(S)NH(CH_3)$ | F | $CF_2CF_3$ |
| $CH_2CH_2CF_2CF_2CF_2CF_3$ | $C(S)NH(CH_3)$ | F | $CF_2CF_2CF_3$ |
| $CH_2CH_2CF_2CF_2CF_2CF_3$ | $C(S)NH(CH_3)$ | Cl | $CF_3$ |
| $CH_2CH_2CF_2CF_2CF_2CF_3$ | $C(S)NH(CH_3)$ | Cl | $CF_2CF_3$ |
| $CH_2CH_2CF_2CF_2CF_2CF_3$ | $C(S)NH(CH_3)$ | Cl | $CF_2CF_2CF_3$ |
| $CH_2CH_2CF_2CF_2CF_2CF_3$ | $C(S)N(CH_3)_2$ | H | $CF_3$ |
| $CH_2CH_2CF_2CF_2CF_2CF_3$ | $C(S)N(CH_3)_2$ | H | $CF_2CF_3$ |
| $CH_2CH_2CF_2CF_2CF_2CF_3$ | $C(S)N(CH_3)_2$ | H | $CF_2CF_2CF_3$ |
| $CH_2CH_2CF_2CF_2CF_2CF_3$ | $C(S)N(CH_3)_2$ | $CH_3$ | $CF_3$ |
| $CH_2CH_2CF_2CF_2CF_2CF_3$ | $C(S)N(CH_3)_2$ | $CH_3$ | $CF_2CF_3$ |
| $CH_2CH_2CF_2CF_2CF_2CF_3$ | $C(S)N(CH_3)_2$ | $CH_3$ | $CF_2CF_2CF_3$ |

TABLE 41

| R¹ | R² | R³ | R⁴ |
|---|---|---|---|
| $CH_2CH_2CF_2CF_2CF_2CF_3$ | $C(S)N(CH_3)_2$ | $CH_2CH_3$ | $CF_3$ |
| $CH_2CH_2CF_2CF_2CF_2CF_3$ | $C(S)N(CH_3)_2$ | $CH_2CH_3$ | $CF_2CF_3$ |
| $CH_2CH_2CF_2CF_2CF_2CF_3$ | $C(S)N(CH_3)_2$ | $CH_2CH_3$ | $CF_2CF_2CF_3$ |
| $CH_2CH_2CF_2CF_2CF_2CF_3$ | $C(S)N(CH_3)_2$ | F | $CF_3$ |
| $CH_2CH_2CF_2CF_2CF_2CF_3$ | $C(S)N(CH_3)_2$ | F | $CF_2CF_3$ |
| $CH_2CH_2CF_2CF_2CF_2CF_3$ | $C(S)N(CH_3)_2$ | F | $CF_2CF_2CF_3$ |
| $CH_2CH_2CF_2CF_2CF_2CF_3$ | $C(S)N(CH_3)_2$ | Cl | $CF_3$ |

TABLE 41-continued

| R¹ | R² | R³ | R⁴ |
|---|---|---|---|
| $CH_2CH_2CF_2CF_2CF_2CF_3$ | $C(S)N(CH_3)_2$ | Cl | $CF_2CF_3$ |
| $CH_2CH_2CF_2CF_2CF_2CF_3$ | $C(S)N(CH_3)_2$ | Cl | $CF_2CF_2CF_3$ |

TABLE 42

| R¹ | R² | R³ | R⁴ |
|---|---|---|---|
| $CF_2CF_2CF_3$ | CN | H | $CF_3$ |
| $CF_2CF_2CF_3$ | CN | H | $CF_2CF_3$ |
| $CF_2CF_2CF_3$ | CN | H | $CF_2CF_2CF_3$ |
| $CF_2CF_2CF_3$ | CN | $CH_3$ | $CF_3$ |
| $CF_2CF_2CF_3$ | CN | $CH_3$ | $CF_2CF_3$ |
| $CF_2CF_2CF_3$ | CN | $CH_3$ | $CF_2CF_2CF_3$ |
| $CF_2CF_2CF_3$ | CN | $CH_2CH_3$ | $CF_3$ |
| $CF_2CF_2CF_3$ | CN | $CH_2CH_3$ | $CF_2CF_3$ |
| $CF_2CF_2CF_3$ | CN | $CH_2CH_3$ | $CF_2CF_2CF_3$ |
| $CF_2CF_2CF_3$ | CN | $CH_2CH_2CH_3$ | $CF_3$ |
| $CF_2CF_2CF_3$ | CN | $CH_2CH_2CH_3$ | $CF_2CF_3$ |
| $CF_2CF_2CF_3$ | CN | $CH_2CH_2CH_3$ | $CF_2CF_2CF_3$ |
| $CF_2CF_2CF_3$ | CN | $CH(CH_3)_2$ | $CF_3$ |
| $CF_2CF_2CF_3$ | CN | $CH(CH_3)_2$ | $CF_2CF_3$ |
| $CF_2CF_2CF_3$ | CN | $CH(CH_3)_2$ | $CF_2CF_2CF_3$ |
| $CF_2CF_2CF_3$ | CN | $CH_2CH_2CH_2CH_3$ | $CF_3$ |
| $CF_2CF_2CF_3$ | CN | $CH_2CH_2CH_2CH_3$ | $CF_2CF_3$ |
| $CF_2CF_2CF_3$ | CN | $CH_2CH_2CH_2CH_3$ | $CF_2CF_2CF_3$ |
| $CF_2CF_2CF_3$ | CN | F | $CF_3$ |
| $CF_2CF_2CF_3$ | CN | F | $CF_2CF_3$ |
| $CF_2CF_2CF_3$ | CN | F | $CF_2CF_2CF_3$ |
| $CF_2CF_2CF_3$ | CN | Cl | $CF_3$ |
| $CF_2CF_2CF_3$ | CN | Cl | $CF_2CF_3$ |
| $CF_2CF_2CF_3$ | CN | Cl | $CF_2CF_2CF_3$ |

TABLE 43

| R¹ | R² | R³ | R⁴ |
|---|---|---|---|
| $CF_2CF_2CF_3$ | $CO_2CH_3$ | H | $CF_3$ |
| $CF_2CF_2CF_3$ | $CO_2CH_3$ | H | $CF_2CF_3$ |
| $CF_2CF_2CF_3$ | $CO_2CH_3$ | H | $CF_2CF_2CF_3$ |
| $CF_2CF_2CF_3$ | $CO_2CH_3$ | $CH_3$ | $CF_3$ |
| $CF_2CF_2CF_3$ | $CO_2CH_3$ | $CH_3$ | $CF_2CF_3$ |
| $CF_2CF_2CF_3$ | $CO_2CH_3$ | $CH_3$ | $CF_2CF_2CF_3$ |
| $CF_2CF_2CF_3$ | $CO_2CH_3$ | $CH_2CH_3$ | $CF_3$ |
| $CF_2CF_2CF_3$ | $CO_2CH_3$ | $CH_2CH_3$ | $CF_2CF_3$ |
| $CF_2CF_2CF_3$ | $CO_2CH_3$ | $CH_2CH_3$ | $CF_2CF_2CF_3$ |
| $CF_2CF_2CF_3$ | $CO_2CH_3$ | $CH_2CH_2CH_3$ | $CF_3$ |
| $CF_2CF_2CF_3$ | $CO_2CH_3$ | $CH_2CH_2CH_3$ | $CF_2CF_3$ |
| $CF_2CF_2CF_3$ | $CO_2CH_3$ | $CH_2CH_2CH_3$ | $CF_2CF_2CF_3$ |
| $CF_2CF_2CF_3$ | $CO_2CH_3$ | F | $CF_3$ |
| $CF_2CF_2CF_3$ | $CO_2CH_3$ | F | $CF_2CF_3$ |
| $CF_2CF_2CF_3$ | $CO_2CH_3$ | F | $CF_2CF_2CF_3$ |
| $CF_2CF_2CF_3$ | $CO_2CH_3$ | Cl | $CF_3$ |
| $CF_2CF_2CF_3$ | $CO_2CH_3$ | Cl | $CF_2CF_3$ |
| $CF_2CF_2CF_3$ | $CO_2CH_3$ | Cl | $CF_2CF_2CF_3$ |
| $CF_2CF_2CF_3$ | $CO_2C(CH_3)_3$ | H | $CF_3$ |
| $CF_2CF_2CF_3$ | $CO_2C(CH_3)_3$ | H | $CF_2CF_3$ |
| $CF_2CF_2CF_3$ | $CO_2C(CH_3)_3$ | H | $CF_2CF_2CF_3$ |
| $CF_2CF_2CF_3$ | $CO_2C(CH_3)_3$ | $CH_3$ | $CF_3$ |
| $CF_2CF_2CF_3$ | $CO_2C(CH_3)_3$ | $CH_3$ | $CF_2CF_3$ |
| $CF_2CF_2CF_3$ | $CO_2C(CH_3)_3$ | $CH_3$ | $CF_2CF_2CF_3$ |
| $CF_2CF_2CF_3$ | $CO_2C(CH_3)_3$ | F | $CF_3$ |
| $CF_2CF_2CF_3$ | $CO_2C(CH_3)_3$ | F | $CF_2CF_3$ |
| $CF_2CF_2CF_3$ | $CO_2C(CH_3)_3$ | F | $CF_2CF_2CF_3$ |

TABLE 44

| R¹ | R² | R³ | R⁴ |
|---|---|---|---|
| $CF_2CF_2CF_3$ | $CO_2C(CH_3)_3$ | Cl | $CF_3$ |
| $CF_2CF_2CF_3$ | $CO_2C(CH_3)_3$ | Cl | $CF_2CF_3$ |
| $CF_2CF_2CF_3$ | $CO_2C(CH_3)_3$ | Cl | $CF_2CF_2CF_3$ |
| $CF_2CF_2CF_3$ | $CONH_2$ | H | $CF_3$ |
| $CF_2CF_2CF_3$ | $CONH_2$ | H | $CF_2CF_3$ |
| $CF_2CF_2CF_3$ | $CONH_2$ | H | $CF_2CF_2CF_3$ |
| $CF_2CF_2CF_3$ | $CONH_2$ | $CH_3$ | $CF_3$ |
| $CF_2CF_2CF_3$ | $CONH_2$ | $CH_3$ | $CF_2CF_3$ |
| $CF_2CF_2CF_3$ | $CONH_2$ | $CH_3$ | $CF_2CF_2CF_3$ |
| $CF_2CF_2CF_3$ | $CONH_2$ | $CH_2CH_3$ | $CF_3$ |
| $CF_2CF_2CF_3$ | $CONH_2$ | $CH_2CH_3$ | $CF_2CF_3$ |
| $CF_2CF_2CF_3$ | $CONH_2$ | $CH_2CH_3$ | $CF_2CF_2CF_3$ |
| $CF_2CF_2CF_3$ | $CONH_2$ | F | $CF_3$ |
| $CF_2CF_2CF_3$ | $CONH_2$ | F | $CF_2CF_3$ |
| $CF_2CF_2CF_3$ | $CONH_2$ | F | $CF_2CF_2CF_3$ |
| $CF_2CF_2CF_3$ | $CONH_2$ | Cl | $CF_3$ |
| $CF_2CF_2CF_3$ | $CONH_2$ | Cl | $CF_2CF_3$ |
| $CF_2CF_2CF_3$ | $CONH_2$ | Cl | $CF_2CF_2CF_3$ |
| $CF_2CF_2CF_3$ | $CONH(CH_3)$ | H | $CF_3$ |
| $CF_2CF_2CF_3$ | $CONH(CH_3)$ | H | $CF_2CF_3$ |
| $CF_2CF_2CF_3$ | $CONH(CH_3)$ | H | $CF_2CF_2CF_3$ |
| $CF_2CF_2CF_3$ | $CONH(CH_3)$ | $CH_3$ | $CF_3$ |
| $CF_2CF_2CF_3$ | $CONH(CH_3)$ | $CH_3$ | $CF_2CF_3$ |
| $CF_2CF_2CF_3$ | $CONH(CH_3)$ | $CH_3$ | $CF_2CF_2CF_3$ |
| $CF_2CF_2CF_3$ | $CONH(CH_3)$ | $CH_2CH_3$ | $CF_3$ |
| $CF_2CF_2CF_3$ | $CONH(CH_3)$ | $CH_2CH_3$ | $CF_2CF_3$ |
| $CF_2CF_2CF_3$ | $CONH(CH_3)$ | $CH_2CH_3$ | $CF_2CF_2CF_3$ |

TABLE 45

| R¹ | R² | R³ | R⁴ |
|---|---|---|---|
| $CF_2CF_2CF_3$ | $CONH(CH_3)$ | F | $CF_3$ |
| $CF_2CF_2CF_3$ | $CONH(CH_3)$ | F | $CF_2CF_3$ |
| $CF_2CF_2CF_3$ | $CONH(CH_3)$ | F | $CF_2CF_2CF_3$ |
| $CF_2CF_2CF_3$ | $CONH(CH_3)$ | Cl | $CF_3$ |
| $CF_2CF_2CF_3$ | $CONH(CH_3)$ | Cl | $CF_2CF_3$ |
| $CF_2CF_2CF_3$ | $CONH(CH_3)$ | Cl | $CF_2CF_2CF_3$ |
| $CF_2CF_2CF_3$ | $CONH(CH_2CH_3)$ | H | $CF_3$ |
| $CF_2CF_2CF_3$ | $CONH(CH_2CH_3)$ | H | $CF_2CF_3$ |
| $CF_2CF_2CF_3$ | $CONH(CH_2CH_3)$ | H | $CF_2CF_2CF_3$ |
| $CF_2CF_2CF_3$ | $CONH(CH_2CH_3)$ | $CH_3$ | $CF_3$ |
| $CF_2CF_2CF_3$ | $CONH(CH_2CH_3)$ | $CH_3$ | $CF_2CF_3$ |
| $CF_2CF_2CF_3$ | $CONH(CH_2CH_3)$ | $CH_3$ | $CF_2CF_2CF_3$ |
| $CF_2CF_2CF_3$ | $CONH(CH_2CH_3)$ | $CH_2CH_3$ | $CF_3$ |
| $CF_2CF_2CF_3$ | $CONH(CH_2CH_3)$ | $CH_2CH_3$ | $CF_2CF_3$ |
| $CF_2CF_2CF_3$ | $CONH(CH_2CH_3)$ | $CH_2CH_3$ | $CF_2CF_2CF_3$ |
| $CF_2CF_2CF_3$ | $CONH(CH_2CH_3)$ | F | $CF_3$ |
| $CF_2CF_2CF_3$ | $CONH(CH_2CH_3)$ | F | $CF_2CF_3$ |
| $CF_2CF_2CF_3$ | $CONH(CH_2CH_3)$ | F | $CF_2CF_2CF_3$ |
| $CF_2CF_2CF_3$ | $CONH(CH_2CH_3)$ | Cl | $CF_3$ |
| $CF_2CF_2CF_3$ | $CONH(CH_2CH_3)$ | Cl | $CF_2CF_3$ |
| $CF_2CF_2CF_3$ | $CONH(CH_2CH_3)$ | Cl | $CF_2CF_2CF_3$ |
| $CF_2CF_2CF_3$ | $CON(CH_3)_2$ | H | $CF_3$ |
| $CF_2CF_2CF_3$ | $CON(CH_3)_2$ | H | $CF_2CF_3$ |
| $CF_2CF_2CF_3$ | $CON(CH_3)_2$ | H | $CF_2CF_2CF_3$ |
| $CF_2CF_2CF_3$ | $CON(CH_3)_2$ | $CH_3$ | $CF_3$ |
| $CF_2CF_2CF_3$ | $CON(CH_3)_2$ | $CH_3$ | $CF_2CF_3$ |
| $CF_2CF_2CF_3$ | $CON(CH_3)_2$ | $CH_3$ | $CF_2CF_2CF_3$ |

TABLE 46

| R¹ | R² | R³ | R⁴ |
|---|---|---|---|
| $CF_2CF_2CF_3$ | $CON(CH_3)_2$ | $CH_2CH_3$ | $CF_3$ |
| $CF_2CF_2CF_3$ | $CON(CH_3)_2$ | $CH_2CH_3$ | $CF_2CF_3$ |
| $CF_2CF_2CF_3$ | $CON(CH_3)_2$ | $CH_2CH_3$ | $CF_2CF_2CF_3$ |
| $CF_2CF_2CF_3$ | $CON(CH_3)_2$ | F | $CF_3$ |
| $CF_2CF_2CF_3$ | $CON(CH_3)_2$ | F | $CF_2CF_3$ |
| $CF_2CF_2CF_3$ | $CON(CH_3)_2$ | F | $CF_2CF_2CF_3$ |
| $CF_2CF_2CF_3$ | $CON(CH_3)_2$ | Cl | $CF_3$ |
| $CF_2CF_2CF_3$ | $CON(CH_3)_2$ | Cl | $CF_2CF_3$ |
| $CF_2CF_2CF_3$ | $CON(CH_3)_2$ | Cl | $CF_2CF_2CF_3$ |
| $CF_2CF_2CF_3$ | $C(S)OCH_3$ | H | $CF_3$ |
| $CF_2CF_2CF_3$ | $C(S)OCH_3$ | H | $CF_2CF_3$ |
| $CF_2CF_2CF_3$ | $C(S)OCH_3$ | H | $CF_2CF_2CF_3$ |
| $CF_2CF_2CF_3$ | $C(S)OCH_3$ | $CH_3$ | $CF_3$ |
| $CF_2CF_2CF_3$ | $C(S)OCH_3$ | $CH_3$ | $CF_2CF_3$ |
| $CF_2CF_2CF_3$ | $C(S)OCH_3$ | $CH_3$ | $CF_2CF_2CF_3$ |
| $CF_2CF_2CF_3$ | $C(S)OCH_3$ | F | $CF_3$ |
| $CF_2CF_2CF_3$ | $C(S)OCH_3$ | F | $CF_2CF_3$ |
| $CF_2CF_2CF_3$ | $C(S)OCH_3$ | F | $CF_2CF_2CF_3$ |
| $CF_2CF_2CF_3$ | $C(S)OCH_3$ | Cl | $CF_3$ |
| $CF_2CF_2CF_3$ | $C(S)OCH_3$ | Cl | $CF_2CF_3$ |
| $CF_2CF_2CF_3$ | $C(S)OCH_3$ | Cl | $CF_2CF_2CF_3$ |
| $CF_2CF_2CF_3$ | $C(S)NH_2$ | H | $CF_3$ |
| $CF_2CF_2CF_3$ | $C(S)NH_2$ | H | $CF_2CF_3$ |
| $CF_2CF_2CF_3$ | $C(S)NH_2$ | H | $CF_2CF_2CF_3$ |
| $CF_2CF_2CF_3$ | $C(S)NH_2$ | $CH_3$ | $CF_3$ |
| $CF_2CF_2CF_3$ | $C(S)NH_2$ | $CH_3$ | $CF_2CF_3$ |
| $CF_2CF_2CF_3$ | $C(S)NH_2$ | $CH_3$ | $CF_2CF_2CF_3$ |

TABLE 47

| R¹ | R² | R³ | R⁴ |
|---|---|---|---|
| $CF_2CF_2CF_3$ | $C(S)NH_2$ | $CH_2CH_3$ | $CF_3$ |
| $CF_2CF_2CF_3$ | $C(S)NH_2$ | $CH_2CH_3$ | $CF_2CF_3$ |
| $CF_2CF_2CF_3$ | $C(S)NH_2$ | $CH_2CH_3$ | $CF_2CF_2CF_3$ |
| $CF_2CF_2CF_3$ | $C(S)NH_2$ | F | $CF_3$ |
| $CF_2CF_2CF_3$ | $C(S)NH_2$ | F | $CF_2CF_3$ |
| $CF_2CF_2CF_3$ | $C(S)NH_2$ | F | $CF_2CF_2CF_3$ |
| $CF_2CF_2CF_3$ | $C(S)NH_2$ | Cl | $CF_3$ |
| $CF_2CF_2CF_3$ | $C(S)NH_2$ | Cl | $CF_2CF_3$ |
| $CF_2CF_2CF_3$ | $C(S)NH_2$ | Cl | $CF_2CF_2CF_3$ |
| $CF_2CF_2CF_3$ | $C(S)NH(CH_3)$ | H | $CF_3$ |
| $CF_2CF_2CF_3$ | $C(S)NH(CH_3)$ | H | $CF_2CF_3$ |
| $CF_2CF_2CF_3$ | $C(S)NH(CH_3)$ | H | $CF_2CF_2CF_3$ |
| $CF_2CF_2CF_3$ | $C(S)NH(CH_3)$ | $CH_3$ | $CF_3$ |
| $CF_2CF_2CF_3$ | $C(S)NH(CH_3)$ | $CH_3$ | $CF_2CF_3$ |
| $CF_2CF_2CF_3$ | $C(S)NH(CH_3)$ | $CH_3$ | $CF_2CF_2CF_3$ |
| $CF_2CF_2CF_3$ | $C(S)NH(CH_3)$ | $CH_2CH_3$ | $CF_3$ |
| $CF_2CF_2CF_3$ | $C(S)NH(CH_3)$ | $CH_2CH_3$ | $CF_2CF_3$ |
| $CF_2CF_2CF_3$ | $C(S)NH(CH_3)$ | $CH_2CH_3$ | $CF_2CF_2CF_3$ |
| $CF_2CF_2CF_3$ | $C(S)NH(CH_3)$ | F | $CF_3$ |
| $CF_2CF_2CF_3$ | $C(S)NH(CH_3)$ | F | $CF_2CF_3$ |
| $CF_2CF_2CF_3$ | $C(S)NH(CH_3)$ | F | $CF_2CF_2CF_3$ |
| $CF_2CF_2CF_3$ | $C(S)NH(CH_3)$ | Cl | $CF_3$ |
| $CF_2CF_2CF_3$ | $C(S)NH(CH_3)$ | Cl | $CF_2CF_3$ |
| $CF_2CF_2CF_3$ | $C(S)NH(CH_3)$ | Cl | $CF_2CF_2CF_3$ |
| $CF_2CF_2CF_3$ | $C(S)N(CH_3)_2$ | H | $CF_3$ |
| $CF_2CF_2CF_3$ | $C(S)N(CH_3)_2$ | H | $CF_2CF_3$ |
| $CF_2CF_2CF_3$ | $C(S)N(CH_3)_2$ | H | $CF_2CF_2CF_3$ |

TABLE 48

| R¹ | R² | R³ | R⁴ |
|---|---|---|---|
| $CF_2CF_2CF_3$ | $C(S)N(CH_3)_2$ | $CH_3$ | $CF_3$ |
| $CF_2CF_2CF_3$ | $C(S)N(CH_3)_2$ | $CH_3$ | $CF_2CF_3$ |
| $CF_2CF_2CF_3$ | $C(S)N(CH_3)_2$ | $CH_3$ | $CF_2CF_2CF_3$ |
| $CF_2CF_2CF_3$ | $C(S)N(CH_3)_2$ | $CH_2CH_3$ | $CF_3$ |
| $CF_2CF_2CF_3$ | $C(S)N(CH_3)_2$ | $CH_2CH_3$ | $CF_2CF_3$ |
| $CF_2CF_2CF_3$ | $C(S)N(CH_3)_2$ | $CH_2CH_3$ | $CF_2CF_2CF_3$ |
| $CF_2CF_2CF_3$ | $C(S)N(CH_3)_2$ | F | $CF_3$ |
| $CF_2CF_2CF_3$ | $C(S)N(CH_3)_2$ | F | $CF_2CF_3$ |
| $CF_2CF_2CF_3$ | $C(S)N(CH_3)_2$ | F | $CF_2CF_2CF_3$ |
| $CF_2CF_2CF_3$ | $C(S)N(CH_3)_2$ | Cl | $CF_3$ |
| $CF_2CF_2CF_3$ | $C(S)N(CH_3)_2$ | Cl | $CF_2CF_3$ |
| $CF_2CF_2CF_3$ | $C(S)N(CH_3)_2$ | Cl | $CF_2CF_2CF_3$ |

TABLE 49

| R¹ | R² | R³ | R⁴ |
|---|---|---|---|
| CF₂CF₂CF₂CF₃ | CN | H | CF₃ |
| CF₂CF₂CF₂CF₃ | CN | H | CF₂CF₃ |
| CF₂CF₂CF₂CF₃ | CN | H | CF₂CF₂CF₃ |
| CF₂CF₂CF₂CF₃ | CN | CH₃ | CF₃ |
| CF₂CF₂CF₂CF₃ | CN | CH₃ | CF₂CF₃ |
| CF₂CF₂CF₂CF₃ | CN | CH₃ | CF₂CF₂CF₃ |
| CF₂CF₂CF₂CF₃ | CN | CH₂CH₃ | CF₃ |
| CF₂CF₂CF₂CF₃ | CN | CH₂CH₃ | CF₂CF₃ |
| CF₂CF₂CF₂CF₃ | CN | CH₂CH₃ | CF₂CF₂CF₃ |
| CF₂CF₂CF₂CF₃ | CN | CH₂CH₂CH₃ | CF₃ |
| CF₂CF₂CF₂CF₃ | CN | CH₂CH₂CH₃ | CF₂CF₃ |
| CF₂CF₂CF₂CF₃ | CN | CH₂CH₂CH₃ | CF₂CF₂CF₃ |
| CF₂CF₂CF₂CF₃ | CN | CH(CH₃)₂ | CF₃ |
| CF₂CF₂CF₂CF₃ | CN | CH(CH₃)₂ | CF₂CF₃ |
| CF₂CF₂CF₂CF₃ | CN | CH(CH₃)₂ | CF₂CF₂CF₃ |
| CF₂CF₂CF₂CF₃ | CN | CH₂CH₂CH₂CH₃ | CF₃ |
| CF₂CF₂CF₂CF₃ | CN | CH₂CH₂CH₂CH₃ | CF₂CF₃ |
| CF₂CF₂CF₂CF₃ | CN | CH₂CH₂CH₂CH₃ | CF₂CF₂CF₃ |
| CF₂CF₂CF₂CF₃ | CN | CH₂CH₂CH₂CH₂CH₃ | CF₃ |
| CF₂CF₂CF₂CF₃ | CN | CH₂CH₂CH₂CH₂CH₃ | CF₂CF₃ |
| CF₂CF₂CF₂CF₃ | CN | CH₂CH₂CH₂CH₂CH₃ | CF₂CF₂CF₃ |
| CF₂CF₂CF₂CF₃ | CN | F | CF₃ |
| CF₂CF₂CF₂CF₃ | CN | F | CF₂CF₃ |
| CF₂CF₂CF₂CF₃ | CN | F | CF₂CF₂CF₃ |
| CF₂CF₂CF₂CF₃ | CN | Cl | CF₃ |
| CF₂CF₂CF₂CF₃ | CN | Cl | CF₂CF₃ |
| CF₂CF₂CF₂CF₃ | CN | Cl | CF₂CF₂CF₃ |

TABLE 50

| R¹ | R² | R³ | R⁴ |
|---|---|---|---|
| CF₂CF₂CF₂CF₃ | CO₂CH₃ | H | CF₃ |
| CF₂CF₂CF₂CF₃ | CO₂CH₃ | H | CF₂CF₃ |
| CF₂CF₂CF₂CF₃ | CO₂CH₃ | H | CF₂CF₂CF₃ |
| CF₂CF₂CF₂CF₃ | CO₂CH₃ | CH₃ | CF₃ |
| CF₂CF₂CF₂CF₃ | CO₂CH₃ | CH₃ | CF₂CF₃ |
| CF₂CF₂CF₂CF₃ | CO₂CH₃ | CH₃ | CF₂CF₂CF₃ |
| CF₂CF₂CF₂CF₃ | CO₂CH₃ | CH₂CH₃ | CF₃ |
| CF₂CF₂CF₂CF₃ | CO₂CH₃ | CH₂CH₃ | CF₂CF₃ |
| CF₂CF₂CF₂CF₃ | CO₂CH₃ | CH₂CH₃ | CF₂CF₂CF₃ |
| CF₂CF₂CF₂CF₃ | CO₂CH₃ | CH₂CH₂CH₃ | CF₃ |
| CF₂CF₂CF₂CF₃ | CO₂CH₃ | CH₂CH₂CH₃ | CF₂CF₃ |
| CF₂CF₂CF₂CF₃ | CO₂CH₃ | CH₂CH₂CH₃ | CF₂CF₂CF₃ |
| CF₂CF₂CF₂CF₃ | CO₂CH₃ | F | CF₃ |
| CF₂CF₂CF₂CF₃ | CO₂CH₃ | F | CF₂CF₃ |
| CF₂CF₂CF₂CF₃ | CO₂CH₃ | F | CF₂CF₂CF₃ |
| CF₂CF₂CF₂CF₃ | CO₂CH₃ | Cl | CF₃ |
| CF₂CF₂CF₂CF₃ | CO₂CH₃ | Cl | CF₂CF₃ |
| CF₂CF₂CF₂CF₃ | CO₂CH₃ | Cl | CF₂CF₂CF₃ |
| CF₂CF₂CF₂CF₃ | CO₂C(CH₃)₃ | H | CF₃ |
| CF₂CF₂CF₂CF₃ | CO₂C(CH₃)₃ | H | CF₂CF₃ |
| CF₂CF₂CF₂CF₃ | CO₂C(CH₃)₃ | H | CF₂CF₂CF₃ |
| CF₂CF₂CF₂CF₃ | CO₂C(CH₃)₃ | CH₃ | CF₃ |
| CF₂CF₂CF₂CF₃ | CO₂C(CH₃)₃ | CH₃ | CF₂CF₃ |
| CF₂CF₂CF₂CF₃ | CO₂C(CH₃)₃ | CH₃ | CF₂CF₂CF₃ |
| CF₂CF₂CF₂CF₃ | CO₂C(CH₃)₃ | F | CF₃ |
| CF₂CF₂CF₂CF₃ | CO₂C(CH₃)₃ | F | CF₂CF₃ |
| CF₂CF₂CF₂CF₃ | CO₂C(CH₃)₃ | F | CF₂CF₂CF₃ |

TABLE 51

| R¹ | R² | R³ | R⁴ |
|---|---|---|---|
| CF₂CF₂CF₂CF₃ | CO₂C(CH₃)₃ | Cl | CF₃ |
| CF₂CF₂CF₂CF₃ | CO₂C(CH₃)₃ | Cl | CF₂CF₃ |
| CF₂CF₂CF₂CF₃ | CO₂C(CH₃)₃ | Cl | CF₂CF₂CF₃ |
| CF₂CF₂CF₂CF₃ | CONH₂ | H | CF₃ |
| CF₂CF₂CF₂CF₃ | CONH₂ | H | CF₂CF₃ |
| CF₂CF₂CF₂CF₃ | CONH₂ | H | CF₂CF₂CF₃ |
| CF₂CF₂CF₂CF₃ | CONH₂ | CH₃ | CF₃ |
| CF₂CF₂CF₂CF₃ | CONH₂ | CH₃ | CF₂CF₃ |
| CF₂CF₂CF₂CF₃ | CONH₂ | CH₃ | CF₂CF₂CF₃ |

TABLE 51-continued

| R¹ | R² | R³ | R⁴ |
|---|---|---|---|
| CF₂CF₂CF₂CF₃ | CONH₂ | CH₂CH₃ | CF₃ |
| CF₂CF₂CF₂CF₃ | CONH₂ | CH₂CH₃ | CF₂CF₃ |
| CF₂CF₂CF₂CF₃ | CONH₂ | CH₂CH₃ | CF₂CF₂CF₃ |
| CF₂CF₂CF₂CF₃ | CONH₂ | F | CF₃ |
| CF₂CF₂CF₂CF₃ | CONH₂ | F | CF₂CF₃ |
| CF₂CF₂CF₂CF₃ | CONH₂ | F | CF₂CF₂CF₃ |
| CF₂CF₂CF₂CF₃ | CONH₂ | Cl | CF₃ |
| CF₂CF₂CF₂CF₃ | CONH₂ | Cl | CF₂CF₃ |
| CF₂CF₂CF₂CF₃ | CONH₂ | Cl | CF₂CF₂CF₃ |
| CF₂CF₂CF₂CF₃ | CONH(CH₃) | H | CF₃ |
| CF₂CF₂CF₂CF₃ | CONH(CH₃) | H | CF₂CF₃ |
| CF₂CF₂CF₂CF₃ | CONH(CH₃) | H | CF₂CF₂CF₃ |
| CF₂CF₂CF₂CF₃ | CONH(CH₃) | CH₃ | CF₃ |
| CF₂CF₂CF₂CF₃ | CONH(CH₃) | CH₃ | CF₂CF₃ |
| CF₂CF₂CF₂CF₃ | CONH(CH₃) | CH₃ | CF₂CF₂CF₃ |
| CF₂CF₂CF₂CF₃ | CONH(CH₃) | CH₂CH₃ | CF₃ |
| CF₂CF₂CF₂CF₃ | CONH(CH₃) | CH₂CH₃ | CF₂CF₃ |
| CF₂CF₂CF₂CF₃ | CONH(CH₃) | CH₂CH₃ | CF₂CF₂CF₃ |

TABLE 52

| R¹ | R² | R³ | R⁴ |
|---|---|---|---|
| CF₂CF₂CF₂CF₃ | CONH(CH₃) | F | CF₃ |
| CF₂CF₂CF₂CF₃ | CONH(CH₃) | F | CF₂CF₃ |
| CF₂CF₂CF₂CF₃ | CONH(CH₃) | F | CF₂CF₂CF₃ |
| CF₂CF₂CF₂CF₃ | CONH(CH₃) | Cl | CF₃ |
| CF₂CF₂CF₂CF₃ | CONH(CH₃) | Cl | CF₂CF₃ |
| CF₂CF₂CF₂CF₃ | CONH(CH₃) | Cl | CF₂CF₂CF₃ |
| CF₂CF₂CF₂CF₃ | CONH(CH₂CH₃) | H | CF₃ |
| CF₂CF₂CF₂CF₃ | CONH(CH₂CH₃) | H | CF₂CF₃ |
| CF₂CF₂CF₂CF₃ | CONH(CH₂CH₃) | H | CF₂CF₂CF₃ |
| CF₂CF₂CF₂CF₃ | CONH(CH₂CH₃) | CH₃ | CF₃ |
| CF₂CF₂CF₂CF₃ | CONH(CH₂CH₃) | CH₃ | CF₂CF₃ |
| CF₂CF₂CF₂CF₃ | CONH(CH₂CH₃) | CH₃ | CF₂CF₂CF₃ |
| CF₂CF₂CF₂CF₃ | CONH(CH₂CH₃) | CH₂CH₃ | CF₃ |
| CF₂CF₂CF₂CF₃ | CONH(CH₂CH₃) | CH₂CH₃ | CF₂CF₃ |
| CF₂CF₂CF₂CF₃ | CONH(CH₂CH₃) | CH₂CH₃ | CF₂CF₂CF₃ |
| CF₂CF₂CF₂CF₃ | CONH(CH₂CH₃) | F | CF₃ |
| CF₂CF₂CF₂CF₃ | CONH(CH₂CH₃) | F | CF₂CF₃ |
| CF₂CF₂CF₂CF₃ | CONH(CH₂CH₃) | F | CF₂CF₂CF₃ |
| CF₂CF₂CF₂CF₃ | CONH(CH₂CH₃) | Cl | CF₃ |
| CF₂CF₂CF₂CF₃ | CONH(CH₂CH₃) | Cl | CF₂CF₃ |
| CF₂CF₂CF₂CF₃ | CONH(CH₂CH₃) | Cl | CF₂CF₂CF₃ |
| CF₂CF₂CF₂CF₃ | CON(CH₃)₂ | H | CF₃ |
| CF₂CF₂CF₂CF₃ | CON(CH₃)₂ | H | CF₂CF₃ |
| CF₂CF₂CF₂CF₃ | CON(CH₃)₂ | H | CF₂CF₂CF₃ |
| CF₂CF₂CF₂CF₃ | CON(CH₃)₂ | CH₃ | CF₃ |
| CF₂CF₂CF₂CF₃ | CON(CH₃)₂ | CH₃ | CF₂CF₃ |
| CF₂CF₂CF₂CF₃ | CON(CH₃)₂ | CH₃ | CF₂CF₂CF₃ |

TABLE 53

| R¹ | R² | R³ | R⁴ |
|---|---|---|---|
| CF₂CF₂CF₂CF₃ | CON(CH₃)₂ | CH₂CH₃ | CF₃ |
| CF₂CF₂CF₂CF₃ | CON(CH₃)₂ | CH₂CH₃ | CF₂CF₃ |
| CF₂CF₂CF₂CF₃ | CON(CH₃)₂ | CH₂CH₃ | CF₂CF₂CF₃ |
| CF₂CF₂CF₂CF₃ | CON(CH₃)₂ | F | CF₃ |
| CF₂CF₂CF₂CF₃ | CON(CH₃)₂ | F | CF₂CF₃ |
| CF₂CF₂CF₂CF₃ | CON(CH₃)₂ | F | CF₂CF₂CF₃ |
| CF₂CF₂CF₂CF₃ | CON(CH₃)₂ | Cl | CF₃ |
| CF₂CF₂CF₂CF₃ | CON(CH₃)₂ | Cl | CF₂CF₃ |
| CF₂CF₂CF₂CF₃ | CON(CH₃)₂ | Cl | CF₂CF₂CF₃ |
| CF₂CF₂CF₂CF₃ | C(S)OCH₃ | H | CF₃ |
| CF₂CF₂CF₂CF₃ | C(S)OCH₃ | H | CF₂CF₃ |
| CF₂CF₂CF₂CF₃ | C(S)OCH₃ | H | CF₂CF₂CF₃ |
| CF₂CF₂CF₂CF₃ | C(S)OCH₃ | CH₃ | CF₃ |
| CF₂CF₂CF₂CF₃ | C(S)OCH₃ | CH₃ | CF₂CF₃ |
| CF₂CF₂CF₂CF₃ | C(S)OCH₃ | CH₃ | CF₂CF₂CF₃ |
| CF₂CF₂CF₂CF₃ | C(S)OCH₃ | F | CF₃ |
| CF₂CF₂CF₂CF₃ | C(S)OCH₃ | F | CF₂CF₃ |
| CF₂CF₂CF₂CF₃ | C(S)OCH₃ | F | CF₂CF₂CF₃ |

TABLE 53-continued

| R¹ | R² | R³ | R⁴ |
|---|---|---|---|
| CF₂CF₂CF₂CF₃ | C(S)OCH₃ | Cl | CF₃ |
| CF₂CF₂CF₂CF₃ | C(S)OCH₃ | Cl | CF₂CF₃ |
| CF₂CF₂CF₂CF₃ | C(S)OCH₃ | Cl | CF₂CF₂CF₃ |
| CF₂CF₂CF₂CF₃ | C(S)NH₂ | H | CF₃ |
| CF₂CF₂CF₂CF₃ | C(S)NH₂ | H | CF₂CF₃ |
| CF₂CF₂CF₂CF₃ | C(S)NH₂ | H | CF₂CF₂CF₃ |
| CF₂CF₂CF₂CF₃ | C(S)NH₂ | CH₃ | CF₃ |
| CF₂CF₂CF₂CF₃ | C(S)NH₂ | CH₃ | CF₂CF₃ |
| CF₂CF₂CF₂CF₃ | C(S)NH₂ | CH₃ | CF₂CF₂CF₃ |

TABLE 54

| R¹ | R² | R³ | R⁴ |
|---|---|---|---|
| CF₂CF₂CF₂CF₃ | C(S)NH₂ | CH₂CH₃ | CF₃ |
| CF₂CF₂CF₂CF₃ | C(S)NH₂ | CH₂CH₃ | CF₂CF₃ |
| CF₂CF₂CF₂CF₃ | C(S)NH₂ | CH₂CH₃ | CF₂CF₂CF₃ |
| CF₂CF₂CF₂CF₃ | C(S)NH₂ | F | CF₃ |
| CF₂CF₂CF₂CF₃ | C(S)NH₂ | F | CF₂CF₃ |
| CF₂CF₂CF₂CF₃ | C(S)NH₂ | F | CF₂CF₂CF₃ |
| CF₂CF₂CF₂CF₃ | C(S)NH₂ | Cl | CF₃ |
| CF₂CF₂CF₂CF₃ | C(S)NH₂ | Cl | CF₂CF₃ |
| CF₂CF₂CF₂CF₃ | C(S)NH₂ | Cl | CF₂CF₂CF₃ |
| CF₂CF₂CF₂CF₃ | C(S)NH(CH₃) | H | CF₃ |
| CF₂CF₂CF₂CF₃ | C(S)NH(CH₃) | H | CF₂CF₃ |
| CF₂CF₂CF₂CF₃ | C(S)NH(CH₃) | H | CF₂CF₂CF₃ |
| CF₂CF₂CF₂CF₃ | C(S)NH(CH₃) | CH₃ | CF₃ |
| CF₂CF₂CF₂CF₃ | C(S)NH(CH₃) | CH₃ | CF₂CF₃ |
| CF₂CF₂CF₂CF₃ | C(S)NH(CH₃) | CH₃ | CF₂CF₂CF₃ |
| CF₂CF₂CF₂CF₃ | C(S)NH(CH₃) | CH₂CH₃ | CF₃ |
| CF₂CF₂CF₂CF₃ | C(S)NH(CH₃) | CH₂CH₃ | CF₂CF₃ |
| CF₂CF₂CF₂CF₃ | C(S)NH(CH₃) | CH₂CH₃ | CF₂CF₂CF₃ |
| CF₂CF₂CF₂CF₃ | C(S)NH(CH₃) | F | CF₃ |
| CF₂CF₂CF₂CF₃ | C(S)NH(CH₃) | F | CF₂CF₃ |
| CF₂CF₂CF₂CF₃ | C(S)NH(CH₃) | F | CF₂CF₂CF₃ |
| CF₂CF₂CF₂CF₃ | C(S)NH(CH₃) | Cl | CF₃ |
| CF₂CF₂CF₂CF₃ | C(S)NH(CH₃) | Cl | CF₂CF₃ |
| CF₂CF₂CF₂CF₃ | C(S)NH(CH₃) | Cl | CF₂CF₂CF₃ |
| CF₂CF₂CF₂CF₃ | C(S)N(CH₃)₂ | H | CF₃ |
| CF₂CF₂CF₂CF₃ | C(S)N(CH₃)₂ | H | CF₂CF₃ |
| CF₂CF₂CF₂CF₃ | C(S)N(CH₃)₂ | H | CF₂CF₂CF₃ |

TABLE 55

| R¹ | R² | R³ | R⁴ |
|---|---|---|---|
| CF₂CF₂CF₂CF₃ | C(S)N(CH₃)₂ | CH₃ | CF₃ |
| CF₂CF₂CF₂CF₃ | C(S)N(CH₃)₂ | CH₃ | CF₂CF₃ |
| CF₂CF₂CF₂CF₃ | C(S)N(CH₃)₂ | CH₃ | CF₂CF₂CF₃ |
| CF₂CF₂CF₂CF₃ | C(S)N(CH₃)₂ | CH₂CH₃ | CF₃ |
| CF₂CF₂CF₂CF₃ | C(S)N(CH₃)₂ | CH₂CH₃ | CF₂CF₃ |
| CF₂CF₂CF₂CF₃ | C(S)N(CH₃)₂ | CH₂CH₃ | CF₂CF₂CF₃ |
| CF₂CF₂CF₂CF₃ | C(S)N(CH₃)₂ | F | CF₃ |
| CF₂CF₂CF₂CF₃ | C(S)N(CH₃)₂ | F | CF₂CF₃ |
| CF₂CF₂CF₂CF₃ | C(S)N(CH₃)₂ | F | CF₂CF₂CF₃ |
| CF₂CF₂CF₂CF₃ | C(S)N(CH₃)₂ | Cl | CF₃ |
| CF₂CF₂CF₂CF₃ | C(S)N(CH₃)₂ | Cl | CF₂CF₃ |
| CF₂CF₂CF₂CF₃ | C(S)N(CH₃)₂ | Cl | CF₂CF₂CF₃ |

TABLE 56

| R¹ | R² | R³ | R⁴ |
|---|---|---|---|
| CF₂CF₂CF₂CF₂CF₃ | CN | H | CF₃ |
| CF₂CF₂CF₂CF₂CF₃ | CN | H | CF₂CF₃ |
| CF₂CF₂CF₂CF₂CF₃ | CN | H | CF₂CF₂CF₃ |
| CF₂CF₂CF₂CF₂CF₃ | CN | CH₃ | CF₃ |
| CF₂CF₂CF₂CF₂CF₃ | CN | CH₃ | CF₂CF₃ |
| CF₂CF₂CF₂CF₂CF₃ | CN | CH₃ | CF₂CF₂CF₃ |
| CF₂CF₂CF₂CF₂CF₃ | CN | CH₂CH₃ | CF₃ |
| CF₂CF₂CF₂CF₂CF₃ | CN | CH₂CH₃ | CF₂CF₃ |

TABLE 56-continued

| R¹ | R² | R³ | R⁴ |
|---|---|---|---|
| CF₂CF₂CF₂CF₂CF₃ | CN | CH₂CH₃ | CF₂CF₂CF₃ |
| CF₂CF₂CF₂CF₂CF₃ | CN | CH₂CH₂CH₃ | CF₃ |
| CF₂CF₂CF₂CF₂CF₃ | CN | CH₂CH₂CH₃ | CF₂CF₃ |
| CF₂CF₂CF₂CF₂CF₃ | CN | CH₂CH₂CH₃ | CF₂CF₂CF₃ |
| CF₂CF₂CF₂CF₂CF₃ | CN | CH(CH₃)₂ | CF₃ |
| CF₂CF₂CF₂CF₂CF₃ | CN | CH(CH₃)₂ | CF₂CF₃ |
| CF₂CF₂CF₂CF₂CF₃ | CN | CH(CH₃)₂ | CF₂CF₂CF₃ |
| CF₂CF₂CF₂CF₂CF₃ | CN | CH₂CH₂CH₂CH₃ | CF₃ |
| CF₂CF₂CF₂CF₂CF₃ | CN | CH₂CH₂CH₂CH₃ | CF₂CF₃ |
| CF₂CF₂CF₂CF₂CF₃ | CN | CH₂CH₂CH₂CH₃ | CF₂CF₂CF₃ |
| CF₂CF₂CF₂CF₂CF₃ | CN | CH₂CH₂CH₂CH₂CH₃ | CF₃ |
| CF₂CF₂CF₂CF₂CF₃ | CN | CH₂CH₂CH₂CH₂CH₃ | CF₂CF₃ |
| CF₂CF₂CF₂CF₂CF₃ | CN | CH₂CH₂CH₂CH₂CH₃ | CF₂CF₂CF₃ |
| CF₂CF₂CF₂CF₂CF₃ | CN | F | CF₃ |
| CF₂CF₂CF₂CF₂CF₃ | CN | F | CF₂CF₃ |
| CF₂CF₂CF₂CF₂CF₃ | CN | F | CF₂CF₂CF₃ |
| CF₂CF₂CF₂CF₂CF₃ | CN | Cl | CF₃ |
| CF₂CF₂CF₂CF₂CF₃ | CN | Cl | CF₂CF₃ |
| CF₂CF₂CF₂CF₂CF₃ | CN | Cl | CF₂CF₂CF₃ |

TABLE 57

| R¹ | R² | R³ | R⁴ |
|---|---|---|---|
| CF₂CF₂CF₂CF₂CF₃ | CO₂CH₃ | H | CF₃ |
| CF₂CF₂CF₂CF₂CF₃ | CO₂CH₃ | H | CF₂CF₃ |
| CF₂CF₂CF₂CF₂CF₃ | CO₂CH₃ | H | CF₂CF₂CF₃ |
| CF₂CF₂CF₂CF₂CF₃ | CO₂CH₃ | CH₃ | CF₃ |
| CF₂CF₂CF₂CF₂CF₃ | CO₂CH₃ | CH₃ | CF₂CF₃ |
| CF₂CF₂CF₂CF₂CF₃ | CO₂CH₃ | CH₃ | CF₂CF₂CF₃ |
| CF₂CF₂CF₂CF₂CF₃ | CO₂CH₃ | CH₂CH₃ | CF₃ |
| CF₂CF₂CF₂CF₂CF₃ | CO₂CH₃ | CH₂CH₃ | CF₂CF₃ |
| CF₂CF₂CF₂CF₂CF₃ | CO₂CH₃ | CH₂CH₃ | CF₂CF₂CF₃ |
| CF₂CF₂CF₂CF₂CF₃ | CO₂CH₃ | CH₂CH₂CH₃ | CF₃ |
| CF₂CF₂CF₂CF₂CF₃ | CO₂CH₃ | CH₂CH₂CH₃ | CF₂CF₃ |
| CF₂CF₂CF₂CF₂CF₃ | CO₂CH₃ | CH₂CH₂CH₃ | CF₂CF₂CF₃ |
| CF₂CF₂CF₂CF₂CF₃ | CO₂CH₃ | F | CF₃ |
| CF₂CF₂CF₂CF₂CF₃ | CO₂CH₃ | F | CF₂CF₃ |
| CF₂CF₂CF₂CF₂CF₃ | CO₂CH₃ | F | CF₂CF₂CF₃ |
| CF₂CF₂CF₂CF₂CF₃ | CO₂CH₃ | Cl | CF₃ |
| CF₂CF₂CF₂CF₂CF₃ | CO₂CH₃ | Cl | CF₂CF₃ |
| CF₂CF₂CF₂CF₂CF₃ | CO₂CH₃ | Cl | CF₂CF₂CF₃ |
| CF₂CF₂CF₂CF₂CF₃ | CO₂C(CH₃)₃ | H | CF₃ |
| CF₂CF₂CF₂CF₂CF₃ | CO₂C(CH₃)₃ | H | CF₂CF₃ |
| CF₂CF₂CF₂CF₂CF₃ | CO₂C(CH₃)₃ | H | CF₂CF₂CF₃ |
| CF₂CF₂CF₂CF₂CF₃ | CO₂C(CH₃)₃ | CH₃ | CF₃ |
| CF₂CF₂CF₂CF₂CF₃ | CO₂C(CH₃)₃ | CH₃ | CF₂CF₃ |
| CF₂CF₂CF₂CF₂CF₃ | CO₂C(CH₃)₃ | CH₃ | CF₂CF₂CF₃ |
| CF₂CF₂CF₂CF₂CF₃ | CO₂C(CH₃)₃ | F | CF₃ |
| CF₂CF₂CF₂CF₂CF₃ | CO₂C(CH₃)₃ | F | CF₂CF₃ |
| CF₂CF₂CF₂CF₂CF₃ | CO₂C(CH₃)₃ | F | CF₂CF₂CF₃ |

TABLE 58

| R¹ | R² | R³ | R⁴ |
|---|---|---|---|
| CF₂CF₂CF₂CF₂CF₃ | CO₂C(CH₃)₃ | Cl | CF₃ |
| CF₂CF₂CF₂CF₂CF₃ | CO₂C(CH₃)₃ | Cl | CF₂CF₃ |
| CF₂CF₂CF₂CF₂CF₃ | CO₂C(CH₃)₃ | Cl | CF₂CF₂CF₃ |
| CF₂CF₂CF₂CF₂CF₃ | CONH₂ | H | CF₃ |
| CF₂CF₂CF₂CF₂CF₃ | CONH₂ | H | CF₂CF₃ |
| CF₂CF₂CF₂CF₂CF₃ | CONH₂ | H | CF₂CF₂CF₃ |
| CF₂CF₂CF₂CF₂CF₃ | CONH₂ | CH₃ | CF₃ |
| CF₂CF₂CF₂CF₂CF₃ | CONH₂ | CH₃ | CF₂CF₃ |
| CF₂CF₂CF₂CF₂CF₃ | CONH₂ | CH₃ | CF₂CF₂CF₃ |
| CF₂CF₂CF₂CF₂CF₃ | CONH₂ | CH₂CH₃ | CF₃ |
| CF₂CF₂CF₂CF₂CF₃ | CONH₂ | CH₂CH₃ | CF₂CF₃ |
| CF₂CF₂CF₂CF₂CF₃ | CONH₂ | CH₂CH₃ | CF₂CF₂CF₃ |
| CF₂CF₂CF₂CF₂CF₃ | CONH₂ | F | CF₃ |
| CF₂CF₂CF₂CF₂CF₃ | CONH₂ | F | CF₂CF₃ |
| CF₂CF₂CF₂CF₂CF₃ | CONH₂ | F | CF₂CF₂CF₃ |
| CF₂CF₂CF₂CF₂CF₃ | CONH₂ | Cl | CF₃ |
| CF₂CF₂CF₂CF₂CF₃ | CONH₂ | Cl | CF₂CF₃ |

TABLE 58-continued

| R¹ | R² | R³ | R⁴ |
|---|---|---|---|
| CF₂CF₂CF₂CF₂CF₃ | CONH₂ | Cl | CF₂CF₂CF₃ |
| CF₂CF₂CF₂CF₂CF₃ | CONH(CH₃) | H | CF₃ |
| CF₂CF₂CF₂CF₂CF₃ | CONH(CH₃) | H | CF₂CF₃ |
| CF₂CF₂CF₂CF₂CF₃ | CONH(CH₃) | H | CF₂CF₂CF₃ |
| CF₂CF₂CF₂CF₂CF₃ | CONH(CH₃) | CH₃ | CF₃ |
| CF₂CF₂CF₂CF₂CF₃ | CONH(CH₃) | CH₃ | CF₂CF₃ |
| CF₂CF₂CF₂CF₂CF₃ | CONH(CH₃) | CH₃ | CF₂CF₂CF₃ |
| CF₂CF₂CF₂CF₂CF₃ | CONH(CH₃) | CH₂CH₃ | CF₃ |
| CF₂CF₂CF₂CF₂CF₃ | CONH(CH₃) | CH₂CH₃ | CF₂CF₃ |
| CF₂CF₂CF₂CF₂CF₃ | CONH(CH₃) | CH₂CH₃ | CF₂CF₂CF₃ |

TABLE 59

| R¹ | R² | R³ | R⁴ |
|---|---|---|---|
| CF₂CF₂CF₂CF₂CF₃ | CONH(CH₃) | F | CF₃ |
| CF₂CF₂CF₂CF₂CF₃ | CONH(CH₃) | F | CF₂CF₃ |
| CF₂CF₂CF₂CF₂CF₃ | CONH(CH₃) | F | CF₂CF₂CF₃ |
| CF₂CF₂CF₂CF₂CF₃ | CONH(CH₃) | Cl | CF₃ |
| CF₂CF₂CF₂CF₂CF₃ | CONH(CH₃) | Cl | CF₂CF₃ |
| CF₂CF₂CF₂CF₂CF₃ | CONH(CH₃) | Cl | CF₂CF₂CF₃ |
| CF₂CF₂CF₂CF₂CF₃ | CONH(CH₂CH₃) | H | CF₃ |
| CF₂CF₂CF₂CF₂CF₃ | CONH(CH₂CH₃) | H | CF₂CF₃ |
| CF₂CF₂CF₂CF₂CF₃ | CONH(CH₂CH₃) | H | CF₂CF₂CF₃ |
| CF₂CF₂CF₂CF₂CF₃ | CONH(CH₂CH₃) | CH₃ | CF₃ |
| CF₂CF₂CF₂CF₂CF₃ | CONH(CH₂CH₃) | CH₃ | CF₂CF₃ |
| CF₂CF₂CF₂CF₂CF₃ | CONH(CH₂CH₃) | CH₃ | CF₂CF₂CF₃ |
| CF₂CF₂CF₂CF₂CF₃ | CONH(CH₂CH₃) | CH₂CH₃ | CF₃ |
| CF₂CF₂CF₂CF₂CF₃ | CONH(CH₂CH₃) | CH₂CH₃ | CF₂CF₃ |
| CF₂CF₂CF₂CF₂CF₃ | CONH(CH₂CH₃) | CH₂CH₃ | CF₂CF₂CF₃ |
| CF₂CF₂CF₂CF₂CF₃ | CONH(CH₂CH₃) | F | CF₃ |
| CF₂CF₂CF₂CF₂CF₃ | CONH(CH₂CH₃) | F | CF₂CF₃ |
| CF₂CF₂CF₂CF₂CF₃ | CONH(CH₂CH₃) | F | CF₂CF₂CF₃ |
| CF₂CF₂CF₂CF₂CF₃ | CONH(CH₂CH₃) | Cl | CF₃ |
| CF₂CF₂CF₂CF₂CF₃ | CONH(CH₂CH₃) | Cl | CF₂CF₃ |
| CF₂CF₂CF₂CF₂CF₃ | CONH(CH₂CH₃) | Cl | CF₂CF₂CF₃ |
| CF₂CF₂CF₂CF₂CF₃ | CON(CH₃)₂ | H | CF₃ |
| CF₂CF₂CF₂CF₂CF₃ | CON(CH₃)₂ | H | CF₂CF₃ |
| CF₂CF₂CF₂CF₂CF₃ | CON(CH₃)₂ | H | CF₂CF₂CF₃ |
| CF₂CF₂CF₂CF₂CF₃ | CON(CH₃)₂ | CH₃ | CF₃ |
| CF₂CF₂CF₂CF₂CF₃ | CON(CH₃)₂ | CH₃ | CF₂CF₃ |
| CF₂CF₂CF₂CF₂CF₃ | CON(CH₃)₂ | CH₃ | CF₂CF₂CF₃ |

TABLE 60

| R¹ | R² | R³ | R⁴ |
|---|---|---|---|
| CF₂CF₂CF₂CF₂CF₃ | CON(CH₃)₂ | CH₂CH₃ | CF₃ |
| CF₂CF₂CF₂CF₂CF₃ | CON(CH₃)₂ | CH₂CH₃ | CF₂CF₃ |
| CF₂CF₂CF₂CF₂CF₃ | CON(CH₃)₂ | CH₂CH₃ | CF₂CF₂CF₃ |
| CF₂CF₂CF₂CF₂CF₃ | CON(CH₃)₂ | F | CF₃ |
| CF₂CF₂CF₂CF₂CF₃ | CON(CH₃)₂ | F | CF₂CF₃ |
| CF₂CF₂CF₂CF₂CF₃ | CON(CH₃)₂ | F | CF₂CF₂CF₃ |
| CF₂CF₂CF₂CF₂CF₃ | CON(CH₃)₂ | Cl | CF₃ |
| CF₂CF₂CF₂CF₂CF₃ | CON(CH₃)₂ | Cl | CF₂CF₃ |
| CF₂CF₂CF₂CF₂CF₃ | CON(CH₃)₂ | Cl | CF₂CF₂CF₃ |
| CF₂CF₂CF₂CF₂CF₃ | C(S)OCH₃ | H | CF₃ |
| CF₂CF₂CF₂CF₂CF₃ | C(S)OCH₃ | H | CF₂CF₃ |
| CF₂CF₂CF₂CF₂CF₃ | C(S)OCH₃ | H | CF₂CF₂CF₃ |
| CF₂CF₂CF₂CF₂CF₃ | C(S)OCH₃ | CH₃ | CF₃ |
| CF₂CF₂CF₂CF₂CF₃ | C(S)OCH₃ | CH₃ | CF₂CF₃ |
| CF₂CF₂CF₂CF₂CF₃ | C(S)OCH₃ | CH₃ | CF₂CF₂CF₃ |
| CF₂CF₂CF₂CF₂CF₃ | C(S)OCH₃ | F | CF₃ |
| CF₂CF₂CF₂CF₂CF₃ | C(S)OCH₃ | F | CF₂CF₃ |
| CF₂CF₂CF₂CF₂CF₃ | C(S)OCH₃ | F | CF₂CF₂CF₃ |
| CF₂CF₂CF₂CF₂CF₃ | C(S)OCH₃ | Cl | CF₃ |
| CF₂CF₂CF₂CF₂CF₃ | C(S)OCH₃ | Cl | CF₂CF₃ |
| CF₂CF₂CF₂CF₂CF₃ | C(S)OCH₃ | Cl | CF₂CF₂CF₃ |
| CF₂CF₂CF₂CF₂CF₃ | C(S)NH₂ | H | CF₃ |
| CF₂CF₂CF₂CF₂CF₃ | C(S)NH₂ | H | CF₂CF₃ |
| CF₂CF₂CF₂CF₂CF₃ | C(S)NH₂ | H | CF₂CF₂CF₃ |
| CF₂CF₂CF₂CF₂CF₃ | C(S)NH₂ | CH₃ | CF₃ |

TABLE 60-continued

| R¹ | R² | R³ | R⁴ |
|---|---|---|---|
| CF₂CF₂CF₂CF₂CF₃ | C(S)NH₂ | CH₃ | CF₂CF₃ |
| CF₂CF₂CF₂CF₂CF₃ | C(S)NH₂ | CH₃ | CF₂CF₂CF₃ |

TABLE 61

| R¹ | R² | R³ | R⁴ |
|---|---|---|---|
| CF₂CF₂CF₂CF₂CF₃ | C(S)NH₂ | CH₂CH₃ | CF₃ |
| CF₂CF₂CF₂CF₂CF₃ | C(S)NH₂ | CH₂CH₃ | CF₂CF₃ |
| CF₂CF₂CF₂CF₂CF₃ | C(S)NH₂ | CH₂CH₃ | CF₂CF₂CF₃ |
| CF₂CF₂CF₂CF₂CF₃ | C(S)NH₂ | F | CF₃ |
| CF₂CF₂CF₂CF₂CF₃ | C(S)NH₂ | F | CF₂CF₃ |
| CF₂CF₂CF₂CF₂CF₃ | C(S)NH₂ | F | CF₂CF₂CF₃ |
| CF₂CF₂CF₂CF₂CF₃ | C(S)NH₂ | Cl | CF₃ |
| CF₂CF₂CF₂CF₂CF₃ | C(S)NH₂ | Cl | CF₂CF₃ |
| CF₂CF₂CF₂CF₂CF₃ | C(S)NH₂ | Cl | CF₂CF₂CF₃ |
| CF₂CF₂CF₂CF₂CF₃ | C(S)NH(CH₃) | H | CF₃ |
| CF₂CF₂CF₂CF₂CF₃ | C(S)NH(CH₃) | H | CF₂CF₃ |
| CF₂CF₂CF₂CF₂CF₃ | C(S)NH(CH₃) | H | CF₂CF₂CF₃ |
| CF₂CF₂CF₂CF₂CF₃ | C(S)NH(CH₃) | CH₃ | CF₃ |
| CF₂CF₂CF₂CF₂CF₃ | C(S)NH(CH₃) | CH₃ | CF₂CF₃ |
| CF₂CF₂CF₂CF₂CF₃ | C(S)NH(CH₃) | CH₃ | CF₂CF₂CF₃ |
| CF₂CF₂CF₂CF₂CF₃ | C(S)NH(CH₃) | CH₂CH₃ | CF₃ |
| CF₂CF₂CF₂CF₂CF₃ | C(S)NH(CH₃) | CH₂CH₃ | CF₂CF₃ |
| CF₂CF₂CF₂CF₂CF₃ | C(S)NH(CH₃) | CH₂CH₃ | CF₂CF₂CF₃ |
| CF₂CF₂CF₂CF₂CF₃ | C(S)NH(CH₃) | F | CF₃ |
| CF₂CF₂CF₂CF₂CF₃ | C(S)NH(CH₃) | F | CF₂CF₃ |
| CF₂CF₂CF₂CF₂CF₃ | C(S)NH(CH₃) | F | CF₂CF₂CF₃ |
| CF₂CF₂CF₂CF₂CF₃ | C(S)NH(CH₃) | Cl | CF₃ |
| CF₂CF₂CF₂CF₂CF₃ | C(S)NH(CH₃) | Cl | CF₂CF₃ |
| CF₂CF₂CF₂CF₂CF₃ | C(S)NH(CH₃) | Cl | CF₂CF₂CF₃ |
| CF₂CF₂CF₂CF₂CF₃ | C(S)N(CH₃)₂ | H | CF₃ |
| CF₂CF₂CF₂CF₂CF₃ | C(S)N(CH₃)₂ | H | CF₂CF₃ |
| CF₂CF₂CF₂CF₂CF₃ | C(S)N(CH₃)₂ | H | CF₂CF₂CF₃ |

TABLE 62

| R¹ | R² | R³ | R⁴ |
|---|---|---|---|
| CF₂CF₂CF₂CF₂CF₃ | C(S)N(CH₃)₂ | CH₃ | CF₃ |
| CF₂CF₂CF₂CF₂CF₃ | C(S)N(CH₃)₂ | CH₃ | CF₂CF₃ |
| CF₂CF₂CF₂CF₂CF₃ | C(S)N(CH₃)₂ | CH₃ | CF₂CF₂CF₃ |
| CF₂CF₂CF₂CF₂CF₃ | C(S)N(CH₃)₂ | CH₂CH₃ | CF₃ |
| CF₂CF₂CF₂CF₂CF₃ | C(S)N(CH₃)₂ | CH₂CH₃ | CF₂CF₃ |
| CF₂CF₂CF₂CF₂CF₃ | C(S)N(CH₃)₂ | CH₂CH₃ | CF₂CF₂CF₃ |
| CF₂CF₂CF₂CF₂CF₃ | C(S)N(CH₃)₂ | F | CF₃ |
| CF₂CF₂CF₂CF₂CF₃ | C(S)N(CH₃)₂ | F | CF₂CF₃ |
| CF₂CF₂CF₂CF₂CF₃ | C(S)N(CH₃)₂ | F | CF₂CF₂CF₃ |
| CF₂CF₂CF₂CF₂CF₃ | C(S)N(CH₃)₂ | Cl | CF₃ |
| CF₂CF₂CF₂CF₂CF₃ | C(S)N(CH₃)₂ | Cl | CF₂CF₃ |
| CF₂CF₂CF₂CF₂CF₃ | C(S)N(CH₃)₂ | Cl | CF₂CF₂CF₃ |

TABLE 63

| R¹ | R² | R³ | R⁴ |
|---|---|---|---|
| CF₂CF₂CF₂CF₂CF₃ | CN | H | CF₃ |
| CF₂CF₂CF₂CF₂CF₃ | CN | H | CF₂CF₃ |
| CF₂CF₂CF₂CF₂CF₃ | CN | H | CF₂CF₂CF₃ |
| CF₂CF₂CF₂CF₂CF₃ | CN | CH₃ | CF₃ |
| CF₂CF₂CF₂CF₂CF₃ | CN | CH₃ | CF₂CF₃ |
| CF₂CF₂CF₂CF₂CF₃ | CN | CH₃ | CF₂CF₂CF₃ |
| CF₂CF₂CF₂CF₂CF₃ | CN | CH₂CH₃ | CF₃ |
| CF₂CF₂CF₂CF₂CF₃ | CN | CH₂CH₃ | CF₂CF₃ |
| CF₂CF₂CF₂CF₂CF₃ | CN | CH₂CH₃ | CF₂CF₂CF₃ |
| CF₂CF₂CF₂CF₂CF₃ | CN | CH₂CH₂CH₃ | CF₃ |
| CF₂CF₂CF₂CF₂CF₃ | CN | CH₂CH₂CH₃ | CF₂CF₃ |
| CF₂CF₂CF₂CF₂CF₃ | CN | CH₂CH₂CH₃ | CF₂CF₂CF₃ |
| CF₂CF₂CF₂CF₂CF₃ | CN | CH(CH₃)₂ | CF₃ |
| CF₂CF₂CF₂CF₂CF₃ | CN | CH(CH₃)₂ | CF₂CF₃ |
| CF₂CF₂CF₂CF₂CF₃ | CN | CH(CH₃)₂ | CF₂CF₂CF₃ |

TABLE 63-continued

| R$^1$ | R$^2$ | R$^3$ | R$^4$ |
|---|---|---|---|
| CF$_2$CF$_2$CF$_2$CF$_2$CF$_2$CF$_3$ | CN | CH$_2$CH$_2$CH$_2$CH$_3$ | CF$_3$ |
| CF$_2$CF$_2$CF$_2$CF$_2$CF$_2$CF$_3$ | CN | CH$_2$CH$_2$CH$_2$CH$_3$ | CF$_2$CF$_3$ |
| CF$_2$CF$_2$CF$_2$CF$_2$CF$_2$CF$_3$ | CN | CH$_2$CH$_2$CH$_2$CH$_3$ | CF$_2$CF$_2$CF$_3$ |
| CF$_2$CF$_2$CF$_2$CF$_2$CF$_2$CF$_3$ | CN | CH$_2$CH$_2$CH$_2$CH$_2$CH$_3$ | CF$_3$ |
| CF$_2$CF$_2$CF$_2$CF$_2$CF$_2$CF$_3$ | CN | CH$_2$CH$_2$CH$_2$CH$_2$CH$_3$ | CF$_2$CF$_3$ |
| CF$_2$CF$_2$CF$_2$CF$_2$CF$_2$CF$_3$ | CN | CH$_2$CH$_2$CH$_2$CH$_2$CH$_3$ | CF$_2$CF$_2$CF$_3$ |
| CF$_2$CF$_2$CF$_2$CF$_2$CF$_2$CF$_3$ | CN | F | CF$_3$ |
| CF$_2$CF$_2$CF$_2$CF$_2$CF$_2$CF$_3$ | CN | F | CF$_2$CF$_3$ |
| CF$_2$CF$_2$CF$_2$CF$_2$CF$_2$CF$_3$ | CN | F | CF$_2$CF$_2$CF$_3$ |
| CF$_2$CF$_2$CF$_2$CF$_2$CF$_2$CF$_3$ | CN | Cl | CF$_3$ |
| CF$_2$CF$_2$CF$_2$CF$_2$CF$_2$CF$_3$ | CN | Cl | CF$_2$CF$_3$ |
| CF$_2$CF$_2$CF$_2$CF$_2$CF$_2$CF$_3$ | CN | Cl | CF$_2$CF$_2$CF$_3$ |

TABLE 64

| R$^1$ | R$^2$ | R$^3$ | R$^4$ |
|---|---|---|---|
| CF$_2$CF$_2$CF$_2$CF$_2$CF$_2$CF$_3$ | CO$_2$CH$_3$ | H | CF$_3$ |
| CF$_2$CF$_2$CF$_2$CF$_2$CF$_2$CF$_3$ | CO$_2$CH$_3$ | H | CF$_2$CF$_3$ |
| CF$_2$CF$_2$CF$_2$CF$_2$CF$_2$CF$_3$ | CO$_2$CH$_3$ | H | CF$_2$CF$_2$CF$_3$ |
| CF$_2$CF$_2$CF$_2$CF$_2$CF$_2$CF$_3$ | CO$_2$CH$_3$ | CH$_3$ | CF$_3$ |
| CF$_2$CF$_2$CF$_2$CF$_2$CF$_2$CF$_3$ | CO$_2$CH$_3$ | CH$_3$ | CF$_2$CF$_3$ |
| CF$_2$CF$_2$CF$_2$CF$_2$CF$_2$CF$_3$ | CO$_2$CH$_3$ | CH$_3$ | CF$_2$CF$_2$CF$_3$ |
| CF$_2$CF$_2$CF$_2$CF$_2$CF$_2$CF$_3$ | CO$_2$CH$_3$ | CH$_2$CH$_3$ | CF$_3$ |
| CF$_2$CF$_2$CF$_2$CF$_2$CF$_2$CF$_3$ | CO$_2$CH$_3$ | CH$_2$CH$_3$ | CF$_2$CF$_3$ |
| CF$_2$CF$_2$CF$_2$CF$_2$CF$_2$CF$_3$ | CO$_2$CH$_3$ | CH$_2$CH$_3$ | CF$_2$CF$_2$CF$_3$ |
| CF$_2$CF$_2$CF$_2$CF$_2$CF$_2$CF$_3$ | CO$_2$CH$_3$ | CH$_2$CH$_2$CH$_3$ | CF$_3$ |
| CF$_2$CF$_2$CF$_2$CF$_2$CF$_2$CF$_3$ | CO$_2$CH$_3$ | CH$_2$CH$_2$CH$_3$ | CF$_2$CF$_3$ |
| CF$_2$CF$_2$CF$_2$CF$_2$CF$_2$CF$_3$ | CO$_2$CH$_3$ | CH$_2$CH$_2$CH$_3$ | CF$_2$CF$_2$CF$_3$ |
| CF$_2$CF$_2$CF$_2$CF$_2$CF$_2$CF$_3$ | CO$_2$CH$_3$ | F | CF$_3$ |
| CF$_2$CF$_2$CF$_2$CF$_2$CF$_2$CF$_3$ | CO$_2$CH$_3$ | F | CF$_2$CF$_3$ |
| CF$_2$CF$_2$CF$_2$CF$_2$CF$_2$CF$_3$ | CO$_2$CH$_3$ | F | CF$_2$CF$_2$CF$_3$ |
| CF$_2$CF$_2$CF$_2$CF$_2$CF$_2$CF$_3$ | CO$_2$CH$_3$ | Cl | CF$_3$ |
| CF$_2$CF$_2$CF$_2$CF$_2$CF$_2$CF$_3$ | CO$_2$CH$_3$ | Cl | CF$_2$CF$_3$ |
| CF$_2$CF$_2$CF$_2$CF$_2$CF$_2$CF$_3$ | CO$_2$CH$_3$ | Cl | CF$_2$CF$_2$CF$_3$ |
| CF$_2$CF$_2$CF$_2$CF$_2$CF$_2$CF$_3$ | CO$_2$C(CH$_3$)$_3$ | H | CF$_3$ |
| CF$_2$CF$_2$CF$_2$CF$_2$CF$_2$CF$_3$ | CO$_2$C(CH$_3$)$_3$ | H | CF$_2$CF$_3$ |
| CF$_2$CF$_2$CF$_2$CF$_2$CF$_2$CF$_3$ | CO$_2$C(CH$_3$)$_3$ | H | CF$_2$CF$_2$CF$_3$ |
| CF$_2$CF$_2$CF$_2$CF$_2$CF$_2$CF$_3$ | CO$_2$C(CH$_3$)$_3$ | CH$_3$ | CF$_3$ |
| CF$_2$CF$_2$CF$_2$CF$_2$CF$_2$CF$_3$ | CO$_2$C(CH$_3$)$_3$ | CH$_3$ | CF$_2$CF$_3$ |
| CF$_2$CF$_2$CF$_2$CF$_2$CF$_2$CF$_3$ | CO$_2$C(CH$_3$)$_3$ | CH$_3$ | CF$_2$CF$_2$CF$_3$ |
| CF$_2$CF$_2$CF$_2$CF$_2$CF$_2$CF$_3$ | CO$_2$C(CH$_3$)$_3$ | F | CF$_3$ |
| CF$_2$CF$_2$CF$_2$CF$_2$CF$_2$CF$_3$ | CO$_2$C(CH$_3$)$_3$ | F | CF$_2$CF$_3$ |
| CF$_2$CF$_2$CF$_2$CF$_2$CF$_2$CF$_3$ | CO$_2$C(CH$_3$)$_3$ | F | CF$_2$CF$_2$CF$_3$ |

TABLE 65

| R$^1$ | R$^2$ | R$^3$ | R$^4$ |
|---|---|---|---|
| CF$_2$CF$_2$CF$_2$CF$_2$CF$_2$CF$_3$ | CO$_2$C(CH$_3$)$_3$ | Cl | CF$_3$ |
| CF$_2$CF$_2$CF$_2$CF$_2$CF$_2$CF$_3$ | CO$_2$C(CH$^3$)$_3$ | Cl | CF$_2$CF$_3$ |
| CF$_2$CF$_2$CF$_2$CF$_2$CF$_2$CF$_3$ | CO$_2$C(CH$^3$)$_3$ | Cl | CF$_2$CF$_2$CF$_3$ |
| CF$_2$CF$_2$CF$_2$CF$_2$CF$_2$CF$_3$ | CONH$_2$ | H | CF$_3$ |
| CF$_2$CF$_2$CF$_2$CF$_2$CF$_2$CF$_3$ | CONH$_2$ | H | CF$_2$CF$_3$ |
| CF$_2$CF$_2$CF$_2$CF$_2$CF$_2$CF$_3$ | CONH$_2$ | H | CF$_2$CF$_2$CF$_3$ |
| CF$_2$CF$_2$CF$_2$CF$_2$CF$_2$CF$_3$ | CONH$_2$ | CH$_3$ | CF$_3$ |
| CF$_2$CF$_2$CF$_2$CF$_2$CF$_2$CF$_3$ | CONH$_2$ | CH$_3$ | CF$_2$CF$_3$ |
| CF$_2$CF$_2$CF$_2$CF$_2$CF$_2$CF$_3$ | CONH$_2$ | CH$_3$ | CF$_2$CF$_2$CF$_3$ |
| CF$_2$CF$_2$CF$_2$CF$_2$CF$_2$CF$_3$ | CONH$_2$ | CH$_2$CH$_3$ | CF$_3$ |
| CF$_2$CF$_2$CF$_2$CF$_2$CF$_2$CF$_3$ | CONH$_2$ | CH$_2$CH$_3$ | CF$_2$CF$_3$ |
| CF$_2$CF$_2$CF$_2$CF$_2$CF$_2$CF$_3$ | CONH$_2$ | CH$_2$CH$_3$ | CF$_2$CF$_2$CF$_3$ |
| CF$_2$CF$_2$CF$_2$CF$_2$CF$_2$CF$_3$ | CONH$_2$ | F | CF$_3$ |
| CF$_2$CF$_2$CF$_2$CF$_2$CF$_2$CF$_3$ | CONH$_2$ | F | CF$_2$CF$_3$ |
| CF$_2$CF$_2$CF$_2$CF$_2$CF$_2$CF$_3$ | CONH$_2$ | F | CF$_2$CF$_2$CF$_3$ |
| CF$_2$CF$_2$CF$_2$CF$_2$CF$_2$CF$_3$ | CONH$_2$ | Cl | CF$_3$ |
| CF$_2$CF$_2$CF$_2$CF$_2$CF$_2$CF$_3$ | CONH$_2$ | Cl | CF$_2$CF$_3$ |
| CF$_2$CF$_2$CF$_2$CF$_2$CF$_2$CF$_3$ | CONH$_2$ | Cl | CF$_2$CF$_2$CF$_3$ |
| CF$_2$CF$_2$CF$_2$CF$_2$CF$_2$CF$_3$ | CONH(CH$_3$) | H | CF$_3$ |
| CF$_2$CF$_2$CF$_2$CF$_2$CF$_2$CF$_3$ | CONH(CH$_3$) | H | CF$_2$CF$_3$ |
| CF$_2$CF$_2$CF$_2$CF$_2$CF$_2$CF$_3$ | CONH(CH$_3$) | H | CF$_2$CF$_2$CF$_3$ |
| CF$_2$CF$_2$CF$_2$CF$_2$CF$_2$CF$_3$ | CONH(CH$_3$) | CH$_3$ | CF$_3$ |
| CF$_2$CF$_2$CF$_2$CF$_2$CF$_2$CF$_3$ | CONH(CH$_3$) | CH$_3$ | CF$_2$CF$_3$ |
| CF$_2$CF$_2$CF$_2$CF$_2$CF$_2$CF$_3$ | CONH(CH$_3$) | CH$_3$ | CF$_2$CF$_2$CF$_3$ |

TABLE 65-continued

| R$^1$ | R$^2$ | R$^3$ | R$^4$ |
|---|---|---|---|
| CF$_2$CF$_2$CF$_2$CF$_2$CF$_2$CF$_3$ | CONH(CH$_3$) | CH$_2$CH$_3$ | CF$_3$ |
| CF$_2$CF$_2$CF$_2$CF$_2$CF$_2$CF$_3$ | CONH(CH$_3$) | CH$_2$CH$_3$ | CF$_2$CF$_3$ |
| CF$_2$CF$_2$CF$_2$CF$_2$CF$_2$CF$_3$ | CONH(CH$_3$) | CH$_2$CH$_3$ | CF$_2$CF$_2$CF$_3$ |

TABLE 66

| R$^1$ | R$^2$ | R$^3$ | R$^4$ |
|---|---|---|---|
| CF$_2$CF$_2$CF$_2$CF$_2$CF$_2$CF$_3$ | CONH(CH$_3$) | F | CF$_3$ |
| CF$_2$CF$_2$CF$_2$CF$_2$CF$_2$CF$_3$ | CONH(CH$_3$) | F | CF$_2$CF$_3$ |
| CF$_2$CF$_2$CF$_2$CF$_2$CF$_2$CF$_3$ | CONH(CH$_3$) | F | CF$_2$CF$_2$CF$_3$ |
| CF$_2$CF$_2$CF$_2$CF$_2$CF$_2$CF$_3$ | CONH(CH$_3$) | Cl | CF$_3$ |
| CF$_2$CF$_2$CF$_2$CF$_2$CF$_2$CF$_3$ | CONH(CH$_3$) | Cl | CF$_2$CF$_3$ |
| CF$_2$CF$_2$CF$_2$CF$_2$CF$_2$CF$_3$ | CONH(CH$_3$) | Cl | CF$_2$CF$_2$CF$_3$ |
| CF$_2$CF$_2$CF$_2$CF$_2$CF$_2$CF$_3$ | CONH(CH$_2$CH$_3$) | H | CF$_3$ |
| CF$_2$CF$_2$CF$_2$CF$_2$CF$_2$CF$_3$ | CONH(CH$_2$CH$_3$) | H | CF$_2$CF$_3$ |
| CF$_2$CF$_2$CF$_2$CF$_2$CF$_2$CF$_3$ | CONH(CH$_2$CH$_3$) | H | CF$_2$CF$_2$CF$_3$ |
| CF$_2$CF$_2$CF$_2$CF$_2$CF$_2$CF$_3$ | CONH(CH$_2$CH$_3$) | CH$_3$ | CF$_3$ |
| CF$_2$CF$_2$CF$_2$CF$_2$CF$_2$CF$_3$ | CONH(CH$_2$CH$_3$) | CH$_3$ | CF$_2$CF$_3$ |
| CF$_2$CF$_2$CF$_2$CF$_2$CF$_2$CF$_3$ | CONH(CH$_2$CH$_3$) | CH$_3$ | CF$_2$CF$_2$CF$_3$ |
| CF$_2$CF$_2$CF$_2$CF$_2$CF$_2$CF$_3$ | CONH(CH$_2$CH$_3$) | CH$_2$CH$_3$ | CF$_3$ |
| CF$_2$CF$_2$CF$_2$CF$_2$CF$_2$CF$_3$ | CONH(CH$_2$CH$_3$) | CH$_2$CH$_3$ | CF$_2$CF$_3$ |
| CF$_2$CF$_2$CF$_2$CF$_2$CF$_2$CF$_3$ | CONH(CH$_2$CH$_3$) | CH$_2$CH$_3$ | CF$_2$CF$_2$CF$_3$ |
| CF$_2$CF$_2$CF$_2$CF$_2$CF$_2$CF$_3$ | CONH(CH$_2$CH$_3$) | F | CF$_3$ |
| CF$_2$CF$_2$CF$_2$CF$_2$CF$_2$CF$_3$ | CONH(CH$_2$CH$_3$) | F | CF$_2$CF$_3$ |
| CF$_2$CF$_2$CF$_2$CF$_2$CF$_2$CF$_3$ | CONH(CH$_2$CH$_3$) | F | CF$_2$CF$_2$CF$_3$ |
| CF$_2$CF$_2$CF$_2$CF$_2$CF$_2$CF$_3$ | CONH(CH$_2$CH$_3$) | Cl | CF$_3$ |
| CF$_2$CF$_2$CF$_2$CF$_2$CF$_2$CF$_3$ | CONH(CH$_2$CH$_3$) | Cl | CF$_2$CF$_3$ |
| CF$_2$CF$_2$CF$_2$CF$_2$CF$_2$CF$_3$ | CONH(CH$_2$CH$_3$) | Cl | CF$_2$CF$_2$CF$_3$ |
| CF$_2$CF$_2$CF$_2$CF$_2$CF$_2$CF$_3$ | CON(CH$_3$)$_2$ | H | CF$_3$ |
| CF$_2$CF$_2$CF$_2$CF$_2$CF$_2$CF$_3$ | CON(CH$_3$)$_2$ | H | CF$_2$CF$_3$ |
| CF$_2$CF$_2$CF$_2$CF$_2$CF$_2$CF$_3$ | CON(CH$_3$)$_2$ | H | CF$_2$CF$_2$CF$_3$ |
| CF$_2$CF$_2$CF$_2$CF$_2$CF$_2$CF$_3$ | CON(CH$_3$)$_2$ | CH$_3$ | CF$_3$ |
| CF$_2$CF$_2$CF$_2$CF$_2$CF$_2$CF$_3$ | CON(CH$_3$)$_2$ | CH$_3$ | CF$_2$CF$_3$ |
| CF$_2$CF$_2$CF$_2$CF$_2$CF$_2$CF$_3$ | CON(CH$_3$)$_2$ | CH$_3$ | CF$_2$CF$_2$CF$_3$ |

TABLE 67

| R$^1$ | R$^2$ | R$^3$ | R$^4$ |
|---|---|---|---|
| CF$_2$CF$_2$CF$_2$CF$_2$CF$_2$CF$_3$ | CON(CH$_3$)$_2$ | CH$_2$CH$_3$ | CF$_3$ |
| CF$_2$CF$_2$CF$_2$CF$_2$CF$_2$CF$_3$ | CON(CH$_3$)$_2$ | CH$_2$CH$_3$ | CF$_2$CF$_3$ |
| CF$_2$CF$_2$CF$_2$CF$_2$CF$_2$CF$_3$ | CON(CH$_3$)$_2$ | CH$_2$CH$_3$ | CF$_2$CF$_2$CF$_3$ |
| CF$_2$CF$_2$CF$_2$CF$_2$CF$_2$CF$_3$ | CON(CH$_3$)$_2$ | F | CF$_3$ |
| CF$_2$CF$_2$CF$_2$CF$_2$CF$_2$CF$_3$ | CON(CH$_3$)$_2$ | F | CF$_2$CF$_3$ |
| CF$_2$CF$_2$CF$_2$CF$_2$CF$_2$CF$_3$ | CON(CH$_3$)$_2$ | F | CF$_2$CF$_2$CF$_3$ |
| CF$_2$CF$_2$CF$_2$CF$_2$CF$_2$CF$_3$ | CON(CH$_3$)$_2$ | Cl | CF$_3$ |
| CF$_2$CF$_2$CF$_2$CF$_2$CF$_2$CF$_3$ | CON(CH$_3$)$_2$ | Cl | CF$_2$CF$_3$ |
| CF$_2$CF$_2$CF$_2$CF$_2$CF$_2$CF$_3$ | CON(CH$_3$)$_2$ | Cl | CF$_2$CF$_2$CF$_3$ |
| CF$_2$CF$_2$CF$_2$CF$_2$CF$_2$CF$_3$ | C(S)OCH$_3$ | H | CF$_3$ |
| CF$_2$CF$_2$CF$_2$CF$_2$CF$_2$CF$_3$ | C(S)OCH$_3$ | H | CF$_2$CF$_3$ |
| CF$_2$CF$_2$CF$_2$CF$_2$CF$_2$CF$_3$ | C(S)OCH$_3$ | H | CF$_2$CF$_2$CF$_3$ |
| CF$_2$CF$_2$CF$_2$CF$_2$CF$_2$CF$_3$ | C(S)OCH$_3$ | CH$_3$ | CF$_3$ |
| CF$_2$CF$_2$CF$_2$CF$_2$CF$_2$CF$_3$ | C(S)OCH$_3$ | CH$_3$ | CF$_2$CF$_3$ |
| CF$_2$CF$_2$CF$_2$CF$_2$CF$_2$CF$_3$ | C(S)OCH$_3$ | CH$_3$ | CF$_2$CF$_2$CF$_3$ |
| CF$_2$CF$_2$CF$_2$CF$_2$CF$_2$CF$_3$ | C(S)OCH$_3$ | F | CF$_3$ |
| CF$_2$CF$_2$CF$_2$CF$_2$CF$_2$CF$_3$ | C(S)OCH$_3$ | F | CF$_2$CF$_3$ |
| CF$_2$CF$_2$CF$_2$CF$_2$CF$_2$CF$_3$ | C(S)OCH$_3$ | F | CF$_2$CF$_2$CF$_3$ |
| CF$_2$CF$_2$CF$_2$CF$_2$CF$_2$CF$_3$ | C(S)OCH$_3$ | Cl | CF$_3$ |
| CF$_2$CF$_2$CF$_2$CF$_2$CF$_2$CF$_3$ | C(S)OCH$_3$ | Cl | CF$_2$CF$_3$ |
| CF$_2$CF$_2$CF$_2$CF$_2$CF$_2$CF$_3$ | C(S)OCH$_3$ | Cl | CF$_2$CF$_2$CF$_3$ |
| CF$_2$CF$_2$CF$_2$CF$_2$CF$_2$CF$_3$ | C(S)NH$_2$ | H | CF$_3$ |
| CF$_2$CF$_2$CF$_2$CF$_2$CF$_2$CF$_3$ | C(S)NH$_2$ | H | CF$_2$CF$_3$ |
| CF$_2$CF$_2$CF$_2$CF$_2$CF$_2$CF$_3$ | C(S)NH$_2$ | H | CF$_2$CF$_2$CF$_3$ |
| CF$_2$CF$_2$CF$_2$CF$_2$CF$_2$CF$_3$ | C(S)NH$_2$ | CH$_3$ | CF$_3$ |
| CF$_2$CF$_2$CF$_2$CF$_2$CF$_2$CF$_3$ | C(S)NH$_2$ | CH$_3$ | CF$_2$CF$_3$ |
| CF$_2$CF$_2$CF$_2$CF$_2$CF$_2$CF$_3$ | C(S)NH$_2$ | CH$_3$ | CF$_2$CF$_2$CF$_3$ |

TABLE 68

| R¹ | R² | R³ | R⁴ |
|---|---|---|---|
| CF₂CF₂CF₂CF₂CF₂CF₃ | C(S)NH₂ | CH₂CH₃ | CF₃ |
| CF₂CF₂CF₂CF₂CF₂CF₃ | C(S)NH₂ | CH₂CH₃ | CF₂CF₃ |
| CF₂CF₂CF₂CF₂CF₂CF₃ | C(S)NH₂ | CH₂CH₃ | CF₂CF₂CF₃ |
| CF₂CF₂CF₂CF₂CF₂CF₃ | C(S)NH₂ | F | CF₃ |
| CF₂CF₂CF₂CF₂CF₂CF₃ | C(S)NH₂ | F | CF₂CF₃ |
| CF₂CF₂CF₂CF₂CF₂CF₃ | C(S)NH₂ | F | CF₂CF₂CF₃ |
| CF₂CF₂CF₂CF₂CF₂CF₃ | C(S)NH₂ | Cl | CF₃ |
| CF₂CF₂CF₂CF₂CF₂CF₃ | C(S)NH₂ | Cl | CF₂CF₃ |
| CF₂CF₂CF₂CF₂CF₂CF₃ | C(S)NH₂ | Cl | CF₂CF₂CF₃ |
| CF₂CF₂CF₂CF₂CF₂CF₃ | C(S)NH(CH₃) | H | CF₃ |
| CF₂CF₂CF₂CF₂CF₂CF₃ | C(S)NH(CH₃) | H | CF₂CF₃ |
| CF₂CF₂CF₂CF₂CF₂CF₃ | C(S)NH(CH₃) | H | CF₂CF₂CF₃ |
| CF₂CF₂CF₂CF₂CF₂CF₃ | C(S)NH(CH₃) | CH₃ | CF₃ |
| CF₂CF₂CF₂CF₂CF₂CF₃ | C(S)NH(CH₃) | CH₃ | CF₂CF₃ |
| CF₂CF₂CF₂CF₂CF₂CF₃ | C(S)NH(CH₃) | CH₃ | CF₂CF₂CF₃ |
| CF₂CF₂CF₂CF₂CF₂CF₃ | C(S)NH(CH₃) | CH₂CH₃ | CF₃ |
| CF₂CF₂CF₂CF₂CF₂CF₃ | C(S)NH(CH₃) | CH₂CH₃ | CF₂CF₃ |
| CF₂CF₂CF₂CF₂CF₂CF₃ | C(S)NH(CH₃) | CH₂CH₃ | CF₂CF₂CF₃ |
| CF₂CF₂CF₂CF₂CF₂CF₃ | C(S)NH(CH₃) | F | CF₃ |
| CF₂CF₂CF₂CF₂CF₂CF₃ | C(S)NH(CH₃) | F | CF₂CF₃ |
| CF₂CF₂CF₂CF₂CF₂CF₃ | C(S)NH(CH₃) | F | CF₂CF₂CF₃ |
| CF₂CF₂CF₂CF₂CF₂CF₃ | C(S)NH(CH₃) | Cl | CF₃ |
| CF₂CF₂CF₂CF₂CF₂CF₃ | C(S)NH(CH₃) | Cl | CF₂CF₃ |
| CF₂CF₂CF₂CF₂CF₂CF₃ | C(S)NH(CH₃) | Cl | CF₂CF₂CF₃ |
| CF₂CF₂CF₂CF₂CF₂CF₃ | C(S)N(CH₃)₂ | H | CF₃ |
| CF₂CF₂CF₂CF₂CF₂CF₃ | C(S)N(CH₃)₂ | H | CF₂CF₃ |
| CF₂CF₂CF₂CF₂CF₂CF₃ | C(S)N(CH₃)₂ | H | CF₂CF₂CF₃ |

TABLE 69

| R¹ | R² | R³ | R⁴ |
|---|---|---|---|
| CF₂CF₂CF₂CF₂CF₂CF₃ | C(S)N(CH₃)₂ | CH₃ | CF₃ |
| CF₂CF₂CF₂CF₂CF₂CF₃ | C(S)N(CH₃)₂ | CH₃ | CF₂CF₃ |
| CF₂CF₂CF₂CF₂CF₂CF₃ | C(S)N(CH₃)₂ | CH₃ | CF₂CF₂CF₃ |
| CF₂CF₂CF₂CF₂CF₂CF₃ | C(S)N(CH₃)₂ | CH₂CH₃ | CF₃ |
| CF₂CF₂CF₂CF₂CF₂CF₃ | C(S)N(CH₃)₂ | CH₂CH₃ | CF₂CF₃ |
| CF₂CF₂CF₂CF₂CF₂CF₃ | C(S)N(CH₃)₂ | CH₂CH₃ | CF₂CF₂CF₃ |
| CF₂CF₂CF₂CF₂CF₂CF₃ | C(S)N(CH₃)₂ | F | CF₃ |
| CF₂CF₂CF₂CF₂CF₂CF₃ | C(S)N(CH₃)₂ | F | CF₂CF₃ |
| CF₂CF₂CF₂CF₂CF₂CF₃ | C(S)N(CH₃)₂ | F | CF₂CF₂CF₃ |
| CF₂CF₂CF₂CF₂CF₂CF₃ | C(S)N(CH₃)₂ | Cl | CF₃ |
| CF₂CF₂CF₂CF₂CF₂CF₃ | C(S)N(CH₃)₂ | Cl | CF₂CF₃ |
| CF₂CF₂CF₂CF₂CF₂CF₃ | C(S)N(CH₃)₂ | Cl | CF₂CF₂CF₃ |

TABLE 70

| R¹ | R² | R³ | R⁴ |
|---|---|---|---|
| CH₂CH₂CH₂CH₂CF₃ | CN | H | CF₃ |
| CH₂CH₂CH₂CH₂CF₃ | CN | H | CF₂CF₃ |
| CH₂CH₂CH₂CH₂CF₃ | CN | H | CF₂CF₂CF₃ |
| CH₂CH₂CH₂CH₂CF₃ | CN | CH₃ | CF₃ |
| CH₂CH₂CH₂CH₂CF₃ | CN | CH₃ | CF₂CF₃ |
| CH₂CH₂CH₂CH₂CF₃ | CN | CH₃ | CF₂CF₂CF₃ |
| CH₂CH₂CH₂CH₂CF₃ | CN | CH₂CH₃ | CF₃ |
| CH₂CH₂CH₂CH₂CF₃ | CN | CH₂CH₃ | CF₂CF₃ |
| CH₂CH₂CH₂CH₂CF₃ | CN | CH₂CH₃ | CF₂CF₂CF₃ |
| CH₂CH₂CH₂CH₂CF₃ | CN | CH₂CH₂CH₃ | CF₃ |
| CH₂CH₂CH₂CH₂CF₃ | CN | CH₂CH₂CH₃ | CF₂CF₃ |
| CH₂CH₂CH₂CH₂CF₃ | CN | CH₂CH₂CH₃ | CF₂CF₂CF₃ |
| CH₂CH₂CH₂CH₂CF₃ | CN | CH(CH₃)₂ | CF₃ |
| CH₂CH₂CH₂CH₂CF₃ | CN | CH(CH₃)₂ | CF₂CF₃ |
| CH₂CH₂CH₂CH₂CF₃ | CN | CH(CH₃)₂ | CF₂CF₂CF₃ |
| CH₂CH₂CH₂CH₂CF₃ | CN | CH₂CH₂CH₂CH₃ | CF₃ |
| CH₂CH₂CH₂CH₂CF₃ | CN | CH₂CH₂CH₂CH₃ | CF₂CF₃ |
| CH₂CH₂CH₂CH₂CF₃ | CN | CH₂CH₂CH₂CH₃ | CF₂CF₂CF₃ |
| CH₂CH₂CH₂CH₂CF₃ | CN | CH₂CH₂CH₂CH₂CH₃ | CF₃ |
| CH₂CH₂CH₂CH₂CF₃ | CN | CH₂CH₂CH₂CH₂CH₃ | CF₂CF₃ |
| CH₂CH₂CH₂CH₂CF₃ | CN | CH₂CH₂CH₂CH₂CH₃ | CF₂CF₂CF₃ |
| CH₂CH₂CH₂CH₂CF₃ | CN | F | CF₃ |
| CH₂CH₂CH₂CH₂CF₃ | CN | F | CF₂CF₃ |
| CH₂CH₂CH₂CH₂CF₃ | CN | F | CF₂CF₂CF₃ |

TABLE 70-continued

| R¹ | R² | R³ | R⁴ |
|---|---|---|---|
| CH₂CH₂CH₂CH₂CF₃ | CN | Cl | CF₃ |
| CH₂CH₂CH₂CH₂CF₃ | CN | Cl | CF₂CF₃ |
| CH₂CH₂CH₂CH₂CF₃ | CN | Cl | CF₂CF₂CF₃ |

TABLE 71

| R¹ | R² | R³ | R⁴ |
|---|---|---|---|
| CH₂CH₂CH₂CH₂CF₃ | CO₂CH₃ | H | CF₃ |
| CH₂CH₂CH₂CH₂CF₃ | CO₂CH₃ | H | CF₂CF₃ |
| CH₂CH₂CH₂CH₂CF₃ | CO₂CH₃ | H | CF₂CF₂CF₃ |
| CH₂CH₂CH₂CH₂CF₃ | CO₂CH₃ | CH₃ | CF₃ |
| CH₂CH₂CH₂CH₂CF₃ | CO₂CH₃ | CH₃ | CF₂CF₃ |
| CH₂CH₂CH₂CH₂CF₃ | CO₂CH₃ | CH₃ | CF₂CF₂CF₃ |
| CH₂CH₂CH₂CH₂CF₃ | CO₂CH₃ | CH₂CH₃ | CF₃ |
| CH₂CH₂CH₂CH₂CF₃ | CO₂CH₃ | CH₂CH₃ | CF₂CF₃ |
| CH₂CH₂CH₂CH₂CF₃ | CO₂CH₃ | CH₂CH₃ | CF₂CF₂CF₃ |
| CH₂CH₂CH₂CH₂CF₃ | CO₂CH₃ | CH₂CH₂CH₃ | CF₃ |
| CH₂CH₂CH₂CH₂CF₃ | CO₂CH₃ | CH₂CH₂CH₃ | CF₂CF₃ |
| CH₂CH₂CH₂CH₂CF₃ | CO₂CH₃ | CH₂CH₂CH₃ | CF₂CF₂CF₃ |
| CH₂CH₂CH₂CH₂CF₃ | CO₂CH₃ | F | CF₃ |
| CH₂CH₂CH₂CH₂CF₃ | CO₂CH₃ | F | CF₂CF₃ |
| CH₂CH₂CH₂CH₂CF₃ | CO₂CH₃ | F | CF₂CF₂CF₃ |
| CH₂CH₂CH₂CH₂CF₃ | CO₂CH₃ | Cl | CF₃ |
| CH₂CH₂CH₂CH₂CF₃ | CO₂CH₃ | Cl | CF₂CF₃ |
| CH₂CH₂CH₂CH₂CF₃ | CO₂CH₃ | Cl | CF₂CF₂CF₃ |
| CH₂CH₂CH₂CH₂CF₃ | CO₂C(CH₃)₃ | H | CF₃ |
| CH₂CH₂CH₂CH₂CF₃ | CO₂C(CH₃)₃ | H | CF₂CF₃ |
| CH₂CH₂CH₂CH₂CF₃ | CO₂C(CH₃)₃ | H | CF₂CF₂CF₃ |
| CH₂CH₂CH₂CH₂CF₃ | CO₂C(CH₃)₃ | CH₃ | CF₃ |
| CH₂CH₂CH₂CH₂CF₃ | CO₂C(CH₃)₃ | CH₃ | CF₂CF₃ |
| CH₂CH₂CH₂CH₂CF₃ | CO₂C(CH₃)₃ | CH₃ | CF₂CF₂CF₃ |
| CH₂CH₂CH₂CH₂CF₃ | CO₂C(CH₃)₃ | F | CF₃ |
| CH₂CH₂CH₂CH₂CF₃ | CO₂C(CH₃)₃ | F | CF₂CF₃ |
| CH₂CH₂CH₂CH₂CF₃ | CO₂C(CH₃)₃ | F | CF₂CF₂CF₃ |

TABLE 72

| R¹ | R² | R³ | R⁴ |
|---|---|---|---|
| CH₂CH₂CH₂CH₂CF₃ | CO₂C(CH₃)₃ | Cl | CF₃ |
| CH₂CH₂CH₂CH₂CF₃ | CO₂C(CH₃)₃ | Cl | CF₂CF₃ |
| CH₂CH₂CH₂CH₂CF₃ | CO₂C(CH₃)₃ | Cl | CF₂CF₂CF₃ |
| CH₂CH₂CH₂CH₂CF₃ | CONH₂ | H | CF₃ |
| CH₂CH₂CH₂CH₂CF₃ | CONH₂ | H | CF₂CF₃ |
| CH₂CH₂CH₂CH₂CF₃ | CONH₂ | H | CF₂CF₂CF₃ |
| CH₂CH₂CH₂CH₂CF₃ | CONH₂ | CH₃ | CF₃ |
| CH₂CH₂CH₂CH₂CF₃ | CONH₂ | CH₃ | CF₂CF₃ |
| CH₂CH₂CH₂CH₂CF₃ | CONH₂ | CH₃ | CF₂CF₂CF₃ |
| CH₂CH₂CH₂CH₂CF₃ | CONH₂ | CH₂CH₃ | CF₃ |
| CH₂CH₂CH₂CH₂CF₃ | CONH₂ | CH₂CH₃ | CF₂CF₃ |
| CH₂CH₂CH₂CH₂CF₃ | CONH₂ | CH₂CH₃ | CF₂CF₂CF₃ |
| CH₂CH₂CH₂CH₂CF₃ | CONH₂ | F | CF₃ |
| CH₂CH₂CH₂CH₂CF₃ | CONH₂ | F | CF₂CF₃ |
| CH₂CH₂CH₂CH₂CF₃ | CONH₂ | F | CF₂CF₂CF₃ |
| CH₂CH₂CH₂CH₂CF₃ | CONH₂ | Cl | CF₃ |
| CH₂CH₂CH₂CH₂CF₃ | CONH₂ | Cl | CF₂CF₃ |
| CH₂CH₂CH₂CH₂CF₃ | CONH₂ | Cl | CF₂CF₂CF₃ |
| CH₂CH₂CH₂CH₂CF₃ | CONH(CH₃) | H | CF₃ |
| CH₂CH₂CH₂CH₂CF₃ | CONH(CH₃) | H | CF₂CF₃ |
| CH₂CH₂CH₂CH₂CF₃ | CONH(CH₃) | H | CF₂CF₂CF₃ |
| CH₂CH₂CH₂CH₂CF₃ | CONH(CH₃) | CH₃ | CF₃ |
| CH₂CH₂CH₂CH₂CF₃ | CONH(CH₃) | CH₃ | CF₂CF₃ |
| CH₂CH₂CH₂CH₂CF₃ | CONH(CH₃) | CH₃ | CF₂CF₂CF₃ |
| CH₂CH₂CH₂CH₂CF₃ | CONH(CH₃) | CH₂CH₃ | CF₃ |
| CH₂CH₂CH₂CH₂CF₃ | CONH(CH₃) | CH₂CH₃ | CF₂CF₃ |
| CH₂CH₂CH₂CH₂CF₃ | CONH(CH₃) | CH₂CH₃ | CF₂CF₂CF₃ |

TABLE 73

| R¹ | R² | R³ | R⁴ |
|---|---|---|---|
| CH₂CH₂CH₂CH₂CF₃ | CONH(CH₃) | F | CF₃ |
| CH₂CH₂CH₂CH₂CF₃ | CONH(CH₃) | F | CF₂CF₃ |
| CH₂CH₂CH₂CH₂CF₃ | CONH(CH₃) | F | CF₂CF₂CF₃ |
| CH₂CH₂CH₂CH₂CF₃ | CONH(CH₃) | Cl | CF₃ |
| CH₂CH₂CH₂CH₂CF₃ | CONH(CH₃) | Cl | CF₂CF₃ |
| CH₂CH₂CH₂CH₂CF₃ | CONH(CH₃) | Cl | CF₂CF₂CF₃ |
| CH₂CH₂CH₂CH₂CF₃ | CONH(CH₂CH₃) | H | CF₃ |
| CH₂CH₂CH₂CH₂CF₃ | CONH(CH₂CH₃) | H | CF₂CF₃ |
| CH₂CH₂CH₂CH₂CF₃ | CONH(CH₂CH₃) | H | CF₂CF₂CF₃ |
| CH₂CH₂CH₂CH₂CF₃ | CONH(CH₂CH₃) | CH₃ | CF₃ |
| CH₂CH₂CH₂CH₂CF₃ | CONH(CH₂CH₃) | CH₃ | CF₂CF₃ |
| CH₂CH₂CH₂CH₂CF₃ | CONH(CH₂CH₃) | CH₃ | CF₂CF₂CF₃ |
| CH₂CH₂CH₂CH₂CF₃ | CONH(CH₂CH₃) | CH₂CH₃ | CF₃ |
| CH₂CH₂CH₂CH₂CF₃ | CONH(CH₂CH₃) | CH₂CH₃ | CF₂CF₃ |
| CH₂CH₂CH₂CH₂CF₃ | CONH(CH₂CH₃) | CH₂CH₃ | CF₂CF₂CF₃ |
| CH₂CH₂CH₂CH₂CF₃ | CONH(CH₂CH₃) | F | CF₃ |
| CH₂CH₂CH₂CH₂CF₃ | CONH(CH₂CH₃) | F | CF₂CF₃ |
| CH₂CH₂CH₂CH₂CF₃ | CONH(CH₂CH₃) | F | CF₂CF₂CF₃ |
| CH₂CH₂CH₂CH₂CF₃ | CONH(CH₂CH₃) | Cl | CF₃ |
| CH₂CH₂CH₂CH₂CF₃ | CONH(CH₂CH₃) | Cl | CF₂CF₃ |
| CH₂CH₂CH₂CH₂CF₃ | CONH(CH₂CH₃) | Cl | CF₂CF₂CF₃ |
| CH₂CH₂CH₂CH₂CF₃ | CON(CH₃)₂ | H | CF₃ |
| CH₂CH₂CH₂CH₂CF₃ | CON(CH₃)₂ | H | CF₂CF₃ |
| CH₂CH₂CH₂CH₂CF₃ | CON(CH₃)₂ | H | CF₂CF₂CF₃ |
| CH₂CH₂CH₂CH₂CF₃ | CON(CH₃)₂ | CH₃ | CF₃ |
| CH₂CH₂CH₂CH₂CF₃ | CON(CH₃)₂ | CH₃ | CF₂CF₃ |
| CH₂CH₂CH₂CH₂CF₃ | CON(CH₃)₂ | CH₃ | CF₂CF₂CF₃ |

TABLE 74

| R¹ | R² | R³ | R⁴ |
|---|---|---|---|
| CH₂CH₂CH₂CH₂CF₃ | CON(CH₃)₂ | CH₂CH₃ | CF₃ |
| CH₂CH₂CH₂CH₂CF₃ | CON(CH₃)₂ | CH₂CH₃ | CF₂CF₃ |
| CH₂CH₂CH₂CH₂CF₃ | CON(CH₃)₂ | CH₂CH₃ | CF₂CF₂CF₃ |
| CH₂CH₂CH₂CH₂CF₃ | CON(CH₃)₂ | F | CF₃ |
| CH₂CH₂CH₂CH₂CF₃ | CON(CH₃)₂ | F | CF₂CF₃ |
| CH₂CH₂CH₂CH₂CF₃ | CON(CH₃)₂ | F | CF₂CF₂CF₃ |
| CH₂CH₂CH₂CH₂CF₃ | CON(CH₃)₂ | Cl | CF₃ |
| CH₂CH₂CH₂CH₂CF₃ | CON(CH₃)₂ | Cl | CF₂CF₃ |
| CH₂CH₂CH₂CH₂CF₃ | CON(CH₃)₂ | Cl | CF₂CF₂CF₃ |
| CH₂CH₂CH₂CH₂CF₃ | C(S)OCH₃ | H | CF₃ |
| CH₂CH₂CH₂CH₂CF₃ | C(S)OCH₃ | H | CF₂CF₃ |
| CH₂CH₂CH₂CH₂CF₃ | C(S)OCH₃ | H | CF₂CF₂CF₃ |
| CH₂CH₂CH₂CH₂CF₃ | C(S)OCH₃ | CH₃ | CF₃ |
| CH₂CH₂CH₂CH₂CF₃ | C(S)OCH₃ | CH₃ | CF₂CF₃ |
| CH₂CH₂CH₂CH₂CF₃ | C(S)OCH₃ | CH₃ | CF₂CF₂CF₃ |
| CH₂CH₂CH₂CH₂CF₃ | C(S)OCH₃ | F | CF₃ |
| CH₂CH₂CH₂CH₂CF₃ | C(S)OCH₃ | F | CF₂CF₃ |
| CH₂CH₂CH₂CH₂CF₃ | C(S)OCH₃ | F | CF₂CF₂CF₃ |
| CH₂CH₂CH₂CH₂CF₃ | C(S)OCH₃ | Cl | CF₃ |
| CH₂CH₂CH₂CH₂CF₃ | C(S)OCH₃ | Cl | CF₂CF₃ |
| CH₂CH₂CH₂CH₂CF₃ | C(S)OCH₃ | Cl | CF₂CF₂CF₃ |
| CH₂CH₂CH₂CH₂CF₃ | C(S)NH₂ | H | CF₃ |
| CH₂CH₂CH₂CH₂CF₃ | C(S)NH₂ | H | CF₂CF₃ |
| CH₂CH₂CH₂CH₂CF₃ | C(S)NH₂ | H | CF₂CF₂CF₃ |
| CH₂CH₂CH₂CH₂CF₃ | C(S)NH₂ | CH₃ | CF₃ |
| CH₂CH₂CH₂CH₂CF₃ | C(S)NH₂ | CH₃ | CF₂CF₃ |
| CH₂CH₂CH₂CH₂CF₃ | C(S)NH₂ | CH₃ | CF₂CF₂CF₃ |

TABLE 75

| R¹ | R² | R³ | R⁴ |
|---|---|---|---|
| CH₂CH₂CH₂CH₂CF₃ | C(S)NH₂ | CH₂CH₃ | CF₃ |
| CH₂CH₂CH₂CH₂CF₃ | C(S)NH₂ | CH₂CH₃ | CF₂CF₃ |
| CH₂CH₂CH₂CH₂CF₃ | C(S)NH₂ | CH₂CH₃ | CF₂CF₂CF₃ |
| CH₂CH₂CH₂CH₂CF₃ | C(S)NH₂ | F | CF₃ |
| CH₂CH₂CH₂CH₂CF₃ | C(S)NH₂ | F | CF₂CF₃ |
| CH₂CH₂CH₂CH₂CF₃ | C(S)NH₂ | F | CF₂CF₂CF₃ |
| CH₂CH₂CH₂CH₂CF₃ | C(S)NH₂ | Cl | CF₃ |
| CH₂CH₂CH₂CH₂CF₃ | C(S)NH₂ | Cl | CF₂CF₃ |
| CH₂CH₂CH₂CH₂CF₃ | C(S)NH₂ | Cl | CF₂CF₂CF₃ |

TABLE 75-continued

| R¹ | R² | R³ | R⁴ |
|---|---|---|---|
| CH₂CH₂CH₂CH₂CF₃ | C(S)NH(CH₃) | H | CF₃ |
| CH₂CH₂CH₂CH₂CF₃ | C(S)NH(CH₃) | H | CF₂CF₃ |
| CH₂CH₂CH₂CH₂CF₃ | C(S)NH(CH₃) | H | CF₂CF₂CF₃ |
| CH₂CH₂CH₂CH₂CF₃ | C(S)NH(CH₃) | CH₃ | CF₃ |
| CH₂CH₂CH₂CH₂CF₃ | C(S)NH(CH₃) | CH₃ | CF₂CF₃ |
| CH₂CH₂CH₂CH₂CF₃ | C(S)NH(CH₃) | CH₃ | CF₂CF₂CF₃ |
| CH₂CH₂CH₂CH₂CF₃ | C(S)NH(CH₃) | CH₂CH₃ | CF₃ |
| CH₂CH₂CH₂CH₂CF₃ | C(S)NH(CH₃) | CH₂CH₃ | CF₂CF₃ |
| CH₂CH₂CH₂CH₂CF₃ | C(S)NH(CH₃) | CH₂CH₃ | CF₂CF₂CF₃ |
| CH₂CH₂CH₂CH₂CF₃ | C(S)NH(CH₃) | F | CF₃ |
| CH₂CH₂CH₂CH₂CF₃ | C(S)NH(CH₃) | F | CF₂CF₃ |
| CH₂CH₂CH₂CH₂CF₃ | C(S)NH(CH₃) | F | CF₂CF₂CF₃ |
| CH₂CH₂CH₂CH₂CF₃ | C(S)NH(CH₃) | Cl | CF₃ |
| CH₂CH₂CH₂CH₂CF₃ | C(S)NH(CH₃) | Cl | CF₂CF₃ |
| CH₂CH₂CH₂CH₂CF₃ | C(S)NH(CH₃) | Cl | CF₂CF₂CF₃ |
| CH₂CH₂CH₂CH₂CF₃ | C(S)N(CH₃)₂ | H | CF₃ |
| CH₂CH₂CH₂CH₂CF₃ | C(S)N(CH₃)₂ | H | CF₂CF₃ |
| CH₂CH₂CH₂CH₂CF₃ | C(S)N(CH₃)₂ | H | CF₂CF₂CF₃ |

TABLE 76

| R¹ | R² | R³ | R⁴ |
|---|---|---|---|
| CH₂CH₂CH₂CH₂CF₃ | C(S)N(CH₃)₂ | CH₃ | CF₃ |
| CH₂CH₂CH₂CH₂CF₃ | C(S)N(CH₃)₂ | CH₃ | CF₂CF₃ |
| CH₂CH₂CH₂CH₂CF₃ | C(S)N(CH₃)₂ | CH₃ | CF₂CF₂CF₃ |
| CH₂CH₂CH₂CH₂CF₃ | C(S)N(CH₃)₂ | CH₂CH₃ | CF₃ |
| CH₂CH₂CH₂CH₂CF₃ | C(S)N(CH₃)₂ | CH₂CH₃ | CF₂CF₃ |
| CH₂CH₂CH₂CH₂CF₃ | C(S)N(CH₃)₂ | CH₂CH₃ | CF₂CF₂CF₃ |
| CH₂CH₂CH₂CH₂CF₃ | C(S)N(CH₃)₂ | F | CF₃ |
| CH₂CH₂CH₂CH₂CF₃ | C(S)N(CH₃)₂ | F | CF₂CF₃ |
| CH₂CH₂CH₂CH₂CF₃ | C(S)N(CH₃)₂ | F | CF₂CF₂CF₃ |
| CH₂CH₂CH₂CH₂CF₃ | C(S)N(CH₃)₂ | Cl | CF₃ |
| CH₂CH₂CH₂CH₂CF₃ | C(S)N(CH₃)₂ | Cl | CF₂CF₃ |
| CH₂CH₂CH₂CH₂CF₃ | C(S)N(CH₃)₂ | Cl | CF₂CF₂CF₃ |

TABLE 77

| R¹ | R² | R³ | R⁴ |
|---|---|---|---|
| CH₂CH₂CH₂CF₂CF₃ | CN | H | CF₃ |
| CH₂CH₂CH₂CF₂CF₃ | CN | H | CF₂CF₃ |
| CH₂CH₂CH₂CF₂CF₃ | CN | H | CF₂CF₂CF₃ |
| CH₂CH₂CH₂CF₂CF₃ | CN | CH₃ | CF₃ |
| CH₂CH₂CH₂CF₂CF₃ | CN | CH₃ | CF₂CF₃ |
| CH₂CH₂CH₂CF₂CF₃ | CN | CH₃ | CF₂CF₂CF₃ |
| CH₂CH₂CH₂CF₂CF₃ | CN | CH₂CH₃ | CF₃ |
| CH₂CH₂CH₂CF₂CF₃ | CN | CH₂CH₃ | CF₂CF₃ |
| CH₂CH₂CH₂CF₂CF₃ | CN | CH₂CH₃ | CF₂CF₂CF₃ |
| CH₂CH₂CH₂CF₂CF₃ | CN | CH₂CH₂CH₃ | CF₃ |
| CH₂CH₂CH₂CF₂CF₃ | CN | CH₂CH₂CH₃ | CF₂CF₃ |
| CH₂CH₂CH₂CF₂CF₃ | CN | CH₂CH₂CH₃ | CF₂CF₂CF₃ |
| CH₂CH₂CH₂CF₂CF₃ | CN | CH(CH₃)₂ | CF₃ |
| CH₂CH₂CH₂CF₂CF₃ | CN | CH(CH₃)₂ | CF₂CF₃ |
| CH₂CH₂CH₂CF₂CF₃ | CN | CH(CH₃)₂ | CF₂CF₂CF₃ |
| CH₂CH₂CH₂CF₂CF₃ | CN | CH₂CH₂CH₂CH₃ | CF₃ |
| CH₂CH₂CH₂CF₂CF₃ | CN | CH₂CH₂CH₂CH₃ | CF₂CF₃ |
| CH₂CH₂CH₂CF₂CF₃ | CN | CH₂CH₂CH₂CH₃ | CF₂CF₂CF₃ |
| CH₂CH₂CH₂CF₂CF₃ | CN | CH₂CH₂CH₂CH₂CH₃ | CF₃ |
| CH₂CH₂CH₂CF₂CF₃ | CN | CH₂CH₂CH₂CH₂CH₃ | CF₂CF₃ |
| CH₂CH₂CH₂CF₂CF₃ | CN | CH₂CH₂CH₂CH₂CH₃ | CF₂CF₂CF₃ |
| CH₂CH₂CH₂CF₂CF₃ | CN | F | CF₃ |
| CH₂CH₂CH₂CF₂CF₃ | CN | F | CF₂CF₃ |
| CH₂CH₂CH₂CF₂CF₃ | CN | F | CF₂CF₂CF₃ |
| CH₂CH₂CH₂CF₂CF₃ | CN | Cl | CF₃ |
| CH₂CH₂CH₂CF₂CF₃ | CN | Cl | CF₂CF₃ |
| CH₂CH₂CH₂CF₂CF₃ | CN | Cl | CF₂CF₂CF₃ |

TABLE 78

| R¹ | R² | R³ | R⁴ |
| --- | --- | --- | --- |
| CH₂CH₂CH₂CF₂CF₃ | CO₂CH₃ | H | CF₃ |
| CH₂CH₂CH₂CF₂CF₃ | CO₂CH₃ | H | CF₂CF₃ |
| CH₂CH₂CH₂CF₂CF₃ | CO₂CH₃ | H | CF₂CF₂CF₃ |
| CH₂CH₂CH₂CF₂CF₃ | CO₂CH₃ | CH₃ | CF₃ |
| CH₂CH₂CH₂CF₂CF₃ | CO₂CH₃ | CH₃ | CF₂CF₃ |
| CH₂CH₂CH₂CF₂CF₃ | CO₂CH₃ | CH₃ | CF₂CF₂CF₃ |
| CH₂CH₂CH₂CF₂CF₃ | CO₂CH₃ | CH₂CH₃ | CF₃ |
| CH₂CH₂CH₂CF₂CF₃ | CO₂CH₃ | CH₂CH₃ | CF₂CF₃ |
| CH₂CH₂CH₂CF₂CF₃ | CO₂CH₃ | CH₂CH₃ | CF₂CF₂CF₃ |
| CH₂CH₂CH₂CF₂CF₃ | CO₂CH₃ | CH₂CH₂CH₃ | CF₃ |
| CH₂CH₂CH₂CF₂CF₃ | CO₂CH₃ | CH₂CH₂CH₃ | CF₂CF₃ |
| CH₂CH₂CH₂CF₂CF₃ | CO₂CH₃ | CH₂CH₂CH₃ | CF₂CF₂CF₃ |
| CH₂CH₂CH₂CF₂CF₃ | CO₂CH₃ | F | CF₃ |
| CH₂CH₂CH₂CF₂CF₃ | CO₂CH₃ | F | CF₂CF₃ |
| CH₂CH₂CH₂CF₂CF₃ | CO₂CH₃ | F | CF₂CF₂CF₃ |
| CH₂CH₂CH₂CF₂CF₃ | CO₂CH₃ | Cl | CF₃ |
| CH₂CH₂CH₂CF₂CF₃ | CO₂CH₃ | Cl | CF₂CF₃ |
| CH₂CH₂CH₂CF₂CF₃ | CO₂CH₃ | Cl | CF₂CF₂CF₃ |
| CH₂CH₂CH₂CF₂CF₃ | CO₂C(CH₃)₃ | H | CF₃ |
| CH₂CH₂CH₂CF₂CF₃ | CO₂C(CH₃)₃ | H | CF₂CF₃ |
| CH₂CH₂CH₂CF₂CF₃ | CO₂C(CH₃)₃ | H | CF₂CF₂CF₃ |
| CH₂CH₂CH₂CF₂CF₃ | CO₂C(CH₃)₃ | CH₃ | CF₃ |
| CH₂CH₂CH₂CF₂CF₃ | CO₂C(CH₃)₃ | CH₃ | CF₂CF₃ |
| CH₂CH₂CH₂CF₂CF₃ | CO₂C(CH₃)₃ | CH₃ | CF₂CF₂CF₃ |
| CH₂CH₂CH₂CF₂CF₃ | CO₂C(CH₃)₃ | F | CF₃ |
| CH₂CH₂CH₂CF₂CF₃ | CO₂C(CH₃)₃ | F | CF₂CF₃ |
| CH₂CH₂CH₂CF₂CF₃ | CO₂C(CH₃)₃ | F | CF₂CF₂CF₃ |

TABLE 79

| R¹ | R² | R³ | R⁴ |
| --- | --- | --- | --- |
| CH₂CH₂CH₂CF₂CF₃ | CO₂C(CH₃)₃ | Cl | CF₃ |
| CH₂CH₂CH₂CF₂CF₃ | CO₂C(CH₃)₃ | Cl | CF₂CF₃ |
| CH₂CH₂CH₂CF₂CF₃ | CO₂C(CH₃)₃ | Cl | CF₂CF₂CF₃ |
| CH₂CH₂CH₂CF₂CF₃ | CONH₂ | H | CF₃ |
| CH₂CH₂CH₂CF₂CF₃ | CONH₂ | H | CF₂CF₃ |
| CH₂CH₂CH₂CF₂CF₃ | CONH₂ | H | CF₂CF₂CF₃ |
| CH₂CH₂CH₂CF₂CF₃ | CONH₂ | CH₃ | CF₃ |
| CH₂CH₂CH₂CF₂CF₃ | CONH₂ | CH₃ | CF₂CF₃ |
| CH₂CH₂CH₂CF₂CF₃ | CONH₂ | CH₃ | CF₂CF₂CF₃ |
| CH₂CH₂CH₂CF₂CF₃ | CONH₂ | CH₂CH₃ | CF₃ |
| CH₂CH₂CH₂CF₂CF₃ | CONH₂ | CH₂CH₃ | CF₂CF₃ |
| CH₂CH₂CH₂CF₂CF₃ | CONH₂ | CH₂CH₃ | CF₂CF₂CF₃ |
| CH₂CH₂CH₂CF₂CF₃ | CONH₂ | F | CF₃ |
| CH₂CH₂CH₂CF₂CF₃ | CONH₂ | F | CF₂CF₃ |
| CH₂CH₂CH₂CF₂CF₃ | CONH₂ | F | CF₂CF₂CF₃ |
| CH₂CH₂CH₂CF₂CF₃ | CONH₂ | Cl | CF₃ |
| CH₂CH₂CH₂CF₂CF₃ | CONH₂ | Cl | CF₂CF₃ |
| CH₂CH₂CH₂CF₂CF₃ | CONH₂ | Cl | CF₂CF₂CF₃ |
| CH₂CH₂CH₂CF₂CF₃ | CONH(CH₃) | H | CF₃ |
| CH₂CH₂CH₂CF₂CF₃ | CONH(CH₃) | H | CF₂CF₃ |
| CH₂CH₂CH₂CF₂CF₃ | CONH(CH₃) | H | CF₂CF₂CF₃ |
| CH₂CH₂CH₂CF₂CF₃ | CONH(CH₃) | CH₃ | CF₃ |
| CH₂CH₂CH₂CF₂CF₃ | CONH(CH₃) | CH₃ | CF₂CF₃ |
| CH₂CH₂CH₂CF₂CF₃ | CONH(CH₃) | CH₃ | CF₂CF₂CF₃ |
| CH₂CH₂CH₂CF₂CF₃ | CONH(CH₃) | CH₂CH₃ | CF₃ |
| CH₂CH₂CH₂CF₂CF₃ | CONH(CH₃) | CH₂CH₃ | CF₂CF₃ |
| CH₂CH₂CH₂CF₂CF₃ | CONH(CH₃) | CH₂CH₃ | CF₂CF₂CF₃ |

TABLE 80

| R¹ | R² | R³ | R⁴ |
| --- | --- | --- | --- |
| CH₂CH₂CH₂CF₂CF₃ | CONH(CH₃) | F | CF₃ |
| CH₂CH₂CH₂CF₂CF₃ | CONH(CH₃) | F | CF₂CF₃ |
| CH₂CH₂CH₂CF₂CF₃ | CONH(CH₃) | F | CF₂CF₂CF₃ |
| CH₂CH₂CH₂CF₂CF₃ | CONH(CH₃) | Cl | CF₃ |
| CH₂CH₂CH₂CF₂CF₃ | CONH(CH₃) | Cl | CF₂CF₃ |
| CH₂CH₂CH₂CF₂CF₃ | CONH(CH₃) | Cl | CF₂CF₂CF₃ |
| CH₂CH₂CH₂CF₂CF₃ | CONH(CH₂CH₃) | H | CF₃ |
| CH₂CH₂CH₂CF₂CF₃ | CONH(CH₂CH₃) | H | CF₂CF₃ |
| CH₂CH₂CH₂CF₂CF₃ | CONH(CH₂CH₃) | H | CF₂CF₂CF₃ |

TABLE 80-continued

| R¹ | R² | R³ | R⁴ |
| --- | --- | --- | --- |
| CH₂CH₂CH₂CF₂CF₃ | CONH(CH₂CH₃) | CH₃ | CF₃ |
| CH₂CH₂CH₂CF₂CF₃ | CONH(CH₂CH₃) | CH₃ | CF₂CF₃ |
| CH₂CH₂CH₂CF₂CF₃ | CONH(CH₂CH₃) | CH₃ | CF₂CF₂CF₃ |
| CH₂CH₂CH₂CF₂CF₃ | CONH(CH₂CH₃) | CH₂CH₃ | CF₃ |
| CH₂CH₂CH₂CF₂CF₃ | CONH(CH₂CH₃) | CH₂CH₃ | CF₂CF₃ |
| CH₂CH₂CH₂CF₂CF₃ | CONH(CH₂CH₃) | CH₂CH₃ | CF₂CF₂CF₃ |
| CH₂CH₂CH₂CF₂CF₃ | CONH(CH₂CH₃) | F | CF₃ |
| CH₂CH₂CH₂CF₂CF₃ | CONH(CH₂CH₃) | F | CF₂CF₃ |
| CH₂CH₂CH₂CF₂CF₃ | CONH(CH₂CH₃) | F | CF₂CF₂CF₃ |
| CH₂CH₂CH₂CF₂CF₃ | CONH(CH₂CH₃) | Cl | CF₃ |
| CH₂CH₂CH₂CF₂CF₃ | CONH(CH₂CH₃) | Cl | CF₂CF₃ |
| CH₂CH₂CH₂CF₂CF₃ | CONH(CH₂CH₃) | Cl | CF₂CF₂CF₃ |
| CH₂CH₂CH₂CF₂CF₃ | CON(CH₃)₂ | H | CF₃ |
| CH₂CH₂CH₂CF₂CF₃ | CON(CH₃)₂ | H | CF₂CF₃ |
| CH₂CH₂CH₂CF₂CF₃ | CON(CH₃)₂ | H | CF₂CF₂CF₃ |
| CH₂CH₂CH₂CF₂CF₃ | CON(CH₃)₂ | CH₃ | CF₃ |
| CH₂CH₂CH₂CF₂CF₃ | CON(CH₃)₂ | CH₃ | CF₂CF₃ |
| CH₂CH₂CH₂CF₂CF₃ | CON(CH₃)₂ | CH₃ | CF₂CF₂CF₃ |

TABLE 81

| R¹ | R² | R³ | R⁴ |
| --- | --- | --- | --- |
| CH₂CH₂CH₂CF₂CF₃ | CON(CH₃)₂ | CH₂CH₃ | CF₃ |
| CH₂CH₂CH₂CF₂CF₃ | CON(CH₃)₂ | CH₂CH₃ | CF₂CF₃ |
| CH₂CH₂CH₂CF₂CF₃ | CON(CH₃)₂ | CH₂CH₃ | CF₂CF₂CF₃ |
| CH₂CH₂CH₂CF₂CF₃ | CON(CH₃)₂ | F | CF₃ |
| CH₂CH₂CH₂CF₂CF₃ | CON(CH₃)₂ | F | CF₂CF₃ |
| CH₂CH₂CH₂CF₂CF₃ | CON(CH₃)₂ | F | CF₂CF₂CF₃ |
| CH₂CH₂CH₂CF₂CF₃ | CON(CH₃)₂ | Cl | CF₃ |
| CH₂CH₂CH₂CF₂CF₃ | CON(CH₃)₂ | Cl | CF₂CF₃ |
| CH₂CH₂CH₂CF₂CF₃ | CON(CH₃)₂ | Cl | CF₂CF₂CF₃ |
| CH₂CH₂CH₂CF₂CF₃ | C(S)OCH₃ | H | CF₃ |
| CH₂CH₂CH₂CF₂CF₃ | C(S)OCH₃ | H | CF₂CF₃ |
| CH₂CH₂CH₂CF₂CF₃ | C(S)OCH₃ | H | CF₂CF₂CF₃ |
| CH₂CH₂CH₂CF₂CF₃ | C(S)OCH₃ | CH₃ | CF₃ |
| CH₂CH₂CH₂CF₂CF₃ | C(S)OCH₃ | CH₃ | CF₂CF₃ |
| CH₂CH₂CH₂CF₂CF₃ | C(S)OCH₃ | CH₃ | CF₂CF₂CF₃ |
| CH₂CH₂CH₂CF₂CF₃ | C(S)OCH₃ | F | CF₃ |
| CH₂CH₂CH₂CF₂CF₃ | C(S)OCH₃ | F | CF₂CF₃ |
| CH₂CH₂CH₂CF₂CF₃ | C(S)OCH₃ | F | CF₂CF₂CF₃ |
| CH₂CH₂CH₂CF₂CF₃ | C(S)OCH₃ | Cl | CF₃ |
| CH₂CH₂CH₂CF₂CF₃ | C(S)OCH₃ | Cl | CF₂CF₃ |
| CH₂CH₂CH₂CF₂CF₃ | C(S)OCH₃ | Cl | CF₂CF₂CF₃ |
| CH₂CH₂CH₂CF₂CF₃ | C(S)NH₂ | H | CF₃ |
| CH₂CH₂CH₂CF₂CF₃ | C(S)NH₂ | H | CF₂CF₃ |
| CH₂CH₂CH₂CF₂CF₃ | C(S)NH₂ | H | CF₂CF₂CF₃ |
| CH₂CH₂CH₂CF₂CF₃ | C(S)NH₂ | CH₃ | CF₃ |
| CH₂CH₂CH₂CF₂CF₃ | C(S)NH₂ | CH₃ | CF₂CF₃ |
| CH₂CH₂CH₂CF₂CF₃ | C(S)NH₂ | CH₃ | CF₂CF₂CF₃ |

TABLE 82

| R¹ | R² | R³ | R⁴ |
| --- | --- | --- | --- |
| CH₂CH₂CH₂CF₂CF₃ | C(S)NH₂ | CH₂CH₃ | CF₃ |
| CH₂CH₂CH₂CF₂CF₃ | C(S)NH₂ | CH₂CH₃ | CF₂CF₃ |
| CH₂CH₂CH₂CF₂CF₃ | C(S)NH₂ | CH₂CH₃ | CF₂CF₂CF₃ |
| CH₂CH₂CH₂CF₂CF₃ | C(S)NH₂ | F | CF₃ |
| CH₂CH₂CH₂CF₂CF₃ | C(S)NH₂ | F | CF₂CF₃ |
| CH₂CH₂CH₂CF₂CF₃ | C(S)NH₂ | F | CF₂CF₂CF₃ |
| CH₂CH₂CH₂CF₂CF₃ | C(S)NH₂ | Cl | CF₃ |
| CH₂CH₂CH₂CF₂CF₃ | C(S)NH₂ | Cl | CF₂CF₃ |
| CH₂CH₂CH₂CF₂CF₃ | C(S)NH₂ | Cl | CF₂CF₂CF₃ |
| CH₂CH₂CH₂CF₂CF₃ | C(S)NH(CH₃) | H | CF₃ |
| CH₂CH₂CH₂CF₂CF₃ | C(S)NH(CH₃) | H | CF₂CF₃ |
| CH₂CH₂CH₂CF₂CF₃ | C(S)NH(CH₃) | H | CF₂CF₂CF₃ |
| CH₂CH₂CH₂CF₂CF₃ | C(S)NH(CH₃) | CH₃ | CF₃ |
| CH₂CH₂CH₂CF₂CF₃ | C(S)NH(CH₃) | CH₃ | CF₂CF₃ |
| CH₂CH₂CH₂CF₂CF₃ | C(S)NH(CH₃) | CH₃ | CF₂CF₂CF₃ |
| CH₂CH₂CH₂CF₂CF₃ | C(S)NH(CH₃) | CH₂CH₃ | CF₃ |
| CH₂CH₂CH₂CF₂CF₃ | C(S)NH(CH₃) | CH₂CH₃ | CF₂CF₃ |
| CH₂CH₂CH₂CF₂CF₃ | C(S)NH(CH₃) | CH₂CH₃ | CF₂CF₂CF₃ |

TABLE 82-continued

| R¹ | R² | R³ | R⁴ |
|---|---|---|---|
| CH₂CH₂CH₂CF₂CF₃ | C(S)NH(CH₃) | F | CF₃ |
| CH₂CH₂CH₂CF₂CF₃ | C(S)NH(CH₃) | F | CF₂CF₃ |
| CH₂CH₂CH₂CF₂CF₃ | C(S)NH(CH₃) | F | CF₂CF₂CF₃ |
| CH₂CH₂CH₂CF₂CF₃ | C(S)NH(CH₃) | Cl | CF₃ |
| CH₂CH₂CH₂CF₂CF₃ | C(S)NH(CH₃) | Cl | CF₂CF₃ |
| CH₂CH₂CH₂CF₂CF₃ | C(S)NH(CH₃) | Cl | CF₂CF₂CF₃ |
| CH₂CH₂CH₂CF₂CF₃ | C(S)N(CH₃)₂ | H | CF₃ |
| CH₂CH₂CH₂CF₂CF₃ | C(S)N(CH₃)₂ | H | CF₂CF₃ |
| CH₂CH₂CH₂CF₂CF₃ | C(S)N(CH₃)₂ | H | CF₂CF₂CF₃ |

TABLE 83

| R¹ | R² | R³ | R⁴ |
|---|---|---|---|
| CH₂CH₂CH₂CF₂CF₃ | C(S)N(CH₃)₂ | CH₃ | CF₃ |
| CH₂CH₂CH₂CF₂CF₃ | C(S)N(CH₃)₂ | CH₃ | CF₂CF₃ |
| CH₂CH₂CH₂CF₂CF₃ | C(S)N(CH₃)₂ | CH₃ | CF₂CF₂CF₃ |
| CH₂CH₂CH₂CF₂CF₃ | C(S)N(CH₃)₂ | CH₂CH₃ | CF₃ |
| CH₂CH₂CH₂CF₂CF₃ | C(S)N(CH₃)₂ | CH₂CH₃ | CF₂CF₃ |
| CH₂CH₂CH₂CF₂CF₃ | C(S)N(CH₃)₂ | CH₂CH₃ | CF₂CF₂CF₃ |
| CH₂CH₂CH₂CF₂CF₃ | C(S)N(CH₃)₂ | F | CF₃ |
| CH₂CH₂CH₂CF₂CF₃ | C(S)N(CH₃)₂ | F | CF₂CF₃ |
| CH₂CH₂CH₂CF₂CF₃ | C(S)N(CH₃)₂ | F | CF₂CF₂CF₃ |
| CH₂CH₂CH₂CF₂CF₃ | C(S)N(CH₃)₂ | Cl | CF₃ |
| CH₂CH₂CH₂CF₂CF₃ | C(S)N(CH₃)₂ | Cl | CF₂CF₃ |
| CH₂CH₂CH₂CF₂CF₃ | C(S)N(CH₃)₂ | Cl | CF₂CF₂CF₃ |

The compound given by the formula (I-B);

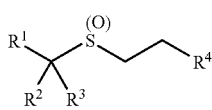
(I-B)

wherein R¹, R², R³ and R⁴ are the combination described in Table 1 to Table 83.

The compound given by the formula (I-C);

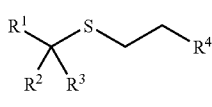
(I-C)

wherein R¹, R², R³ and R⁴ are the combination described in Table 1 to Table 83.

Next, the production of intermediate of the present compound will be illustrated by Reference Production Examples.

Reference Production Example 1

9.6 g of 1-bromo-3,3,3-trifluoropropane and 5 g of thiobenzoic acid were dissolved to 30 ml of N,N-dimethylformamide, and 1.45 g of sodium hydride (60% in oil) was added thereto under ice cooling. The mixture was stirred at room temperature for 12 hours. 10% hydrochloric acid was added to the reaction mixture and the mixture was extracted by ethyl acetate. The organic layer was washed respectively with 10% hydrochloric acid and saturated aqueous solution of sodium chloride, dried over anhydrous magnesium sulfate and concentrated under reduced pressure. The residue was subjected to silica gel chromatography to obtain 6.90 g of S-(3,3,3-trifluoropropyl)benzenethioate given by the below formula:

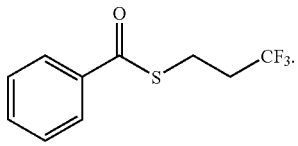

¹H-NMR (CDCl₃, TMS): δ (ppm) 7.97 (d, 2H), 7.58-7.62 (m, 1H), 7.47 (dd, 2H), 3.24 (t, 2H), 2.44-2.56 (m, 2H)

Reference Production Example 2

9.9 g of 1-iodo-3,3,4,4,4-pentafluorobutane and 5 g of thiobenzoic acid were dissolved to 30 ml of N,N-dimethylformamide, and 5.0 g of potassium carbonate was added thereto under ice cooling. The mixture was stirred at room temperature for 20 hours. 10% hydrochloric acid was added to the reaction mixture and the mixture was extracted by ethyl acetate. The organic layer was washed respectively with 10% hydrochloric acid and saturated aqueous solution of sodium chloride, dried over anhydrous magnesium sulfate and concentrated under reduced pressure. The residue was subjected to silica gel chromatography to obtain 7.90 g of S-(3,3,4,4,4-pentafluorobutyl)benzenethioate given by the below formula:

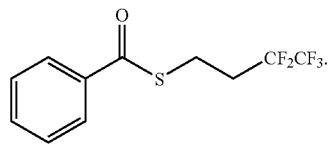

¹H-NMR (CDCl₃, TMS): δ (ppm) 7.95 (d, 2H), 7.58-7.65 (m, 1H), 7.47 (dd, 2H), 3.27 (t, 2H), 2.38-2.53 (m, 2H)

Reference Production Example 3

2.0 g of 1-iodo-3,3,4,4,5,5,5-heptafluoropentane and 0.9 g of thiobenzoic acid were dissolved to 20 ml of N,N-dimethylformamide, and 0.9 g of potassium carbonate was added thereto under ice cooling. The mixture was stirred at room temperature for 20 hours. 10% hydrochloric acid was added to the reaction mixture and the mixture was extracted by ethyl acetate. The organic layer was washed respectively with 10% hydrochloric acid and saturated aqueous solution of sodium chloride, dried over anhydrous magnesium sulfate and concentrated under reduced pressure. The residue was subjected to silica gel chromatography to obtain 1.75 g of S-(3,3,4,4,5,5,5-heptafluoropentyl)benzenethioate given by the below formula:

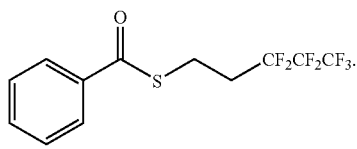

¹H-NMR (CDCl₃, TMS): δ (ppm) 7.95 (d, 2H), 7.58-7.64 (m, 1H), 7.47 (dd, 2H), 3.29 (t, 2H), 2.40-2.56 (m, 2H)

Reference Production Example 4

10 g of S-(3,3,3-trifluoropropyl)benzenethioate was dissolved to 50 ml of tetrahydrofuran and 8.4 ml of sodium methoxide (28% (w/w) methanol solution) was added thereto under ice cooling. Furthermore, 5.1 g of bromoacetonitrile was added dropwise thereto and the mixture was stirred at room temperature for 2 hours. 10% hydrochloric acid was added to the reaction mixture and the mixture was extracted by ethyl acetate. The organic layer was washed respectively with 10% hydrochloric acid and saturated aqueous solution of sodium chloride, dried over anhydrous magnesium sulfate and concentrated under reduced pressure. The residue was dissolved to 40 ml of acetic acid and 20 ml of peracetic acid (32% (w/w) acetic acid solution) was added thereto under ice cooling. Then the mixture was stirred at 60° C. for 10 hours. The reaction mixture was dropped to room temperature and poured into water, then extracted by ethyl acetate. The organic layer was washed respectively with saturated aqueous solution of sodium hydrogen carbonate and saturated aqueous solution of sodium chloride, dried over anhydrous magnesium sulfate and concentrated under reduced pressure. The obtained residue was subjected to silica gel chromatography to obtain 7.04 g of (3,3,3-trifluoropropylsulfonyl)acetonitrile given by the below formula:

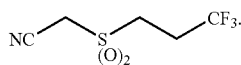

$^1$H-NMR (CDCl$_3$, TMS): δ (ppm) 4.06 (s, 2H), 3.48-3.55 (m, 2H), 2.72-2.84 (m, 2H)

Reference Production Example 5

7.1 g of S-(3,3,4,4,4-pentafluorobutyl)benzenethioate was dissolved to 50 ml of tetrahydrofuran and 4.9 ml of sodium methoxide (28% (w/w) methanol solution) was added thereto under ice cooling. Furthermore, 3.0 g of bromoacetonitrile was added dropwise thereto and the mixture was stirred at room temperature for 20 hours. 10% hydrochloric acid was added to the reaction mixture and the mixture was extracted by ethyl acetate. The organic layer was washed respectively with 10% hydrochloric acid and saturated aqueous solution of sodium chloride, dried over anhydrous magnesium sulfate and concentrated under reduced pressure. The residue was dissolved to 40 ml of acetic acid and 20 ml of peracetic acid (32% (w/w) acetic acid solution) was added thereto under ice cooling. Then the mixture was stirred at 60° C. for 8 hours. The reaction mixture was dropped to room temperature and poured into water, then extracted by ethyl acetate. The organic layer was washed respectively with saturated aqueous solution of sodium hydrogen carbonate and saturated aqueous solution of sodium chloride, dried over anhydrous magnesium sulfate and concentrated under reduced pressure. The obtained residue was subjected to silica gel chromatography to obtain 5.47 g of (3,3,4,4,4-pentafluorobutylsulfonyl)acetonitrile given by the below formula:

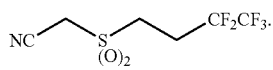

$^1$H-NMR (CDCl$_3$, TMS): δ (ppm) 4.07 (s, 2H), 3.51-3.58 (m, 2H), 2.65-2.78 (m, 2H)

Reference Production Example 6

9.7 g of S-(3,3,4,4,5,5,5-heptafluoropentyl)benzenethioate was dissolved to 30 ml of tetrahydrofuran and 5.7 ml of sodium methoxide (28% (w/w) methanol solution) was added thereto under ice cooling. Furthermore, 3.5 g of bromoacetonitrile was added dropwise thereto and the mixture was stirred at room temperature for 10 hours. 10% hydrochloric acid was added to the reaction mixture and the mixture was extracted by ethyl acetate. The organic layer was washed respectively with 10% hydrochloric acid and saturated aqueous solution of sodium chloride, dried over anhydrous magnesium sulfate and concentrated under reduced pressure. The residue was dissolved to 40 ml of acetic acid and 20 ml of peracetic acid (32% (w/w) acetic acid solution) was added thereto under ice cooling. Then the mixture was stirred at 60° C. for 6 hours. The reaction mixture was dropped to room temperature and poured into water, then extracted by ethyl acetate. The organic layer was washed respectively with saturated aqueous solution of sodium hydrogen carbonate and saturated aqueous solution of sodium chloride, dried over anhydrous magnesium sulfate and concentrated under reduced pressure. The obtained residue was subjected to silica gel chromatography to obtain 6.54 g of S-(3,3,4,4,5,5,5-heptafluoropentylsulfonyl)acetonitrile given by the below formula:

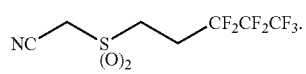

$^1$H-NMR (CDCl$_3$, TMS): δ (ppm) 4.09 (s, 2H), 3.54-3.59 (m, 2H), 2.69-2.84 (m, 2H)

Reference Production Example 7

10 g of methyl thioglycolate and 21 g of 1-iodo-3,3,3-trifluoropropane were dissolved to 200 ml of N,N-dimethylformamide and 13 g of potassium carbonate was added thereto under ice cooling. The mixture was stirred at room temperature for 20 hours. 10% hydrochloric acid was added to the reaction mixture and the mixture was extracted by ethyl acetate. The organic layer was washed respectively with 10% hydrochloric acid and saturated aqueous solution of sodium chloride, dried over anhydrous magnesium sulfate and concentrated under reduced pressure. The residue was dissolved to 100 ml of acetic acid and 50 ml of peracetic acid (32% (w/w) acetic acid solution) was added thereto under ice cooling. Then the mixture was stirred at 60° C. for 16 hours. The reaction mixture was cooled to room temperature and poured into water, then extracted by ethyl acetate. The organic layer was washed respectively with saturated aqueous solution of sodium hydrogen carbonate and saturated aqueous solution of sodium chloride, dried over anhydrous magnesium sulfate and concentrated under reduced pressure. The obtained residue was subjected to silica gel chromatography to obtain 14.1 g of methyl (3,3,3-trifluoropropylsulfonyl)acetate given by the below formula:

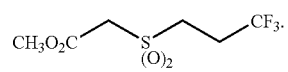

$^1$H-NMR (CDCl$_3$, TMS): δ (ppm) 4.05 (s, 2H), 3.84 (s, 3H), 3.49-3.57 (m, 2H), 2.66-2.79 (m, 2H)

Reference Production Example 8

10 g of methyl thioglycolate and 26 g of 1-iodo-3,3,4,4,4-pentafluorobutane were dissolved to 100 ml of N,N-dimethylformamide and 13 g of potassium carbonate was added thereto under ice cooling. The mixture was stirred at room temperature for 20 hours. 10% hydrochloric acid was added to the reaction mixture and the mixture was extracted by ethyl acetate. The organic layer was washed respectively with 10% hydrochloric acid and saturated aqueous solution of sodium chloride, dried over anhydrous magnesium sulfate and concentrated under reduced pressure. The residue was dissolved to 100 ml of acetic acid and 50 ml of peracetic acid (32% (w/w) acetic acid solution) was added thereto under ice cooling. Then the mixture was stirred at 60° C. for 16 hours. The reaction mixture was cooled to room temperature and poured into water, then extracted by ethyl acetate. The organic layer was washed respectively with saturated aqueous solution of sodium hydrogen carbonate and saturated aqueous solution of sodium chloride, dried over anhydrous magnesium sulfate and concentrated under reduced pressure. The obtained residue was subjected to silica gel chromatography to obtain 23.1 g of methyl (3,3,4,4-pentafluorobutylsulfonyl)acetate given by the below formula:

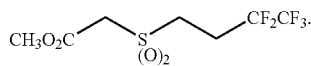

$^1$H-NMR (CDCl$_3$, TMS): δ (ppm) 4.05 (s, 2H), 3.86 (s, 3H), 3.52-3.59 (m, 2H), 2.59-2.75 (m, 2H)

Reference Production Example 9

5 g of methyl thioglycolate and 15 g of 1-iodo 3,3,4,4,5,5,5-heptafluoropentane were dissolved to 50 ml of N,N-dimethylformamide and 6.5 g of potassium carbonate was added thereto under ice cooling. The mixture was stirred at room temperature for 10 hours. 10% hydrochloric acid was added to the reaction mixture and the mixture was extracted by ethyl acetate. The organic layer was washed respectively with 10% hydrochloric acid and saturated aqueous solution of sodium chloride, dried over anhydrous magnesium sulfate and concentrated under reduced pressure. The residue was dissolved to 50 ml of acetic acid and 20 ml of peracetic acid (32% (w/w) acetic acid solution) was added thereto under ice cooling. Then the mixture was stirred at 60° C. for 4 hours. The reaction mixture was cooled to room temperature and poured into water, then extracted by ethyl acetate. The organic layer was washed respectively with saturated aqueous solution of sodium hydrogen carbonate and saturated aqueous solution of sodium chloride, dried over anhydrous magnesium sulfate and concentrated under reduced pressure. The obtained residue was subjected to silica gel chromatography to obtain 12.6 g of methyl (3,3,4,4,5,5,5-heptafluoropentylsulfonyl)acetate given by the below formula:

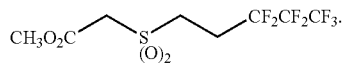

$^1$H-NMR (CDCl$_3$, TMS): δ (ppm) 4.06 (s, 2H), 3.86 (s, 3H), 3.52-3.59 (m, 2H), 2.63-2.78 (m, 2H)

Reference Production Example 10

0.3 g of methyl 5,5,6,6,6-pentafluoro-2-(3,3,3-trifluoropropylsulfonyl)hexanoate was dissolved to 30 ml of methanol. An aqueous solution of potassium hydroxide (a mixed solution of 0.3 g of potassium hydroxide and 5 ml of water) was added thereto at room temperature and the mixture was stirred at the same temperature for 24 hours. 10% hydrochloric acid was added to the reaction mixture and the mixture was extracted by ethyl acetate. The organic layer was washed with saturated aqueous solution of sodium chloride, dried over anhydrous magnesium sulfate and concentrated under reduced pressure to obtain 0.28 g of 5,5,6,6,6-pentafluoro-2-(3,3,3-trifluoropropylsulfonyl)hexanoic acid given by the below formula:

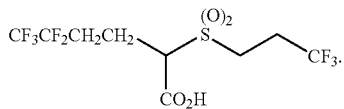

$^1$H-NMR (CDCl$_3$, TMS): δ (ppm) 3.91-3.98 (m, 1H), 3.48-3.56 (m, 2H), 2.64-2.78 (m, 2H), 2.23-2.54 (m, 4H)

Reference Production Example 11

0.5 g of methyl 2-methyl-5,5,6,6,6-pentafluoro-2-(3,3,4,4,4-pentafluorobutylsulfonyl)hexanoate was dissolved to 30 ml of methanol. An aqueous solution of potassium hydroxide (a mixed solution of 0.3 g of potassium hydroxide and 5 ml of water) was added thereto at room temperature and the mixture was stirred at the same temperature for 6 hours. 10% hydrochloric acid was added to the reaction mixture and the mixture was extracted by ethyl acetate. The organic layer was washed with saturated aqueous solution of sodium chloride, dried over anhydrous magnesium sulfate and concentrated under reduced pressure to obtain 0.48 g of 2-methyl-5,5,6,6,6-pentafluoro-2-(3,3,4,4,4-pentafluorobutylsulfonyl)hexanoic acid given by the below formula:

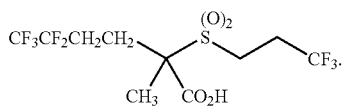

$^1$H-NMR (CDCl$_3$, TMS): δ (ppm) 3.48-3.54 (m, 2H), 2.67-2.78 (m, 2H), 2.18-2.56 (m, 4H), 1.73 (s, 3H)

Reference Production Example 12

0.5 g of methyl 2-ethyl-5,5,6,6,6-pentafluoro-2-(3,3,3-trifluoropropylsulfonyl)hexanoate was dissolved to 30 ml of methanol. An aqueous solution of potassium hydroxide (a mixed solution of 0.3 g of potassium hydroxide and 5 ml of water) was added thereto at room temperature and the mixture was stirred at the same temperature for 10 hours. 10% hydrochloric acid was added to the reaction mixture and the mixture was extracted by ethyl acetate. The organic layer was washed with saturated aqueous solution of sodium chloride, dried over anhydrous magnesium sulfate and concentrated under reduced pressure to obtain 0.48 g of 2-ethyl-5,5,6,6,6-pentafluoro-2-(3,3,3-trifluoropropylsulfonyl)hexanoic acid given by the below formula:

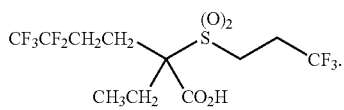

$^1$H-NMR (CDCl$_3$, TMS): δ (ppm) 3.35-3.71 (m, 2H), 2.08-2.78 (m, 8H), 1.10 (t, 3H)

Reference Production Example 13

20 g of ethyl 2-mercaptopropionate and 33 g of 1-iodo-3,3,3-trifluoropropane were dissolved to 200 ml of N,N-dimethylformamide and 21 g of potassium carbonate was added thereto under ice cooling. The mixture was stirred at room temperature for 4 hours. 10% hydrochloric acid was added to the reaction mixture and the mixture was extracted by ethyl acetate. The organic layer was washed respectively with 10% hydrochloric acid and saturated aqueous solution of sodium chloride, dried over anhydrous magnesium sulfate and concentrated under reduced pressure. The residue was dissolved to 100 ml of acetic acid and 30 ml of peracetic acid (30% (w/w) acetic acid solution) was added thereto under ice cooling. Then the mixture was stirred at 60° C. for 4 hours. The reaction mixture was dropped to room temperature and poured into water, then extracted by ethyl acetate. The organic layer was washed respectively with saturated aqueous solution of sodium hydrogen carbonate and saturated aqueous solution of sodium chloride, dried over anhydrous magnesium sulfate and concentrated under reduced pressure. The obtained residue was subjected to silica gel chromatography to obtain 36.3 g of ethyl 2-(3,3,3-trifluoropropylsulfonyl)propionate given by the below formula:

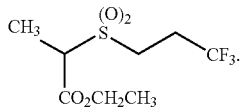

$^1$H-NMR (CDCl$_3$, TMS): δ (ppm) 4.24-4.38 (m, 2H), 3.94 (q, 1H), 3.37-3.55 (m, 2H), 2.62-2.78 (m, 2H), 1.69 (d, 3H), 1.34 (t, 3H)

Referential Production Example 14

40 g of 5,5,6,6,6-pentafluorohexanenitrile was added dropwise with 11 ml of bromine and 2 ml of phosphorus tribromide at room temperature, followed by stirring at 90° C. for 6 hours. The reaction mixture was dropped to room temperature. The reaction mixture was poured into water, followed by extraction with ethyl acetate. The organic layer was subsequently washed with saturated aqueous solution of sodium thiosulfate and saturated aqueous solution of sodium chloride, dried over anhydrous magnesium sulfate, and then concentrated under reduced pressure. The obtained residue was subjected to silica gel chromatography to obtain 17.5 g of 2-bromo-5,5,6,6,6-pentafluorohexanenitrile given by the below formula:

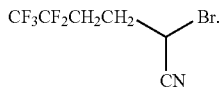

$^1$H-NMR (CDCl$_3$, TMS): δ (ppm) 3.95-4.04 (m, 1H), 3.49-3.57 (m, 2H), 2.06-2.78 (m, 6H)

Referential Production Example 15

0.5 g of methyl 5,5,6,6,7,7,7-heptafluoro-2-(3,3,4,4,4-pentafluorobutylsulfonyl)heptanoate was dissolved to 30 ml of methanol, added with an aqueous solution of potassium hydroxide (a mixed solution of 0.3 g of potassium hydroxide and 5 ml of water) at room temperature, and then stirred at the same temperature for 2 days. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure to obtain 0.48 g of 5,5,6,6,7,7,7-heptafluoro-2-(3,3,4,4,4-pentafluorobutylsulfonyl)heptanoic acid given by the below formula:

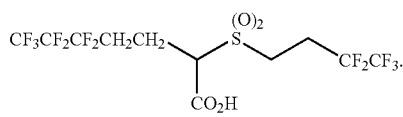

$^1$H-NMR (CDCl$_3$, TMS): δ (ppm) 3.95-4.04 (m, 1H), 3.49-3.57 (m, 2H), 2.06-2.78 (m, 6H)

Referential Production Example 16

1.2 g of methyl 5,5,6,6,7,7,7-heptafluoro-2-methyl-2-(3,3,4,4,4-pentafluorobutylsulfonyl)heptanoate was dissolved to 30 ml of methanol, added with an aqueous solution of potassium hydroxide (a mixed solution of 0.8 g of potassium hydroxide and 10 ml of water) at room temperature, and then stirred at the same temperature for 2 days. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure to obtain 1.10 g of 5,5,6,6,7,7,7-heptafluoro-2-methyl-2-(3,3,4,4,4-pentafluorobutylsulfonyl)heptanoic acid given by the below formula:

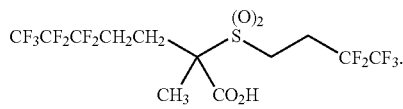

$^1$H-NMR (CDCl$_3$, TMS): δ (ppm) 3.50-3.58 (m, 2H), 2.14-2.77 (m, 6H), 1.75 (s, 3H)

Referential Production Example 17

0.5 g of methyl 5,5,6,6,6-pentafluoro-2-(3,3,4,4,4-pentafluorobutylsulfonyl)hexanoate was dissolved to 50 ml of methanol, added with an aqueous solution of potassium hydroxide (a mixed solution of 0.4 g of potassium hydroxide and 5 ml of water) at room temperature, and then stirred at the same temperature for 1 day. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure to obtain 0.48 g of 5,5,6,6,6-pentafluoro-2-(3,3,4,4,4-pentafluorobutylsulfonyl)hexanoic acid given by the below formula:

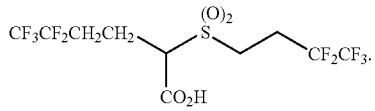

$^1$H-NMR (CDCl$_3$, TMS): δ (ppm) 3.95-4.01 (m, 1H), 3.50-3.56 (m, 2H), 2.22-2.75 (m, 6H)

Referential Production Example 18

0.9 g of methyl 2-methyl-5,5,6,6,6-pentafluoro-2-(3,3,4,4,4-pentafluorobutylsulfonyl)hexanoate was dissolved to 50 ml of methanol, added with an aqueous solution of potassium hydroxide (a mixed solution of 0.7 g of potassium hydroxide and 5 ml of water) at room temperature, and then stirred at the same temperature for 1 day. The reaction mixture was added with 10% hydrochloric acid, followed by extraction with ethyl acetate. The organic layer was washed with saturated aqueous solution of sodium chloride, dried over anhydrous magnesium sulfate, and then concentrated under reduced pressure to obtain 0.78 g of 2-methyl-5,5,6,6,6-pentafluoro-2-(3,3,4,4,4-pentafluorobutylsulfonyl)hexanoic acid given by the below formula:

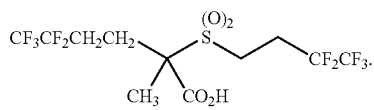

$^1$H-NMR (CDCl$_3$, TMS): δ (ppm) 3.50-3.59 (m, 2H), 2.16-2.75 (m, 6H), 75 (s, 3H)

Formulation Examples are exemplified below. In addition, "part" means part by weight.

Formulation Example 1

9 parts of each of the present compounds (1) to (103) are dissolved in 37.5 parts of xylene and 37.5 parts of N,N-dimethylformamide, and 10 parts of polyoxyethylene styryl phenyl ether and 6 parts of calcium dodecylbenzenesulfonate are added thereto, followed by stirring and mixing well, to give an emulsifiable concentrate for each compound.

Formulation Example 2

To 40 parts of each of the present compounds (1) to (103) are added 5 parts of SORPOL 5060 (registered trade name for TOHO KAGAKU KOGYO), followed by mixing well. To the mixture are added 32 parts of CARPLEX #80 (registered trade name for SHIONOGI & Co., synthetic hydrated silicone oxide fine powder) and 23 parts of 300 mesh diatomaceous earth, followed by mixing with a juice mixer, to give a wettable powder for each compound.

Formulation Example 3

To 3 parts of each of the present compounds (1) to (103) are added 5 parts of synthetic hydrated silicon oxide fine powder, 5 parts of sodium dodecylbenzenesulfonate, 30 parts of bentonite, and 57 parts of clay, followed by stirring and mixing well. Then an appropriate amount of water is added to this mixture, followed by further stirring, granulating with a granulator, and air drying, to give a granule for each compound.

Formulation Example 4

4.5 parts of each of the present compounds (1) to (103), 1 part of synthetic hydrated silicon oxide fine powder, 1 part of Doriresu B (Sankyo Co., Ltd.) as a flocculant and 7 parts of clay are well mixed with a mortar, followed by stirring and mixing with a juice mixer. To the resulting mixture are added 86.5 parts of cut clay, followed by stirring and mixing well, to give a dust for each compound.

Formulation Example 5

10 parts of each of the present compounds (1) to (103), 35 parts of white carbon containing 50 parts of polyoxyethylene alkyl ether sulfate ammonium salt and 55 parts of water are mixed and pulverized by the wet grinding method to give a formulation for each compound.

Formulation Example 6

0.5 parts of each of the present compounds (1) to (103) are dissolved in 10 parts of dichloromethane, and the resulting solution is mixed with 89.5 parts of Iso-Par M (isoparaffine: registered trade name for EXXON CHEMICAL LTD) to give an oil solution.

Formulation Example 7

0.1 parts of each of the present compounds (1) to (103) and 49.9 parts of NEO-CHIOZOL (CHUO KASEI Co., LTD) are charged into aerosol can, and aerosol valve is fixed to the can. Then 25 parts of dimethyl ether and 25 parts of LPG are filled in the can, followed and fitting an actuator on it, to give an oil aerosol.

Formulation Example 8

0.6 parts of each of the present compounds (1) to (103), 0.01 parts of BHT, 5 parts of xylene, 3.39 parts of deodorized kerosene and 1 part of emulsifier [Atmos 300 (registered trade name for ATMOS CHEMICAL LTD)] are mixed and dissolved. The solution obtained and 50 parts of distilled water are charged into aerosol container, and a valve is fixed to the container. 40 Parts of propellant (LPG) are charged under pressure through the valve to give an aqueous aerosol.

The following test example will demonstrate that the present compounds are useful as an active ingredient of noxious arthropod controlling agent.

Test Example 1

The formulation obtained in Formulation Example 5 using the present compounds (1), (2), (3), (4), (5), (6), (8), (9), (11), (12), (13), (14), (15), (16), (17), (18), (20), (21), (22), (23), (24), (25), (26), (27), (29), (30), (31), (32), (33), (34), (35), (36), (37), (38), (39), (40), (41), (44), (45), (46), (47), (48), (49), (50), (52), (53), (55), (56), (57), (58), (59), (60), (61), (63), (64), (65), (67), (68), (71), (72), (73), (74), (75), (78), (79), (80), (81), (82), (83), (84), (86), (87), (88), (89), (90), (91), (93), (94), (96), (97), (100), (101), (102) and (103) respectively, was diluted with water so that the active ingredient concentration came to 55.6 ppm to prepare a test solution.

50 g of molding Bonsoru 2 (available from Sumitomo Chemical Co., Ltd.) was put into a polyethylene cup having five holes of 5 mm in diameter, and 10 to 15 seeds of rice were planted in the polyethylene cup. The rice plants were grown until the second foliage leaves developed and then treated with the test solution, which had been prepared as described above and was absorbed in a volume of 45 ml from the bottom of the cup. The rice plants were left in a greenhouse at 25° C. for 6 days and then cut into the same height of 5 cm. Thirty first-instar larvae of brown planthoppers (*Nilaparvata*

*lugens*) were set free on the rice plants, which were then left in the greenhouse at 25° C. On the 6th day after the release of brown planthopper larvae, the number of brown planthoppers parasitic on the rice plants was examined. As a result, in the treatment with each of the present compounds (1), (2), (3), (4), (5), (6), (8), (9), (11), (12), (13), (14), (15), (16), (17), (18), (20), (21), (22), (23), (24), (25), (26), (27), (29), (30), (31), (32), (33), (34), (35), (36), (37), (38), (39), (40), (41), (44), (45), (46), (47), (48), (49), (50), (52), (53), (55), (56), (57), (58), (59), (60), (61), (63), (64), (65), (67), (68), (71), (72), (73), (74), (75), (78), (79), (80), (81), (82), (83), (84), (86), (87), (88), (89), (90), (91), (93), (94), (96), (97), (100), (101), (102) and (103),
the number of parasitic insects on the 6th day after the treatment was not greater than 3.

Test Example 2

The formulation obtained according to Formulation Example 5 using the present compounds (1), (2), (3), (4), (5), (6), (8), (9), (10), (11), (12), (13), (14), (15), (16), (17), (18), (19), (20), (21), (22), (23), (25), (26), (28), (29), (30), (31), (32), (33), (34), (35), (36), (37), (38), (39), (40), (41), (43), (44), (45), (46), (47), (48), (49), (50), (52), (53), (55), (56), (57), (58), (59), (60), (61), (63), (64), (65), (66), (67), (68), (69), (78), (71), (72), (73), (74), (75), (78), (79), (80), (81), (82), (84), (86), (87), (88), (89), (90), (91), (93), (94), (95), (96), (97), (99), (100), (101), (102) and (103) respectively, was diluted with water so that the active ingredient concentration came to 500 ppm to prepare a test solution.

On the bottom of a polyethylene cup having a diameter of 5.5 cm, a filter paper having the same diameter was laid, and 0.7 ml of the above test solution was added dropwise on the filter paper, followed by putting 30 mg of sucrose on it uniformly as a bait. Ten female *Musca domestica* imagoes were set free in the polyethylene cup and covered it with a lid. After 24 hours, the number of surviving and dead *Musca domestica* was examined and the rate of dead pests was calculated.

As a result, in the treatment with each of the present compounds (1), (2), (3), (4), (5), (6), (8), (9), (10), (11), (12), (13), (14), (15), (16), (17), (18), (19), (20), (21), (22), (23), (25), (26), (28), (29), (30), (31), (32), (33), (34), (35), (36), (37), (38), (39), (40), (41) (43), (44), (45), (46), (47), (48), (49), (50), (52), (53), (55), (56), (57), (58), (59), (60), (61), (63), (64), (65) (66), (67), (68), (69), (70), (71), (72), (73), (74), (75), (78), (79), (80), (81), (82), (84), (86), (87), (88), (89), (90), (91), (93), (94), (95), (96), (97), (99), (100), (101), (102) and (103), the rate of dead pests was 70% or more.

Test Example 3

The formulation obtained according to Formulation Example 5 using the present compounds (1), (2), (3), (4), (5), (6), (7), (8), (9), (10), (11), (12), (13), (14), (15), (16), (17), (20), (21), (23), (26), (29), (30), (31), (32), (33), (34), (35), (36), (37), (38), (39), (40), (41), (44), (45), (46), (47), (49), (50), (52), (53), (55), (56), (57), (58), (59), (60), (61), (63), (64), (65), (67), (68), (69), (70), (71), (72), (73), (74), (75), (78), (79), (80), (81), (84), (86), (87), (88), (89), (90), (91), (93), (94), (96), (97), (100), (101), (102) and (103) respectively, was diluted with water so that the active ingredient concentration came to 500 ppm to prepare a test solution.

On the bottom of a polyethylene cup having a diameter of 5.5 cm, a filter paper having the same diameter was laid, and 0.7 ml of the above test solution was added dropwise on the filter paper, followed by putting 30 mg of sucrose on it uniformly as a bait. Two male *Blattella germanica* imagoes were set free in the polyethylene cup and covered it with a lid. After 6 days, the number of surviving and dead *Blattella germanica* was examined and the rate of dead pests was calculated.

As a result, in the treatment with each of the present compounds (1), (2), (3), (4), (5), (6), (7), (8), (9), (10), (11), (12), (13), (14), (15), (16), (17), (20), (21), (23), (26), (29), (30), (31), (32), (33), (34), (35), (36), (37), (38), (39), (40), (41), (44), (45), (46), (47), (49), (50), (52), (53), (55), (56), (57), (58), (59), (60), (61), (63), (64), (65), (67), (68), (69), (70), (71), (72), (73), (74), (75), (78), (79), (80), (81), (84), (86), (87), (88), (89), (90), (91), (93), (94), (96), (97), (100), (101), (102) and (103) the rate of dead pests was 100%.

Test Example 4

The formulation obtained according to Formulation Example 5 using the present compounds (1), (2), (3), (4), (5), (6), (7), (8), (9), (10), (11), (12), (13), (14), (15), (16), (17), (18), (19), (20), (21), (22), (23), (24), (25), (26), (29), (30), (31), (32), (33), (34), (35), (36), (37), (38), (39), (40), (41), (42) (45), (46), (47), (49), (50), (51), (52), (53), (56), (57), (58), (59), (60), (61), (63), (65), (67), (68), (69), (70), (71), (72), (73), (74), (75), (76), (78), (79), (80), (81), (82), (83), (84), (86), (87), (88), (89), (90), (91), (92), (93), (94), (95), (96), (97), (100), (102) and (103) respectively, was diluted with water so that the active ingredient concentration came to 500 ppm to prepare a test solution.

0.7 ml of above test solution was added to 100 ml of ion exchanged water (active ingredient concentration: 3.5 ppm). Twenty last-instar larvae of *Culex pipiens pallens* were set free in the solution. After one day, the number of surviving and dead *Culex pipiens pallens* was examined and the rate of dead pests was calculated.

As a result, in the treatment with each of the present compounds (1), (2), (3), (4), (5), (6), (7), (8), (9), (10), (11), (12), (13), (14), (15), (16), (17), (18), (19), (20), (21), (22), (23), (24), (25), (26), (29), (30), (31), (32), (33), (34), (35), (36), (37), (38), (39), (40), (41), (42), (45), (46), (47), (49), (50), (51), (52), (53), (56), (57), (58), (59), (60), (61), (63), (65), (67), (68), (69), (70), (71), (72), (73), (74), (75), (76), (78), (79), (80), (81), (82), (83), (84), (86), (87), (88), (89), (90), (91), (92), (93), (94), (95), (96), (97), (100), (102) and (103), the rate of dead pests was not less than 90%.

INDUSTRIAL APPLICABILITY

The present compounds are useful for an active ingredient of noxious arthropod agent.

The invention claimed is:
1. An organic sulfur compound given by the formula [I]:

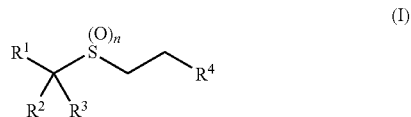

wherein
$R^1$ represents a C3-C6 fluoroalkyl group,
$R^2$ represents a group represented by $C(=O)R^5$ or a group represented by $C(=S)R^6$,
$R^3$ represents a hydrogen atom, a halogen atom or a C1-C4 alkyl group,
$R^4$ represents a C1-C5 fluoroalkyl group, $R^5$ and $R^6$ independently represent an amino group optionally substituted by one or two C1-C4 alkyl group(s) or a C2-C5 cyclic amino group, n represents 0, 1 or 2.

2. The organic sulfur compound according to claim 1, wherein n is 2.

3. The organic sulfur compound according to claim 1, wherein $R^2$ is a group represented by $C(=O)R^5$.

4. The organic sulfur compound according to claim 1, wherein $R^2$ is a group represented by $C(=O)R^5$ and $R^5$ is an amino group optionally substituted by one or two C1-C4 alkyl group(s).

5. The organic sulfur compound according to claim 1, wherein $R^2$ is a group represented by $C(=O)R^5$ and $R^5$ is an amino group.

6. The organic sulfur compound according to claim 1, wherein $R^3$ is a halogen atom.

7. A noxious arthropod controlling agent comprising the organic sulfur compound according to claim 1 and an inert carrier.

8. A method for controlling noxious arthropods, which comprises applying an effective amount of the organic sulfur compound according to claim 1 to noxious arthropods or at a habitat of noxious arthropods.

* * * * *